US011083862B2

(12) United States Patent
Bornholdt et al.

(10) Patent No.: US 11,083,862 B2
(45) Date of Patent: Aug. 10, 2021

(54) RESPIRATORY MASK SYSTEM

(71) Applicant: Fisher & Paykel Healthcare Limited, Auckland (NZ)

(72) Inventors: Melissa Catherine Bornholdt, Auckland (NZ); Jonathan Mark Downey, Auckland (NZ); Bruce Michael Walls, Auckland (NZ); Adam Luke Gilbert, Auckland (NZ); Janine Elizabeth Collins, Auckland (NZ); Chris Onin Limpin Hipolito, Auckland (NZ); Thomas Mark Richardson, Auckland (NZ); Silas Sao Jin Siew, Auckland (NZ); James Patrick O'Connor, Auckland (NZ); Christopher John Large, Auckland (NZ); Tony William Spear, Auckland (NZ); Matthew Roger Stephenson, London (GB); Paul Mathew Freestone, Auckland (NZ); Jake Baker Hocking, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 356 days.

(21) Appl. No.: 16/085,156

(22) PCT Filed: Mar. 15, 2017

(86) PCT No.: PCT/NZ2017/050025
§ 371 (c)(1),
(2) Date: Sep. 14, 2018

(87) PCT Pub. No.: WO2017/160166
PCT Pub. Date: Sep. 21, 2017

(65) Prior Publication Data
US 2019/0151592 A1  May 23, 2019

Related U.S. Application Data

(60) Provisional application No. 62/308,654, filed on Mar. 15, 2016, provisional application No. 62/324,139, (Continued)

(51) Int. Cl.
*A61M 16/06* (2006.01)

(52) U.S. Cl.
CPC .... *A61M 16/0683* (2013.01); *A61M 16/0616* (2014.02); *A61M 16/0666* (2013.01)

(58) Field of Classification Search
CPC .......... A61M 16/0057; A61M 16/0066; A61M 16/024; A61M 16/06; A61M 16/0605;
(Continued)

(56) References Cited

U.S. PATENT DOCUMENTS

2002/0005201 A1   1/2002   Gradon et al.
2006/0042629 A1   3/2006   Geist
(Continued)

FOREIGN PATENT DOCUMENTS

EP        2 731 655         7/2017
WO     WO 2004/073778      9/2004
(Continued)

OTHER PUBLICATIONS

Aug. 31, 2017, International Search Report and Written Opinion for International Application No. PCT/NZ2017/050025 filed on Mar. 15, 2017.

*Primary Examiner* — Annette Dixon
(74) *Attorney, Agent, or Firm* — Knobbe, Marten, Olson & Bear, LLP

(57) ABSTRACT

A respiratory mask system comprising a mask interface comprising a frame for a headgear assembly. The frame comprises a body comprising a first surface and a substantially opposing second surface. The body further comprises (Continued)

a gas inlet and optionally an outlet vent. The gas inlet may be substantially elliptical in shape. The frame may comprise a recessed region for receiving a yoke of a headgear assembly to attach the headgear to the mask interface. The respiratory mask system may also comprise a yoke for attaching to the frame.

15 Claims, 128 Drawing Sheets

Related U.S. Application Data filed on Apr. 18, 2016, provisional application No. 62/402,301, filed on Sep. 30, 2016.

(58) Field of Classification Search
CPC .......... A61M 16/0611; A61M 16/0616; A61M 16/0622; A61M 16/0633; A61M 16/0644; A61M 16/0666; A61M 16/0683; A61M 16/0694; A61M 16/0816; A61M 16/0825; A61M 16/0875; A61M 16/208; A61M 16/22; A61M 2016/0661; A61M 2039/2426; A61M 2202/0014; A61M 2202/0085; A61M 2202/0225; A61M 2205/0216; A61M 2205/42; A61M 2205/587; A61M 2206/14; A61M 2210/0618; A62B 18/084; Y10T 24/1959; Y10T 24/32

See application file for complete search history.

(56) References Cited

U.S. PATENT DOCUMENTS

| 2013/0008447 | A1 | 1/2013 | Gunaratham et al. |
|---|---|---|---|
| 2015/0283347 | A1 | 10/2015 | Barlow et al. |
| 2016/0015921 | A1 | 1/2016 | Harrison et al. |
| 2016/0058966 | A1 | 3/2016 | O'Donnell et al. |
| 2019/0217039 | A1* | 7/2019 | Hocking ........... A61M 16/0683 |

FOREIGN PATENT DOCUMENTS

| WO | WO 2008/106716 | 9/2008 |
|---|---|---|
| WO | WO 2009/108995 | 9/2009 |
| WO | WO 2014/175752 | 10/2014 |
| WO | WO 2015/193833 | 12/2015 |

\* cited by examiner

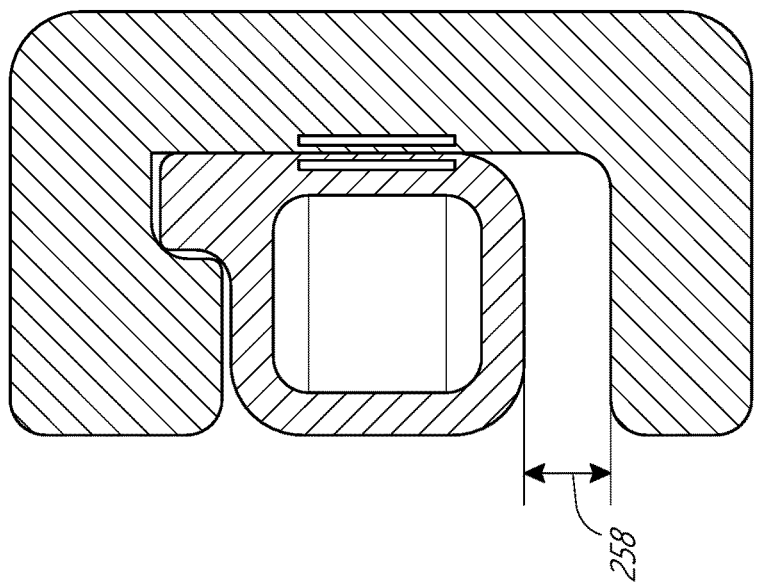
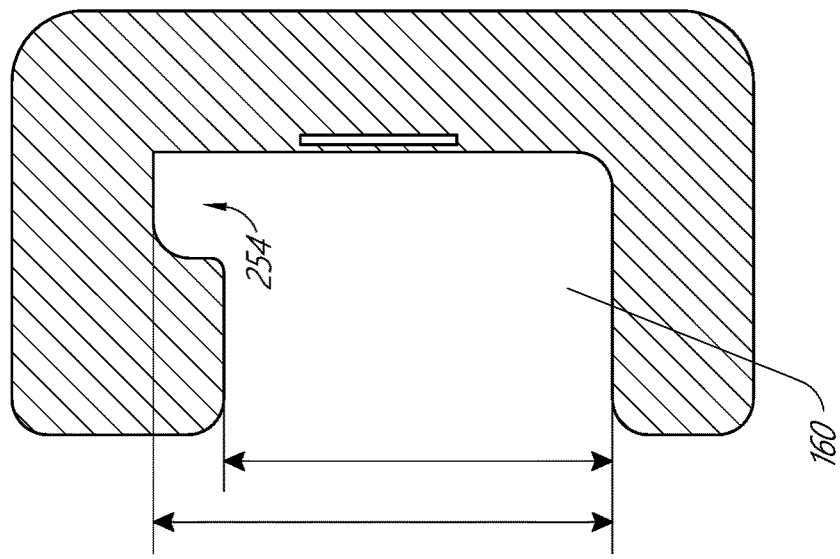
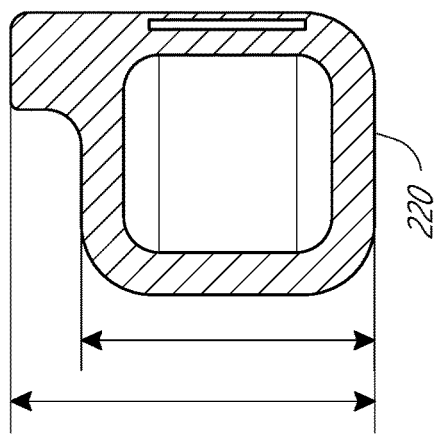
FIG. 58

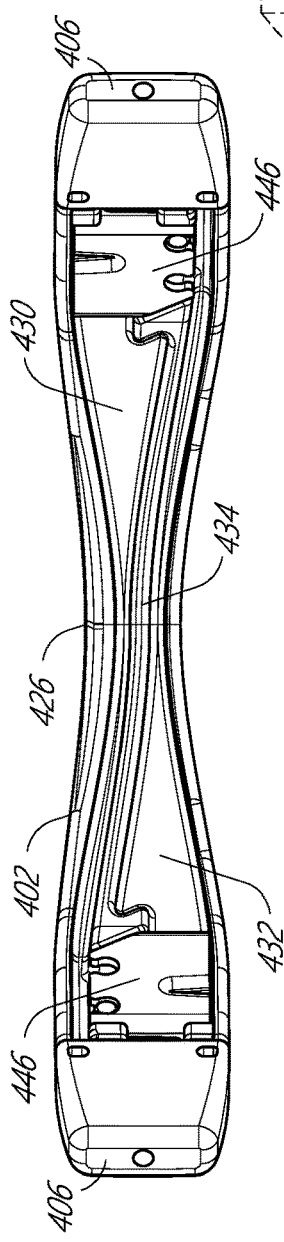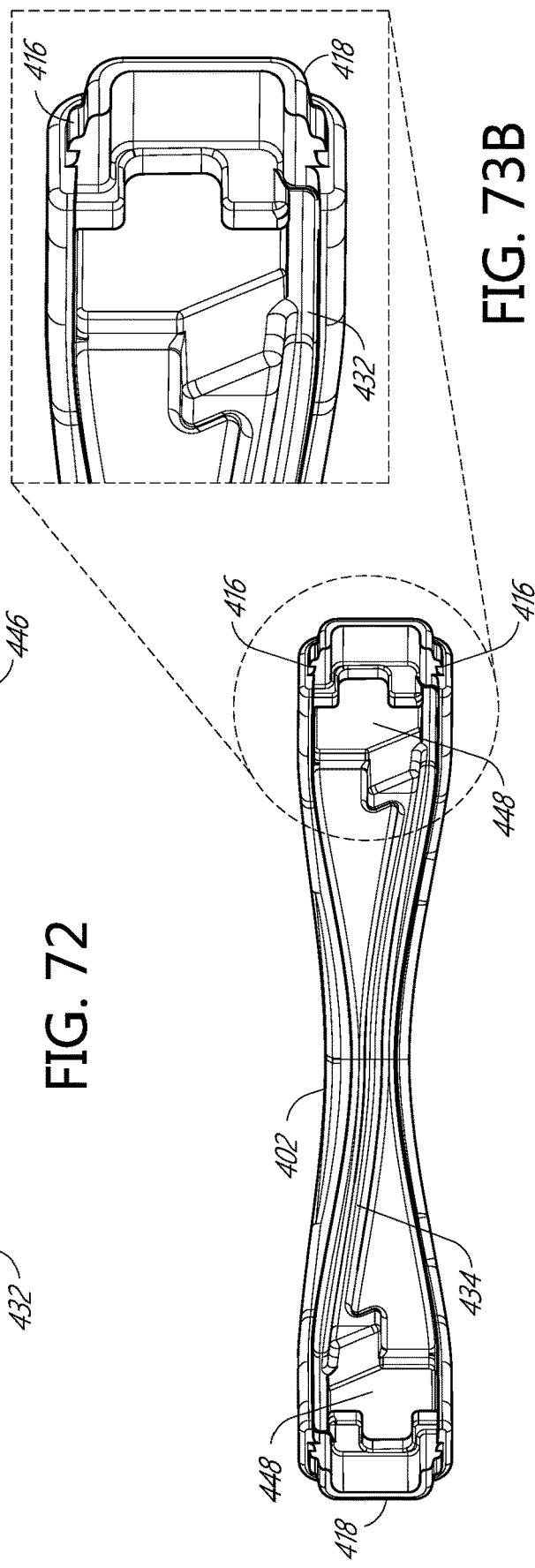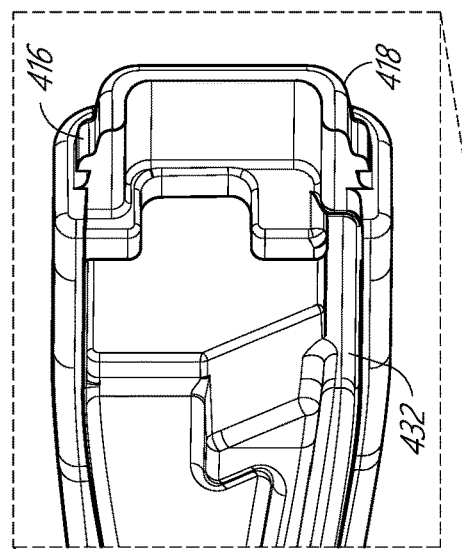

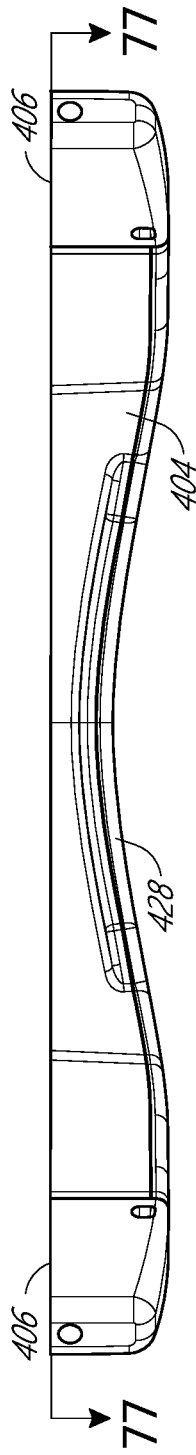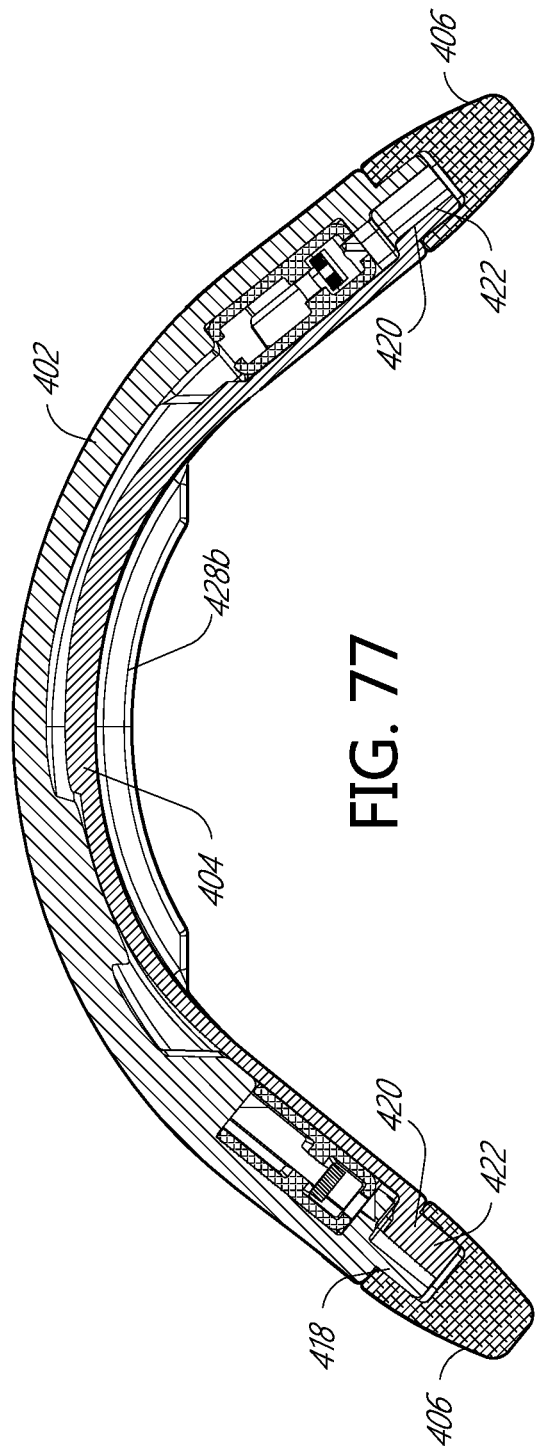

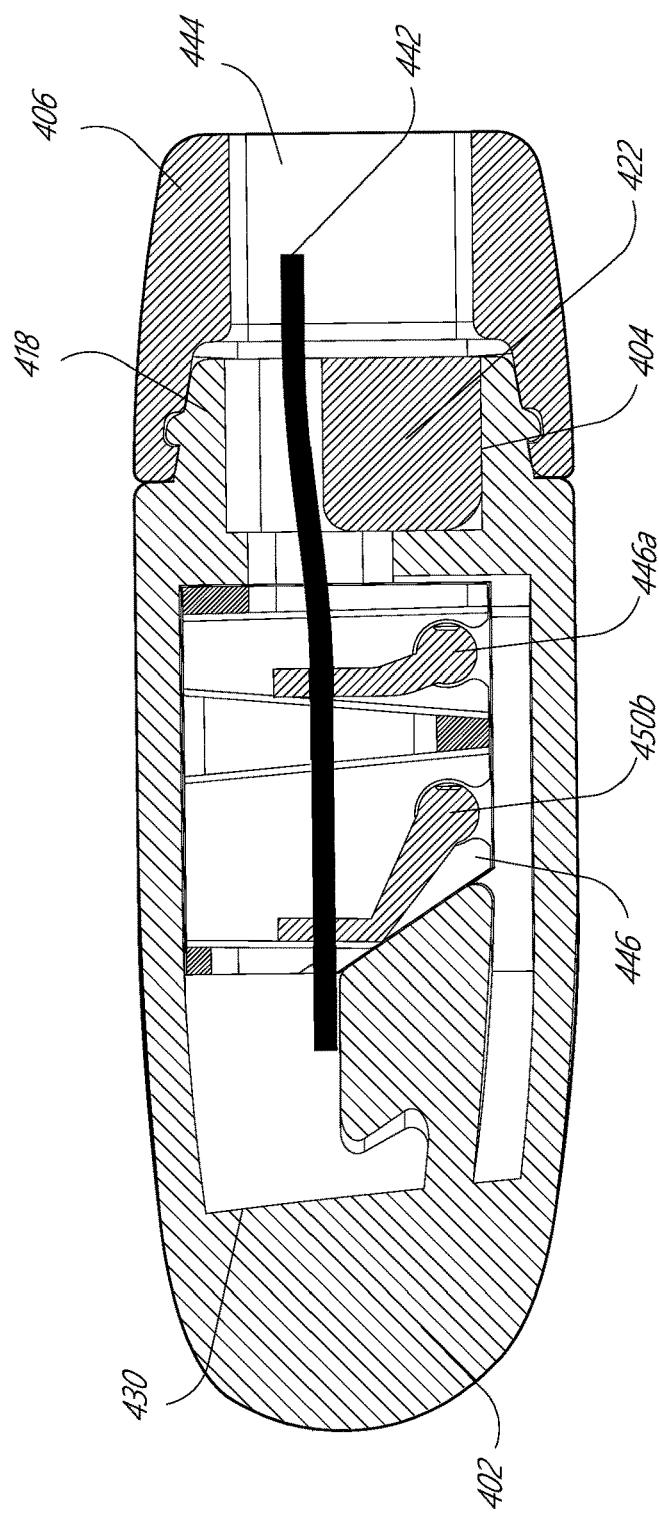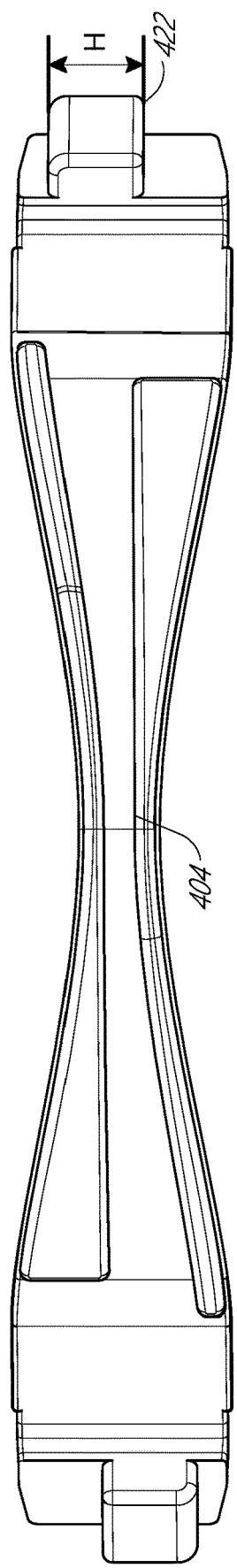
FIG. 83
FIG. 84

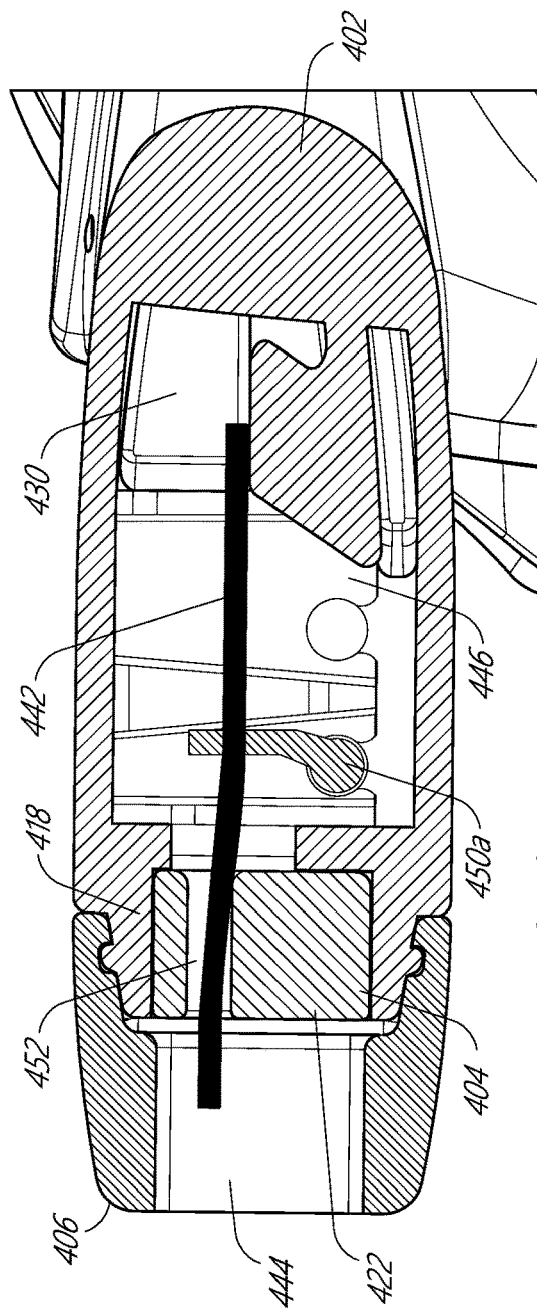
FIG. 85
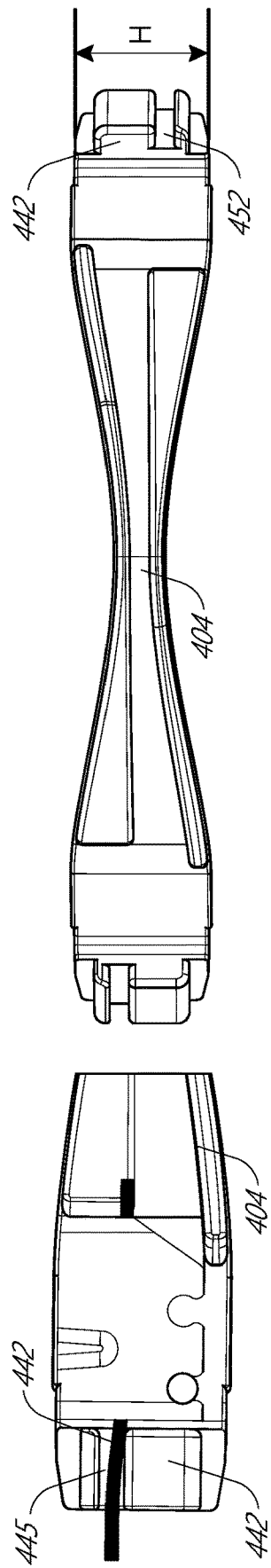
FIG. 87
FIG. 86

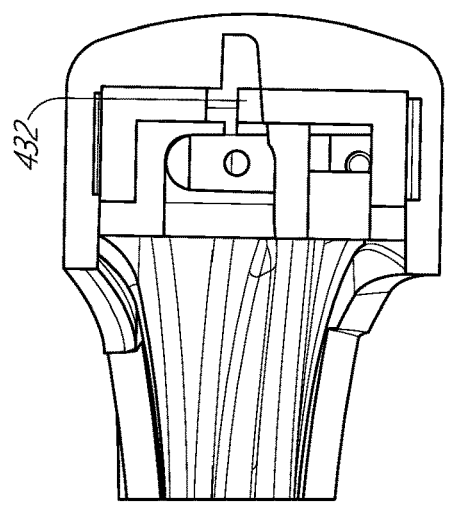
FIG.90
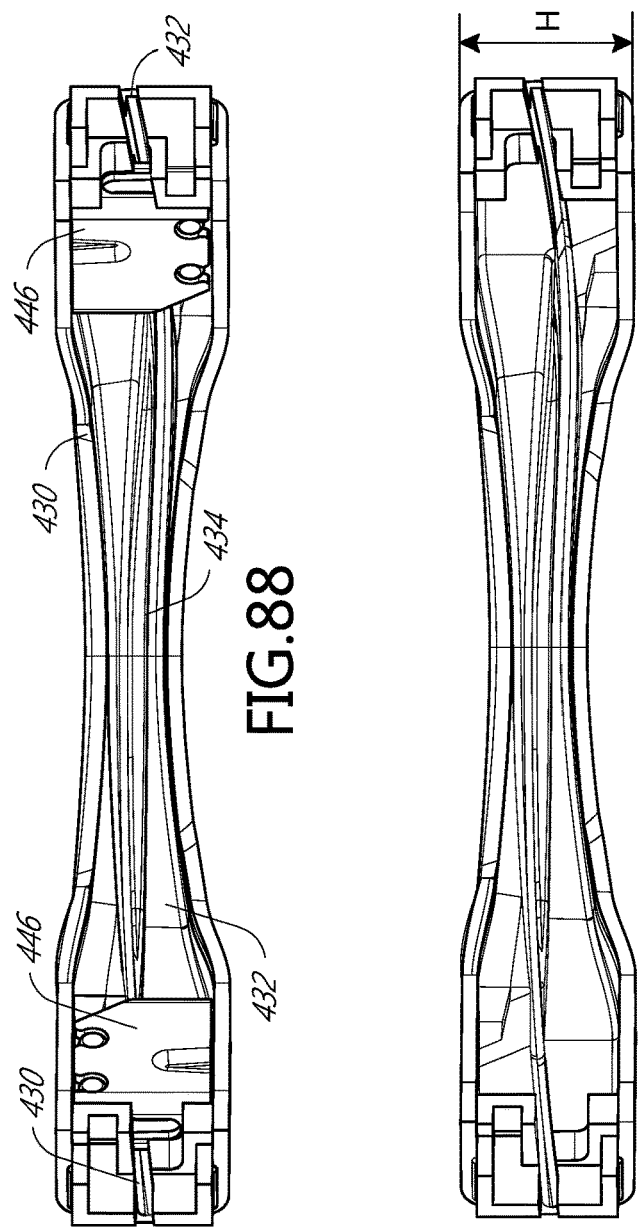
FIG.88
FIG.89

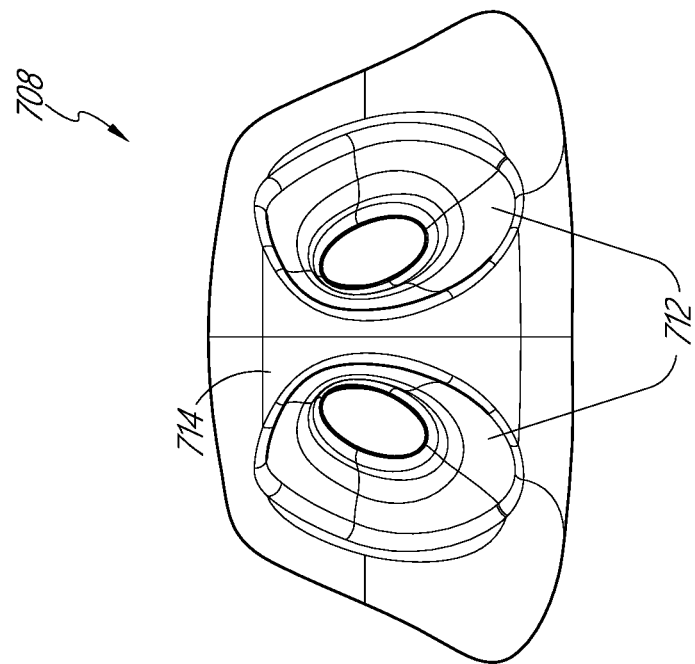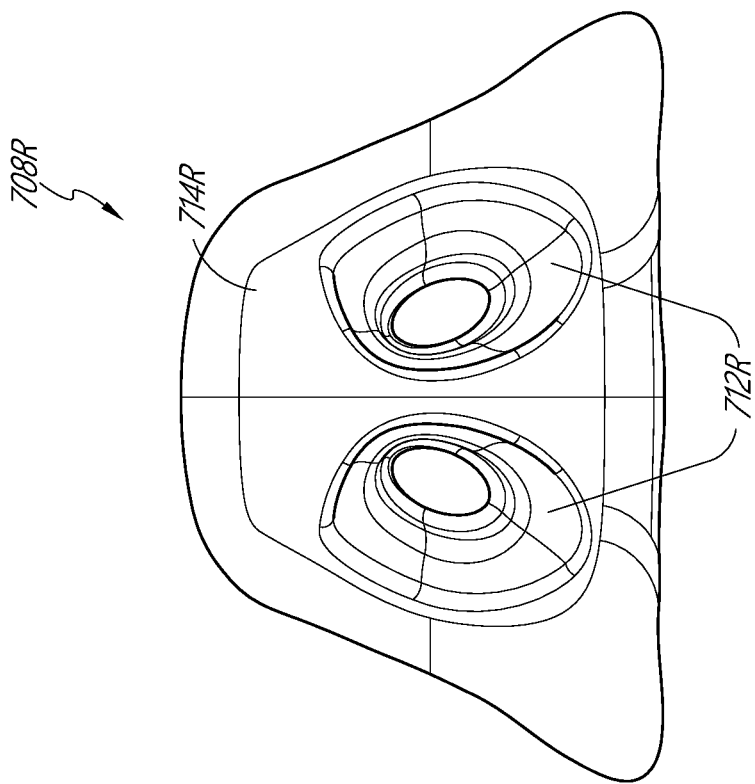
FIG. 97

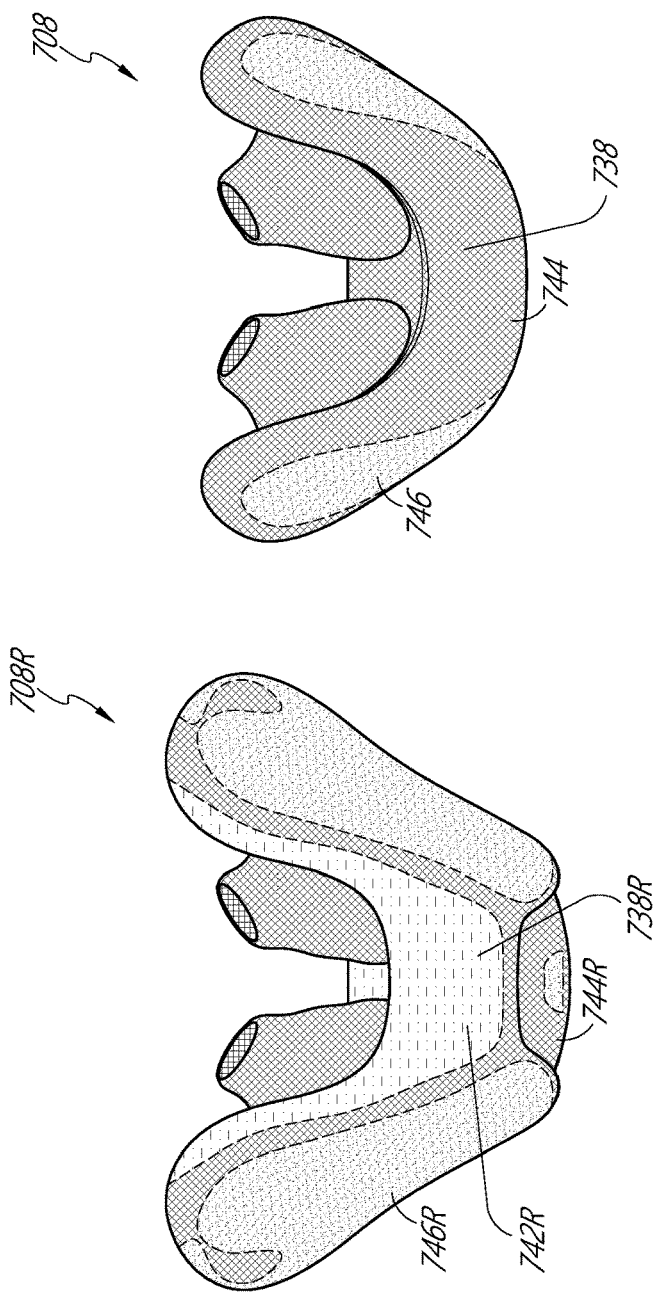
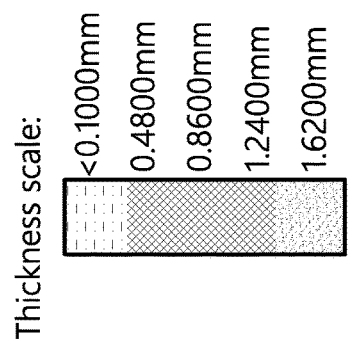
FIG. 104

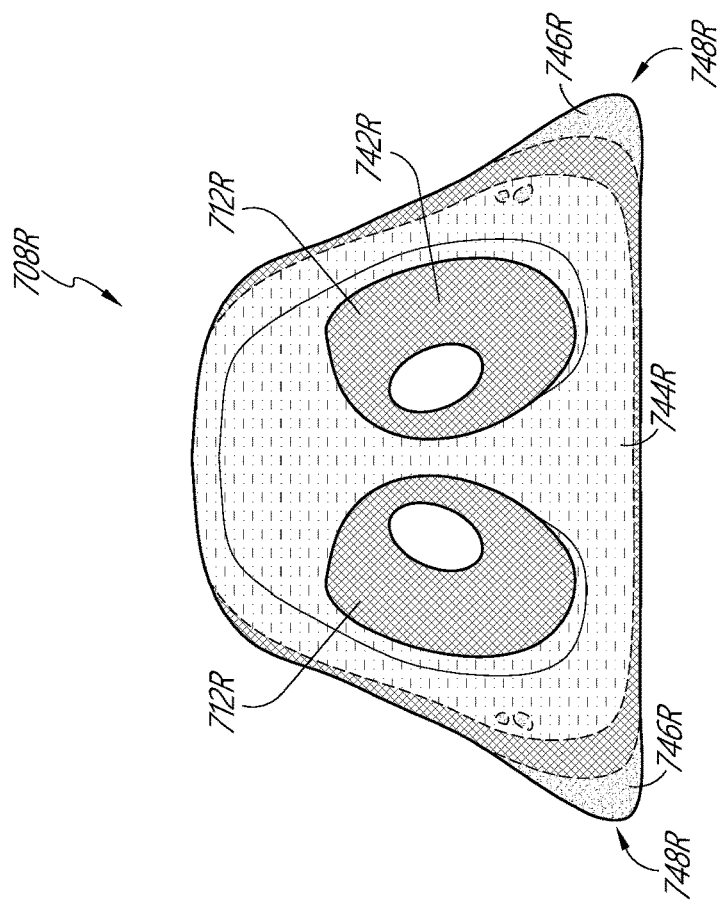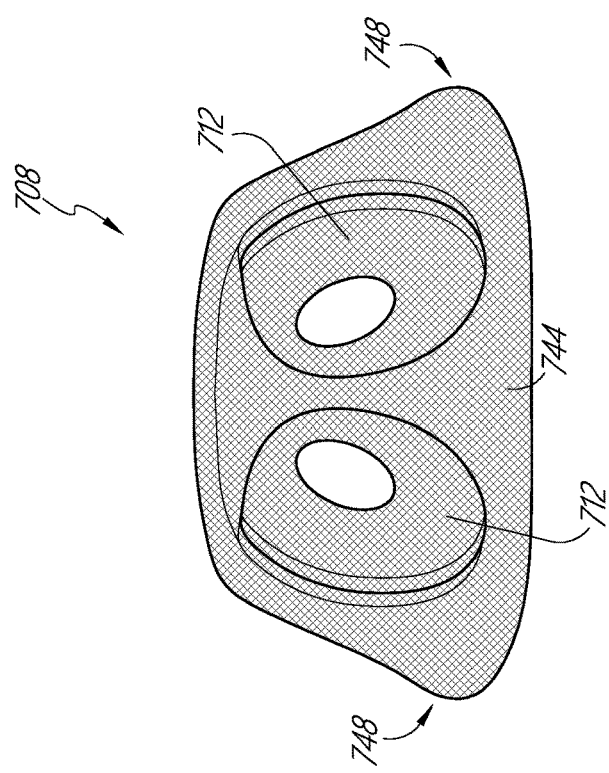
FIG. 105

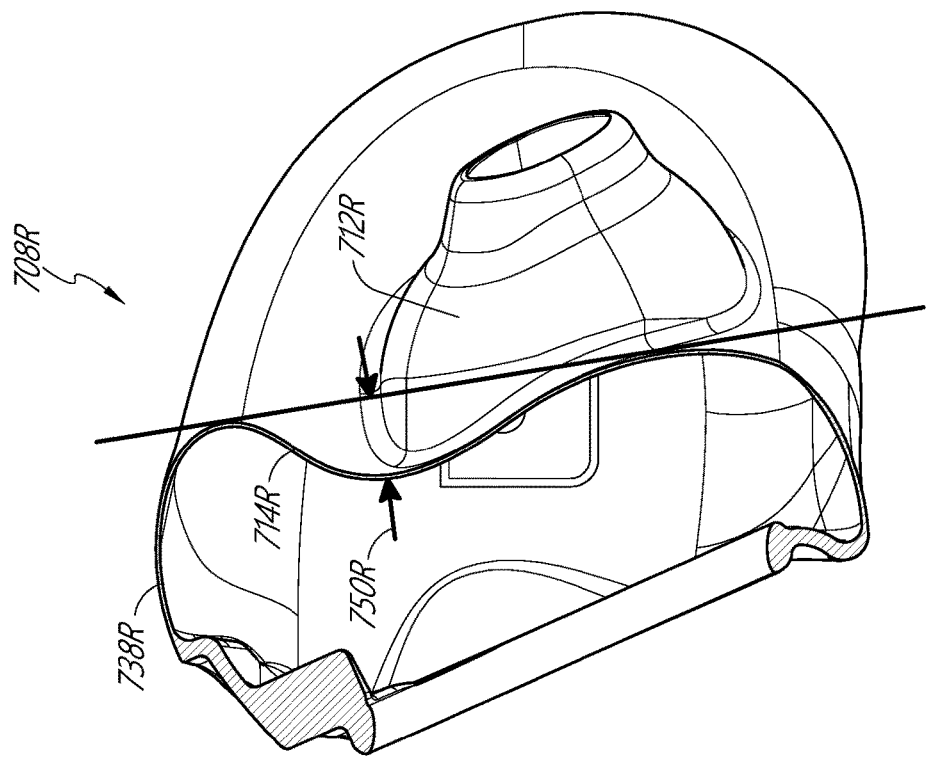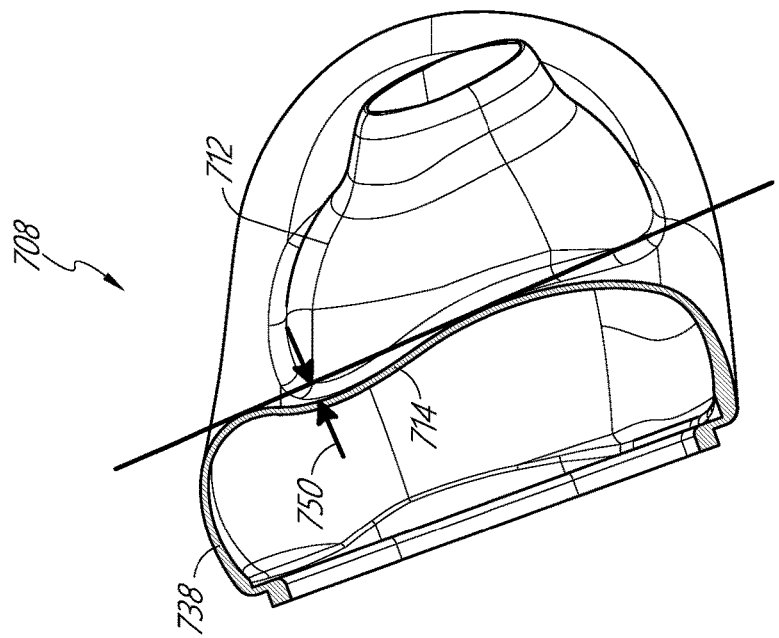
FIG. 106

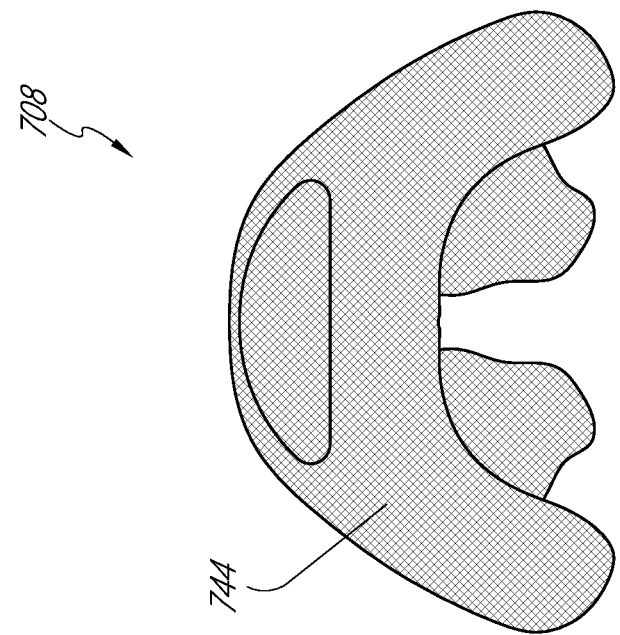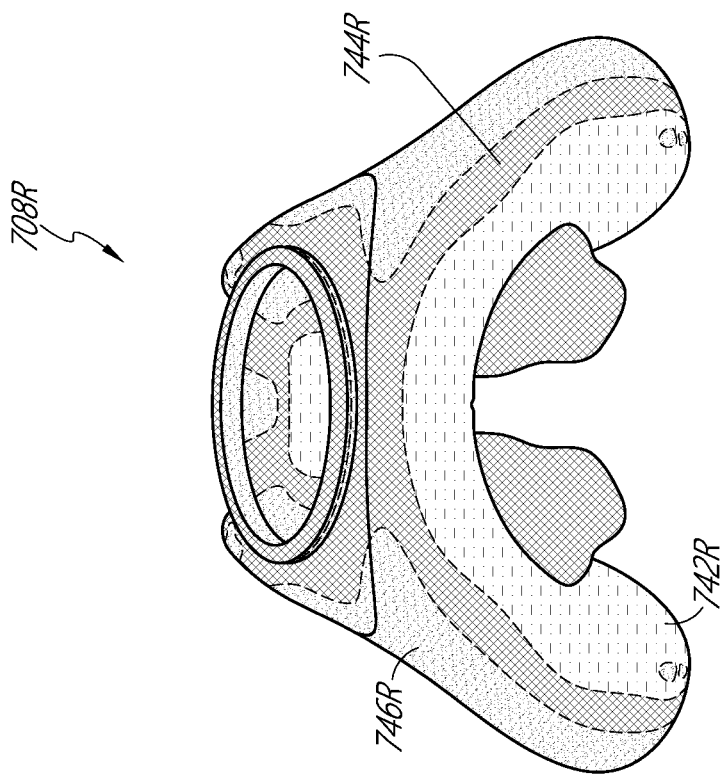
FIG. 107

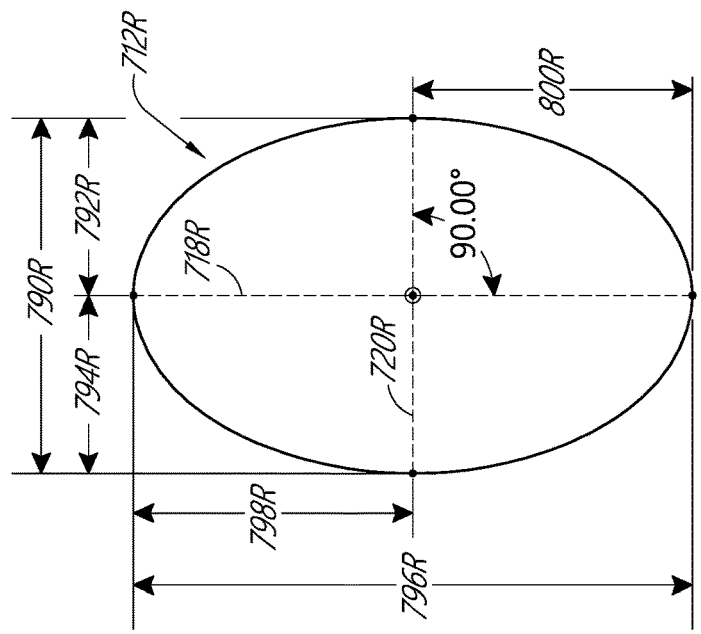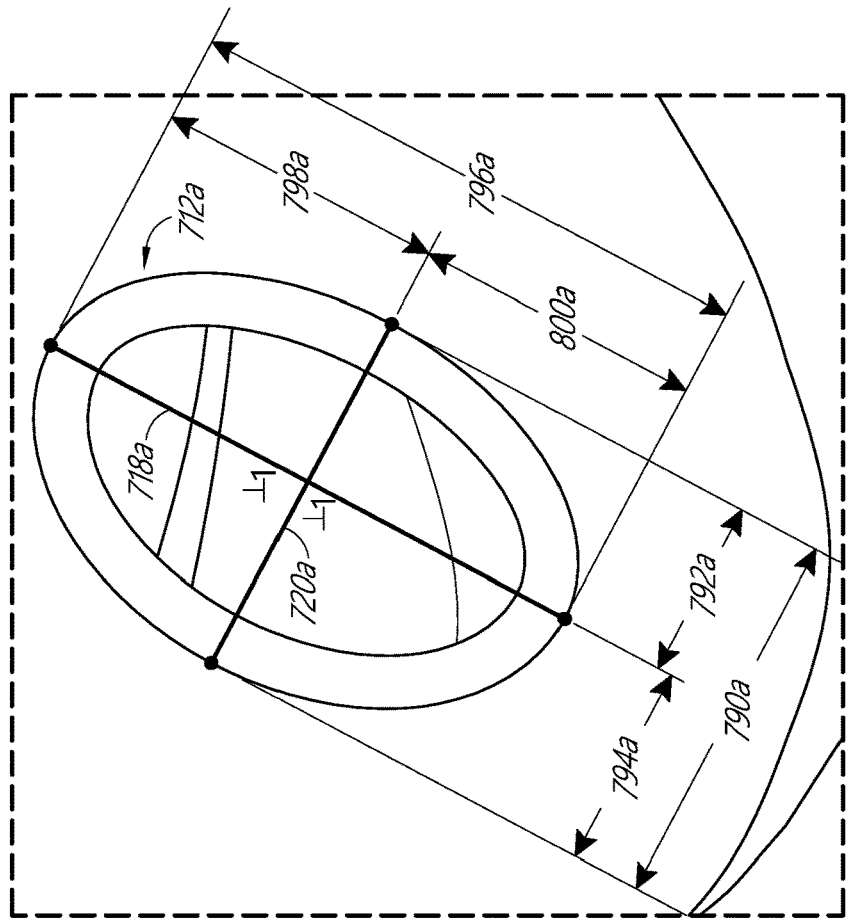
FIG. 123

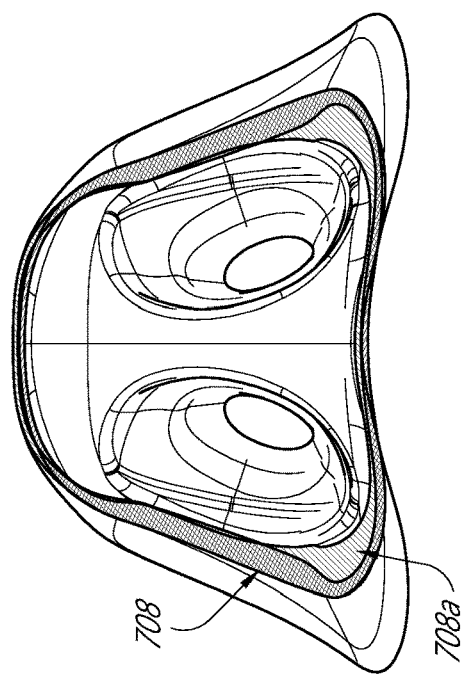
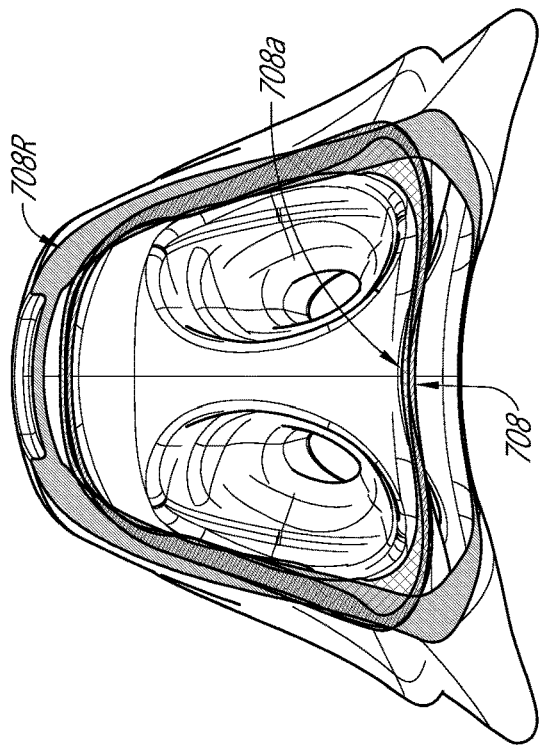
FIG. 132

RESPIRATORY MASK SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference herein and made a part of the present disclosure.

BACKGROUND

Field

The present disclosure generally relates to a respiratory mask system for the delivery of respiratory therapy to a patient. More particularly, the present disclosure relates to various components of a respiratory mask system.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which secures the airway in an open position such that the patient's breathing and sleep are not interrupted.

Respiratory masks typically comprise a patient interface and a headgear, wherein the patient interface is configured to deliver the supply of continuous positive air pressure to the patient's airway via a seal or cushion that forms an airtight seal in or around the patient's nose and/or mouth. Respiratory masks are available in a range of styles including full-face, nasal, direct nasal and oral masks, which create an airtight seal with the nose and/or mouth. The seal or cushion is held in place on the patient's face by the headgear. In order to maintain an airtight seal the headgear should provide support to the patient interface such that it is held in a stable position relative to the patient's face during use. Such respiratory masks may also be used to deliver NIV and other therapies.

SUMMARY

The systems and devices described herein have innovative aspects, no single one of which is indispensable or solely responsible for their desirable attributes. Without limiting the scope of the claims, some of the advantageous features will now be summarized.

In a first aspect, the invention provides a respiratory mask system comprising a mask interface comprising a frame for a headgear assembly, wherein the frame comprises a body comprising a first surface and a substantially opposing second surface, and wherein the body further comprises a gas inlet and an outlet vent.

In one form, the frame is configured so that the gas inlet is angled at around 10 to 450 from vertical.

The gas inlet may comprise a substantially elliptical shape, wherein the gas inlet lies substantially longitudinally along the length of the frame.

In one form, the frame may comprise an opening defined by a substantially continuous edge provided by a seal flange projecting from the rear surface of the frame.

The gas inlet may be substantially elliptical in shape. Preferably, the substantially elliptical gas inlet extends longitudinally between left and right sides of the frame.

The mask interface may also comprise a seal configured to attach to the frame. The seal may comprise a front surface and a rear surface and a gas inlet opening that may substantially correspond with the gas inlet opening of the frame. The gas inlet opening of the seal may comprise a substantially continuous lip configured to attach to the seal flange.

In one form, the gas inlet of the frame comprises a separator that extends between two substantially opposing points on the continuous edge to separate the opening into the gas inlet and the outlet vent.

Optionally, the seal forms part of a seal assembly that further comprises an inner clip and an outer clip, the inner and outer clips each comprising a collar comprising a gas inlet opening, wherein the inner clip further comprises a divider that spans across the gas inlet opening of the inner clip to separate the opening into a gas inlet aperture and a vent aperture.

The inner clip may be attached to the seal flange of the frame so that the gas inlet aperture substantially aligns with the gas inlet of the frame and the vent aperture substantially aligns with the outlet vent of the frame. Preferably, the seal flange comprises one or more recesses within which a portion of the inner clip may be held.

In one form, the inner clip comprises a hooked flange extending around at least a portion of its outer periphery and the outer clip also comprises a hooked flange extending around at least a portion of its periphery. The inner and outer clips may be attached together to cause the hooked flanges of each clip to face each other and form a seal channel in between. The seal may comprise a substantially continuous lip configured to be held within the seal channel.

In one form, the outlet vent may be located above the gas inlet when the frame is in use. In another form, the outlet vent may be located below the gas inlet when the frame is in use.

Optionally, the gas inlet and the outlet vent are located substantially centrally along the length of the frame.

Preferably, a diffuser is located within the outlet vent.

In one form, the respiratory mask system also comprises a headgear assembly comprising a yoke configured to attach to the frame. The frame may comprise a recessed region within which the yoke may be held.

In a second aspect, the invention provides a respiratory mask system comprising a mask interface comprising a frame for a headgear assembly, wherein the frame comprises a body comprising a front surface and a substantially opposing rear surface, wherein the front surface comprises a recessed region within which a yoke of a headgear assembly may be located.

In one form, the recessed region may comprise a channel that substantially extends across a length of the frame. Preferably, the channel is configured to lie substantially horizontally across the frame when the frame is in use. The channel may comprise two side regions, each side region being located at an opposite end of the channel, and a substantially central region located between the two side regions.

In one form, the channel may comprise extension members that extend from either side of the body of the frame.

Preferably, the frame comprises a gas inlet. The gas inlet may comprise a substantially elliptical shape, wherein the gas inlet lies substantially longitudinally along the length of the frame.

Preferably, the frame also comprises an outlet vent. In one form, at least a portion of the outlet vent may be located within the channel. Optionally, the entire outlet vent may be located within the channel. The outlet vent may comprise a diffuser.

Preferably, the frame is substantially curved outwardly from left to right. In one form, the front surface of the frame is substantially curved outwardly from the top to bottom.

In one form, the channel may comprise a first wall forming an upper surface, a second wall forming a lower surface that substantially opposes the first wall, and a channel floor forming a rear surface that extends between the first and second walls. In another form, the channel consists of a rear surface and a lower surface.

Preferably, the lower surface of the channel comprises a recessed region. The recessed region may be located substantially adjacent to the outlet vent.

In one form, the upper surface of the channel may comprise a recessed region. The recessed region of the upper surface may be located substantially adjacent to the outlet vent.

In one form, the lower surface of the channel may angle inwardly toward the rear surface of the channel.

In one form, the upper surface of the channel may angle inwardly toward the rear surface of the channel.

In one form, the height of the rear surface of the channel may be substantially defined by the distance between the upper and lower surfaces of the channel. Preferably, the height of the rear surface of the channel at its central region is less than the height of the channel at one or both side regions.

In one form, the lower surface of the channel may have a depth substantially defined by the distance between the rear surface of the channel and a distal end of the second edge. Preferably, the depth of the lower surface is greater in the central region of the channel than at the side regions.

In one form, the frame may comprise at least one attachment feature for attaching a headgear yoke to the frame. In one form, the at least one attachment feature may comprise an attachment aperture, a magnet, or an attachment tab. In one form, the at least one attachment feature may be located on the rear surface of the channel.

In one form, the at least one attachment feature may be an attachment aperture located on the rear surface of the channel. In one form, an attachment aperture may be located at each side region of the rear surface of the channel. The at least one attachment aperture may be configured to receive a projecting attachment feature of a headgear yoke to attach the headgear yoke to the frame.

In one form, the at least one attachment feature comprises at least one magnet located in the channel of the frame. Preferably, the at least one magnet is located on the rear surface of the channel. In one form, a plurality of magnets are located on the rear surface of the channel. Preferably, the magnets are spaced equidistant from each other. The magnet(s) may be located along a centre-line extending along the length of the channel. Alternatively, the magnet(s) may be located to one side of a centre-line extending along the length of the channel. In one form, the magnet(s) may be located closer to the upper surface of the channel than to the lower surface of the channel. Optionally, the channel may comprise one or more recesses in which one or more may be located.

In one form, the at least one attachment feature comprises at least one attachment tab that extends across at least a portion of the channel. Preferably, at least one attachment tab extends from either the upper surface or lower surface of the channel and projects toward the substantially opposing channel surface. In one form, an attachment projects from the upper surface of the channel and a recess is provided between a rear surface of the attachment tab and the rear surface of the channel.

In one form, the at least one attachment feature comprises a latch that extends across the entire height of the channel from the upper surface to the lower surface of the channel. In one form, the at least one latch may be removable. Optionally, the at least one latch may be configured to attach to a lock provided on the frame. In one form, the at least one attachment tab may be configured to attach to the lock in a snap-fit arrangement. In other form, the at least one latch may be configured to attach to a lock provided on the yoke. Preferably, the at least one latch is hingedly attached to the frame.

In a third aspect, the invention provides a respiratory mask system comprising a yoke for a headgear assembly, wherein the yoke comprises a body comprising: a front surface with a width defined by the distance between a top surface and a bottom surface of the yoke and a length defined by the distance between opposing ends of the yoke; and a middle portion located between two side portions, the side portions being located at or near the ends of the yoke, wherein the width of the yoke at the middle portion is less than the width of the yoke at the side portions.

In one form, the middle portion of the top surface of the yoke may be curved inwardly.

In one form, the middle portion of the bottom surface of the yoke may be curved inwardly. In yet another form, the bottom surface of the yoke may lie in substantially the same plane along the length of the yoke.

In one form, the front surface of the middle portion of the yoke may slope rearward from the top surface to the bottom surface.

In one form, the front surface of the side portions of the yoke may slope forward from the top surface to the bottom surface. Alternatively, the front surface of the side portions may be substantially perpendicular to the bottom and/or top surface.

In one form, the middle portion of the yoke tapers from the front surface to the rear surface.

In one form, the top surface of the middle portion slopes downward from the rear surface to the front surface.

In one form, the bottom surface of the middle portion slopes upward from the front surface to the rear surface.

In one form, at least a portion of the yoke body may be covered in a textile covering. Preferably, the textile covering is a knit fabric that is substantially stretchable in at least one direction. Preferably, the yoke is injection moulded into the textile covering.

In one form, the yoke body may comprise a rear surface comprising a pair of locating members. Each locating member may be located on one side portion of the yoke.

In one form, each locating member projects from the rear surface of the yoke and comprises an alignment surface that slopes outwardly from the rear surface toward the ends of the yoke.

In one form, each alignment surface may be orientated at an angle so that the alignment surfaces are closer together near the bottom surface than near the top surface of the yoke.

In one form, at least one locating member may comprise a substantially curved projection that is formed at or near the ends of the yoke and that may project from the rear surface of the yoke.

Preferably, at least one locating member is integrally formed with the yoke body.

In one form, one or more locating members may be formed from an overmoulding located at or near each end of the yoke.

In one form, one locating member may comprise a hook and the other locating member may comprise a post.

In one form, a tab may project from the top surface of the yoke. Preferably, the tab projects from the middle portion of the yoke. Optionally, the tab comprises a flange that projects from the top surface and substantially along the length of the yoke.

In one form, one or more magnets may be located on the rear surface of the yoke. The rear surface may comprise one or more recesses in which one or more magnets may be held. The magnet(s) may be placed equidistantly apart. The magnet(s) may be located along a centre-line extending along the length of the yoke. In another form, a flange may project from the top surface of the yoke such that the height of the yoke is defined by the distance between the bottom surface and the distal edge of the flange, wherein the magnet(s) may be located closer to the bottom surface of the yoke than to the distal edge of the flange.

In one form, the yoke body may comprise a material that is substantially stretchable along its length and the yoke may comprise one or more attachment features for engaging with one or more complementary attachment features provided on a frame of a respiratory mask system to attach the yoke to the frame.

In one form, the stretchable yoke body may comprise at least one attachment feature comprising a hook configured to engage with a corresponding hook, recess or opening of a frame to attach the yoke to the frame.

In one form, the yoke may comprise a collector for one or more filaments, the yoke forming part of an automatically adjustable headgear assembly.

In a fourth aspect, the invention provides a respiratory mask system comprising a frame according to the first or second aspect of the invention and a yoke according to the third aspect of the invention. The frame and yoke may comprise any feature or combination of features as described in relation to the first, second, and third aspects of the invention above.

In some embodiments, a respiratory mask system includes a mask frame and a yoke. The mask frame includes an inlet configured to be coupled to a gas conduit in use, a yoke channel, and a retention bump. The yoke channel extends longitudinally across the mask frame and is defined by an upper wall, a rear wall, and a lower wall. The retention bump protrudes downward into the yoke channel from the upper wall. The yoke is configured to be at least partially disposed in the yoke channel. The yoke includes a retention notch in an upper surface of the yoke. The retention bump is configured to snap fit into the retention notch when the yoke and mask frame are coupled together.

The retention notch can be positioned along a corner between a front wall and a top wall of the yoke. The yoke can include a yoke front and a yoke back coupled to the yoke front. The yoke front can include the retention notch.

In some embodiments, a respiratory mask system includes a mask frame and a yoke. The mask frame includes an inlet configured to be coupled to a gas conduit in use, a yoke channel, and an anti-rotation groove. The yoke channel extends longitudinally across the mask frame and is defined by an upper wall, a rear wall, and a lower wall. The anti-rotation groove is recessed into the rear wall and extends along a length of the yoke channel. The yoke is configured to be at least partially disposed in the yoke channel. The yoke includes a tongue projecting rearward from the yoke. The tongue is configured to be disposed in the anti-rotation groove when the yoke and mask frame are coupled together. The interaction between the anti-rotation groove and the tongue is configured to inhibit rotational disengagement of the yoke from the mask frame.

The yoke can include a yoke front coupled to a yoke back. The tongue can include a front tongue extending from the yoke front and a back tongue extending from the yoke back. The front tongue can be disposed under the back tongue such that an upper surface of the front tongue abuts a lower surface of the back tongue.

In some embodiments, a yoke configured to be coupled to a mask frame of a respiratory mask system includes a front wall extending from a first lateral end to a second lateral end; a rear wall extending from a first lateral end to a second lateral end, the front wall and the rear wall defining an inner cavity therebetween; a first end cap coupled to the first lateral ends of the front wall and the rear wall and a second end cap coupled to the second lateral ends of the front wall and the rear wall, each end cap comprising a filament entry hole configured to receive a filament of a self-adjusting headgear mechanism; and a line track divider dividing the inner cavity into an upper line track and a lower line track. The yoke can further include a first washer housing disposed between the front wall and the rear wall adjacent the first end cap and a second washer housing disposed between the front wall and the rear wall adjacent the second end cap. In some embodiments, the upper line track extends from the first washer housing to the second end cap above the second washer housing, and the lower line track extends from the second washer housing to the first end cap below the first washer housing.

The yoke can include a yoke front that includes the front wall and a yoke back that includes the rear wall and is coupled to the yoke front. The upper line track can be at least partially defined by an upper wall of the yoke front and the line track divider, and the lower line track can be at least partially defined by a lower wall of the yoke front and the line track divider.

In some configurations, a nasal seal for a respiratory mask system includes a body portion defining an inlet and at least partially defining a user-contacting surface of the nasal seal. A pair of nasal prongs is supported by the body portion and is configured to engage the nostrils of a user. The body portion comprises a bridge portion extending laterally between the pair of nasal prongs on an upper portion of the seal. The bridge portion defines a bridge depth between a front surface and a rear surface of the nasal seal, wherein the bridge depth is less than one-half of an overall depth of the nasal seal.

In some configurations, a rearward-most point of the nasal seal is rearward of a rearward-most surface of the pair of nasal prongs.

In some configurations, the bridge depth is less than or equal to two-fifths of the overall depth.

In some configurations, the bridge depth is one-third of the overall depth.

In some configurations, the bridge depth is equal to or less than 15 mm, 13.5 mm or 11 mm.

In some configurations, the overall depth is equal to or less than 35 mm, 32.5 mm or 30 mm.

In some configurations, wall thicknesses equal to or greater than 1 mm are limited to outer side walls or a front wall of the nasal seal.

In some configurations, a transition between an upper wall and the outer side walls or a transition between a lower wall and the outer side walls is less than 1 mm.

In some configurations, a minimum wall thickness of the user-contacting surface defined by the body portion of the nasal seal is equal to or greater than 0.3 mm.

In some configurations, the minimum wall thickness of the user-contacting surface defined by the body portion of the nasal seal is equal to or greater than 0.45 mm.

In some configurations, an overall width of the nasal seal is equal to or less than 65 mm.

In some configurations, the overall width is equal to or less than 61 mm or 58.5 mm.

In some configurations, an overall height of the nasal seal is equal to or less than 40 mm.

In some configurations, the overall height is equal to or less than 35.5 or 35.2 mm.

In some configurations, a sealing area of the nasal seal is equal to or less than 1000 mm$^2$.

In some configurations, the sealing area is equal to or less than 907 mm$^2$ or 883 mm$^2$.

In some configurations, the inlet is generally D shaped.

In some configurations, a clip assembly is secured to the inlet of the seal body, wherein the clip assembly is configured to allow the nasal seal to be removably connected to a frame.

In some configurations, the clip assembly defines an inlet and a vent.

In some configurations, the vent comprises a diffuser.

In some configurations, the vent is defined by a clip member.

In some configurations, the clip member of the vent is removable.

In some configurations, the inlet has a maximum height of between 12-16 mm or 14 mm.

In some configurations, the inlet has a maximum width of between 25-30 mm or 27 mm.

In some configurations, the nasal seal is combined with a frame. The seal and frame assembly can further comprise a headgear arrangement.

In some configurations, the headgear arrangement is self-adjusting or comprises one or more directional locks.

In some embodiments, a respiratory mask system includes a mask frame and a yoke. The mask frame includes an inlet configured to be coupled to a gas conduit in use and a yoke channel. The yoke channel extends longitudinally across the mask frame and is defined by an upper wall, a rear wall, and a lower wall. The mask frame further includes at least one recess in at least one of the upper wall and lower wall of the yoke channel. The yoke is configured to be at least partially disposed in the yoke channel. The yoke includes at least one protrusion projecting rearward from the yoke and configured to be disposed in the at least one recess when the yoke is disposed in the yoke channel.

The at least one recess and the at least one protrusion can have a rectangular profile.

In some embodiments, a yoke configured to be coupled to a mask frame of a respiratory mask system includes a yoke front including a first central connector and a yoke back including a second central connector. The first and second central connectors are configured to be coupled together to at least partially secure the yoke front and the yoke back together.

In some embodiments, the first central connector is or includes a protrusion projecting rearwardly from the yoke front, the second central connector is or includes an aperture in the yoke back, and the protrusion is configured to be received in the aperture. In some embodiments, the first central connector is or includes a protrusion projecting rearwardly from the yoke front, the second central connector is or includes a recess in a front surface of the yoke back, and the protrusion is configured to be received in the recess. In some embodiments, the yoke front includes an upper alignment groove recessed into a rear surface of the yoke front and extending along a length of the yoke front proximate an upper edge of the yoke front, the yoke rear includes an upper alignment bead protruding forward from a front surface of the yoke rear, and the upper alignment bead is configured to be received in the upper alignment groove when the yoke front and yoke rear are coupled together. In some embodiments, the yoke front includes a lower alignment groove recessed into a rear surface of the yoke front and extending along a length of the yoke front proximate a lower edge of the yoke front, the yoke rear includes a lower alignment bead protruding forward from a front surface of the yoke rear, and the lower alignment bead is configured to be received in the lower alignment groove when the yoke front and yoke rear are coupled together.

In some embodiments, a yoke configured to be coupled to a mask frame of a respiratory mask system includes a yoke frontl extending from a first lateral end to a second lateral end; a yoke rear extending from a first lateral end to a second lateral end, the yoke front and the yoke rear coupled together and defining an inner cavity therebetween; a first end cap coupled to the first lateral ends of the yoke front and the yoke rear and a second end cap coupled to the second lateral ends of the yoke front and the yoke rear, each end cap comprising a filament entry hole configured to receive a filament of a self-adjusting headgear mechanism; and a line track divider dividing the inner cavity into an upper line track and a lower line track. The yoke can further include a first washer housing disposed between the front wall and the rear wall adjacent the first end cap and a second washer housing disposed between the front wall and the rear wall adjacent the second end cap. In some embodiments, the upper line track extends from the first washer housing to the second end cap above the second washer housing, and the lower line track extends from the second washer housing to the first end cap below the first washer housing.

In some embodiments, the upper line track extends into the second end cap and the lower line track extends into the first end cap. In some embodiments, the first and second end caps are configured to be hinged onto the first and second lateral ends of the front wall and the rear wall, respectively, during assembly. In some such embodiments, the yoke rear includes a first retention protrusion extending rearwardly from the yoke rear proximate the first lateral end of the yoke rear, the yoke front includes a second retention protrusion extending forwardly from the yoke front proximate the first lateral end of the yoke front, the first retention protrusion has a greater length than the second retention protrusion, the first end cap includes a retention hole on one side of the end cap configured to receive the first retention feature and a notch on an opposite side of the end cap configured to receive the second retention protrusion, and during assembly, the first retention protrusion and retention hole are engaged and then the first end cap is pivoted over the first lateral ends of the yoke front and yoke rear to engage the second retention protrusion and the notch. In some embodiments, the first and second washer housings are U-shaped. In some such embodiments, the second washer housing is orientated as an upward-facing U-shape and the first washer housing is oriented as a downward-facing U-shape.

In some embodiments, a respiratory mask system includes a mask frame and a yoke. The mask frame includes an inlet configured to be coupled to a gas conduit in use and a yoke channel extending longitudinally across the mask frame and defined by an upper wall, a rear wall, and a lower wall. The yoke is configured to be at least partially disposed in the yoke channel.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made.

Terms such as "top", "bottom", "upper", "lower", "front", "back", "left", "right", "rear", and "side" describe the orientation and/or location of portions of the components or elements within a consistent but arbitrary frame of reference which is made clear by reference to the text and the associated drawings describing the components or elements under discussion. Moreover, terms such as "first", "second", "third", and so on may be used to describe separate components. Such terminology may include the words specifically mentioned above, derivatives thereof, and words of similar import.

BRIEF DESCRIPTION OF THE DRAWINGS

FIGS. 57A to 57C and FIG. 58 are cross-sectional side views of the frame and yoke of FIG. 55A and demonstrating one method of locating the yoke within the channel of the frame;

FIG. 72 is a rear view of a yoke front portion of the yoke of FIG. 66 including washer housings and end caps;

FIG. 73A is a rear view of the yoke front with the washer housings and end caps removed;

FIG. 73B is a close up rear view of a lateral end of the yoke front as indicated in FIG. 73A;

FIG. 76 is a rear view of a bottom half of the yoke back;

FIG. 77 is a section view taken along line 77-77 in FIG. 76;

FIG. 83 is a section view of a lateral portion of an alternative embodiment of the yoke;

FIG. 84 is a front view of the yoke back of FIG. 83;

FIG. 85 is a section view of a lateral portion of an alternative embodiment of the yoke showing the yoke front;

FIG. 86 is a partial section view of the yoke of FIG. 85 showing the yoke back;

FIG. 87 is a front view of the yoke back of FIGS. 85-86;

FIG. 88 is a rear view of an alternative embodiment of the yoke showing the yoke front and including the washer housings;

FIG. 89 is a rear view of the yoke front of FIG. 88 with the washer housings removed;

FIG. 90 is a lateral end view of the yoke front of FIGS. 88-89;

FIG. 97 shows rear views of the seals of FIG. 96;

FIG. 104 shows top views of the seals of FIG. 96 showing regions of different thickness;

FIG. 105 shows rear views of the seals of FIG. 96;

FIG. 106 shows sectional views of the seals of FIG. 96;

FIG. 107 shows top views of the seals of FIG. 96;

FIG. 118 is a horizontal sectioned view of the superimposed seals of the first and second seals of FIG. 108;

FIG. 119 is a front view of a seal assembly incorporating the second seal of FIG. 108; the seal assembly could alternatively incorporate the first seal of FIG. 108;

FIG. 120 is a vertical sectioned view of the seal assembly of FIG. 119;

FIG. 121 is a front view of an alternative of the seal assembly of FIG. 119;

FIG. 122 is a front perspective view of the seal assembly of FIG. 121;

FIGS. 123-132 illustrate additional views of the first seal, the second seal and the prior art seal;

FIG. 133 is a front view of an example embodiment of an assembled frame, cushion, and yoke;

FIG. 134 is a partial perspective view of the yoke of FIG. 133 disconnected from the frame;

FIG. 135 is a section view of the assembled frame and yoke taken along line 135-135 in FIG. 133;

FIG. 136A is a rear view of a yoke rear portion of the yoke of FIG. 133;

FIG. 136B is a front view of the yoke rear portion of FIG. 136A;

FIG. 136C is a rear view of a yoke front portion of the yoke of FIG. 133;

Figure 133:
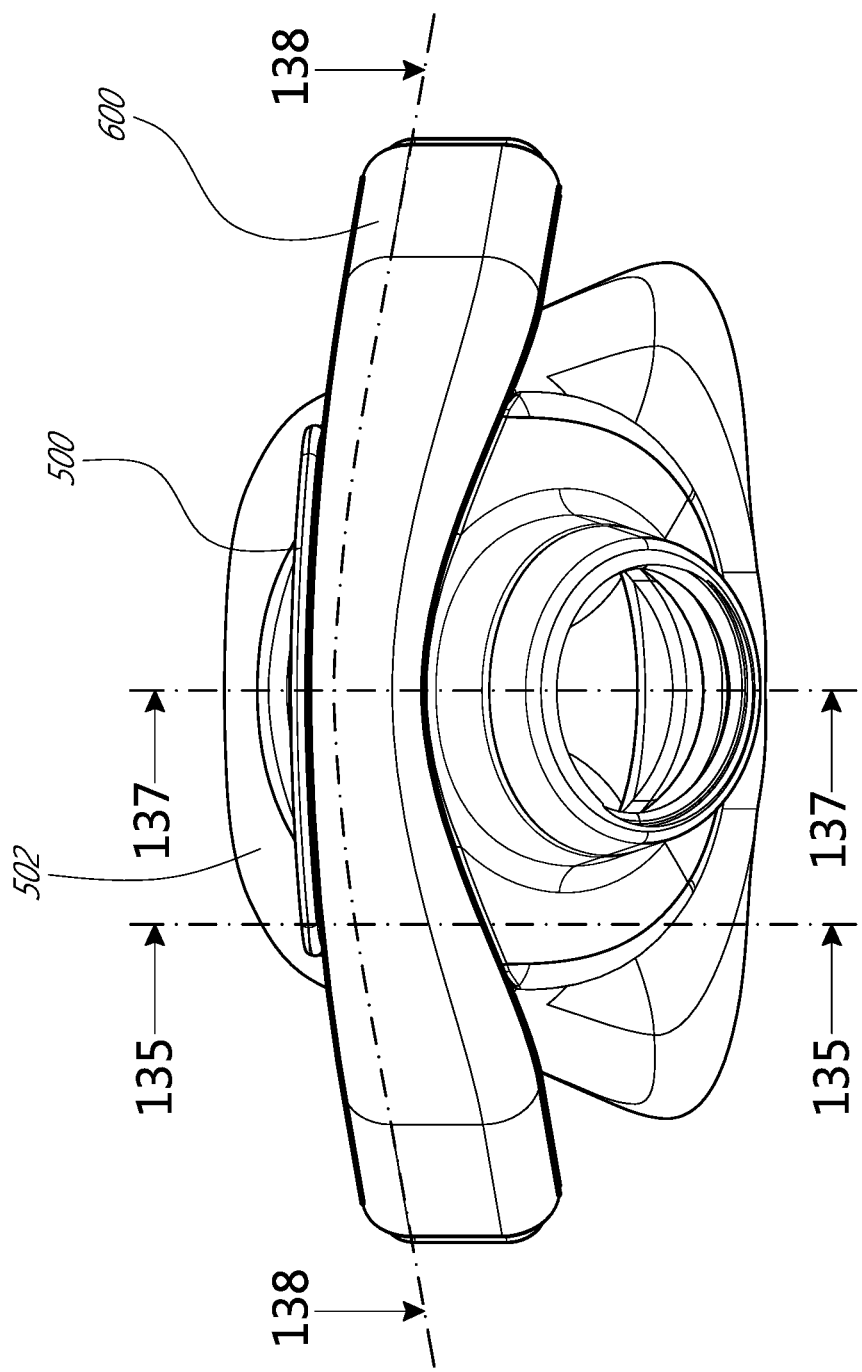
Figure 137:
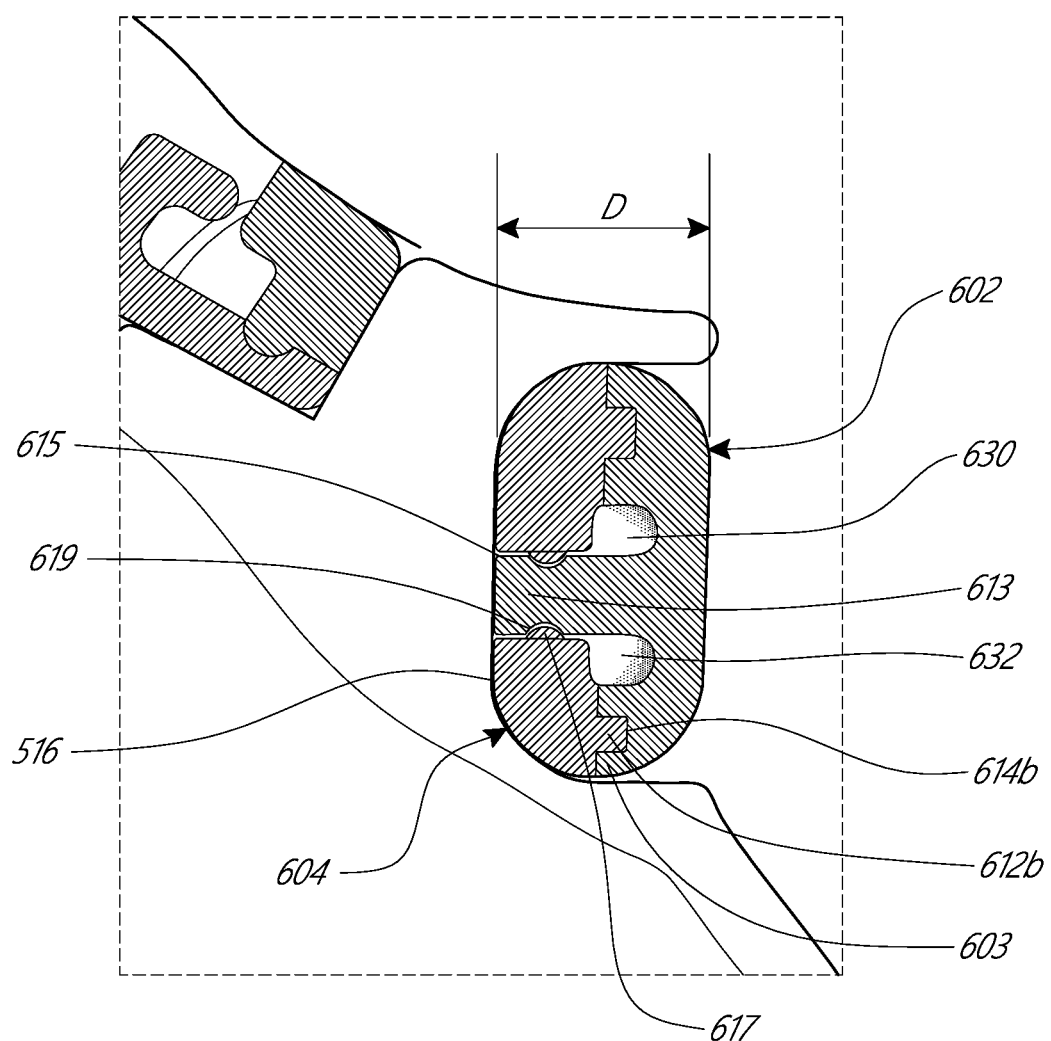
Figure 138:
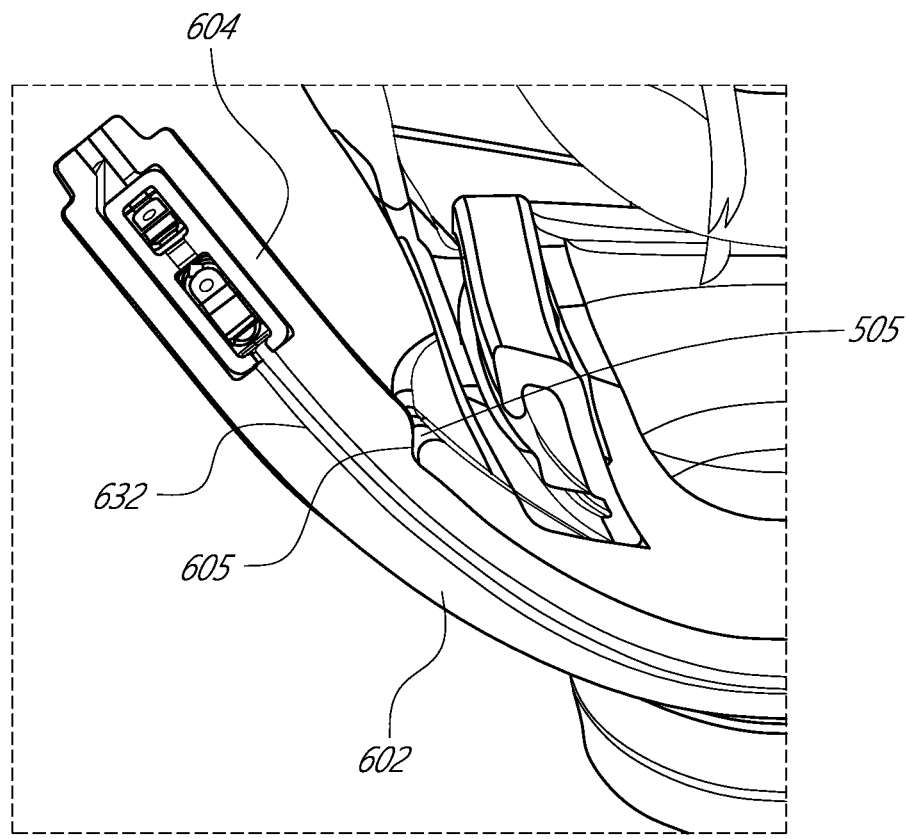
Figure 139:
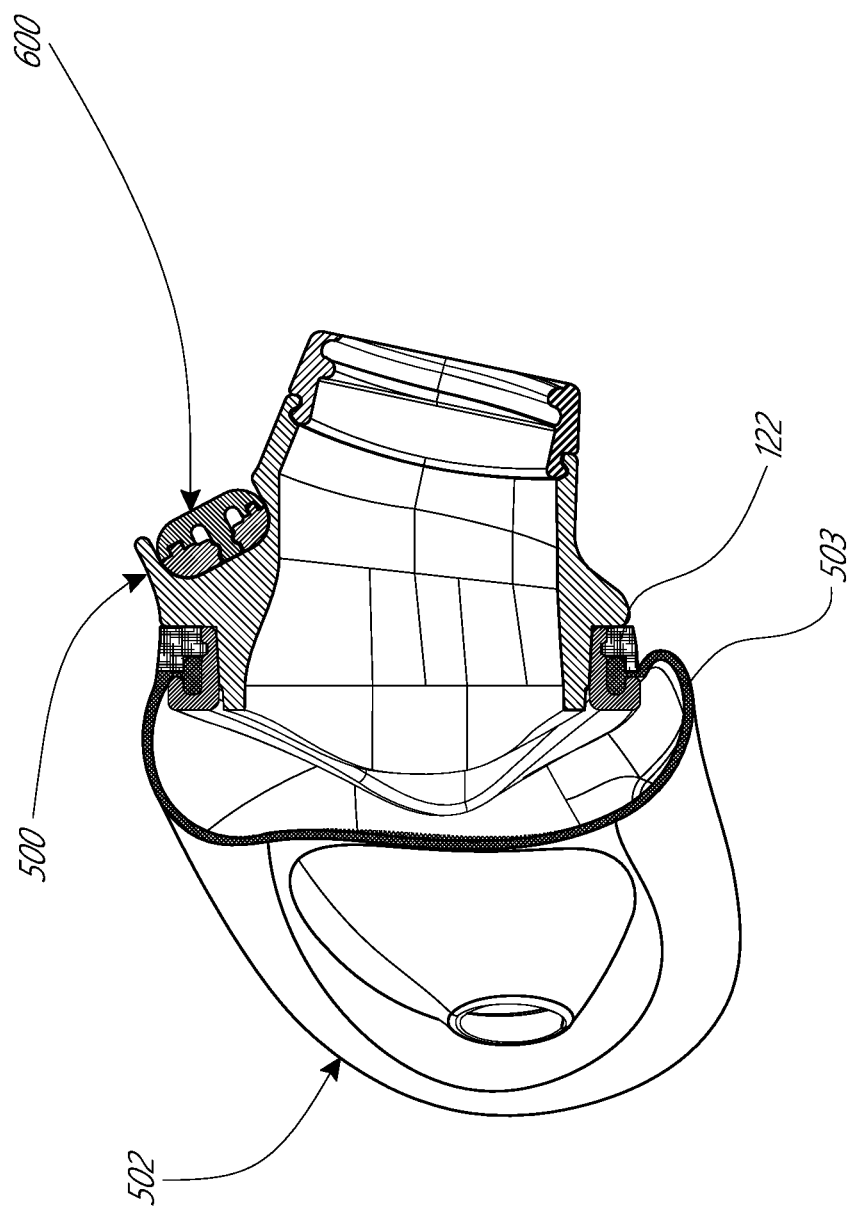
Figure 140:
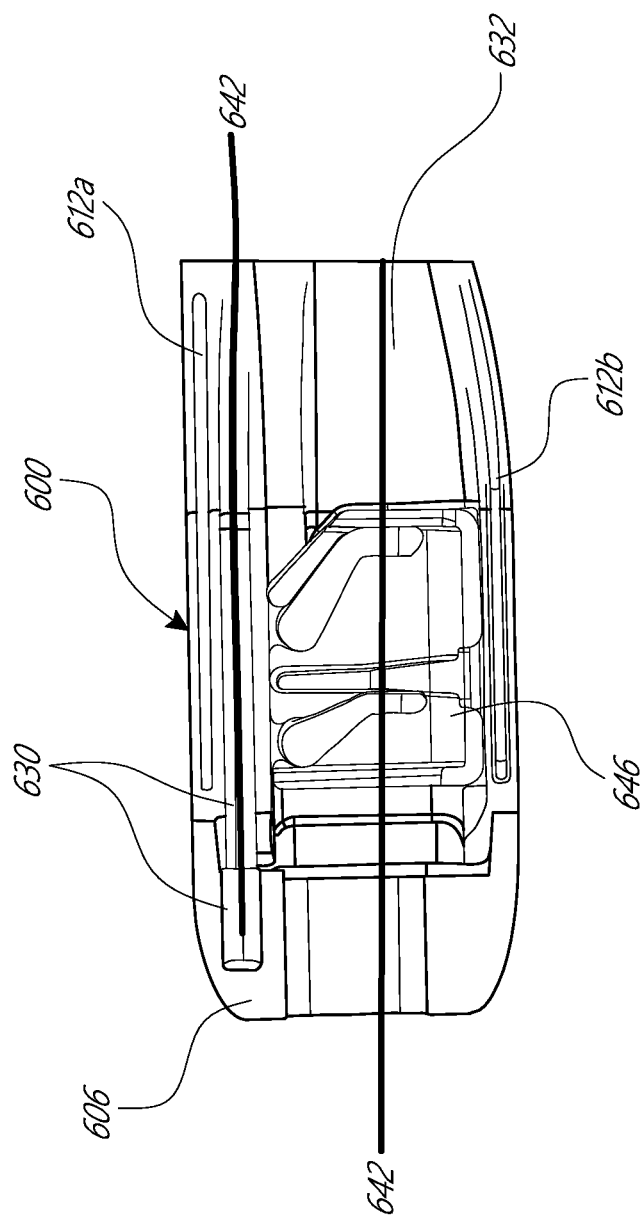
Figure 142:
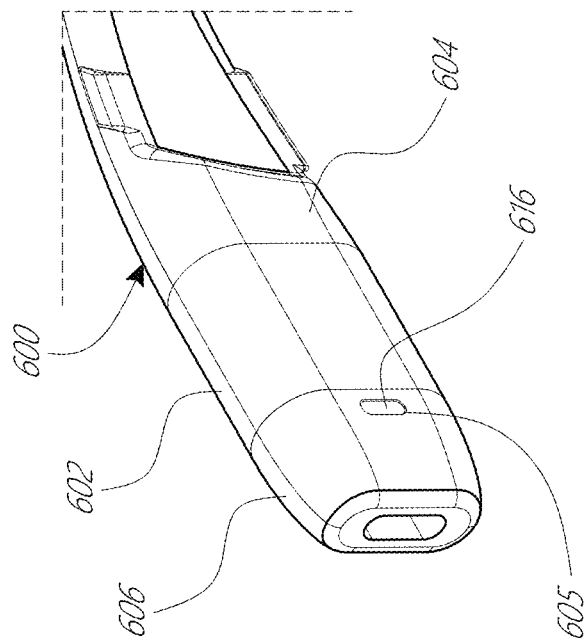
Figure 141:
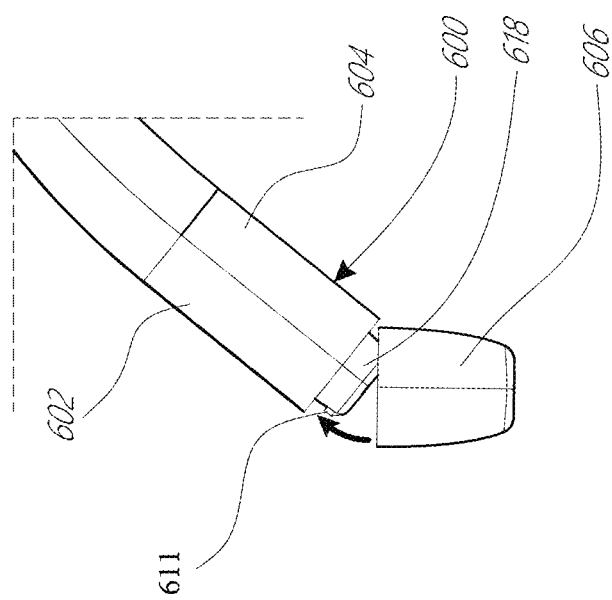
Figure 143:
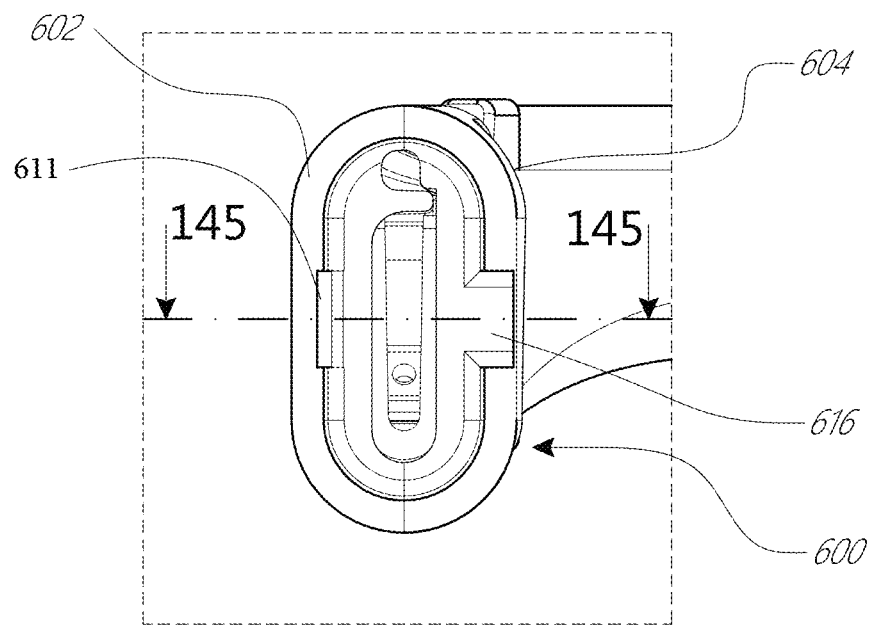
Figure 144:
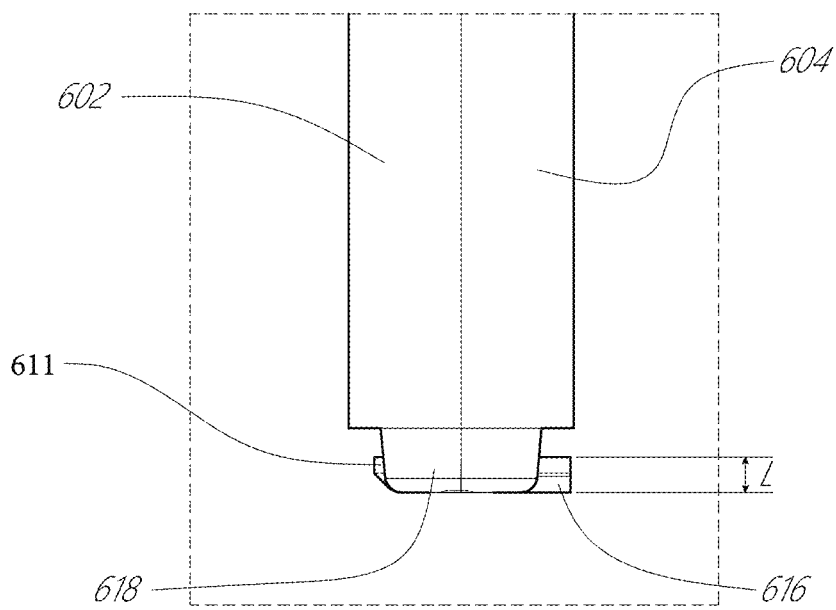
Figure 145:
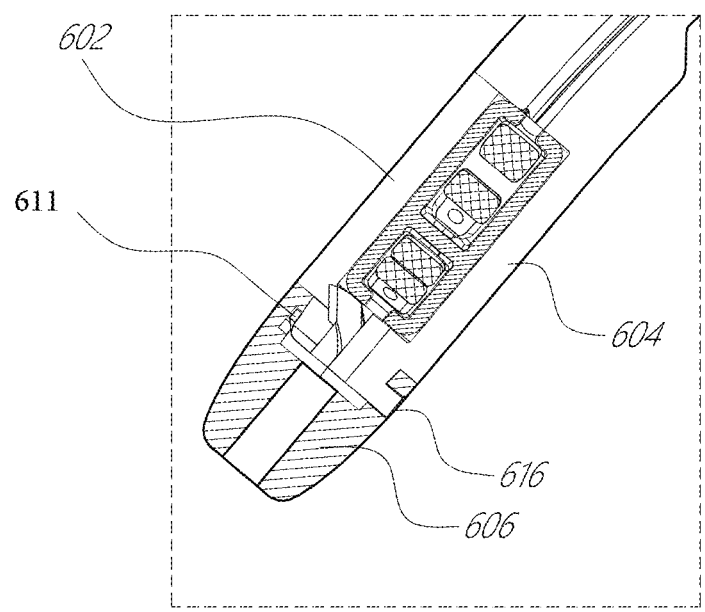
Figure 146:
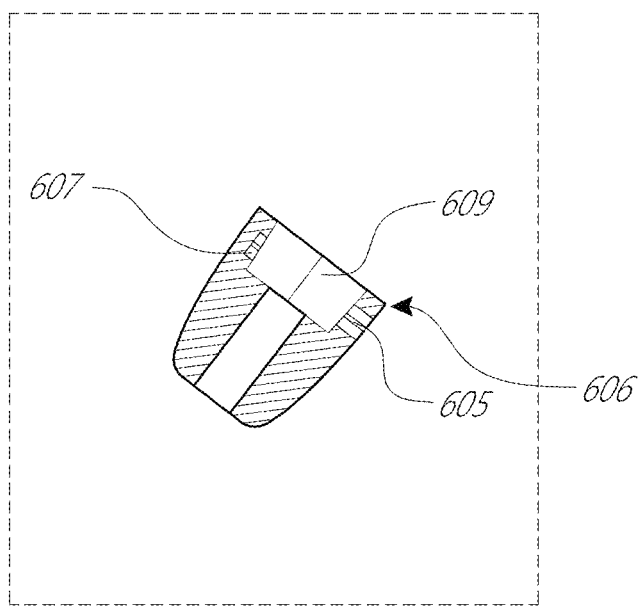
Figure 147:
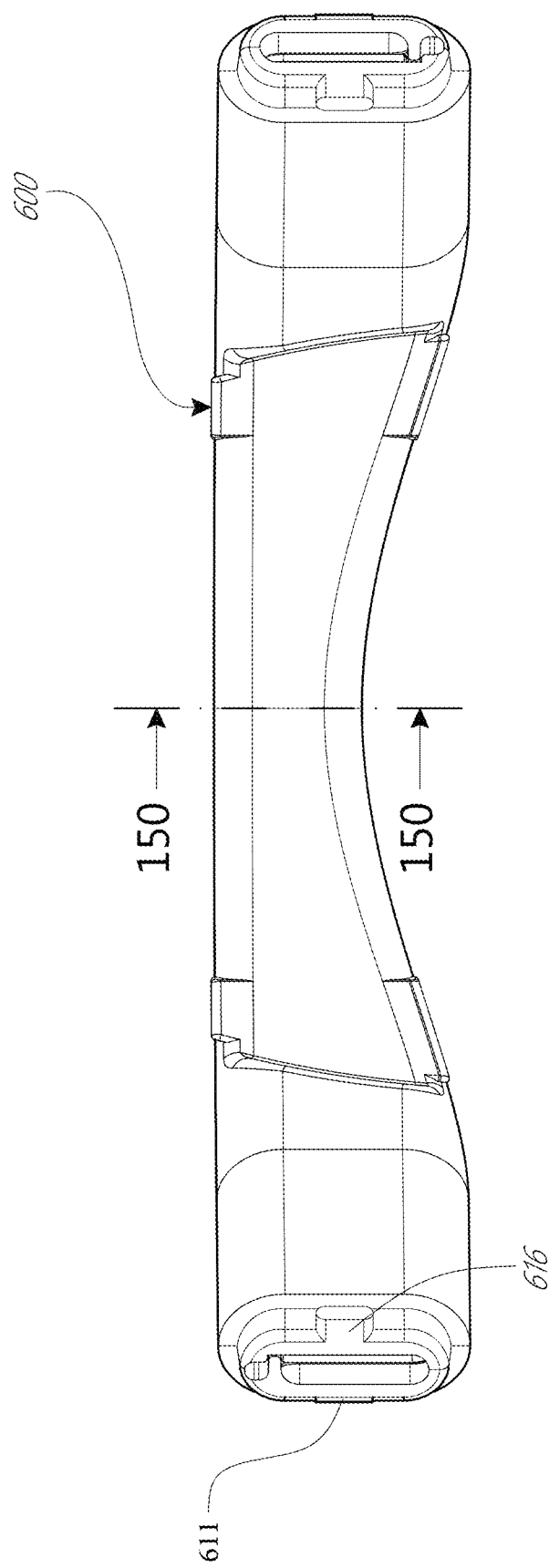
Figure 148:
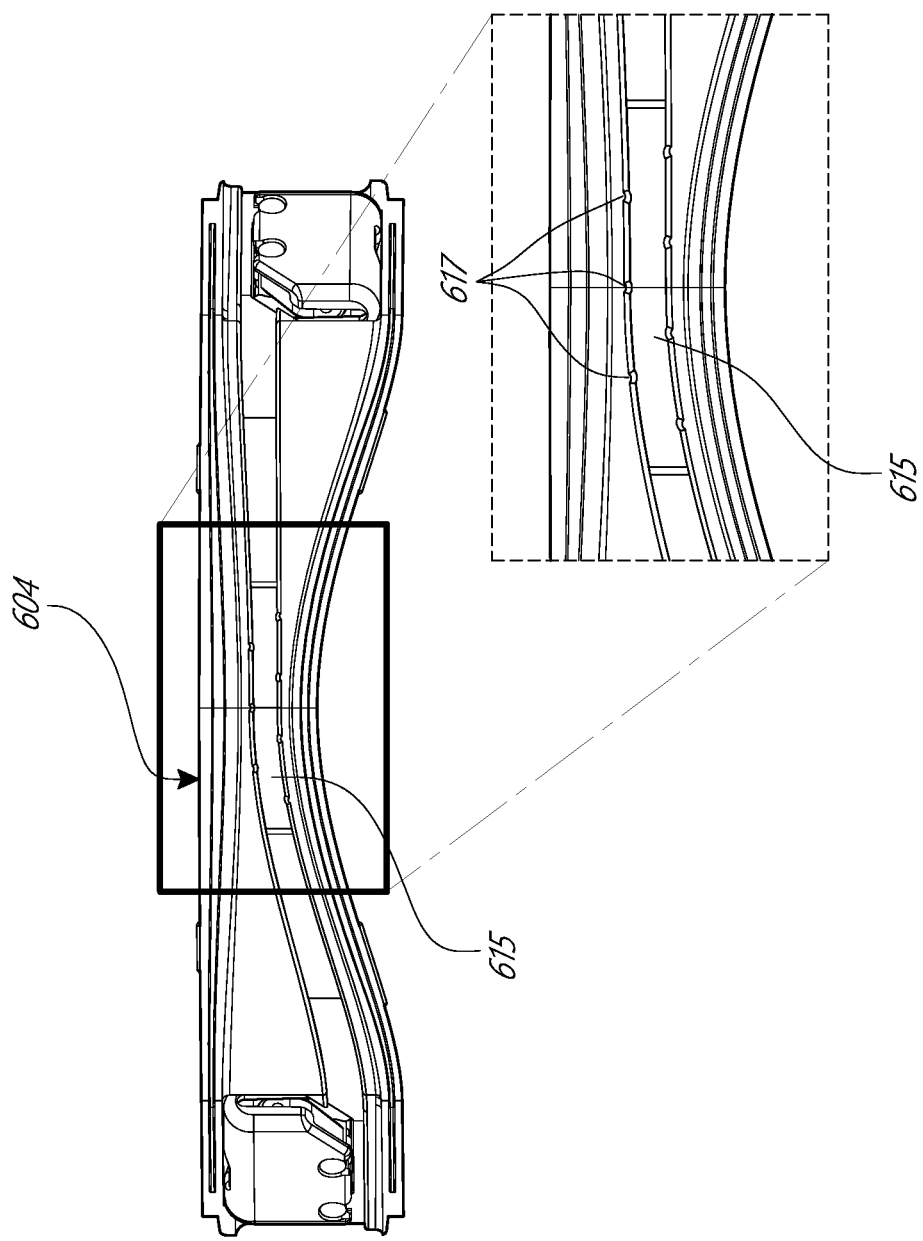
Figure 149:
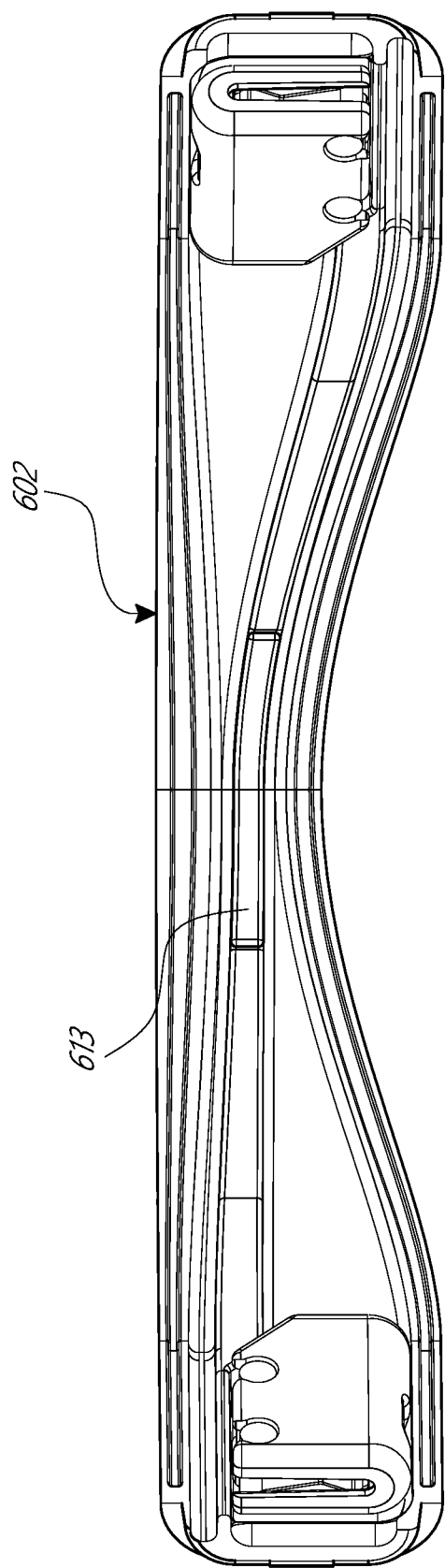
Figure 150:
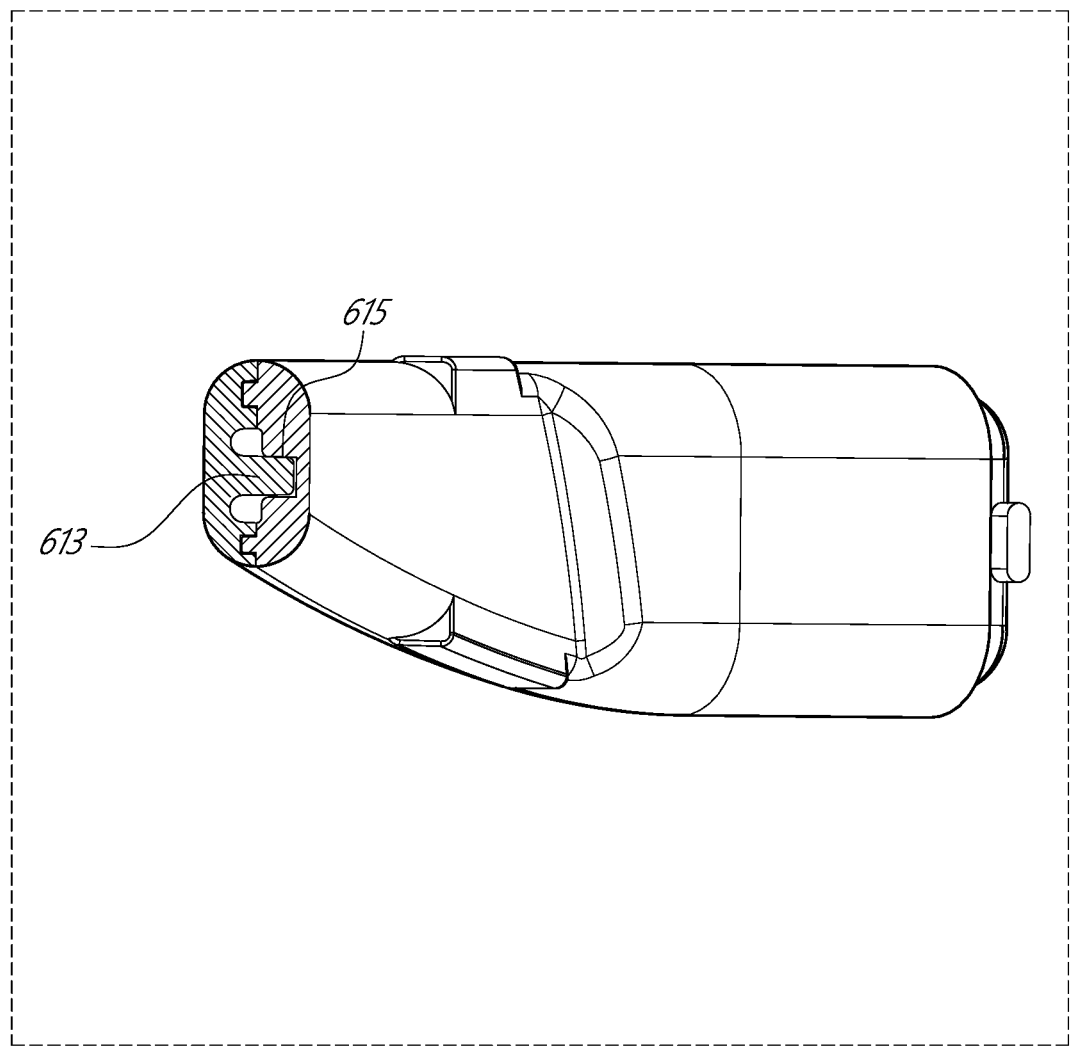

FIG. 137 is a section view of the assembled frame and yoke of FIG. 133 taken along line 137-137 in FIG. 133;

FIG. 138 is a section view of the assembled frame and yoke of FIG. 133 taken along line 138-138 in FIG. 133;

FIG. 139 is a section view of the cushion of FIG. 133;

FIG. 140 is a partial section view of an alternative embodiment of the yoke showing components of a headgear adjustment mechanism;

FIG. 141 shows a method of coupling an end cap onto an end of the yoke;

FIG. 142 is a partial rear perspective view of the assembled end cap and yoke of FIG. 141;

FIG. 143 is an end view of a yoke end of the yoke of FIG. 141;

FIG. 144 is a top view of the yoke end of FIG. 143;

FIG. 145 is a section view of the end cap coupled to the yoke end taken along line 145-145 in FIG. 143;

FIG. 146 is a section view of the end cap of FIG. 145;

FIG. 147 is a rear view of the yoke of FIGS. 141-145;

FIG. 148 is a front view of an alternative embodiment of a yoke back;

FIG. 149 is a rear view of an alternative embodiment of a yoke front configured to be coupled to the yoke back of FIG. 148; and FIG. 150 is a section view of the yoke back of FIG. 148 and yoke front of FIG. 149 assembled together taken along line 150-150 in FIG. 147.

DETAILED DESCRIPTION

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Referring to FIGS. 1 to 6, the present disclosure relates to a respiratory mask system or mask assembly 100 for the delivery of respiratory therapy to a patient. The mask system may comprise a mask interface 102, such as a seal and frame assembly and a headgear 200. The mask interface 102 and headgear 200 may comprise a connection system to attach the headgear 200 to the mask interface 102. Various forms of connection systems may be used to attach the headgear 200 to the mask interface 102. Similarly, the mask interface 102 may be coupled to at least one and possibly multiple different types of headgear.

The mask interface 102 or seal and frame assembly may comprise a seal 104, for sealing around and/or underneath a patient's mouth and/or nose, and a frame 106 for supporting the seal 104 and attaching the seal 104 to the headgear 200. The frame 106 may also comprise a gas inlet 108 configured to attach to a gas conduit 110 for delivering a gas to the patient via the mask interface 102.

The headgear 200 of the respiratory mask system is used to hold the mask interface 102 to the patient's face. The headgear 200 is typically attached to the mask interface 102 and wraps around the rear of the patient's head to seal the mask interface 102 against the patient's face.

In one form, the headgear 200 may comprise a yoke 202 or collector, which is configured to attach to the mask interface 102, as will be described later in this specification.

The yoke 202 may be configured to attach to straps of the headgear 200. In the embodiment shown in FIG. 5, the headgear 200 comprises an assembly of straps, including a rear strap 204 configured to wrap behind a patient's head, an upper strap 206 configured to wrap over the top of a patient's head, and a pair of front straps 208 configured to extend along the patient's cheeks during use. In one form, each front strap 208 is attached to the rear strap 204 of the headgear 200, e.g., to a free end 207 of the rear strap 204 or a connector coupled to the free end 207, by a rear connector 205. In another form, the rear strap 204 comprises side extensions that form front straps to extend along the patient's cheeks during use.

In one form, the headgear can be automatically adjustable and/or can incorporate one or more directional locks that allow the headgear to reduce in length with a relatively low amount of resistance and resist an increase in length of the headgear. In some configurations, a locking force of the directional locks can be overcome to allow lengthening of the headgear for donning of the interface assembly. In some forms the yoke may form a collector for filaments used in an automatically adjustable headgear system. In this form, the yoke may incorporate one or more directional locks, each of which can comprise a washer mechanism, which may be configured to frictionally engage with the filament during elongation of the headgear, but allows relatively friction-free movement during retraction of the headgear. The washer mechanism may be incorporated into the ends of the yoke/collector and the body of the yoke/collector may be substantially hollow to receive the filaments within the body. The headgear or any portion thereof can be configured in accordance with any of the embodiments disclosed in Applicant's U.S. Publication No. 2016/0082217, U.S. application Ser. No. 14/856,193, filed Sep. 16, 2015, and PCT Publication No. WO2016/043603, the entireties of which are incorporated by reference herein.

Each front strap 208 may comprise a free end to which may be attached a connector 209. Each connector 209 may engage with a complementary strap connector 203 located on the yoke 202. Preferably, the yoke 202 is substantially elongate and comprises a strap connector 203 located at or near each end of the yoke 202.

Figure 1:
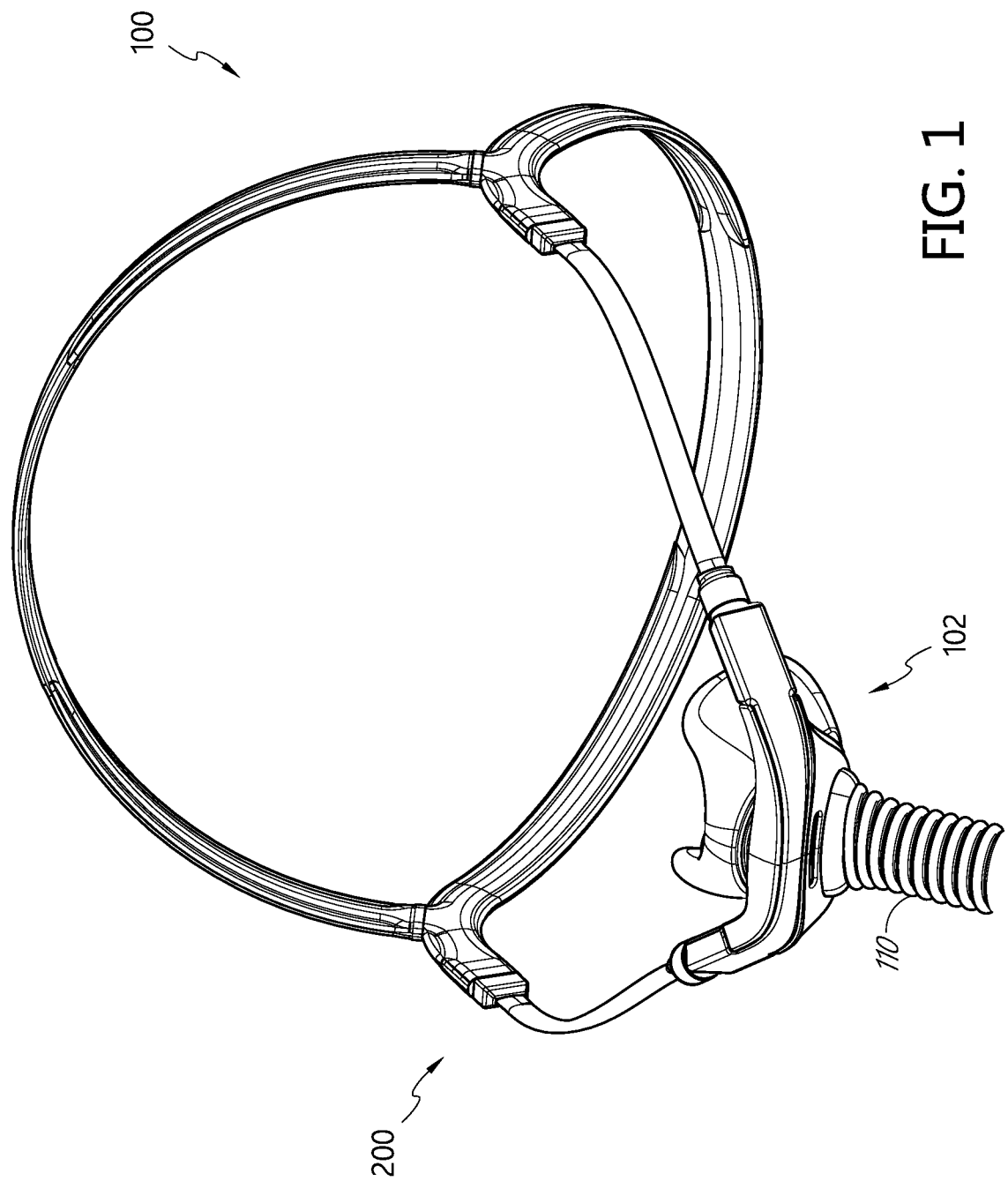
FIG. 1 is a perspective view of a mask assembly, including a headgear assembly, a seal assembly, and a frame assembly.
Figure 2:
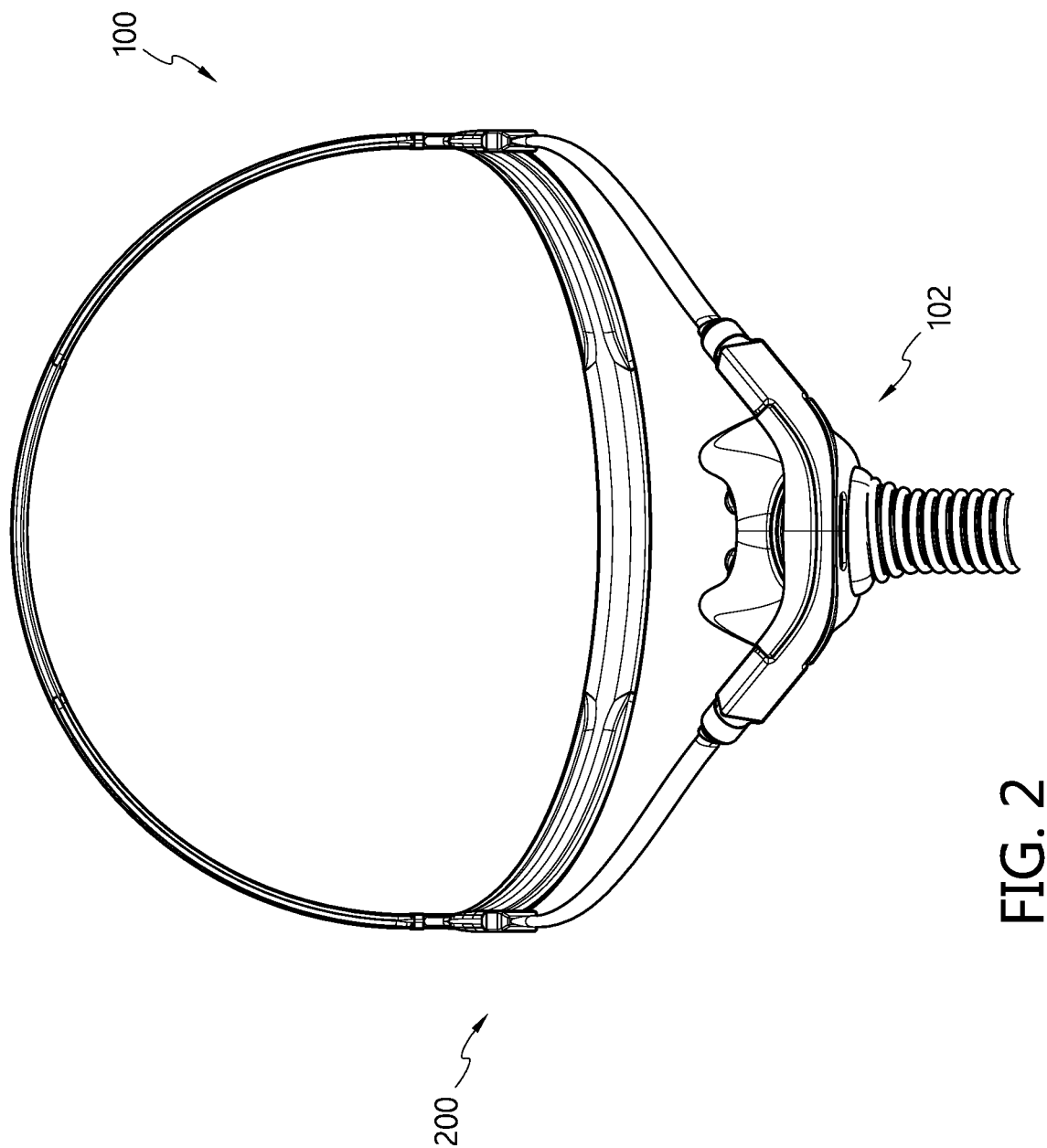
FIGS. 2 to 4 are a front view, side view, and a rear perspective view, respectively, of the mask assembly of FIG. 1.
Figure 3:
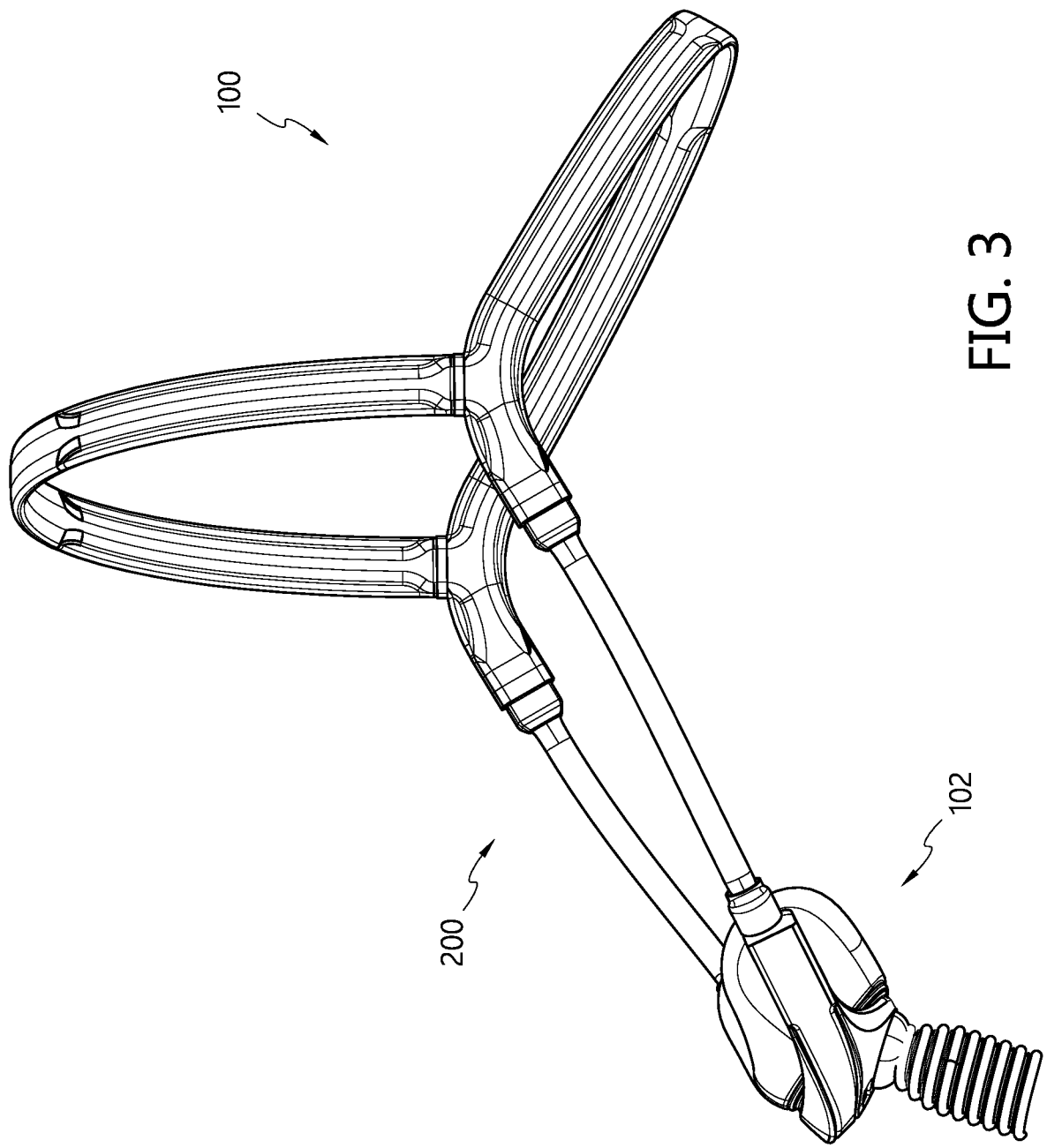
Figure 4:
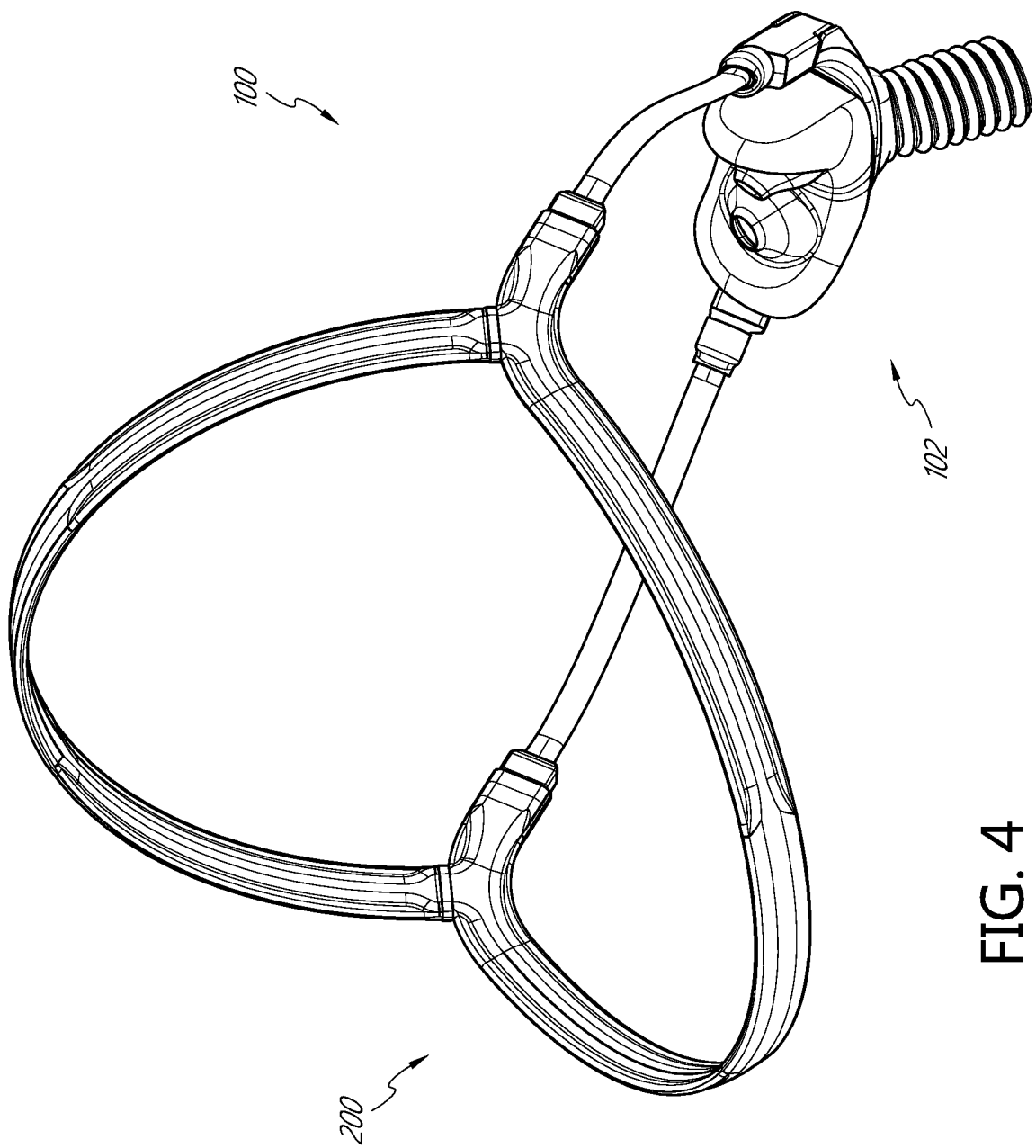
Figure 5:
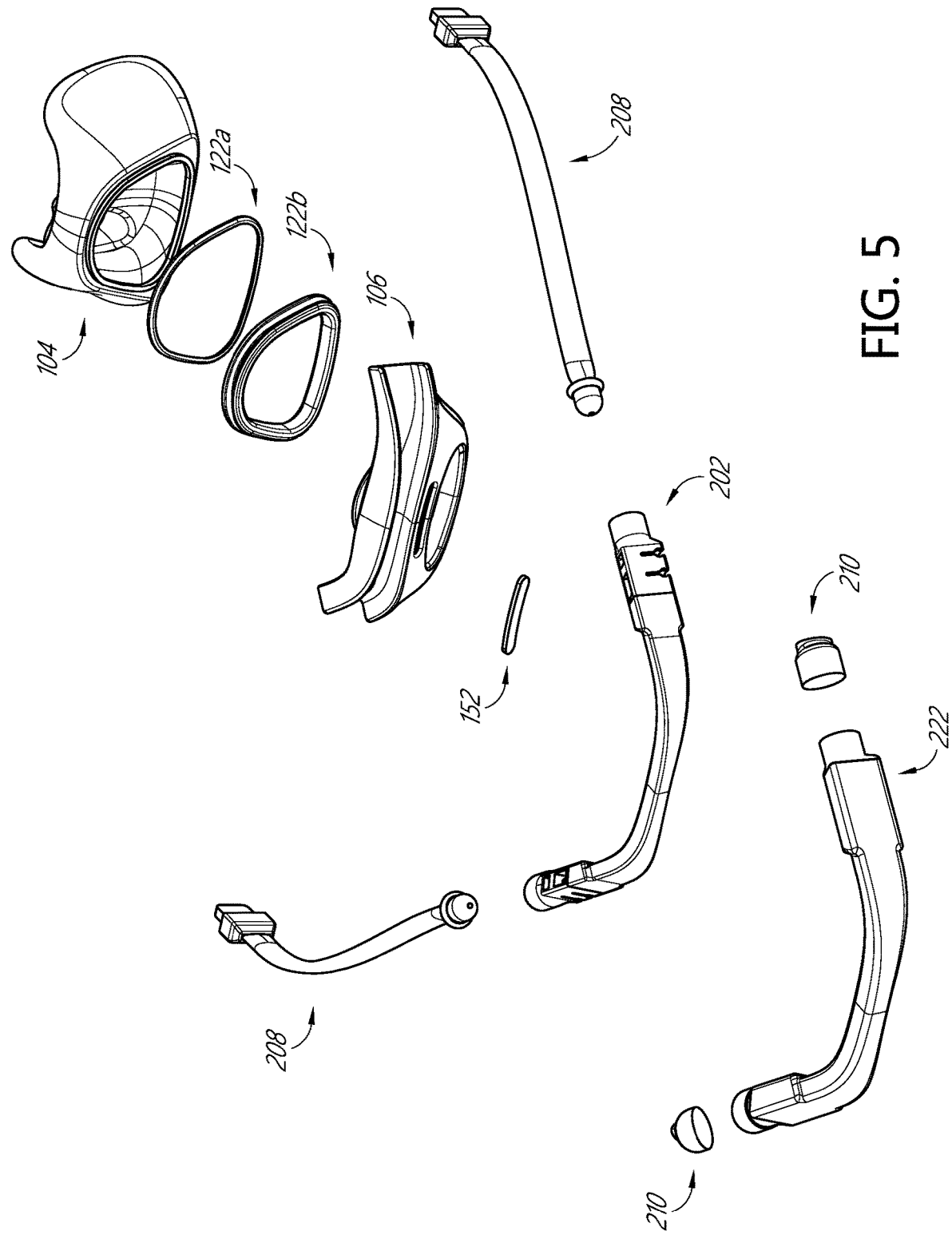
FIG. 5 is an exploded view of the seal assembly, frame assembly, and a front portion of the headgear assembly.
Figure 6:
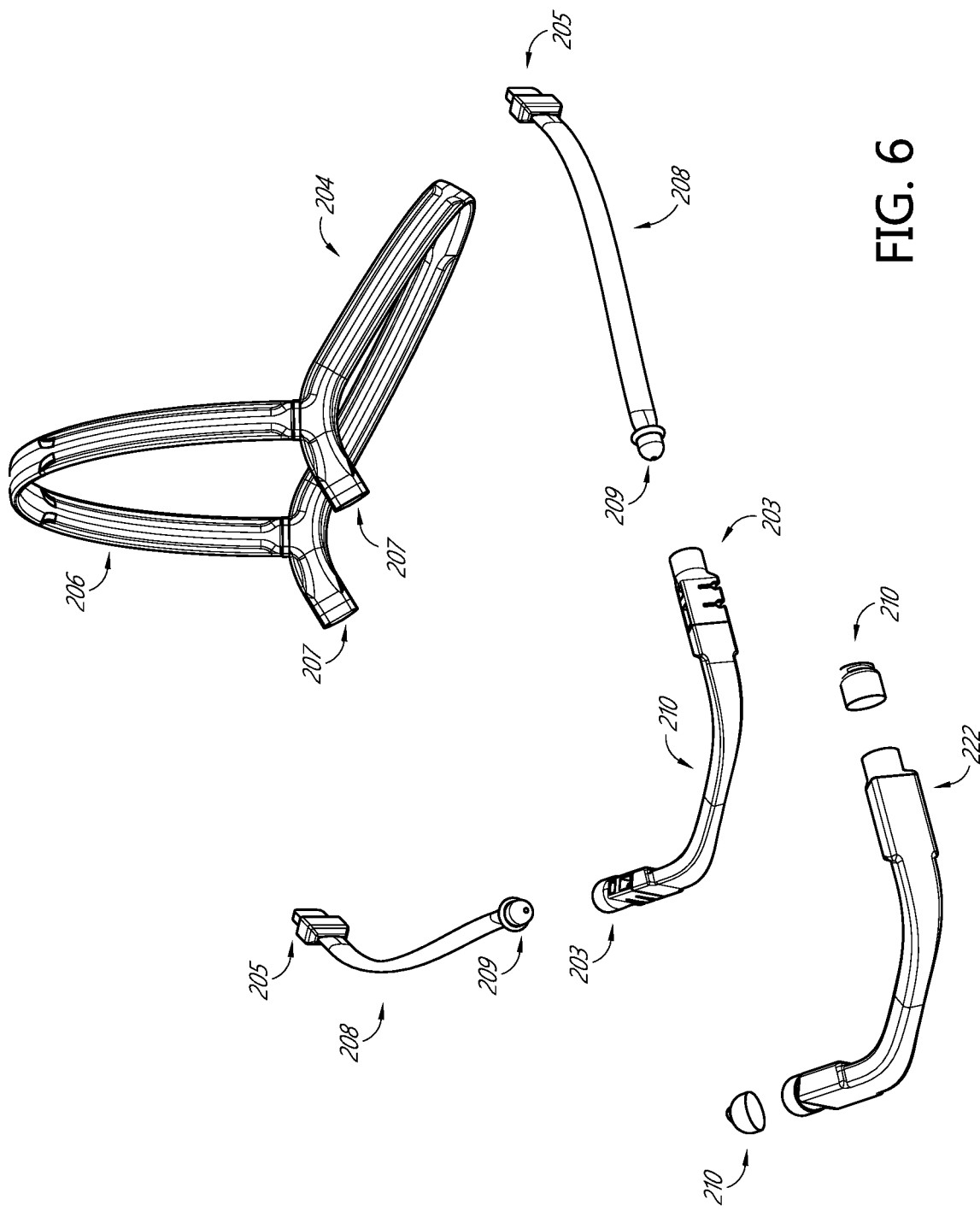
FIG. 6 is an exploded view of one form of headgear assembly.

The connection between the front straps 208 and yoke 202 may be any suitable form of connection, such as a snap-fit connection, a screw and thread type connection, or a hooked connection. In one form, as shown in FIG. 6, each strap connector 203 comprises a cap 210 located at each end of the yoke 202. Each cap 210 may comprise an opening, such as an aperture or recess, configured to receive the connector 209 of the front strap 208 in a snap-fit arrangement to attach the yoke 202 to the front straps 208 of the headgear 200.

As mentioned above, the yoke 202 may also be configured to attach to the frame 106 of the mask interface 102. In one form, the frame 106 may comprise a recessed region configured to receive at least a portion of the yoke 202 therein when the yoke 202 and frame 106 are attached together.

Turning to FIGS. 7 to 26, various forms of mask interface 102 will now be described in further detail.

The mask interface 102 may comprise a frame 106 having a body comprising a first surface or front surface 112 and a substantially opposing second surface or rear surface 114. The frame 106 may also comprise a gas inlet 108 for attaching to a gas conduit and an outlet vent 140.

In one form, the frame 106 is configured so that the gas inlet 108 is angled at around 10 to 450 from vertical. In this configuration, the gas conduit 110 may sit comfortably away from the patient's chin, but not so far away as to create sufficient torque to pull the mask interface away from the patient's face.

The mask interface 102 may comprise a seal 104 having a front or distal surface and a rear surface or proximal surface. The rear surface of the seal may be configured to substantially seal against a patient's face during use. The seal may be configured to fit over a patient's mouth, nose, or both. In one form, the seal comprises nasal pillows that substantially seal around a patient's nares. The seal 104 may also comprise a gas inlet aperture 118 that substantially corresponds with the opening of the gas inlet 108 of the frame 106. The frame 106 and seal 104 may be fitted together so that the gas inlet openings of each part substantially align with each other to provide the mask interface with a gas inlet. In another form, the mask interface is a non-sealing interface such as a nasal cannula configured for high flow therapy.

In one form, the gas inlet 108 of the frame 106 may be defined by a substantially continuous edge. The edge may be provided by a seal flange 120 projecting from the rear surface of the frame 106. A seal 104 or seal assembly may be configured to seal against the seal flange 120 to attach the seal to the frame.

In one form, a seal assembly, comprising a seal 104 and one or more seal clips 122, is configured to attach to the seal flange 120 of the frame. In the embodiment illustrated in FIG. 10, the seal assembly comprises a seal having a gas inlet opening defined by a substantially continuous lip 124. The lip may extend around the entire gas inlet opening or one or more gaps may be formed in the lip so that the lip forms a substantially continuous flange or series of flanges. A channel 126 may be formed between the lip 124 and the front surface 128 of the seal 104. The seal may be formed of a stretchable, resilient material, such as silicon or rubber for example, that can stretch under tension but will substantially return to its original shape after removal of the tension force. The lip 124 of the gas inlet 108 of the seal may be configured to stretch around the seal flange 120 of the frame 106 so that an inner face of the gas inlet 108 substantially surrounds and seals against an outer surface of the seal flange 120. The seal assembly may also comprise a stretchable but tight-fitting, seal clip 122 or ring that may be positioned within the channel 126 of the lip to clamp the seal against the seal flange.

Optionally, the seal flange 120 and/or seal 104 comprise one or more attachment features to help locate and/or attach the seal 104 to the frame 106. For example, the frame 106 may comprise one or more projections configured to be held within one or more recesses provided in the seal to help prevent the seal rotating relative to the frame and to help prevent the seal from pulling off the seal flange. Typically, the one or more projections are provided on the seal flange and the one or more corresponding recesses are provided on the inner surface of the gas inlet opening of the seal. Alternatively, the recesses may be located on the frame and the projections may be located on the seal. In yet another form, one or more recesses may be provided on the outer surface of the seal flange and the lip of the seal is configured to rest within the recess(es) to help prevent the seal from being inadvertently pulled off the seal flange. It is envisaged that other suitable forms of attaching the seal to the frame may be used without departing from the scope of the present disclosure.

In another form, the seal assembly may comprise a seal 104, an inner clip 122a and an outer clip 122b. The inner and outer clips may form a collar or ring that defines an opening forming the gas inlet 108. The gas inlet 108 may be substantially the same shape and dimensions as that of the frame. The inner clip 122a may comprise an inner surface configured to substantially surround and seal against the outer surface of the seal flange 120.

Figure 13:
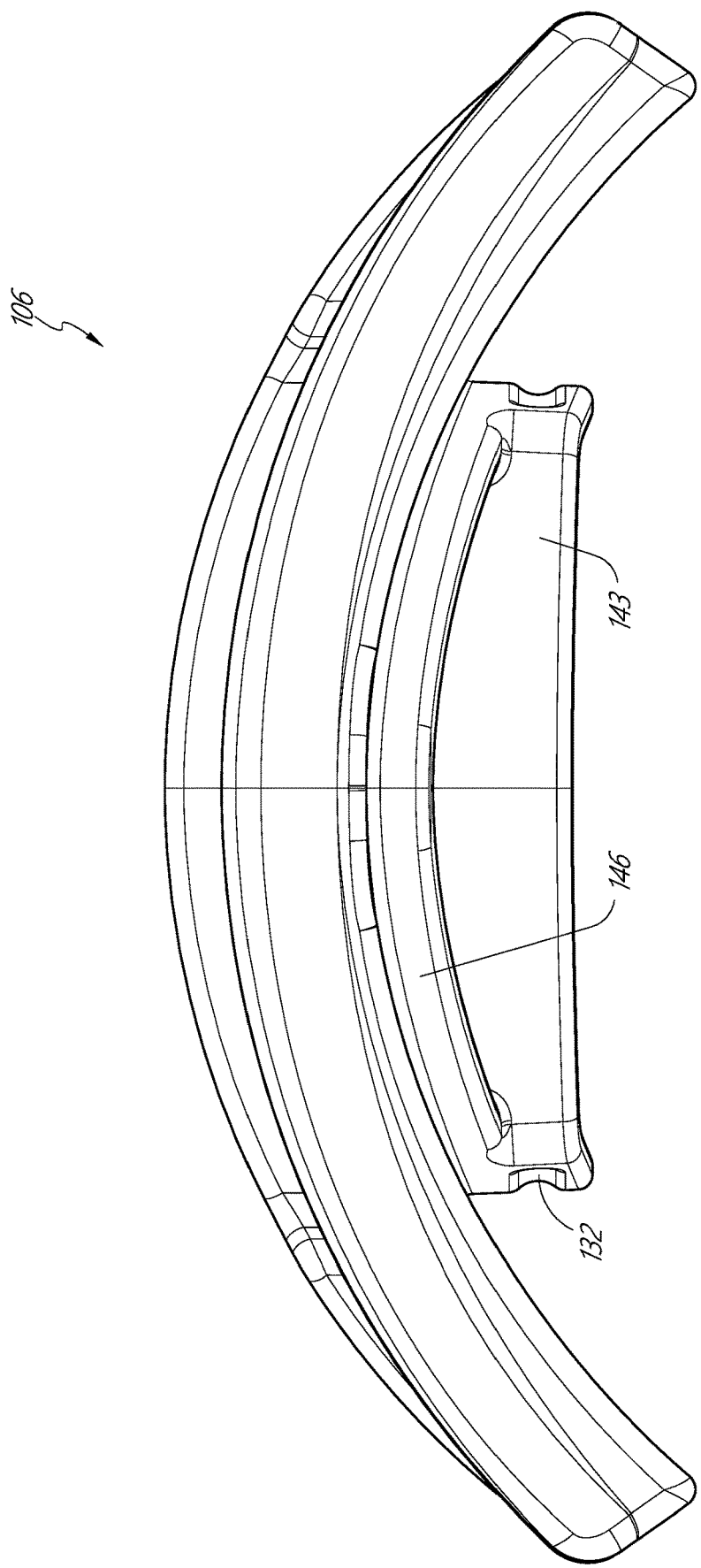
FIG. 13 is a top view of the frame of FIG. 11.
Figure 15:
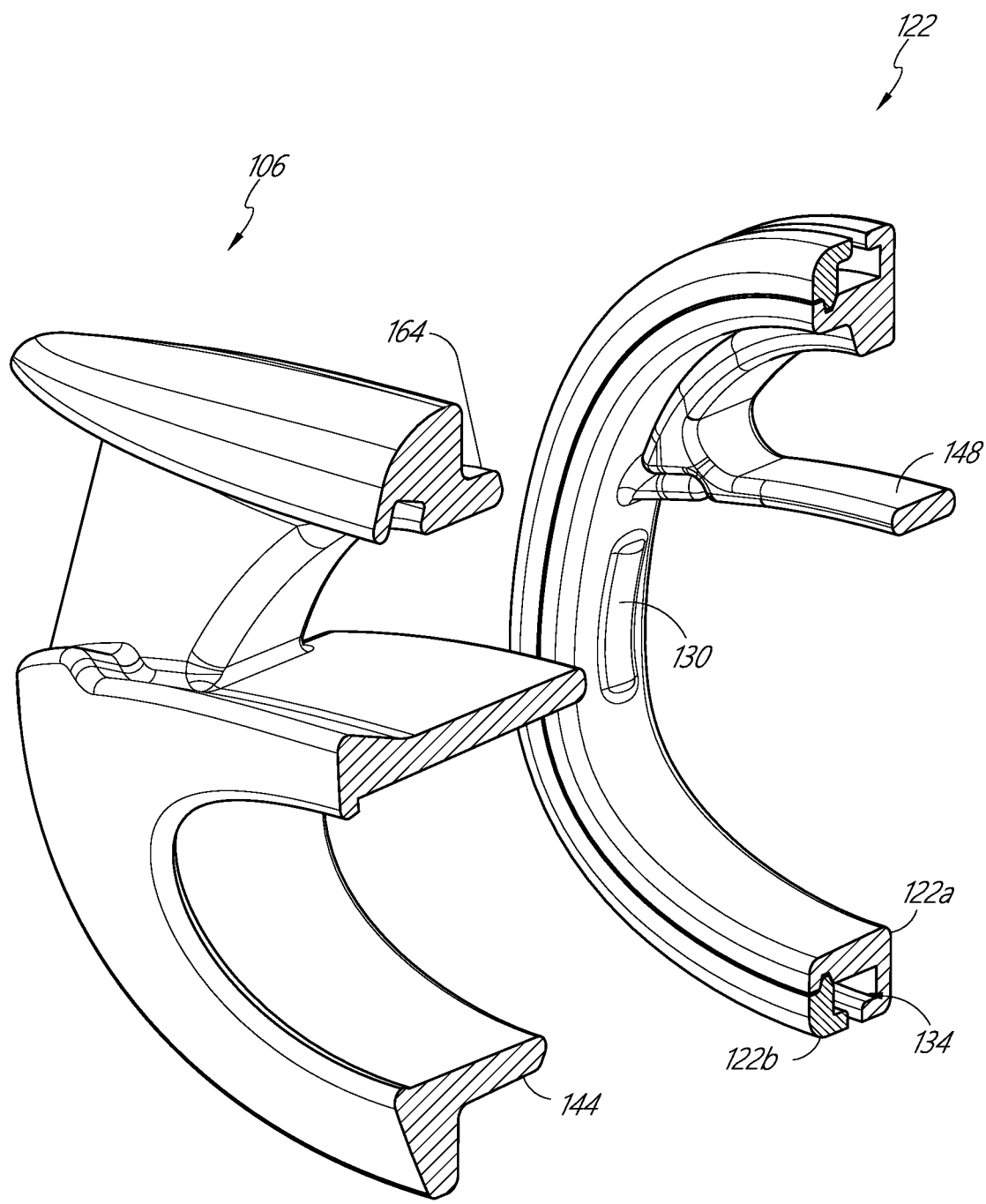
FIG. 15 is a cross-sectional exploded front perspective view of the frame and seal clip assembly of FIG. 14.

In one form, one or more projections (for example, similar to protrusions 130 shown in, for example, FIG. 15) are located on substantially opposing sides of the inner surface of the inner clip and are configured to be received within the snap recesses of the seal flange (for example, similar to snap recesses 132 shown in, for example, FIG. 13) when the inner clip 122*a* is pushed over the seal flange. In other forms, the outer surface of the seal flange may comprise one or more projections configured to be received within one or more recesses located on the inner surface of the inner clip or seal. The inner clip 122*a* may be formed of a stretchable or semi-stretchable material to help push the tight fitting inner clip 122*a* over the seal flange 120.

The inner clip 122*a* may comprise a seal locator for attaching the seal 104 to the inner clip 122*a* and therefore to the frame 106. The seal locator may comprise one or more hooks, flanges, or other projections that may engage with one or more hooks, flanges, or other projections, openings or recesses located on the seal to attach the seal and inner clip together. It is envisaged that alternative forms of attachment may also be suitable.

Figure 7:
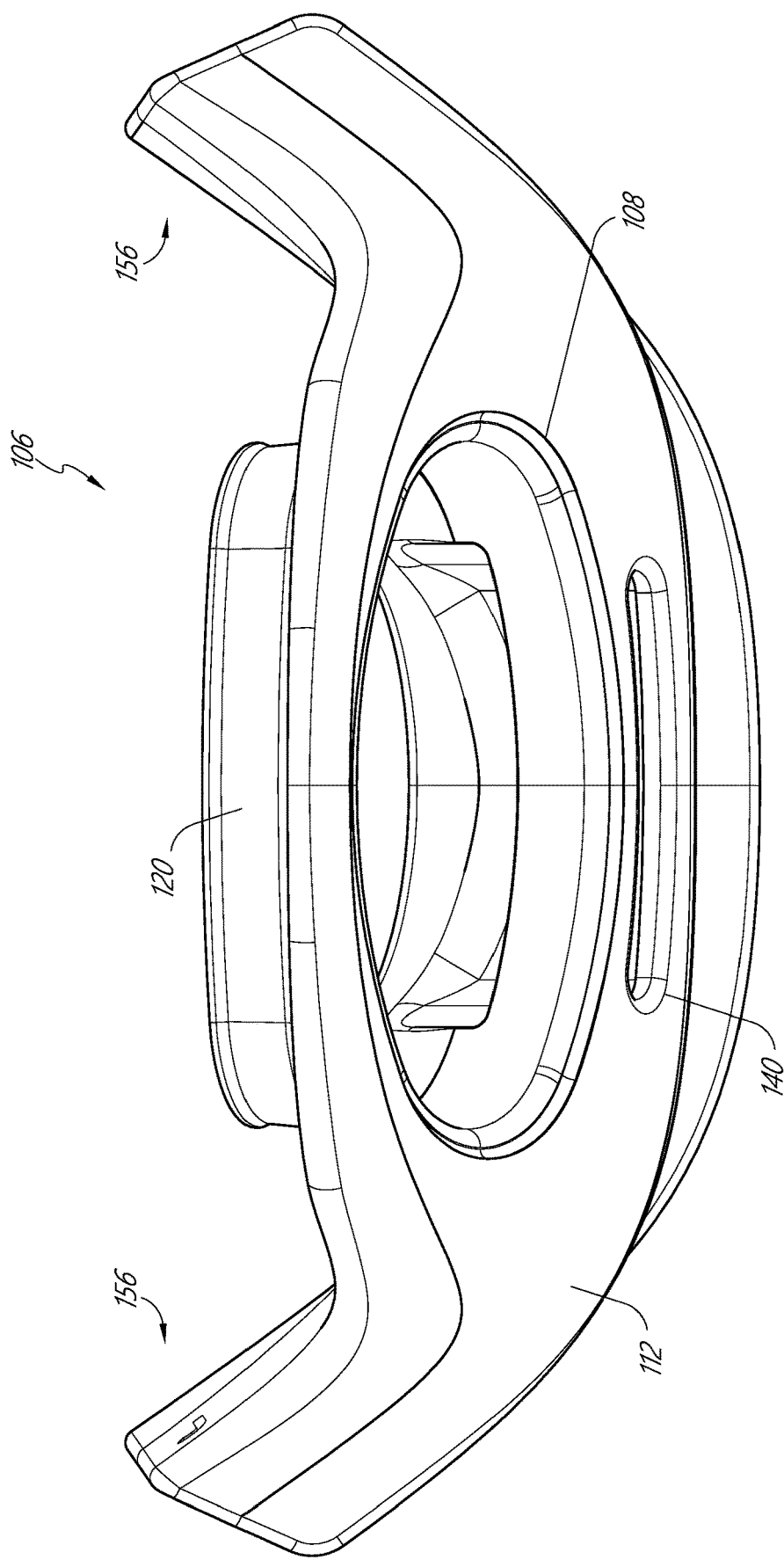
FIG. 7 is a bottom view f one form of frame with vent aperture.
Figure 8:
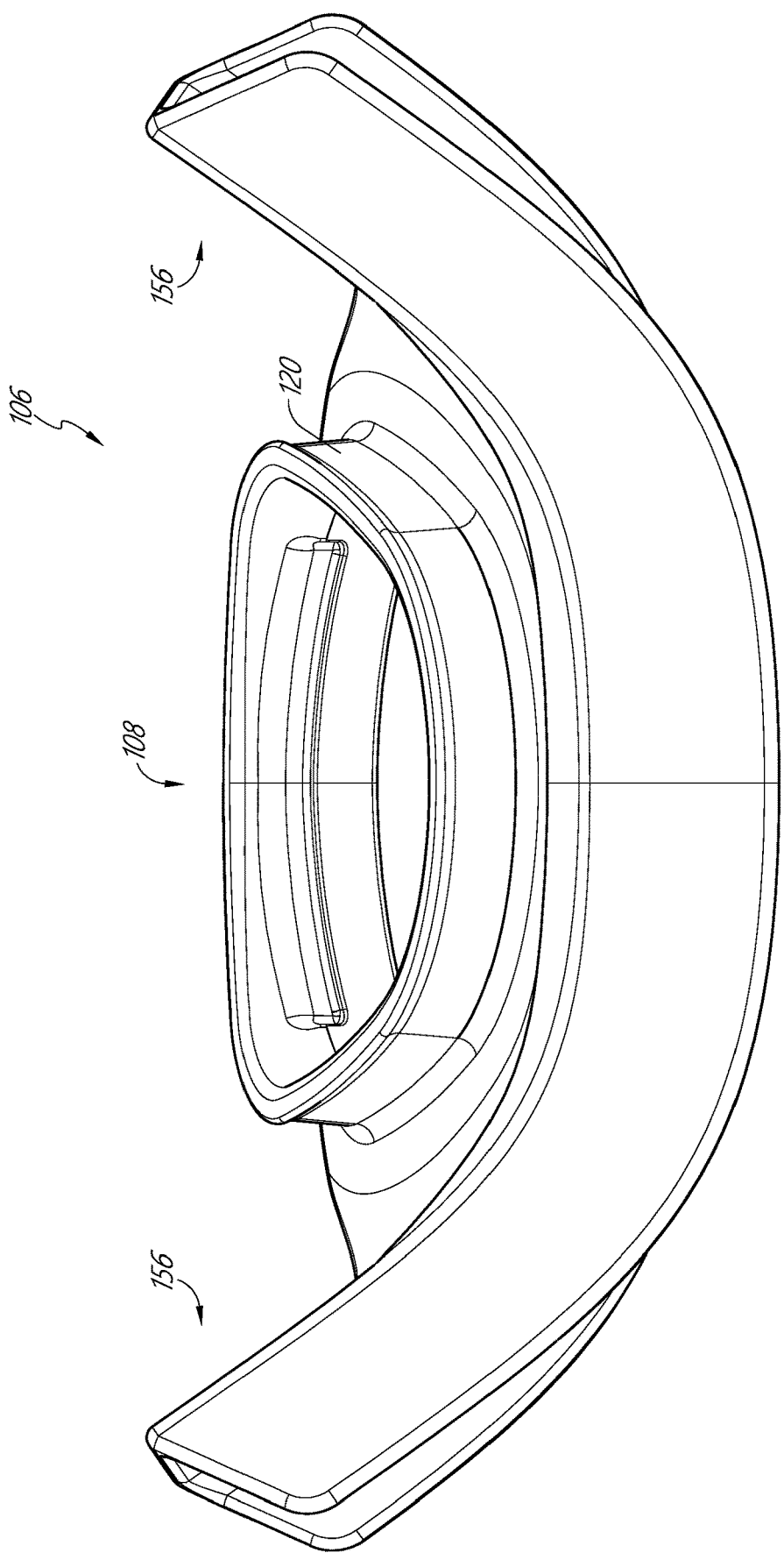
FIG. 8 is a top view of the frame of FIG. 7.
Figure 9:
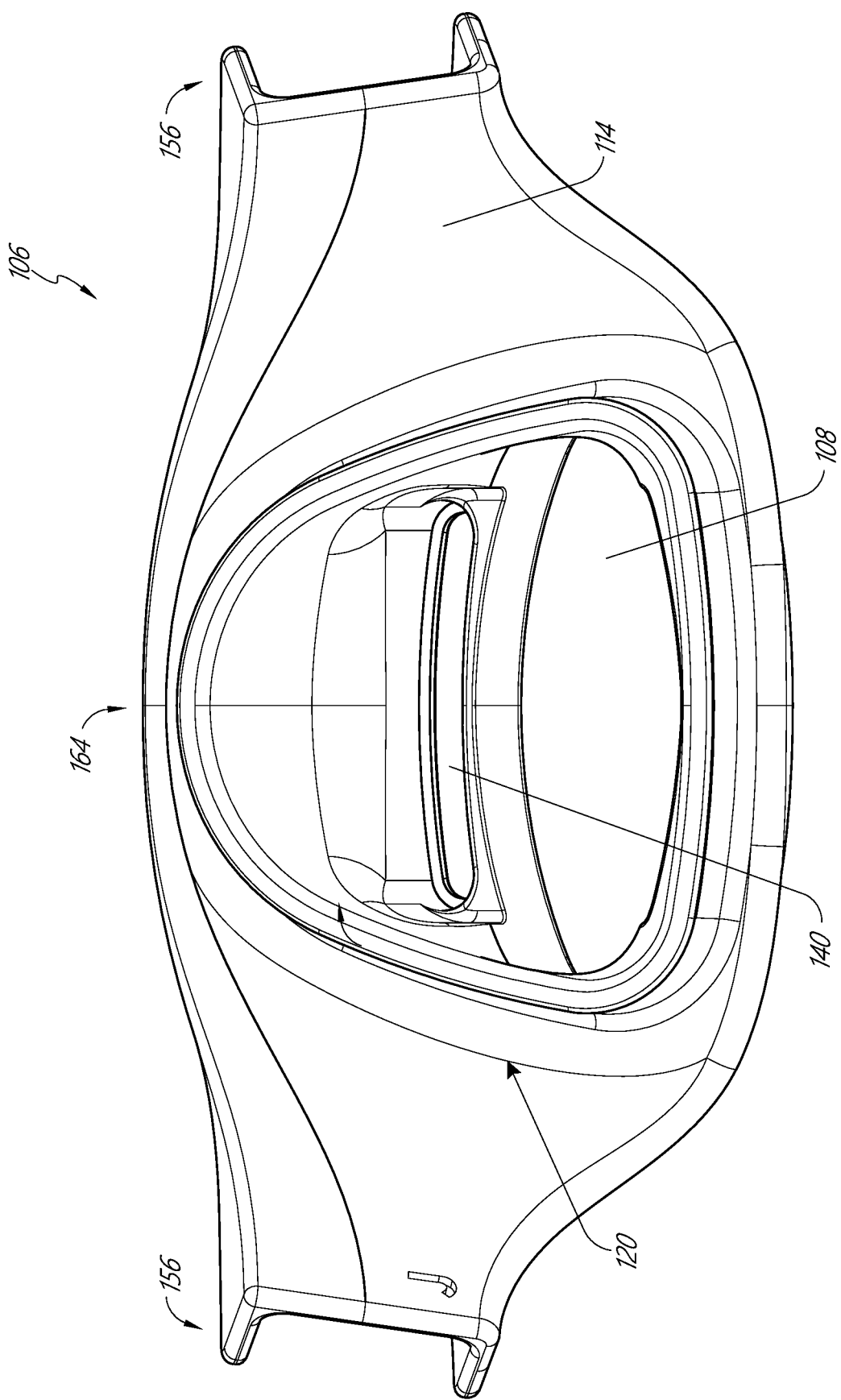
FIG. 9 is a rear view of the frame of FIG. 7.
Figure 10:
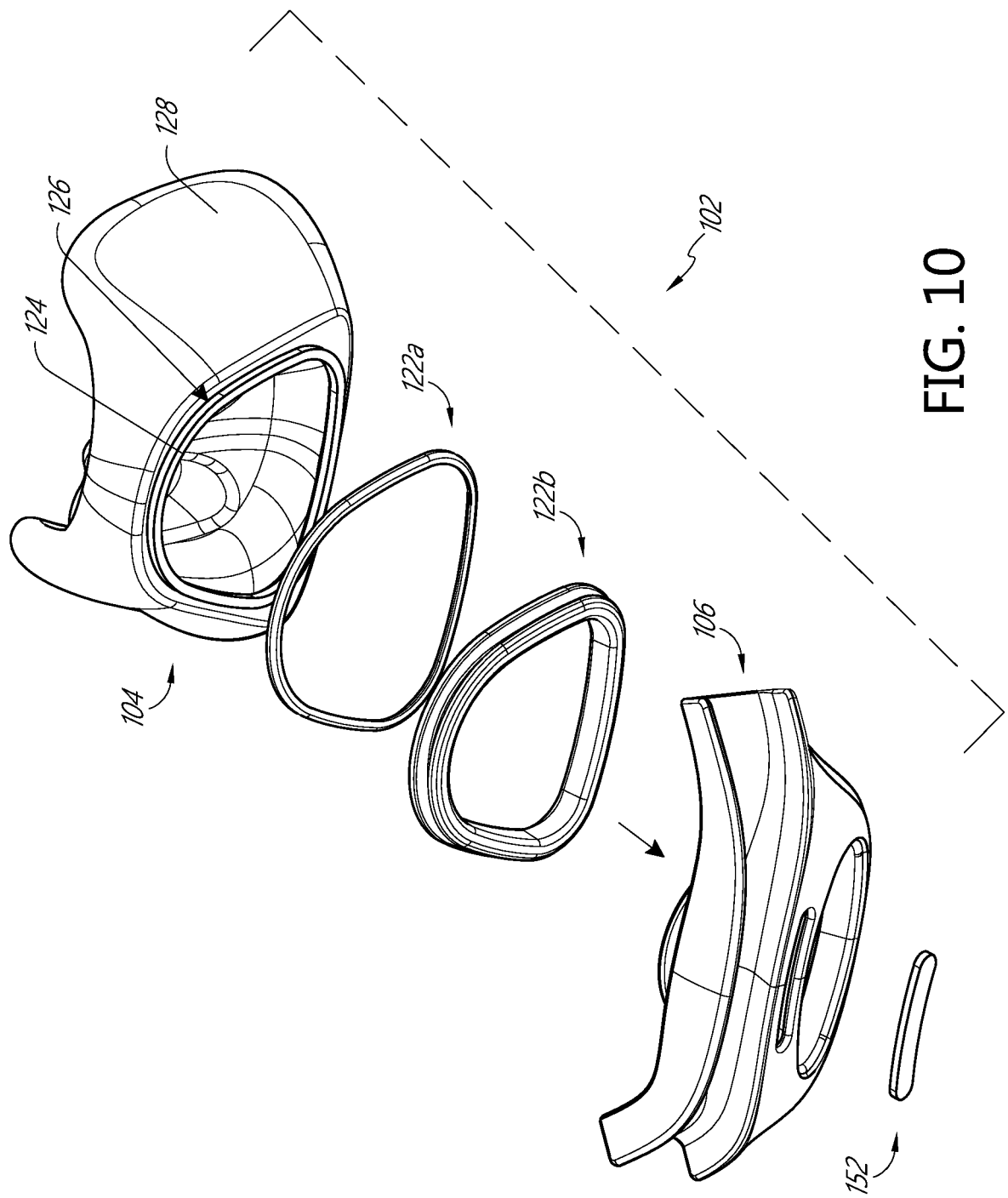
FIG. 10 is an exploded view of one form of seal assembly and frame assembly.
Figure 14:
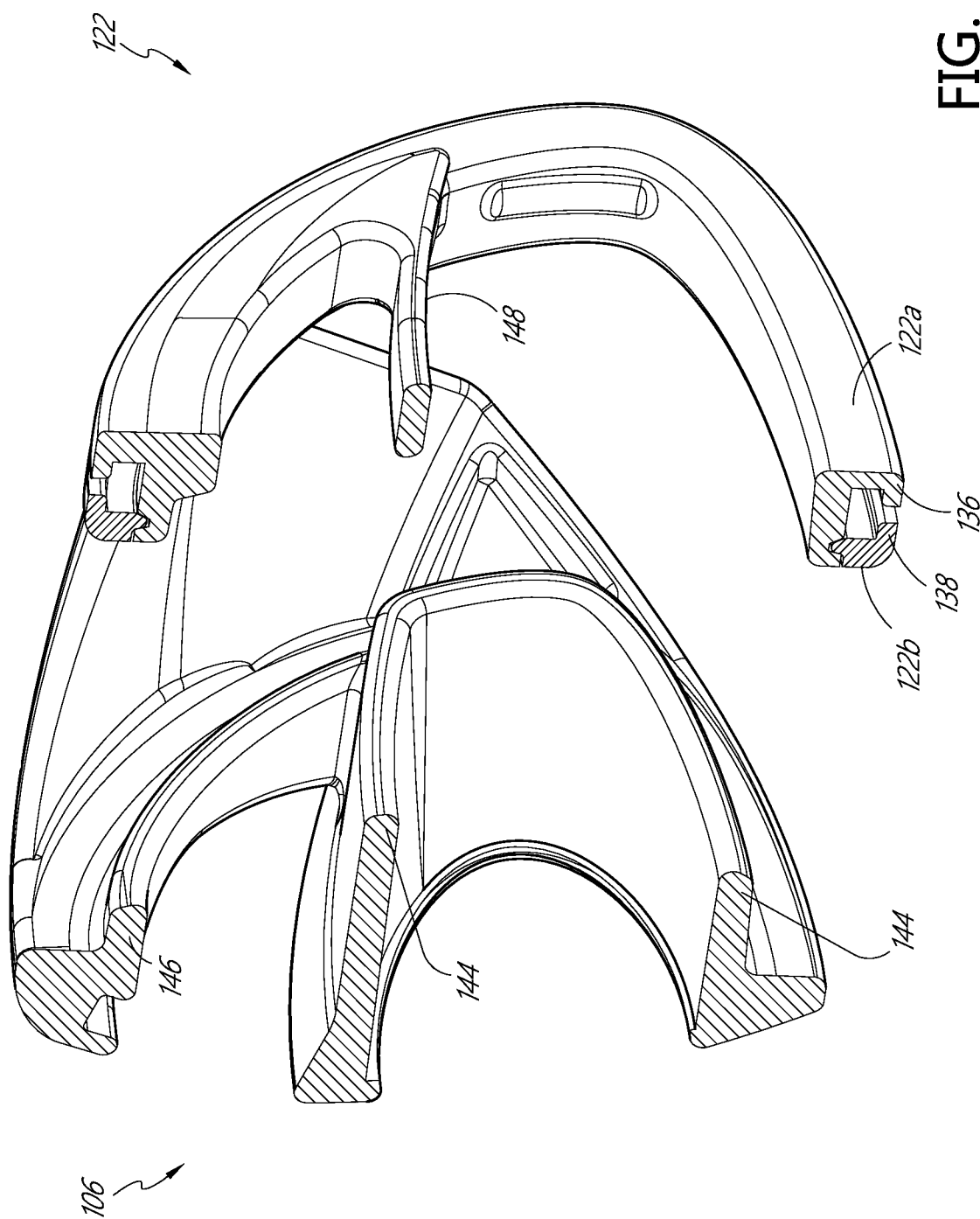
FIG. 14 is a cross-sectional exploded rear perspective view of one form of frame and seal clip assembly, the frame having a vent aperture.
Figure 16:
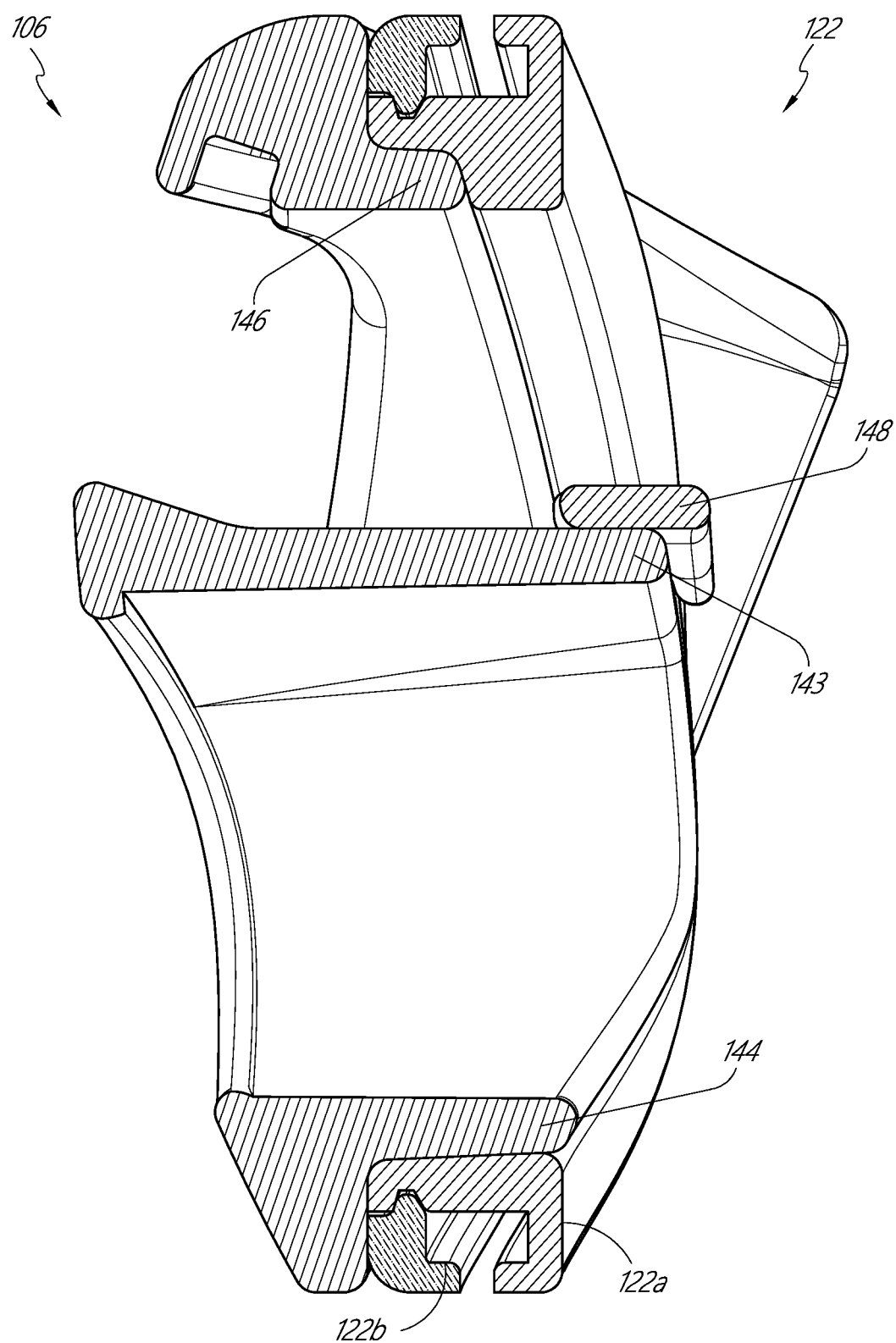
FIG. 16 is a cross-sectional side view of a frame and seal clip assembly when attached together.
Figure 17:
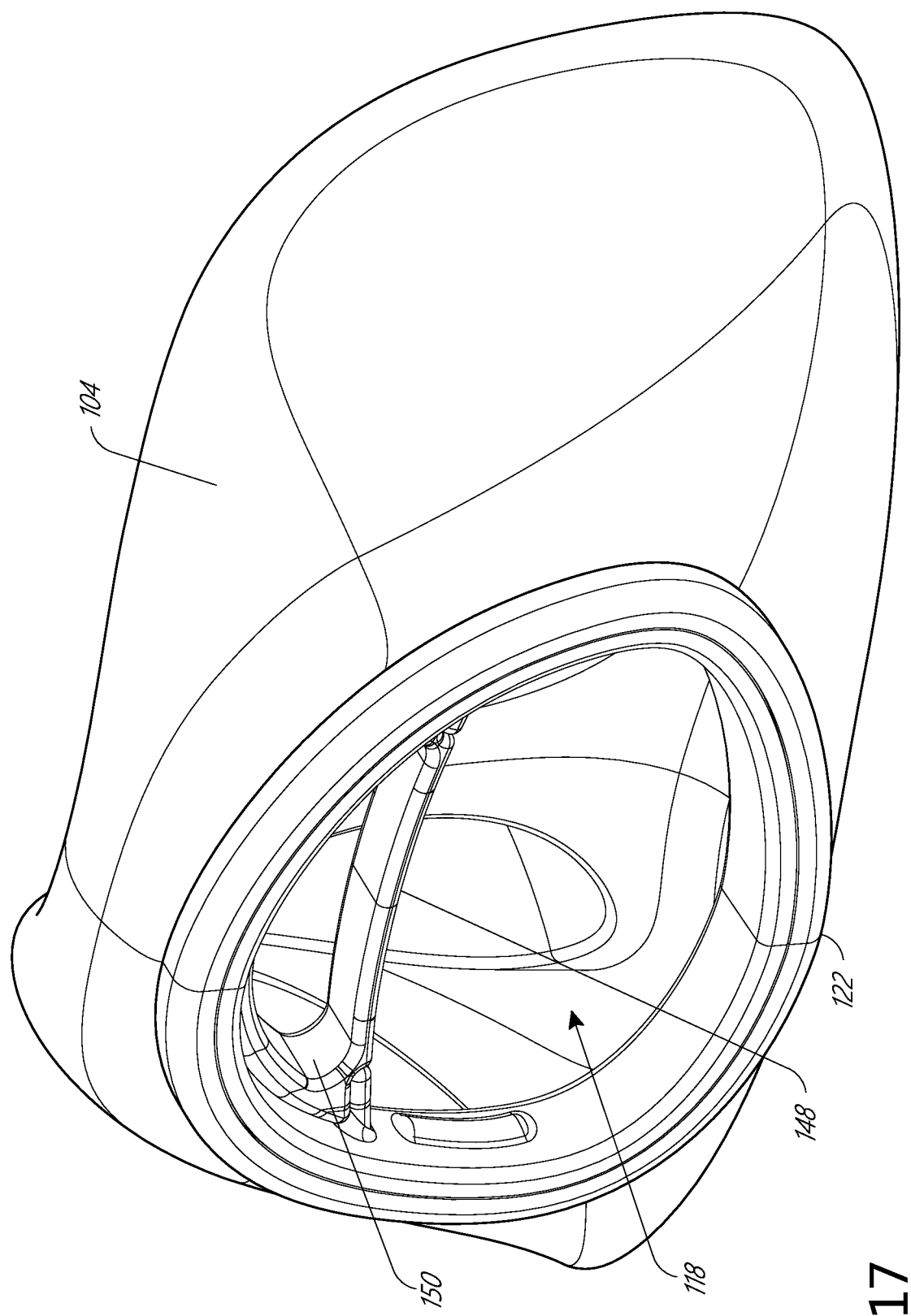
FIG. 17 is a perspective view of one form of seal assembly, including a seal clip having a vent aperture.
Figure 18:
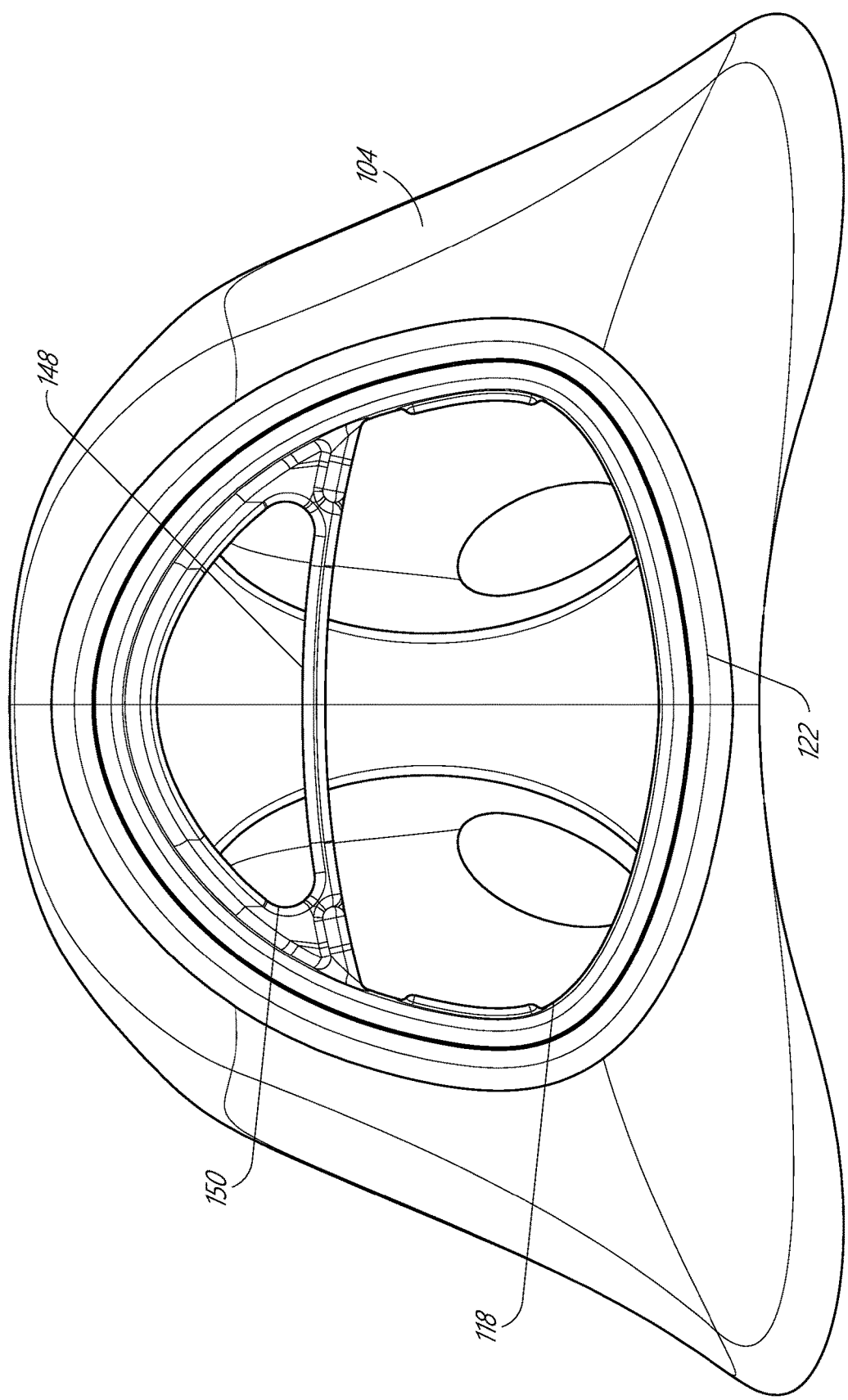
FIG. 18 is a front view of the seal assembly of FIG. 17.
Figure 24:
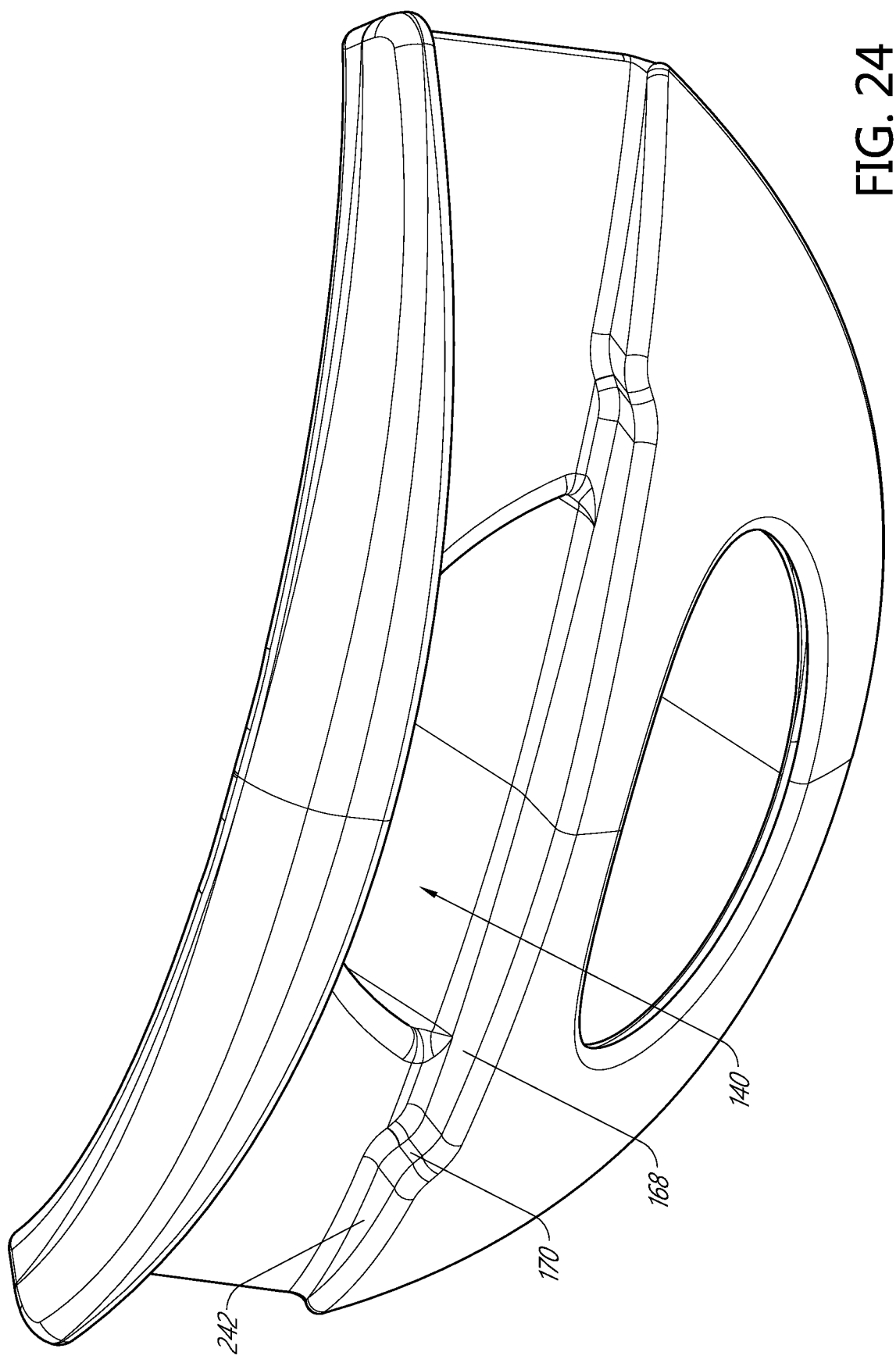
FIGS. 24 to 26 are a perspective view from above, front view, and side view of another form of frame.
Figure 25:
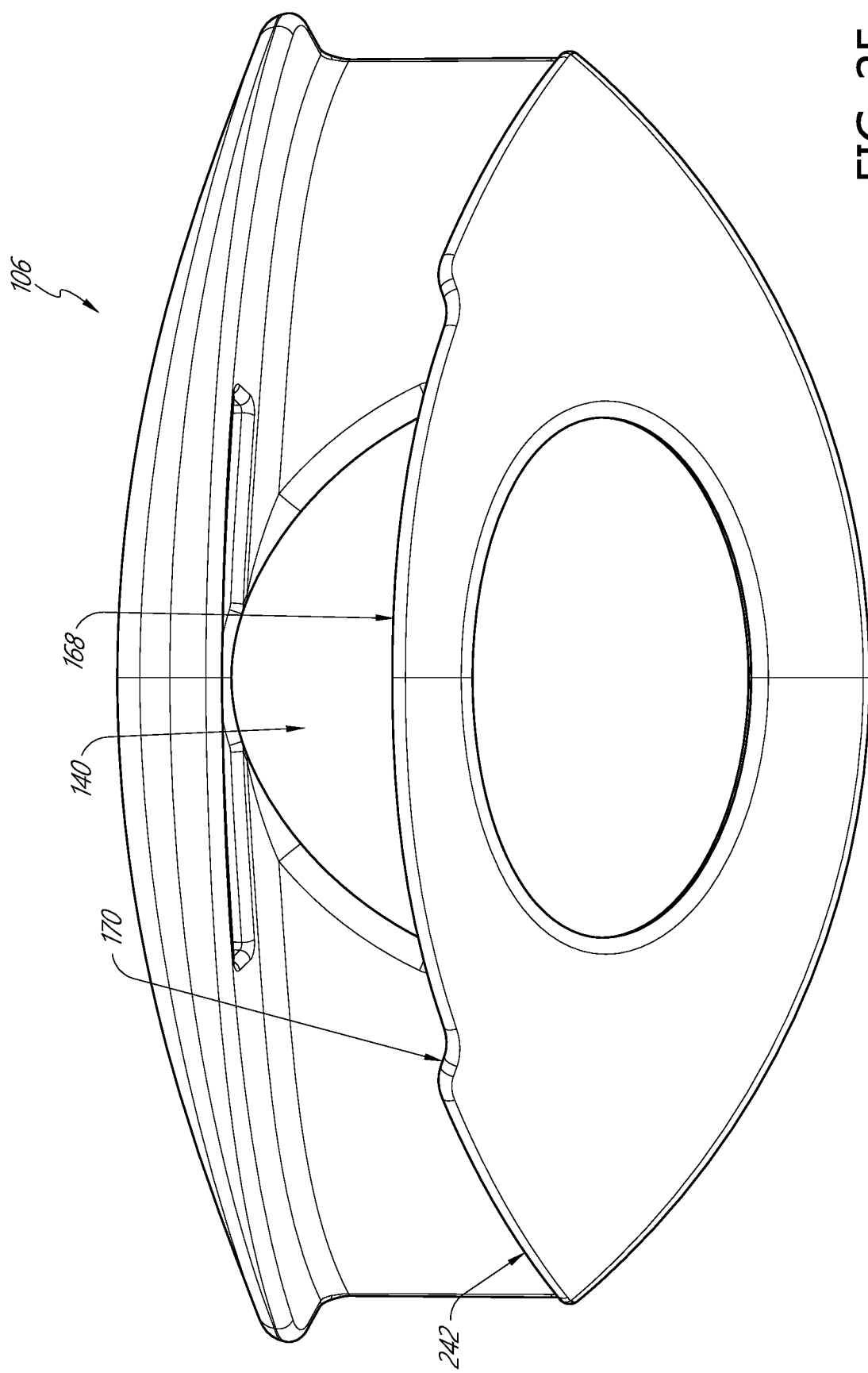
Figure 26:
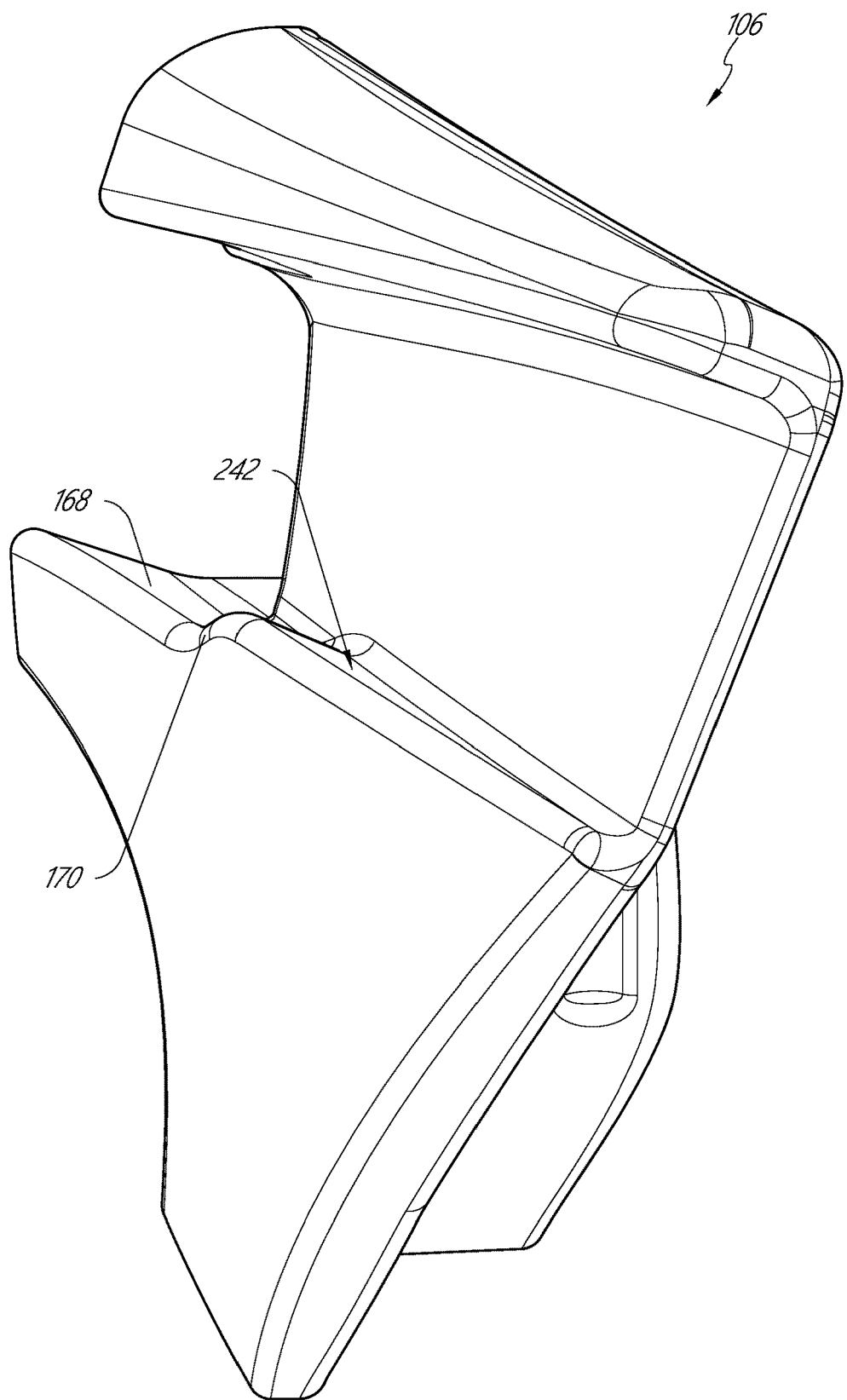
Figure 27:
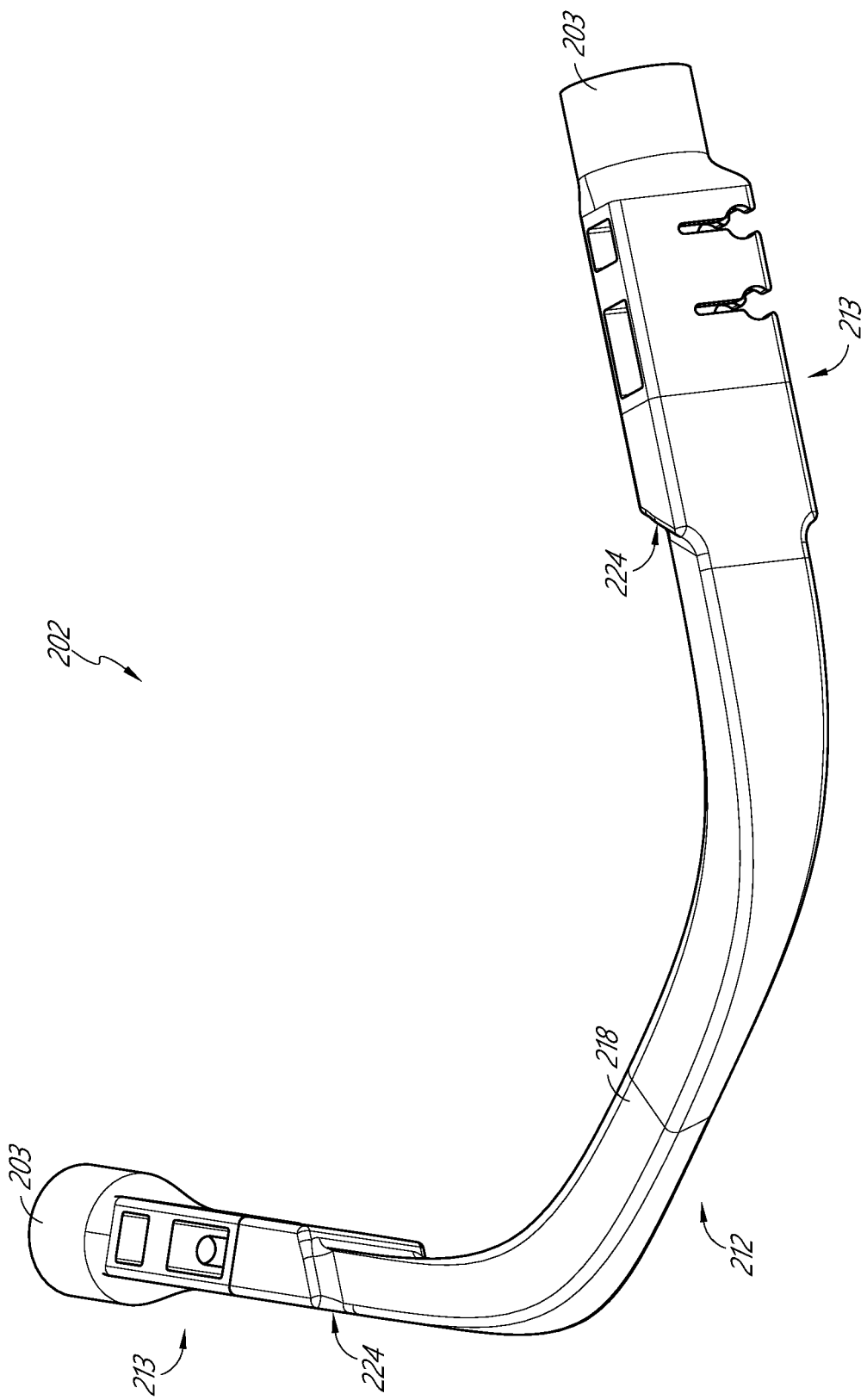
FIG. 27 is a perspective view of one form of yoke, and in some embodiments, a collector, for a headgear assembly.
Figure 28:
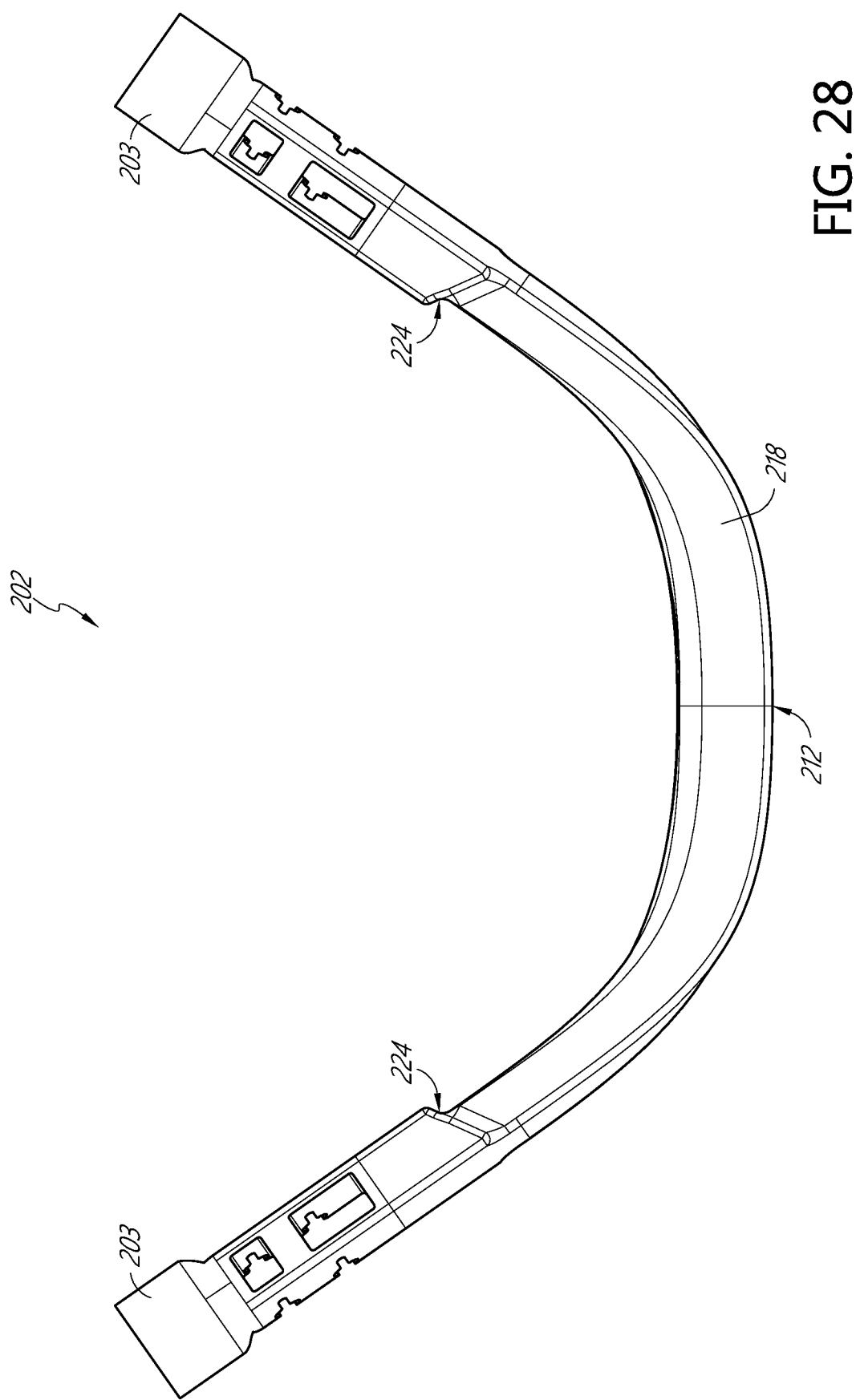
FIG. 28 is a top view of the yoke of FIG. 27.
Figure 29:
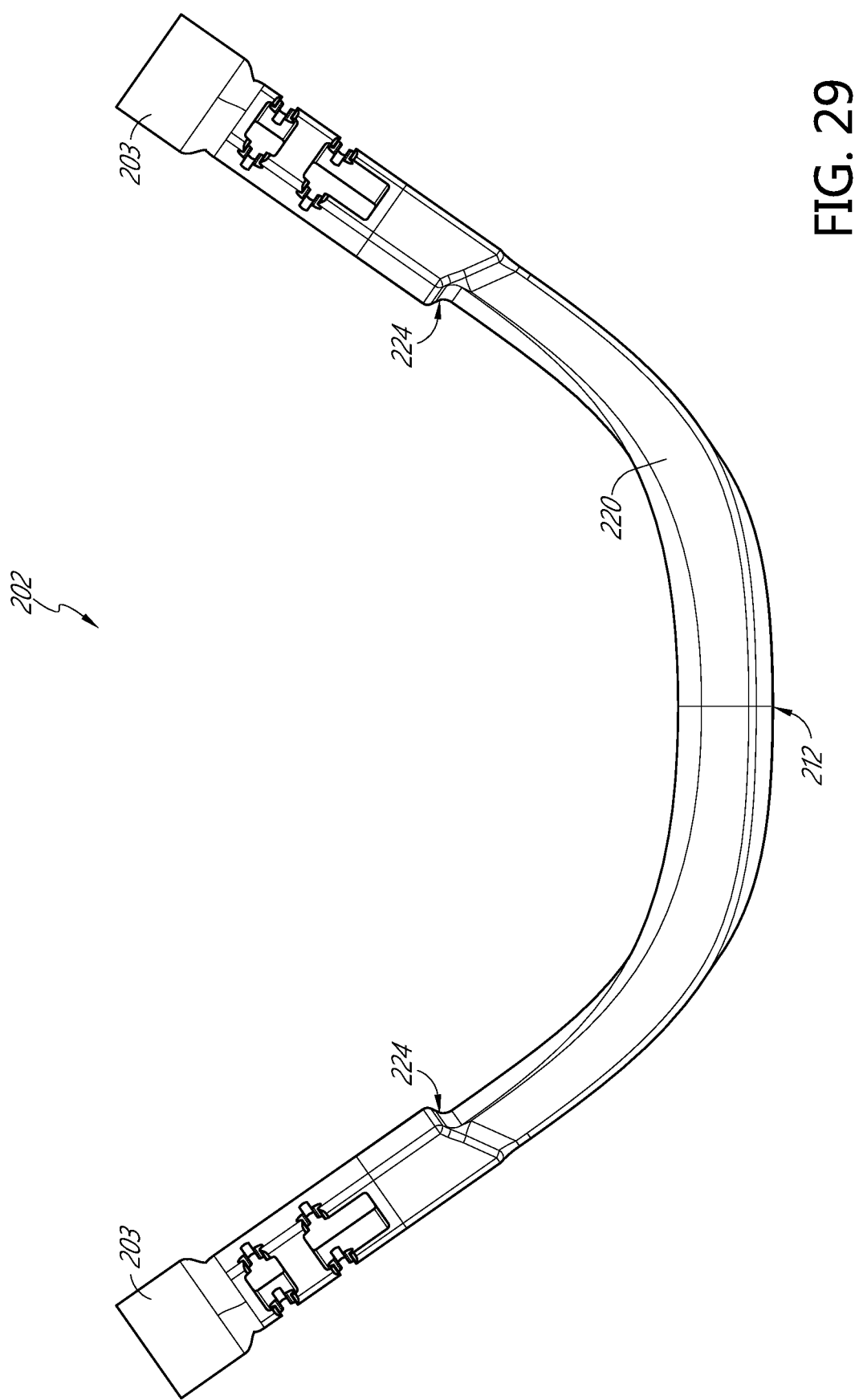
FIG. 29 is a bottom view of the yoke.

As shown in FIGS. 14-16, the outer clip 122*b* may engage with the inner clip 122*a* to form a seal locator comprising a channel 134 within which a portion of the seal 104 may be held to attach the seal 104 to the clips 122*a*, 122*b* and therefore to the frame 106. For example, an outer surface of the inner clip may comprise a hooked flange 136 that extends around at least a portion of the outer periphery of the inner clip. Preferably, the hooked flange extends around the entire outer periphery of the inner clip 122*a*. A hooked flange 138 may also extend around at least a portion of or preferably the entire outer periphery of the outer clip 122*b*. The inner and outer clip may be configured to join together so that the hooked flanges of each clip face toward each other and form a seal channel 134 in between. The seal channel may be substantially shaped like an inverted "T". The seal may comprise an inlet/outlet opening defined by a substantially continuous lip. The seal lip may form a "T" shape when viewed in cross-section and may be dimensioned to fit within the seal channel by pushing the seal onto the clip assembly. In this way, the frame and seal assembly may be attached together to form a gas inlet extending between the frame and seal. Optionally, the mask frame comprises an outlet vent 140 formed in the body of the frame, such as on the front surface of the frame, as shown in FIG. 7, or in a recessed region of the frame, as shown in FIG. 24 and described later in this specification.

In one form, as shown in FIGS. 11 to 20, the mask interface may comprise an outlet vent 140 located near or adjacent to the gas inlet 108. For example, the frame may comprise a flange projecting from the rear surface of the frame and providing a substantially continuous edge to define an opening in the frame. A separator 142 may extend between two substantially opposing points on the substantially continuous edge of the opening to separate the opening into a gas inlet 108 or inlet aperture and an adjacent outlet vent 140 or vent aperture.

Figure 11:
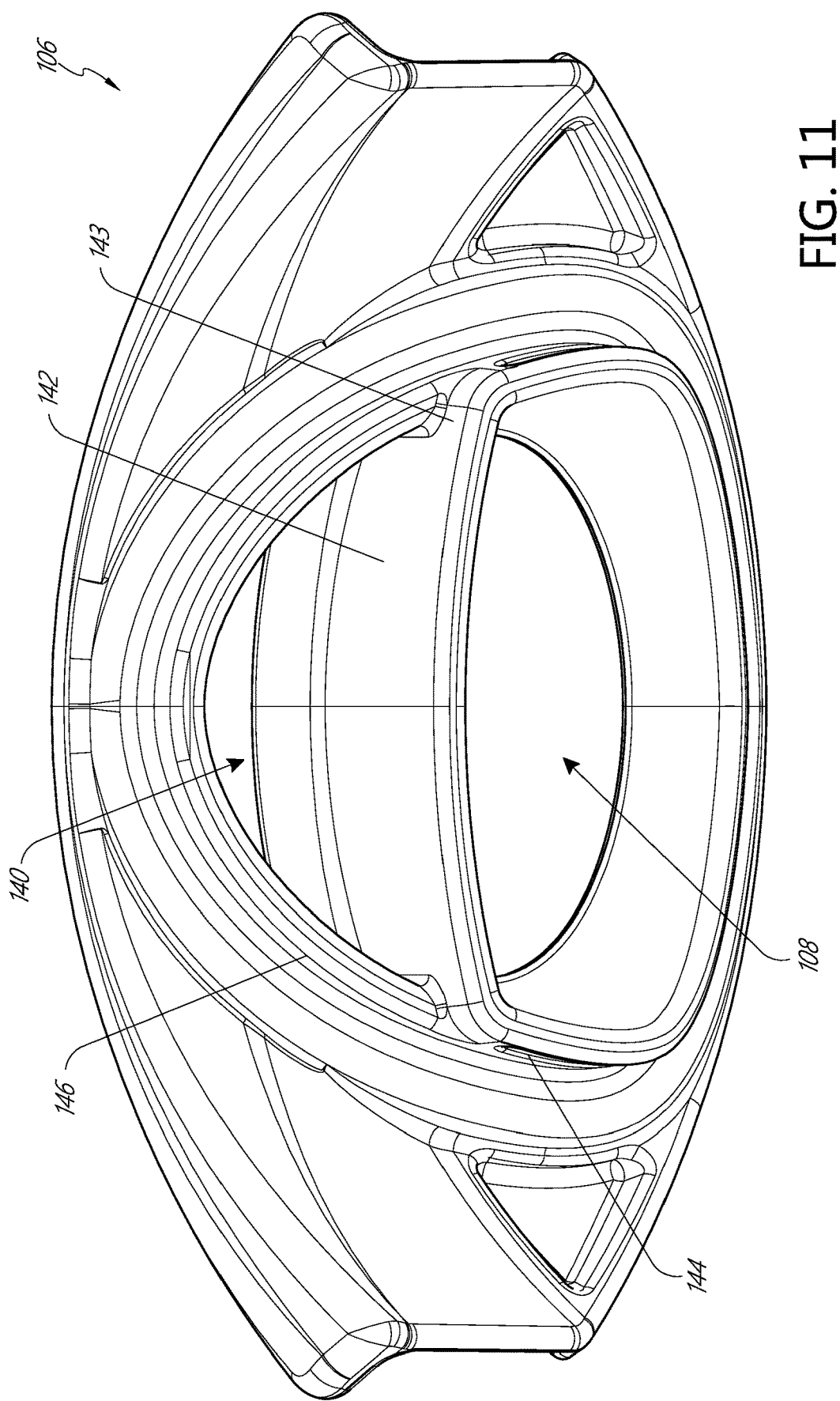
FIG. 11 is a rear perspective view of one form of frame.
Figure 12:
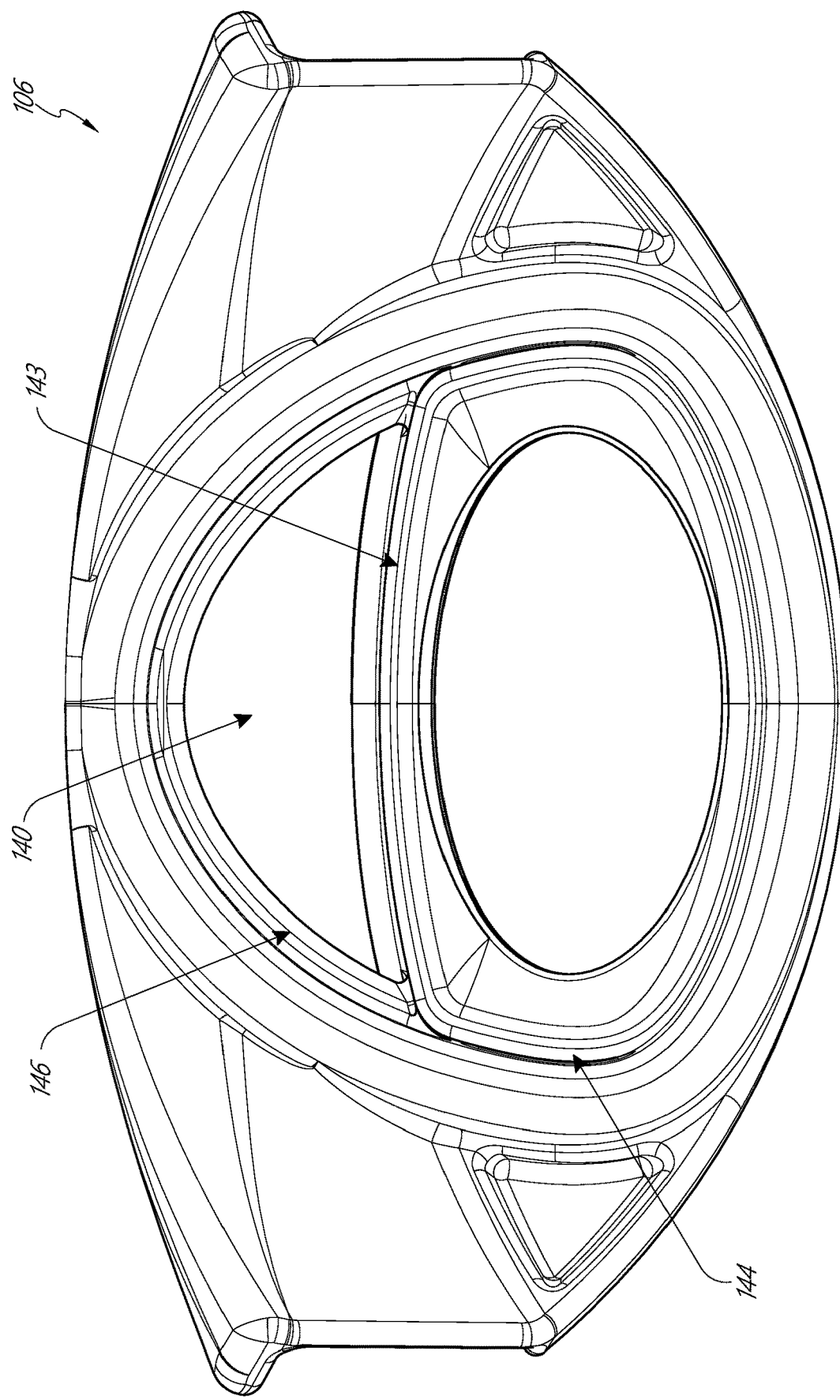
FIG. 12 is a rear view of the frame of FIG. 11.

The portion of the flange adjacent the gas inlet 108 may project further from the rear surface of the frame (i.e. may be deeper) than the portion of the flange adjacent the outlet vent. The separator 142 may also project from the rear surface of the frame and may join with the further projecting flange, so that the separator 142 and flange together form a seal flange 144. The seal flange 144 provides a substantially continuous edge around the gas inlet 108. The portion of the seal flange formed by the separator 142 is referred to herein as the upper seal flange 143, as shown in FIGS. 11 to 13. The area of the projecting flange adjacent the outlet vent 140 is referred to herein as the vent flange 146.

Optionally, the seal flange 144 and/or the vent flange 146 comprise one or more attachment features configured to help locate the seal on the frame and/or to attach the seal to the frame. In one form, the attachment features may comprise one or more recesses and/or projections configured to engage with one or more corresponding projections and/or recesses provided on the seal or seal assembly. For example, the seal flange 144 may comprise snap recesses 132 located on substantially opposing sides of the outer surface of the seal flange 144 as shown in FIG. 13. Each snap recess 132 is configured to receive one or more projections (e.g., protrusions 130 shown in FIG. 15) extending from an inner surface of the seal or seal assembly (e.g., from the seal clip 122, or the inner clip 122*a*, as shown) to help hold the seal or seal assembly in position against the seal flange.

A seal or seal assembly may be attached to the frame by sealing against the seal flange 120.

In one form, the seal assembly comprises a seal 104, an inner clip 122*a* and an outer clip 122*b*, as described above. In this form, the inner and outer clips each comprise a collar or ring having an opening, but the inner clip may also comprise a divider 148 that spans across the opening of the inner clip to separate the opening into a gas inlet aperture 118 and a vent aperture 150. The gas inlet aperture 118 and vent aperture 150 may be substantially the same shape and dimensions as the gas inlet 108 and outlet vent 140 of the frame 106. The inner clip 122*a* may comprise an inner surface configured to substantially surround the outer surface of both the seal flange 144 and vent flange 146. In this position, the divider 148 of the inner clip 122*a* may extend across the upper seal flange 143, as shown best in FIG. 16. The inner clip 122*a* is configured so that it may be pushed over the seal flange 144 to form a seal against the outer surface of the seal flange 144. The remaining portion of the inner clip 122*a* that surrounds the vent aperture may either seal against the outlet vent 140 of the frame 106 or may simply abut the outlet vent 140. It is not necessary for a seal to be formed between the vent aperture 150 and outlet vent 140. Consequently, the fitting of the seal assembly to the frame is simplified. Additionally, the depth of the vent flange 146 does not need to be as large as the depth of the seal flange 144 and as a result, the bulk of the frame may be minimized or reduced.

One or more projections 130 may be located on substantially opposing sides of the inner surface of the inner clip 122*a* and are configured to be received within the snap recesses 132 of the seal flange 144 when the inner clip 122*a* is pushed over the seal flange 144 and vent flange 146. In other forms, the outer surface of the seal flange 144 and/or vent flange 146 may comprise one or more projections configured to be received within one or more recesses located on the inner surface of the inner clip 122*a* or seal 104.

In at least one embodiment, the inner clip 122*a* may be connected to the seal flange 144 by way of a taper fit. The seal flange 144 tapers as the seal flange 144 extends rearwardly, away from the gas inlet 108. The inner clip 122*a* may include a corresponding, oppositely oriented taper, such that a distal opening of the inner clip 122*a* is larger than the proximal opening of the inner clip 122*a*.

In another embodiment, the inner clip 122*a* may be formed of a stretchable or semi-stretchable material to help push the tight fitting inner clip 122a over the seal and vent flanges 144, 146 of the frame 106.

The inner clip 122a may comprise a seal locator for attaching the seal 104 to the inner clip 122a and therefore to the frame 106. The seal locator may comprise one or more hooks, flanges, or other projections that may engage with one or more hooks, flanges, or other projections, openings or recesses located on the seal to attach the seal 104 and inner clip 122a together. It is envisaged that alternative forms of attachment may also be suitable.

As described above, the outer clip 122b may engage with the inner clip 122a to form a seal locator comprising a channel 134 within which a portion of the seal 104 may be held to attach the seal 104 to the clips 122a, 122b and therefore to the frame 106. For example, an outer surface of the inner clip 122a may comprise a hooked flange 136 that extends around at least a portion of the outer periphery of the inner clip 122a. Preferably, the hooked flange extends around the entire outer periphery of the inner clip 122a. A hooked flange 138 may also extend around at least a portion of or preferably the entire outer periphery of the outer clip 122b. The inner and outer clip 122a, 122b may be configured to join together so that the hooked flanges 136, 138 of each clip face toward each other and form a seal channel 134 in between. The seal channel 134 may be substantially shaped like an inverted "T". The seal may comprise an inlet/outlet opening defined by a substantially continuous lip. The seal lip may form a "T" shape when viewed in cross-section and may be dimensioned to fit within the seal channel 134 by pushing the seal 104 onto the clip assembly. In this way, the frame 106 and seal assembly may be attached together to form a gas inlet and an outlet vent extending between the frame and seal.

Figure 19:
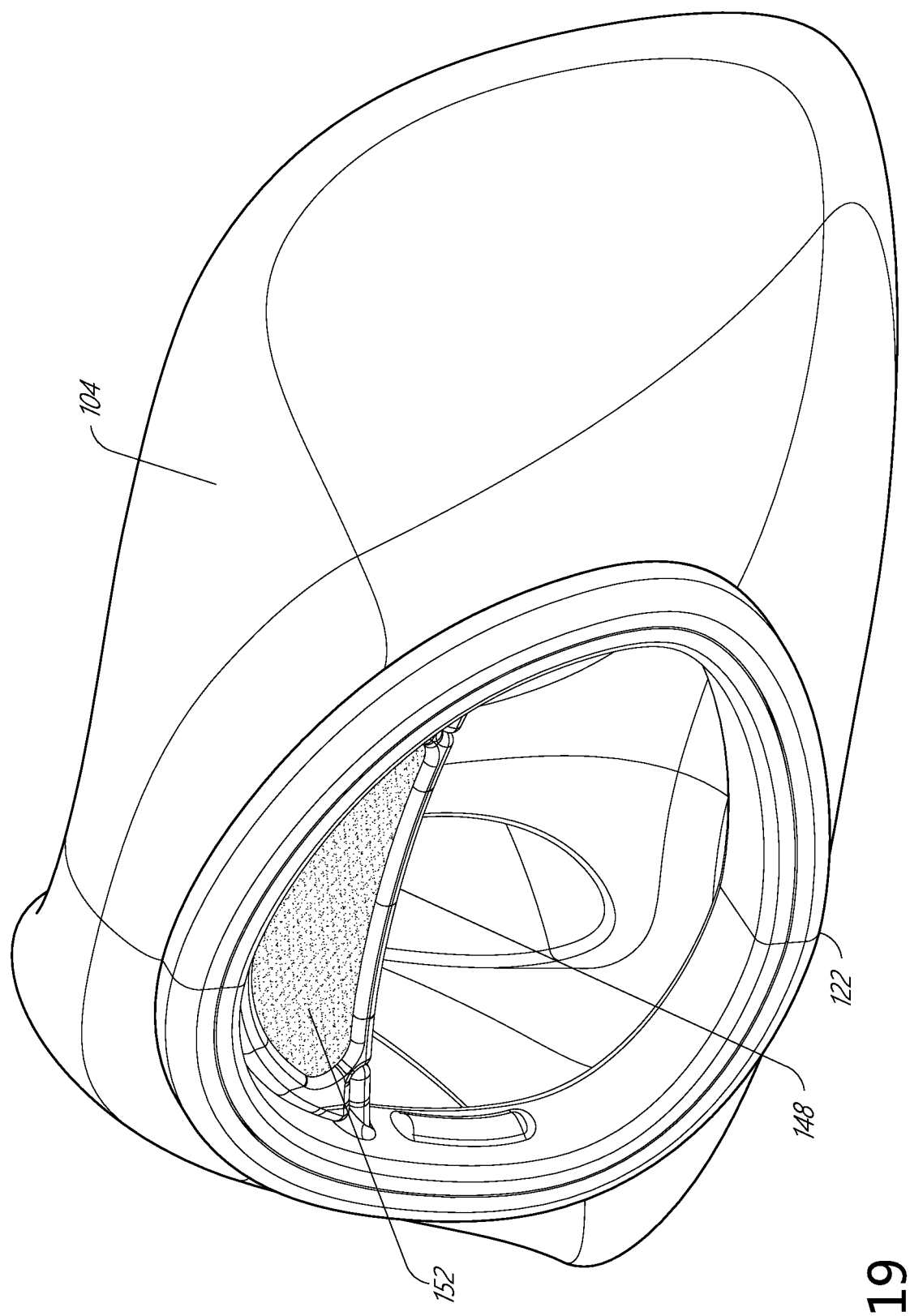
FIG. 19 is a perspective view of another form of seal assembly, including a seal clip having a vent aperture and diffuser.
Figure 20:
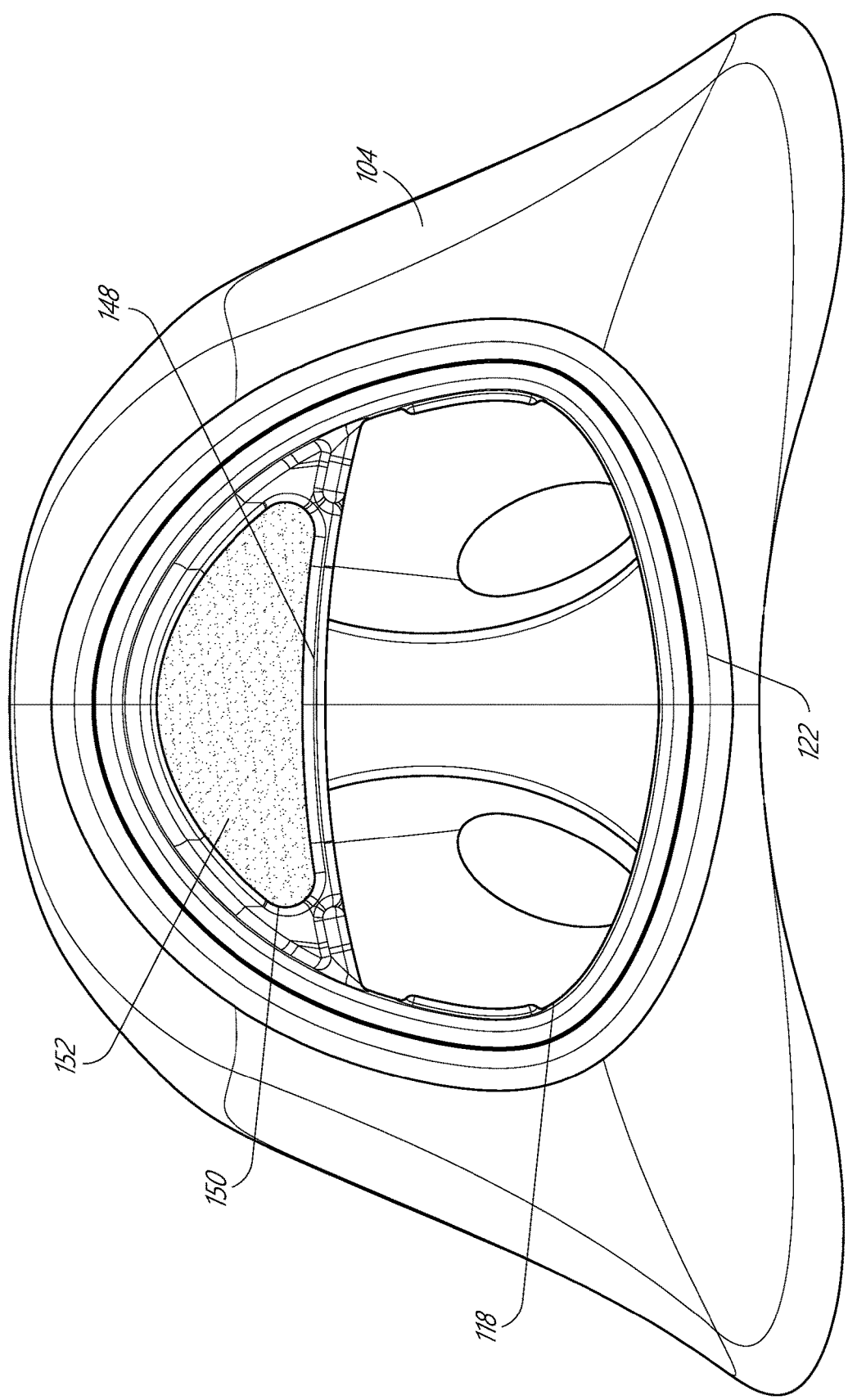
FIG. 20 is a front view of the seal assembly of FIG. 19.
Figure 21:
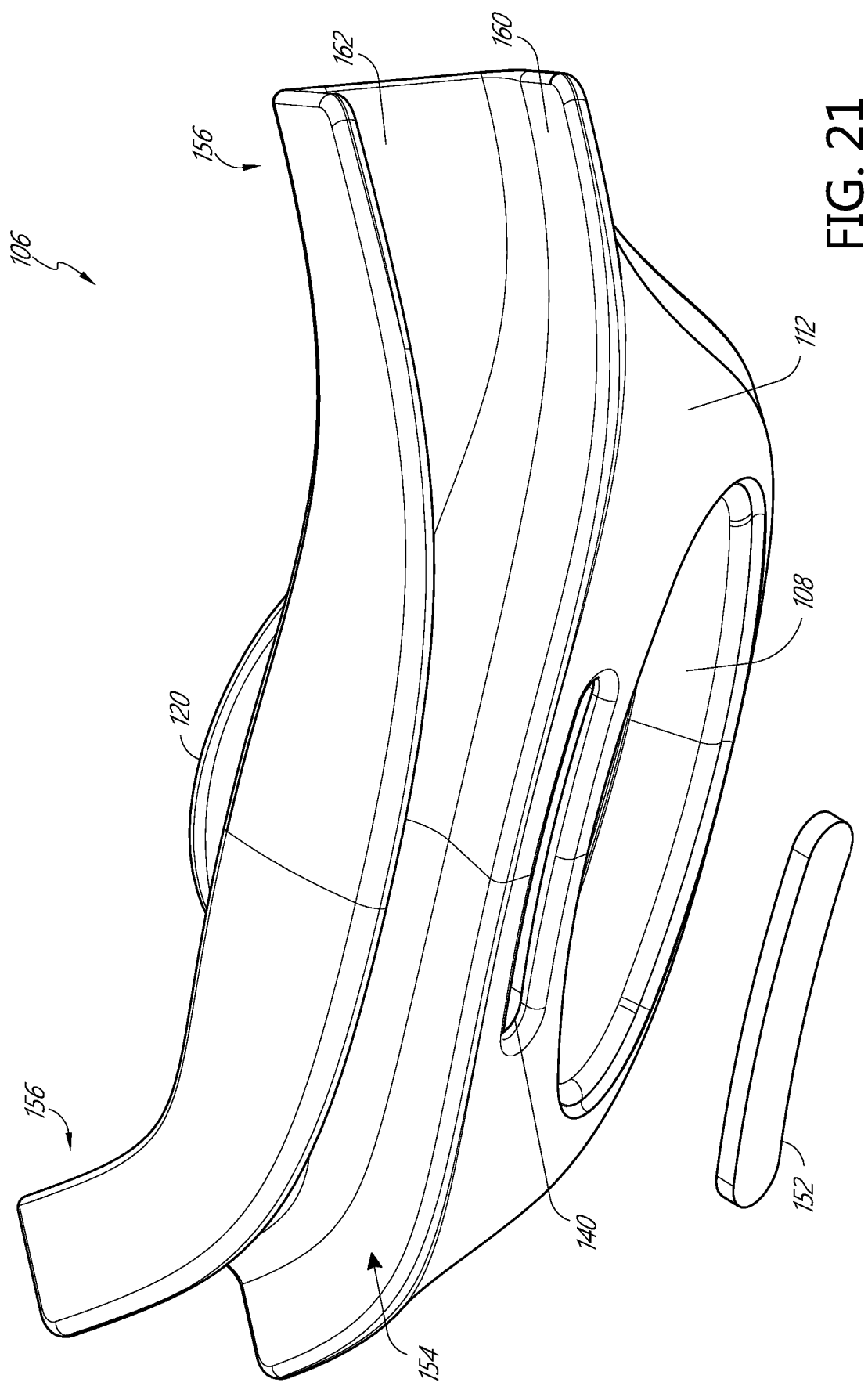
FIG. 21 is an exploded perspective view of one form of frame and diffuser.

In one form, the mask interface 102 also comprises a diffuser 152. The diffuser 152 may be permanently or removably located within the outlet vent 140. The diffuser may be located within the frame 106 or within the seal assembly, when the seal assembly comprises a vent aperture 150 within which the diffuser 152 may be located, as shown in FIGS. 19 and 20. By locating the diffuser 152 in the seal assembly, the diffuser 152 may be readily cleaned each time that the seal assembly is removed from the frame 106 and cleaned. If the mask interface is used with a respiratory mask system for treating sleep apnoea, it is likely that the seal assembly and diffuser 152 may be cleaned as frequently as every morning, whereas other mask components are cleaned less frequently.

Additionally, by positioning the diffuser 152 in the seal assembly, exhausted air is diffused as the exhausted air exits the breathing chamber of the seal assembly, and before the exhausted air contacts any other mask components or has an opportunity to generate noise or entrain surrounding air. As such, the exhausted air can then be further vented through or around other frame parts with less noise, draft/entrainment, and/or jetting. In at least some embodiments, it is possible to conceal the exhaust arrangement, thus providing a more desirable mask aesthetic.

In one form, the gas inlet 108 is substantially elliptical in shape. The gas inlet 108 may extend longitudinally between the left and right sides of the frame 106 so that the gas inlet 108 is wider than it is high. The outlet vent 140 may be located above the gas inlet 108 when the frame 106 is in use. In another form, the outlet vent 140 may be located below the gas inlet 108 when the frame 106 is in use. The gas inlet 108 and the outlet vent 140 may be located substantially centrally along the length of the frame 106.

Turning now to FIGS. 21 to 59A and 59B, various forms of frame and yoke connection systems will now be described.

In one form, the frame 106 comprises a body having a first surface or front surface 112; a second surface or rear surface 114; and a gas inlet 108. In one form, the front surface 112 of the frame 106 may be angled downwardly toward a bottom edge of the frame 106 and the gas inlet 108 is formed within the angled front surface. The frame 106 may also optionally comprise an outlet vent 140. In some forms, the outlet vent 140 may comprise a diffuser 152. In some forms, the frame 106 may comprise features as described above in relation to the embodiments shown in FIGS. 1 to 20 and may be configured to attach to a seal 104 or seal assembly, as described above.

The front surface of the frame 106 comprises a recessed region configured to receive at least a portion of a yoke 202 of a headgear 200 therein. In one form, the recessed region comprises a channel 154 extending across the length of the front surface 112 of the frame 106 from left to right. The channel 154 may comprise extension members that project from either side of the frame body.

The channel 154 may be defined by a first wall, forming an upper surface 158, a second wall, forming a lower surface 160 that substantially opposes the first wall, and a channel floor forming a rear surface 162 that extends between the first and second walls. The channel 154 may comprise two side regions 156 or channel extensions, each side region being located at an opposite end of the channel, and a central region 164 or middle portion located substantially centrally between the two side regions 156.

Figure 22:
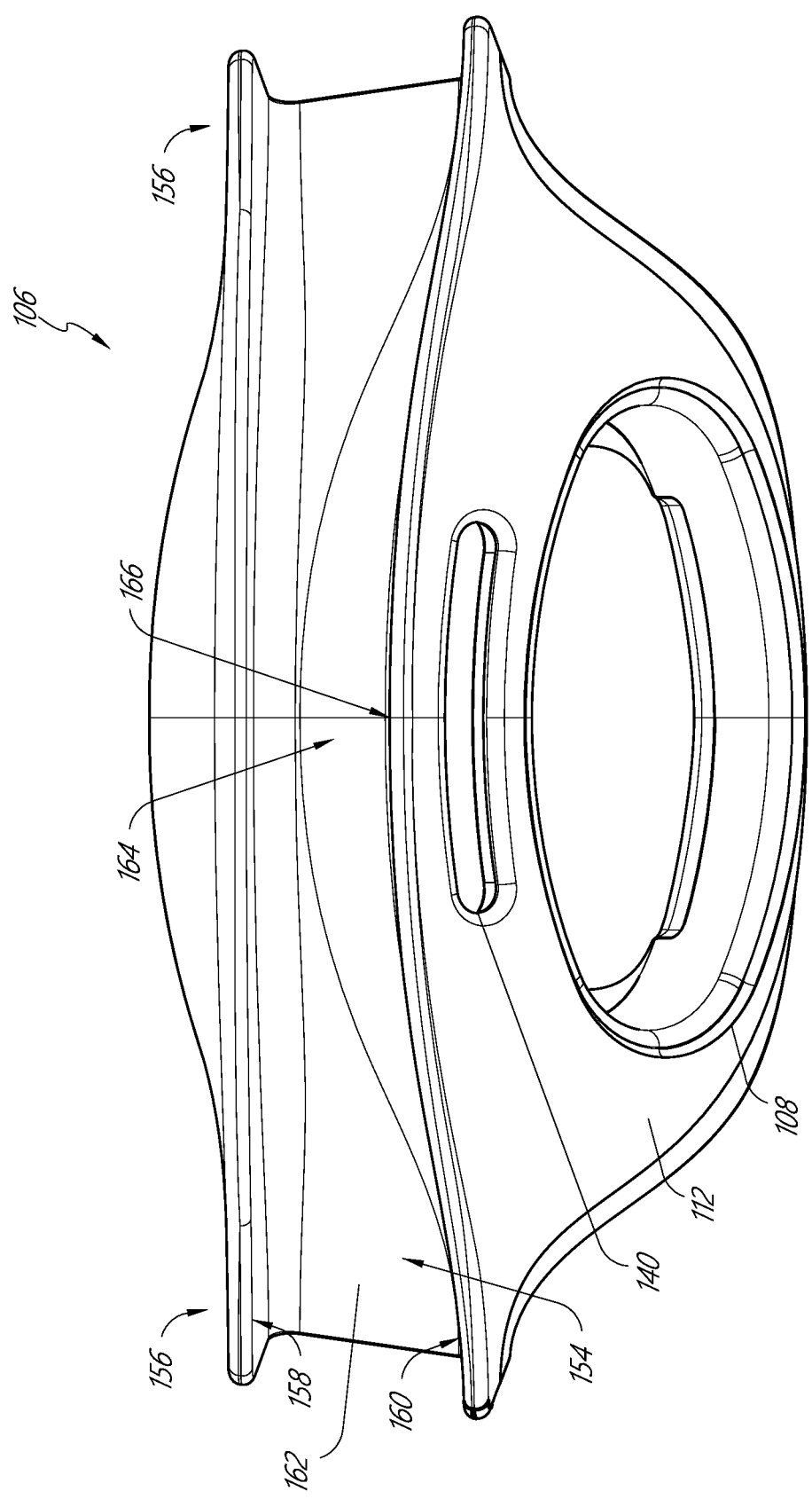
FIG. 22 is a front view of the frame of FIG. 21.
Figure 23:
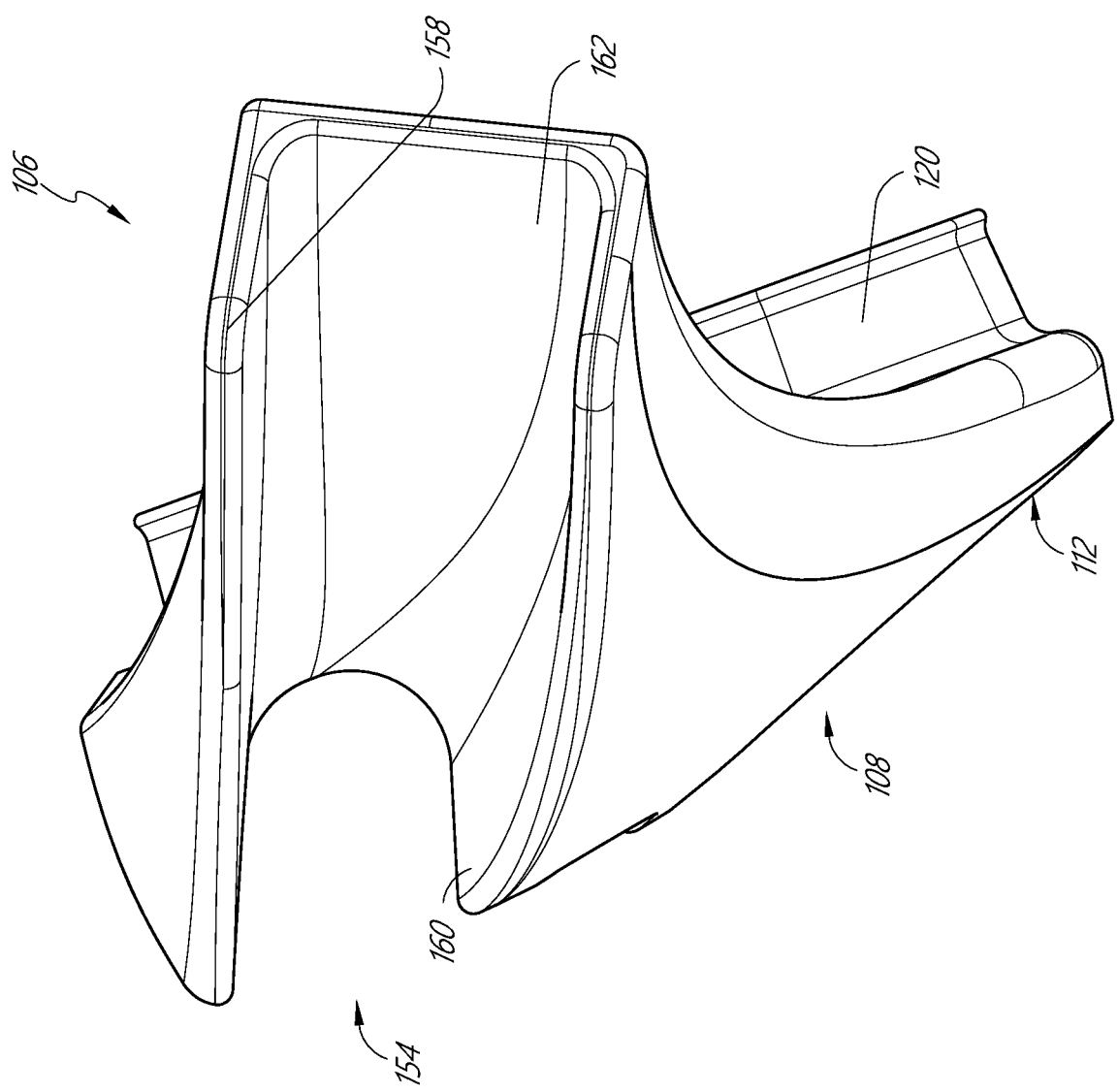
FIG. 23 is a left side view of the frame of FIG. 21, the right side being a mirror image.

In one form, the height of the rear surface 162 of the channel 154 may be substantially defined by the distance between the first and second walls of the channel. At its central region 164, the height of the rear surface 162 of the channel 154 may be less than the height of the channel 154 at one or both side regions 156. For example, the second wall or lower surface 160 may curve or angle toward the first wall or upper surface 158 to form a peak 166 as shown in FIG. 22. Preferably, the peak 166 is located at a central point along the length of the channel 154.

In one form, the lower surface 160 of the channel 154 may angle inwardly toward the rear surface 162 of the channel 154.

In one form, the upper surface 158 of the channel 154 may angle inwardly toward the rear surface 162 of the channel 154.

In one form, the lower surface 160 of the channel 154 may have a depth substantially defined by the distance between the rear surface 162 of the channel 154 and the front surface 112 of the frame 106. The depth of the lower surface 160 may be greater in the central region 164 of the channel 154 than at the side regions 156 or ends of the channel 154. For example, the lower surface 160 may taper towards the ends of the channel 154.

The frame 106 and channel 154 may be substantially curved from left to right to conform to some extent to the curves around a patient's nose or mouth. Alternatively, or additionally, the frame 106 may slope or curve downwardly from top to bottom.

In one form, the frame 106 may comprise an outlet vent 140 located below the central region 164 of the channel 154 (for example, as shown in FIG. 22). In another form, at least a portion of the outlet vent 140 may be located within the channel 154. In yet another form, the entire outlet vent 140 may be located within the channel 154, such as within the rear surface 162 of the channel 154. The outlet vent 140 may comprise a single aperture formed in the frame 106 and/or channel 154, or the outlet vent 140 may comprise multiple apertures. In one form, the outlet vent 140 comprises a plurality of small localised apertures. In another form, the outlet vent 140 comprises an aperture in the form of a slot.

In one form, the lower surface 160 of the channel 154 may comprise a recessed region 168, as shown in FIG. 24. The recessed region 168 may be located at a substantially central region of the lower surface 160. The recessed region 168 may be formed by a downward curve, by downwardly sloping surfaces meeting at a point, or by a stepped down region, for example. The stepped down region may comprise a substantially perpendicular transitional edge or a sloping transitional edge 170 between the recessed and non-recessed areas of the lower surface. The recessed region 168 may be located substantially adjacent to the outlet vent 140. Alternatively or additionally, the upper surface 158 of the channel 154 may comprise a recessed region, which may be located substantially adjacent to the outlet vent 140. The recessed regions in the upper and/or lower surfaces of the channel may provide a fluid flow path from an outlet vent 140 formed in the channel 154 to the atmosphere. This feature will be discussed in further detail later in this specification.

To attach a headgear 200 to the mask interface, at least a portion of a yoke 202 for the headgear 200 may be held within the channel 154 of the frame 106.

FIGS. 27 to 33 illustrate one form of yoke 202 that may be used to attach a headgear 200 to a frame 106. The yoke 202 may be used to attach any suitable closed loop, headgear 200 to the frame. For example, in some forms the yoke 202 may form a collector for filaments, or other core elements, used in an automatically adjustable or self-adjusting headgear system. In this form, the yoke 202 may comprise a washer mechanism, which may be configured to frictionally engage with the filament during elongation of the headgear, but allows relatively friction-free movement during retraction of the headgear. The washer mechanism may be incorporated into the ends of the yoke/collector and the body of the yoke/collector may be substantially hollow to receive the filaments within the body.

In one form, the yoke 202 may comprise a substantially elongate body having distal ends. The yoke 202 may be angled or curved along its length and may comprise a middle portion 212 located between two side portions 213. In one form, the side portions 213 comprise a pair of arms extending from the middle portion 212 and terminating at the distal ends of the yoke 202.

The yoke 202 may comprise a front surface 214, a rear surface 216, a top surface 218, and a bottom surface 220.

The front surface 214 may have a width defined by the distance between the top surface 218 and bottom surface 220 of the yoke 202 and may have a length defined by the distance between opposing ends of the yoke 202.

The cross-section of the yoke 202 may vary along the length of the yoke. For example, in one form, the width of the middle portion 212 of the yoke 202 is less than the width of the side portions 213 of the yoke to create a yoke 202 with a thinner central region and flared ends. By providing a yoke 202 with a thin central region, the height of the rear surface 162 of the channel 154 of the frame 106 may be thinner, which provides additional space on the frame body in which to locate a larger, gas inlet 108 and optionally also an outlet vent 140.

In another form, the top surface 218 of the middle portion 212 of the yoke 202 may be curved inwardly toward the bottom surface 220.

Figure 30:
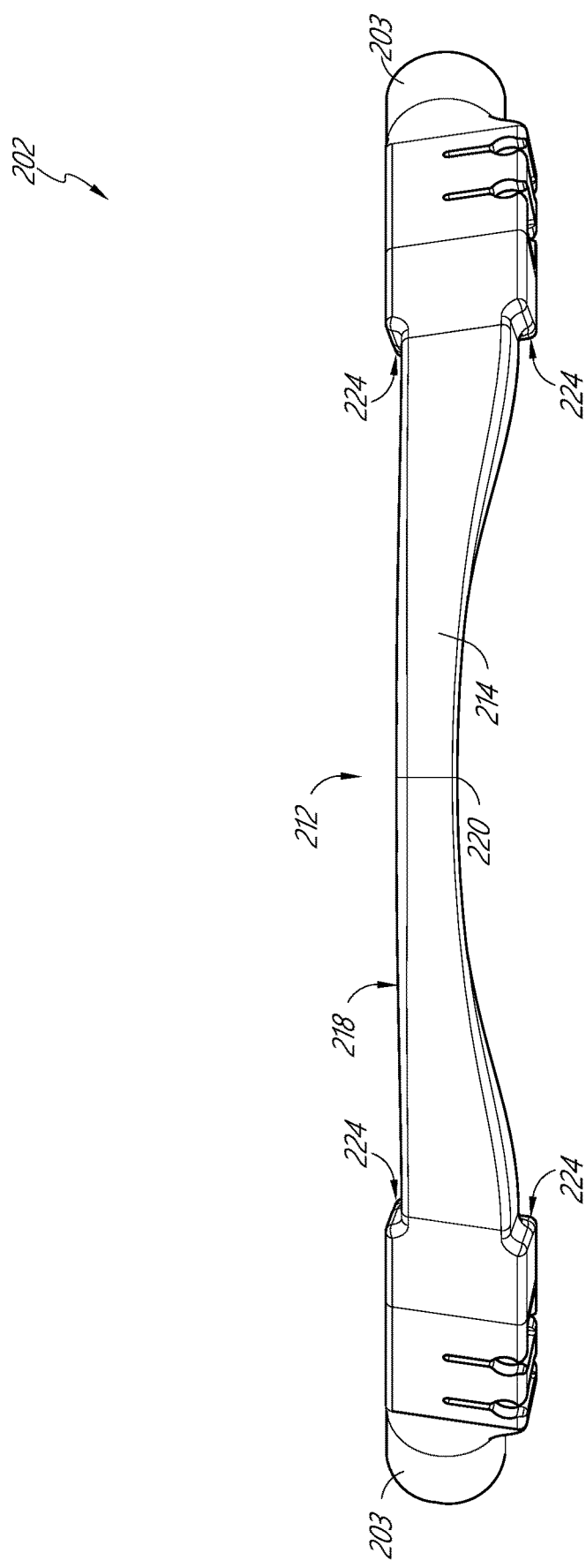
FIG. 30 is a front view of the yoke.
Figure 31:
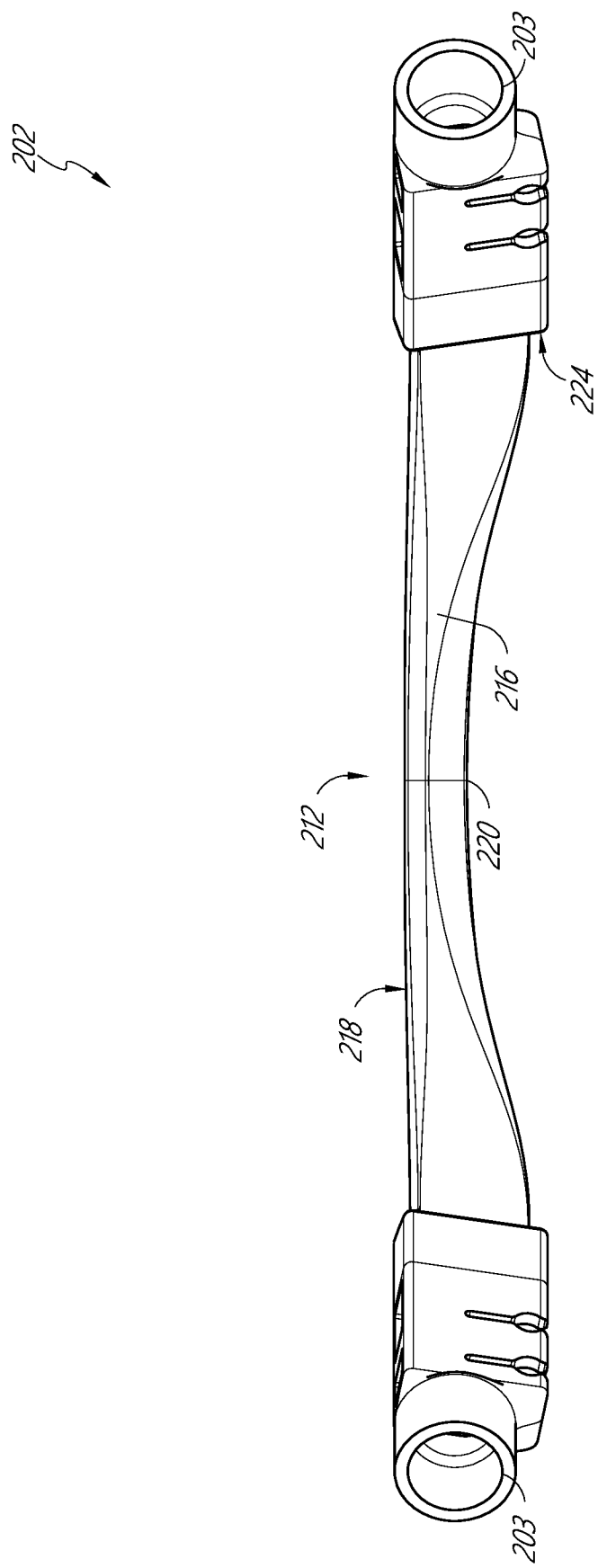
FIG. 31 is a rear view of the yoke.
Figure 32:
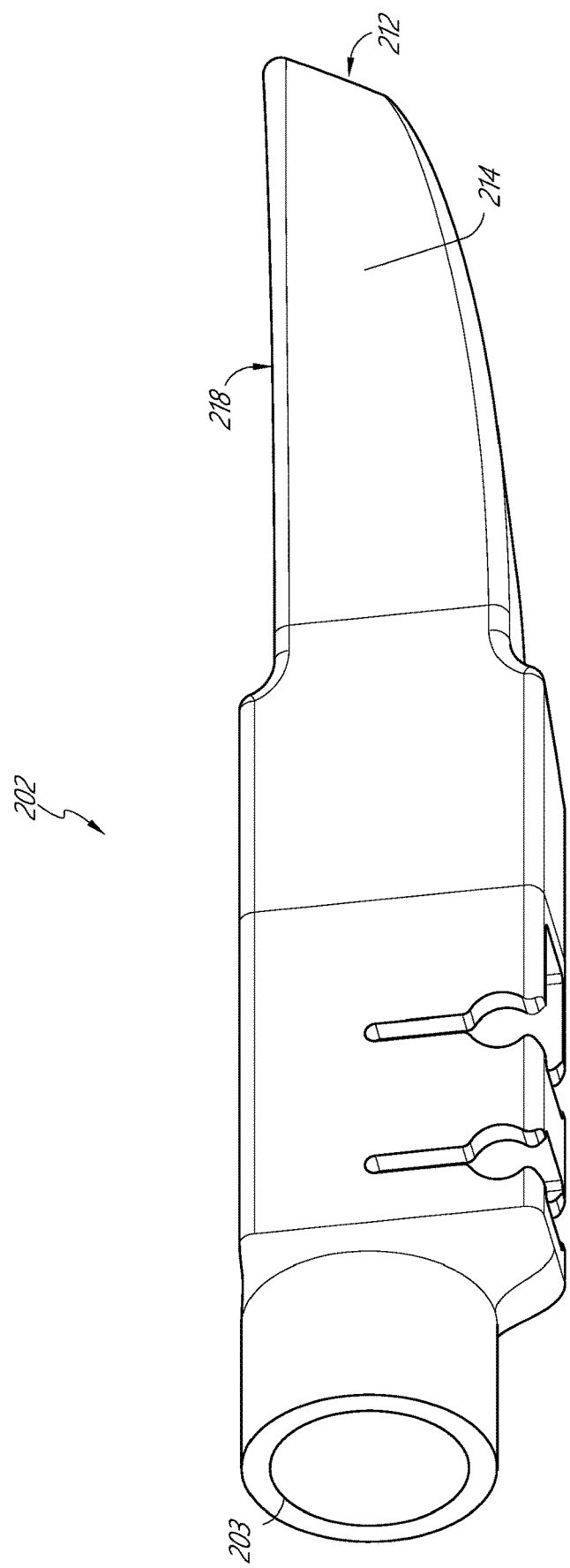
FIG. 32 is a right side view of the yoke.

In yet another form, the bottom surface 220 of the yoke 202 may be curved inwardly towards the top surface 218 (for example, as shown in FIG. 30) or the bottom surface 220 may lie in substantially the same plane along the length of the yoke 202.

In one form, the front surface 214 or distal surface of the middle portion 212 of the yoke 202 may slope rearward from the top surface 218 to the bottom surface 220 of the yoke 202.

In one form, the front surface 214 of the side portions 213 of the yoke 202 may slope forward from the top surface 218 to the bottom surface 220 of the yoke.

In another form, the front surface 214 of the side portions 213 may be substantially perpendicular to the bottom 220 and/or top surface 218 of the yoke 202.

In one form, the top surface 218 and/or bottom surface 220 of the side portions 213 of the yoke may be configured to lie in a substantially horizontal plane when the yoke 202 is located in the frame 106 during use. In this configuration, the side portions 213 may provide useful gripping regions by which a user can hold and maneuver the yoke 202.

In one form, the top surface 218 of the middle portion 212 of the yoke 202 may slope downward from the rear surface 216 to the front surface 214. In one form, the bottom surface 220 of the middle portion 212 of the yoke 202 may slope upward from the front surface 214 to the rear surface 216. When both of these forms of yoke 202 are combined, the body of the yoke tapers toward its rear surface.

Figure 33:
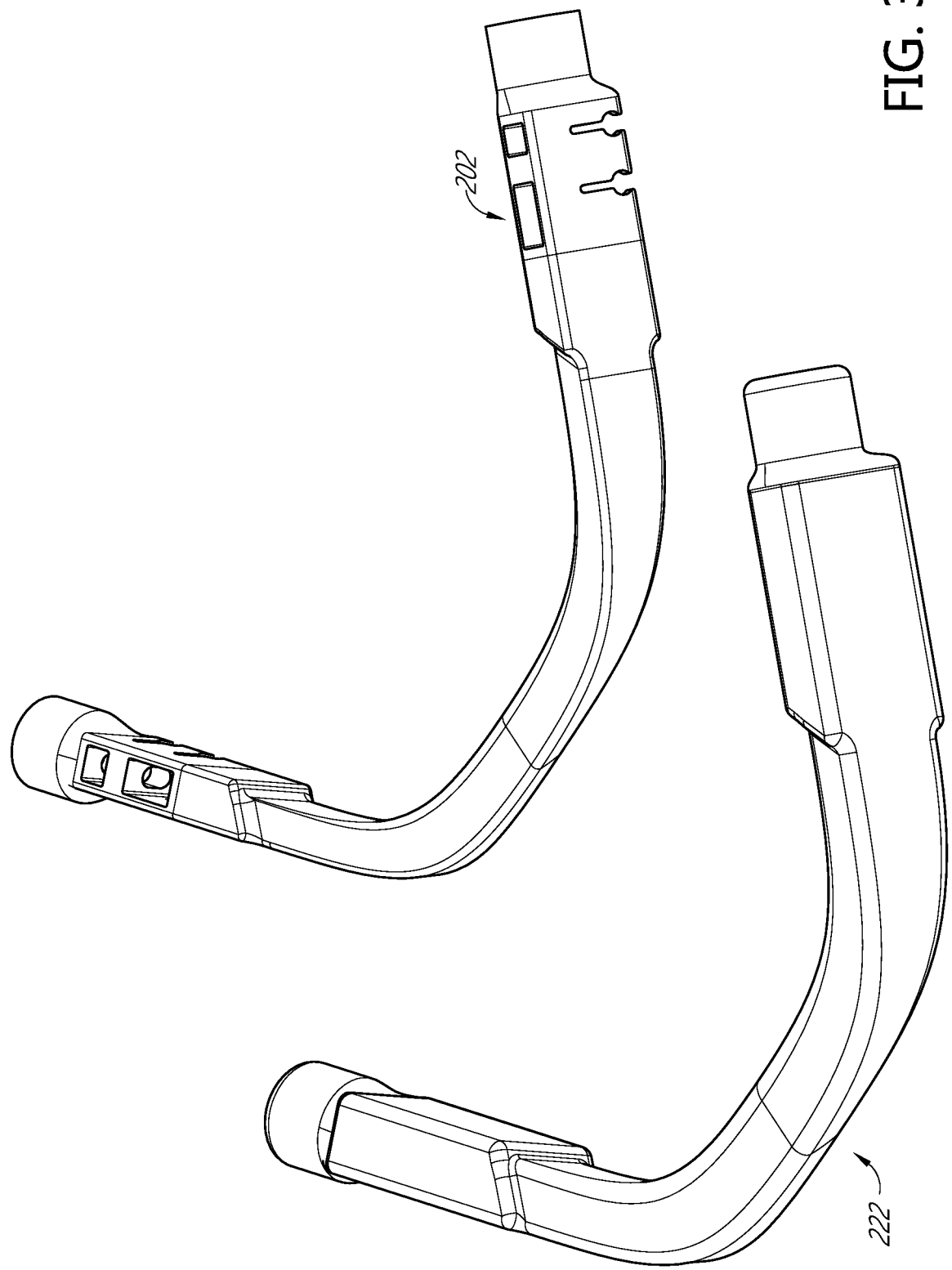
FIG. 33 is an exploded view of a yoke and a yoke covering.
Figure 34:
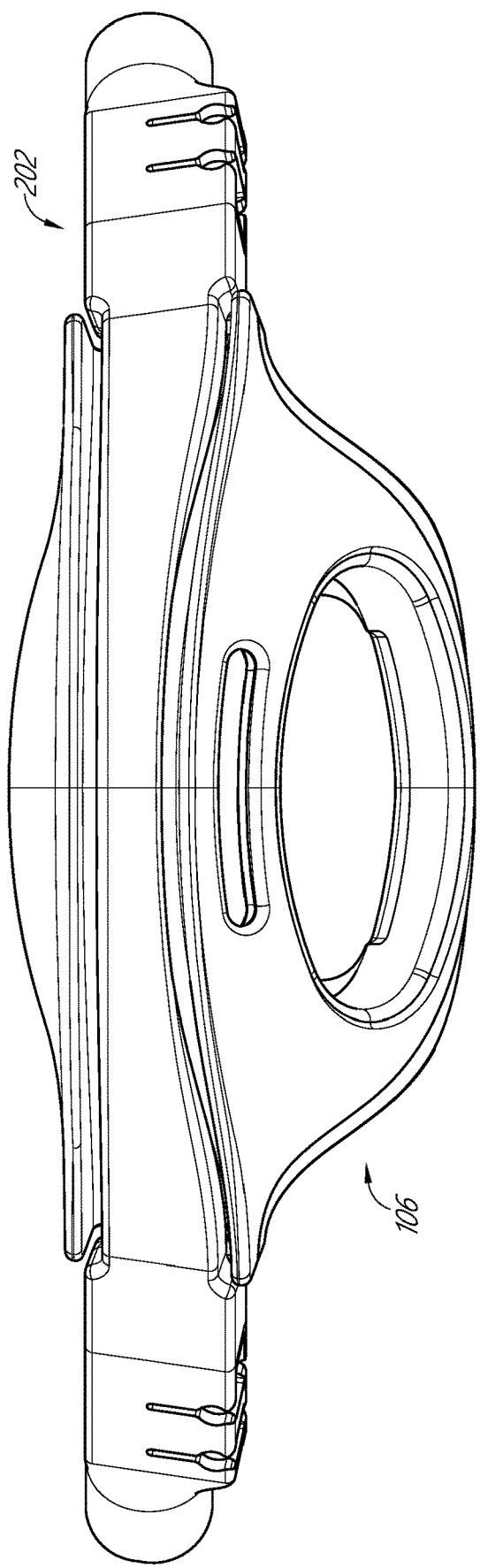
FIGS. 34 to 38 are front view, top view, bottom view, rear view, and left side view of an assembled yoke and frame.
Figure 35:
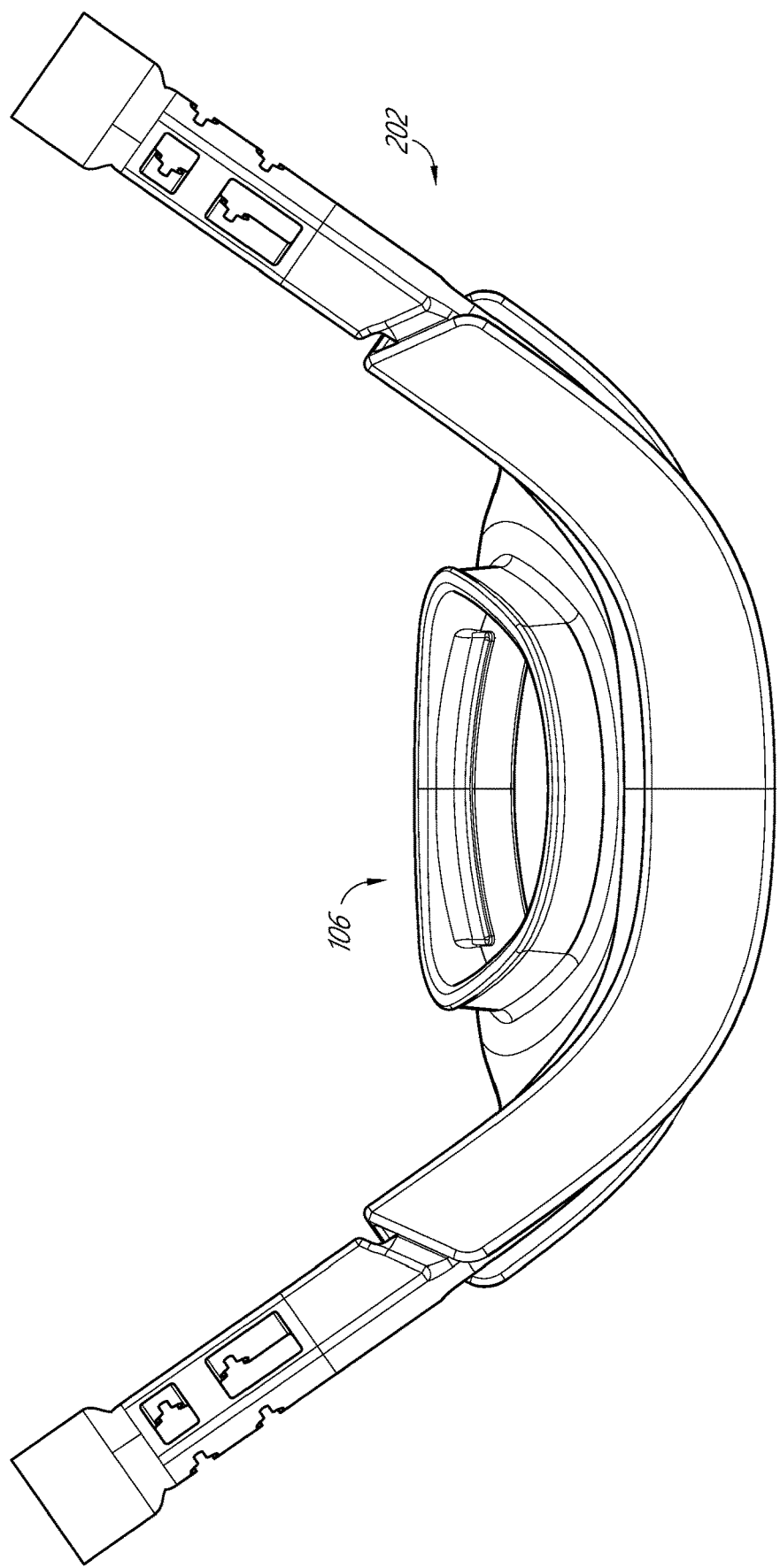
Figure 36:
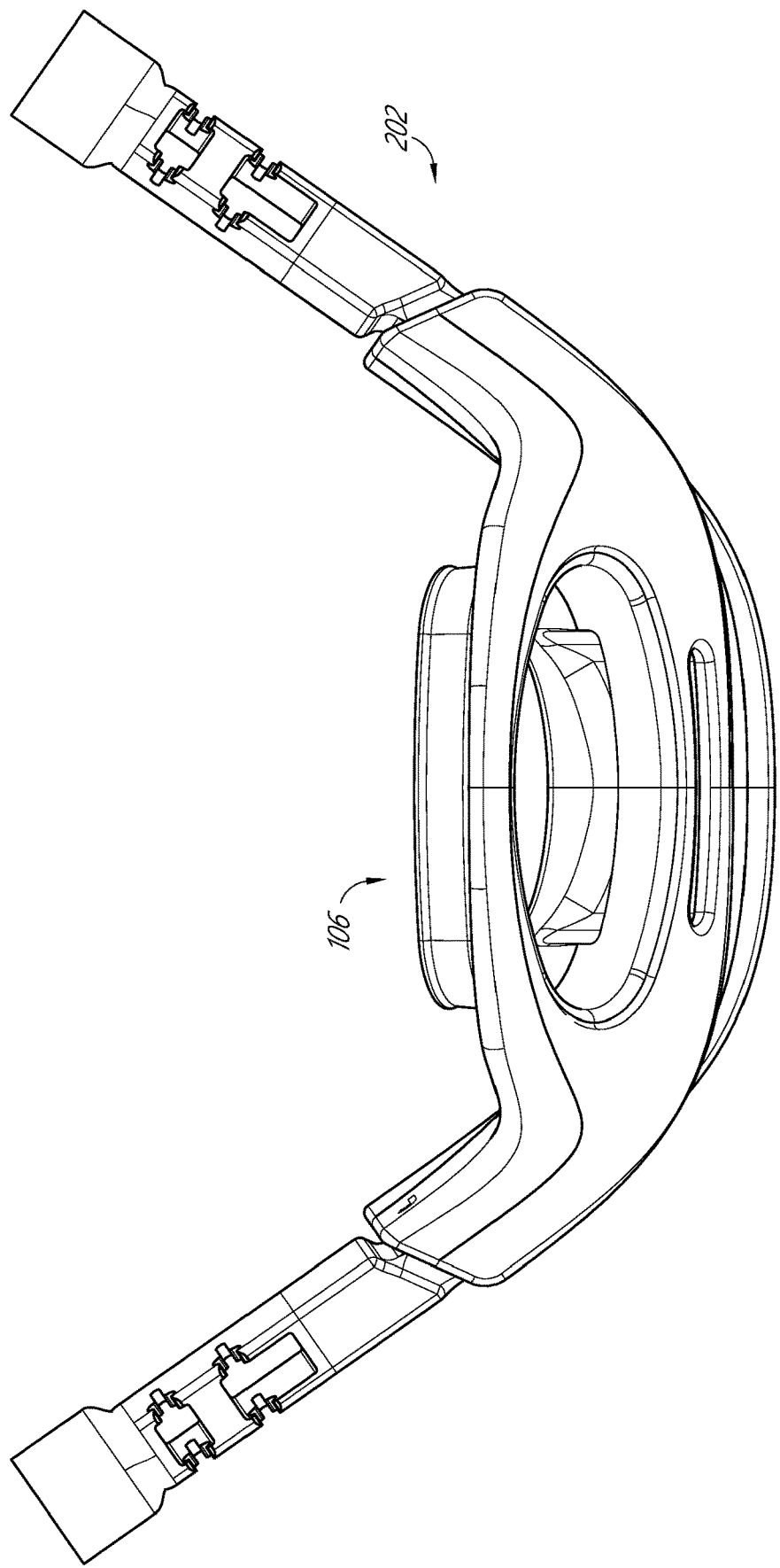
Figure 37:
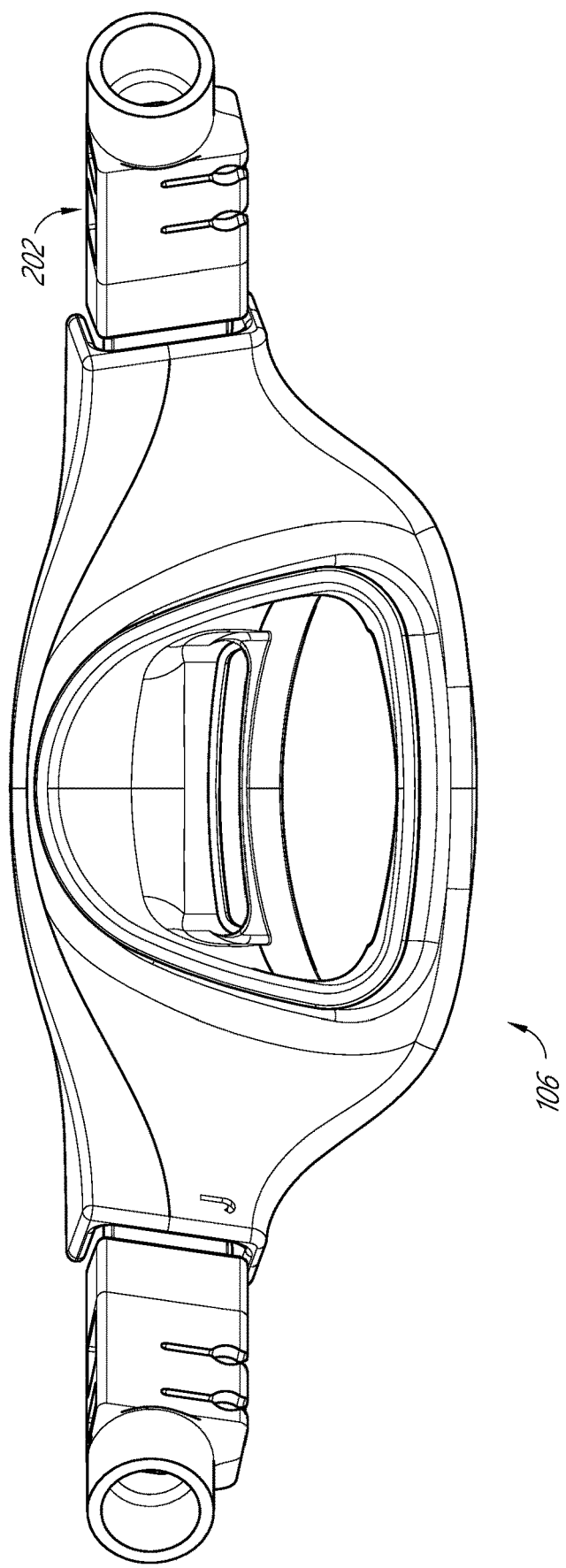
Figure 38:
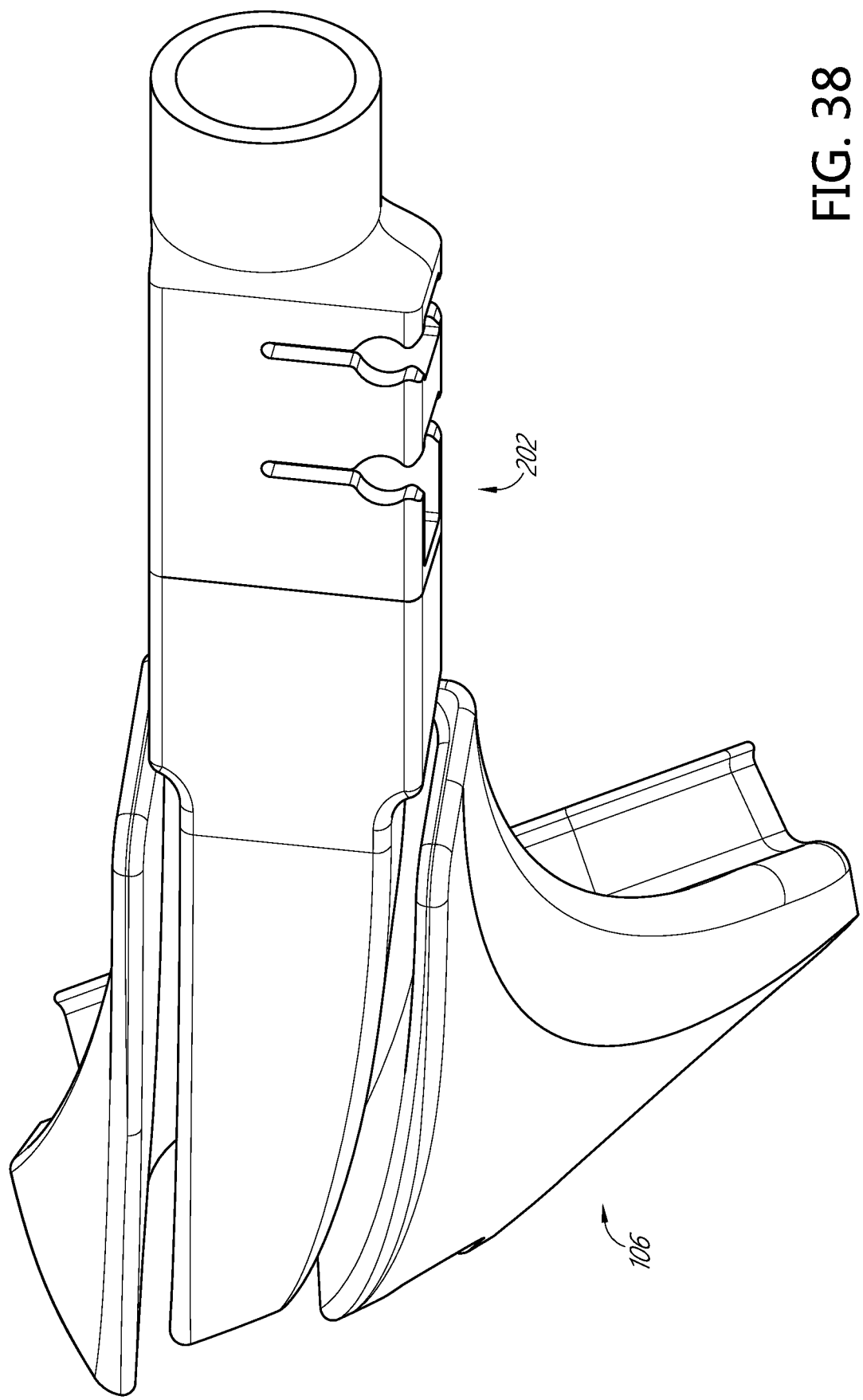

At least a portion of the yoke body may be covered in a textile covering 222, as shown in FIG. 33. Preferably, the textile covering 222 is a knit fabric that is substantially stretchable in at least one direction. It is also preferable that the fabric does not wrinkle. The textile covering 222 can help to provide a snug fit between the yoke 202 and frame 106, without the need for high tolerance manufacture, which may be required in some forms where the yoke 202 and frame 106 comprise hard surfaces that engage with each other to attach the yoke 202 to the frame 106.

The textile covering 222 may be any suitable covering, such as a sheath that is fitted over the yoke 202, a textile wrap, or a textile coating, for example. In one form, the yoke 202 may be injection moulded within the textile covering 222.

The yoke 202 may be configured to provide one or more alignment surfaces 224 configured to abut the frame 106 in order to locate the yoke 202 correctly on the frame 106. In one form, the yoke 202 may comprise a pair of alignment surfaces 224, each alignment surface 224 being located on or near the side portions of the yoke 202 and being configured to abut corresponding alignment surfaces on the left and right sides of the frame 106.

The alignment surfaces 224 of the yoke 202 may project from the rear surface 216 of the yoke 202, the top surface 218 of the yoke 202, the bottom surface 220 of the yoke 202 or from any two or more of the rear surface 216, top surface 218, and bottom surface 220. In one form, the top surface 218, rear surface 216, and bottom surface 220 of at least one side portion 213 of the yoke 202 extend beyond the top surface 218, rear surface 216, and bottom surface 220 of the middle portion 212 of the yoke 202. Each transitional surface formed between the top, rear, and bottom surfaces of the middle portion 212 and side portion 213 of the yoke 202 comprises an alignment surface 224. In this form, the middle portion 212 of the yoke 202 may be located within the channel 154 of the frame 106 and the alignment surfaces 224 may abut corresponding alignment surfaces provided on the frame, as shown in FIGS. 34 to 40. In one form, the outer edges of the channel 154 form the corresponding alignment surfaces of the frame 106.

In one form, as described above, an outlet vent 140 is provided in the rear surface 162 of the channel 154 and a recessed region 168 is provided in the lower surface 160 of the channel 154. In this form, when the yoke 202 is held within the channel 154, a gap is formed between the yoke 202 and the recessed lower surface 160 of the channel 154. The outlet vent 140 and adjacent gap form a fluid flow path through which gas can exit the mask interface. Additionally or alternatively, a gap may be provided between the yoke 202 and the upper surface of the channel 154 to form a second or alternate fluid flow path through which gas can exit the mask interface.

By providing an outlet vent 140 within the attachment channel 154 of the frame 106, the size of the frame may be kept relatively small. Furthermore, if these forms also comprise a gas inlet 108 having an elliptical shape that extends longitudinally from one side of the frame 106 to the other, the height of the frame 106 may be minimized or reduced to provide a more compact, substantially low profile mask interface.

Figure 39:
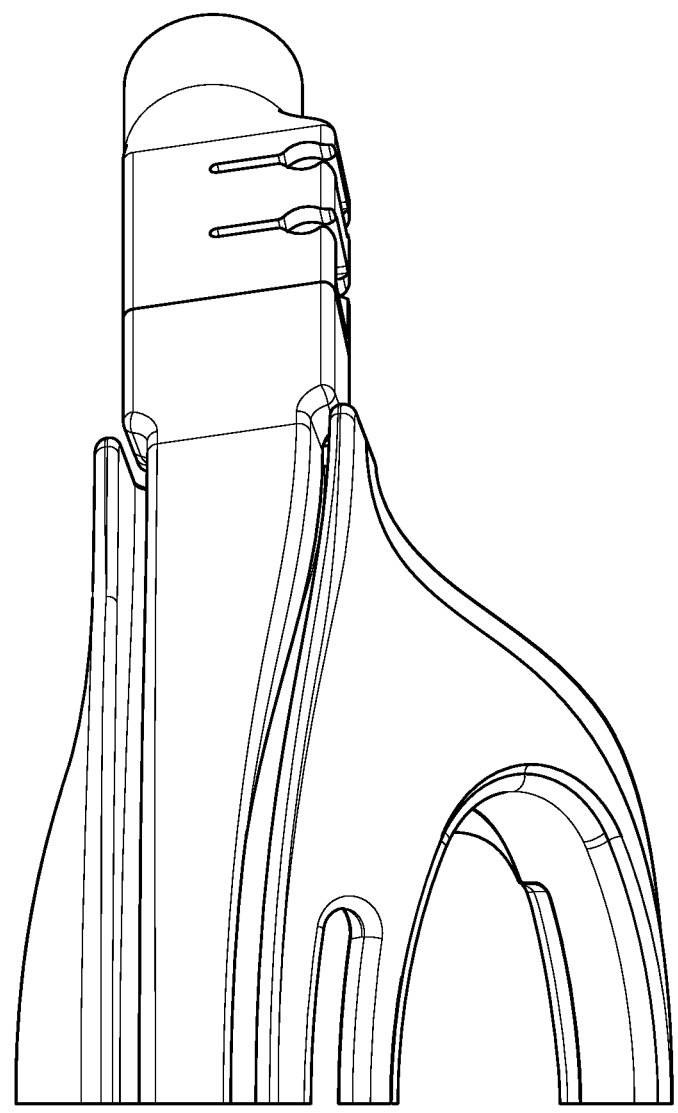
FIG. 39 is a schematic of a yoke to frame connection.

Many different options exist for attaching the yoke 202 to the frame 106. For example, the yoke 202 and channel 154 of the frame 106 may be configured so that at least a portion of the yoke 202, such as the middle portion 212, may simply be pushed into the channel 154 and may be held snugly within the channel 154 due to the frictional and/or clamping forces between the yoke 202 and frame 106. Where the yoke 202 comprises a fabric covering 222, the covering 222 may help fill any gap 172 between the yoke 202 and channel 154 walls (e.g., due to the channel 154 having a height $H_C$ greater than a height $H_Y$ of the yoke 202), as shown in FIG. 39, to hold the yoke 202 snugly within the channel 154. The fabric covering 222 may also increase the frictional forces that hold the yoke 202 in place.

Figure 40B:
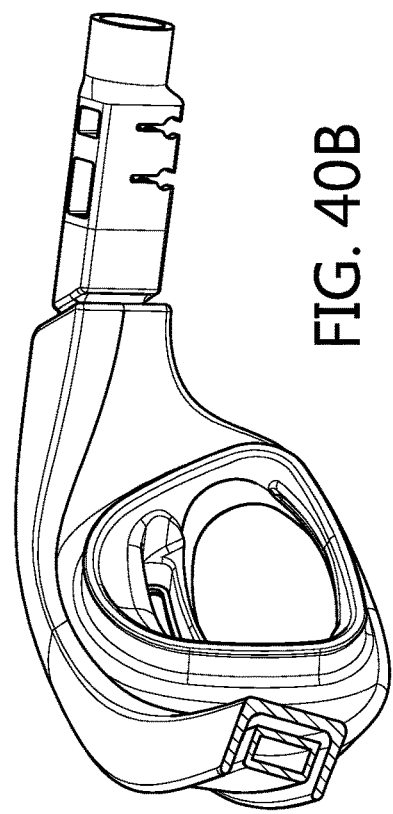
FIGS. 40B to D are cross sectional views of the assembled yoke and frame.
Figure 40D:
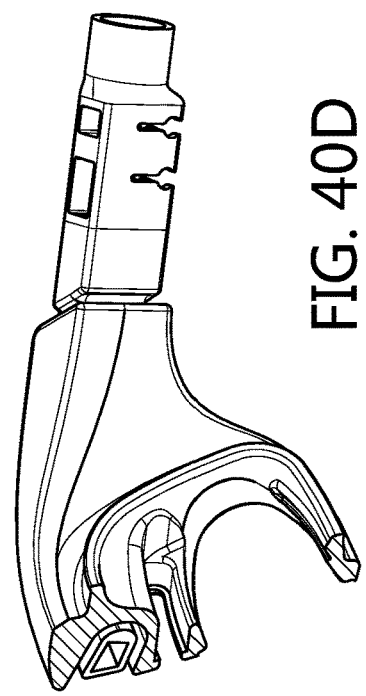
Figure 40A:
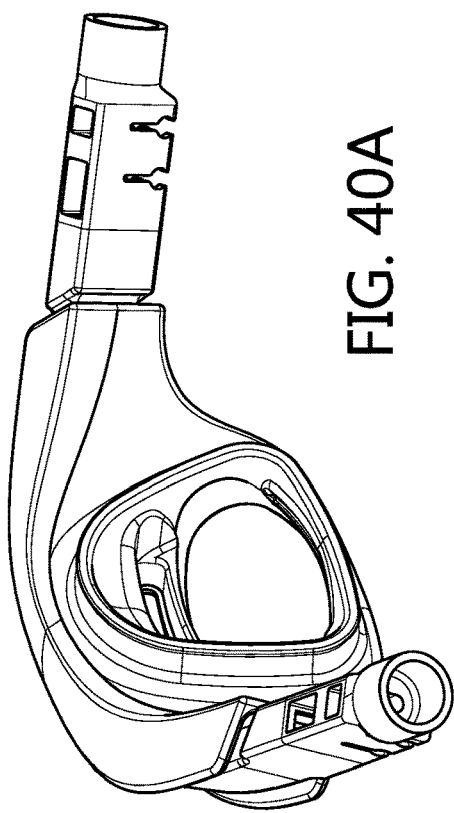
FIG. 40A is a rear perspective view of the assembled yoke and frame.
Figure 40C:
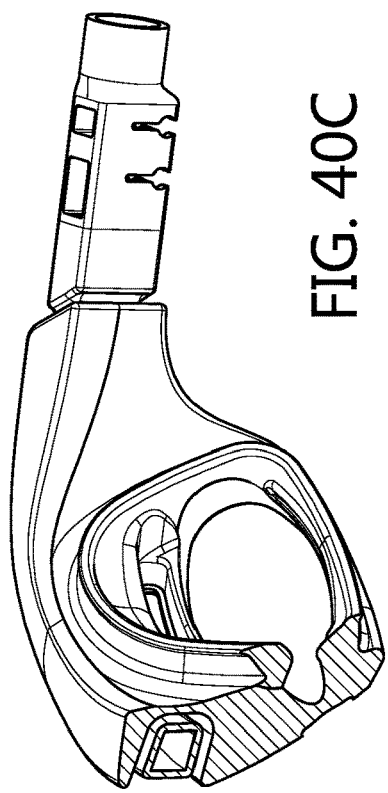

FIGS. 40A to 40D are cross sectional views of the assembled yoke 202 and frame 106 according to at least one embodiment. FIG. 40A shows the yoke 202 held in the correct position within the channel 154 of the frame 106. FIGS. 40B to 40D illustrate how the cross-section of the yoke 202 (and channel 154) may change along its length. For example, the side portions 213 of the yoke 202 may have a substantially rectangular cross-section, as shown in FIG. 40B, whereas the cross-section of the yoke 202 can change to become more trapezoidal in shape at the middle portion 212 of the yoke 202, as shown in FIG. 40D. In other words, moving along the yoke 202 from the ends to the middle portion 212, the body of the yoke 202 gradually tapers towards the rear surface 162 until it reaches its maximum taper at the middle portion 212 of the yoke 202. This configuration helps to locate and centre the yoke 202 in the channel 154 of the frame 106. The shape of the channel 154 may follow a similar transformation between the side regions and central region of the channel 154.

In this form illustrated in FIGS. 40A to 40D, the height of the rear surface 216 of the yoke 202 is at its lowest at the middle portion 212 and at its highest at or near the ends of the yoke. At the middle portion 212 of the yoke 202, the rear surface 216 is also lower in height than the front surface 214, whereas at or near the ends of the yoke 202, the front surface 214 and rear surface 216 are substantially the same height. The front surface 214 of the yoke 202 may also slope downwardly and rearwardly at the middle portion 212 and may be substantially vertical at the side portions 213. This gradually twisting front surface 214 of the yoke 202 helps to hold the yoke 202 in position within the channel 154 of the frame 106.

Optionally, the height of the middle portion 212 of the yoke 202 is less than the height of the side portions 213. In this form, when the yoke 202 is placed within a channel 154 having an outlet vent 140 formed therein, a gap is provided between the middle portion 212 and the upper surface 158 and/or lower surface 160 of the channel 154. The gap provides a fluid flow path through which gas can exit the mask interface through the outlet vent 140 and between the yoke 202 and channel wall.

The yoke 202 may be covered in a textile covering 222, as described above. The frictional forces created between the textile covering 222 and frame 106 and the slightly compressible nature of the textile covering 222 may help to hold the yoke 202 within the channel 154 of the frame 106.

FIGS. 41 to 59 illustrate various forms of connection systems between the yoke 202 and frame 106. In each connection system, the yoke and/or frame may comprise one or more attachment features to help hold and/or locate the yoke within the channel of the frame.

Figure 41A:
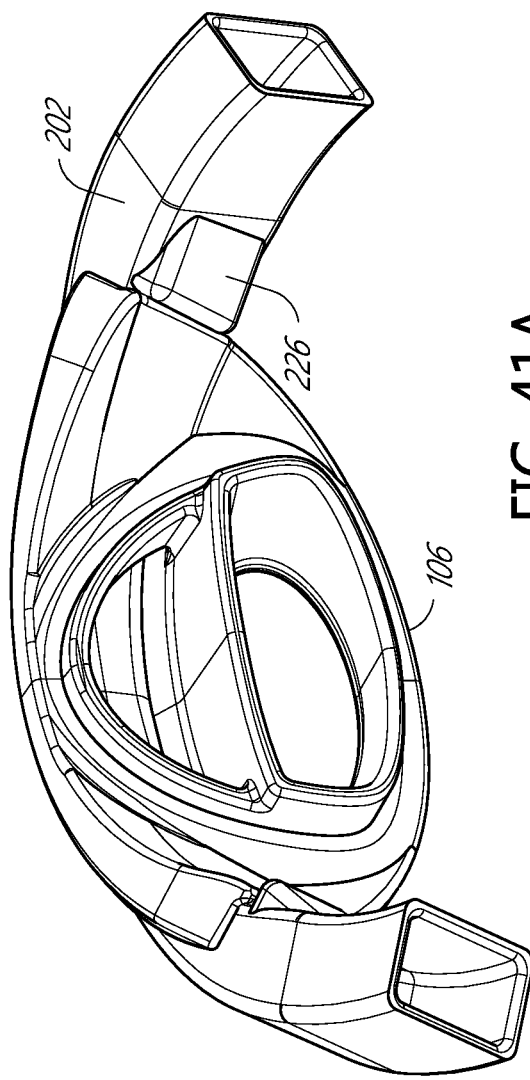
FIG. 41A is a rear perspective view from above showing a frame and yoke attached together.
Figure 41C:
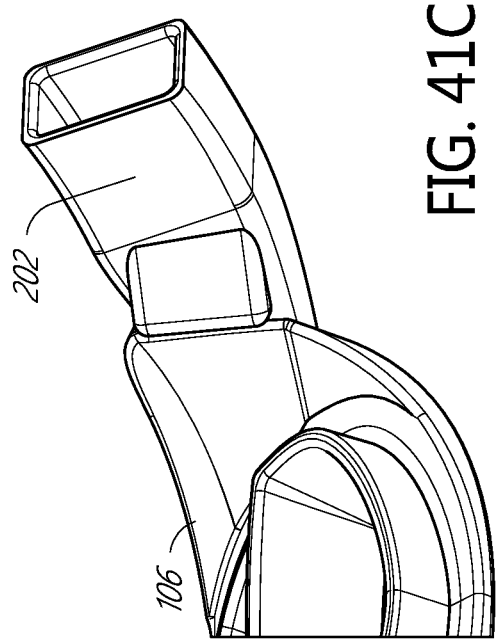
FIG. 41C is a partial rear perspective view showing the frame and yoke combination of FIG. 41A from below.
Figure 41B:
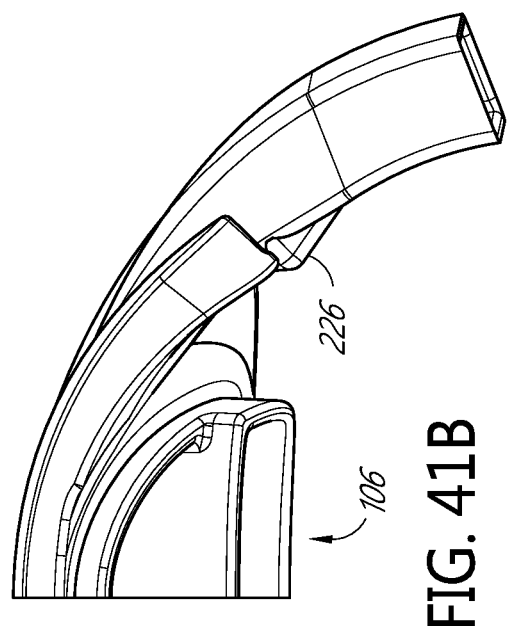
FIG. 41B is a partial bottom view of the frame and yoke combination of FIG. 41A.
Figure 42A:
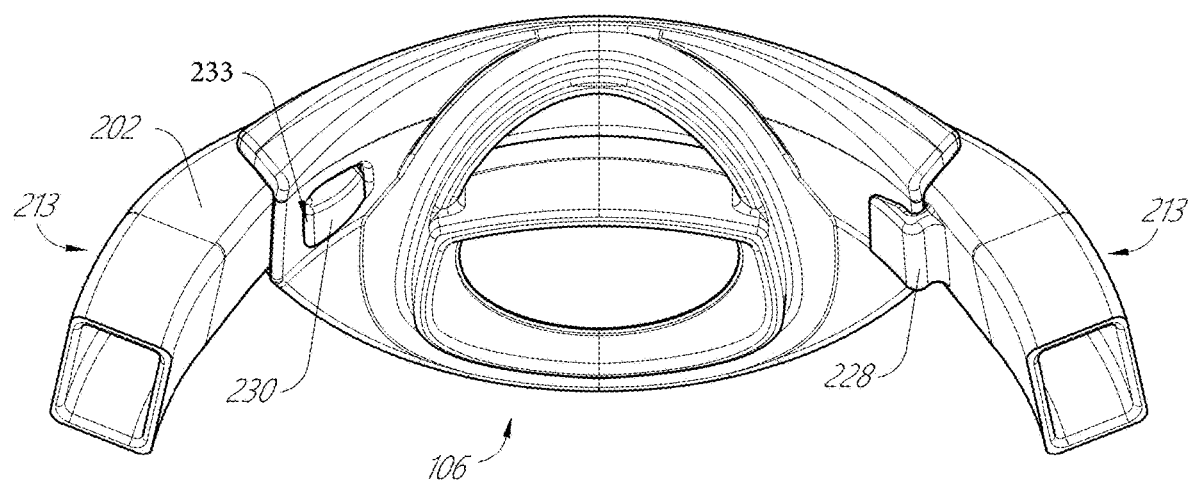
FIG. 42A is a rear perspective view of another form of frame and yoke attached together using a hook and post configuration.
Figure 42B:
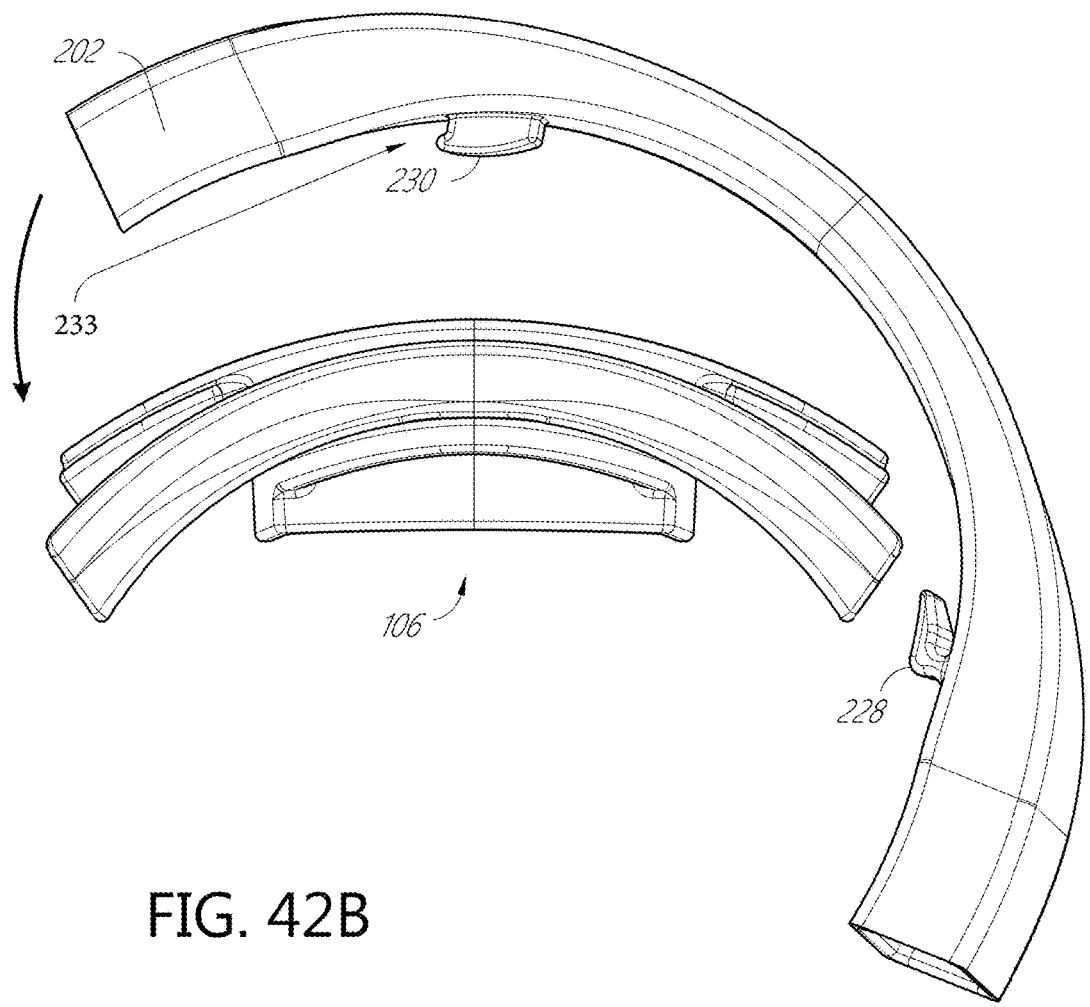
FIG. 42B is a schematic view of the configuration of FIG. 42A from above and illustrating how the yoke may be attached to the frame.
Figure 43A:
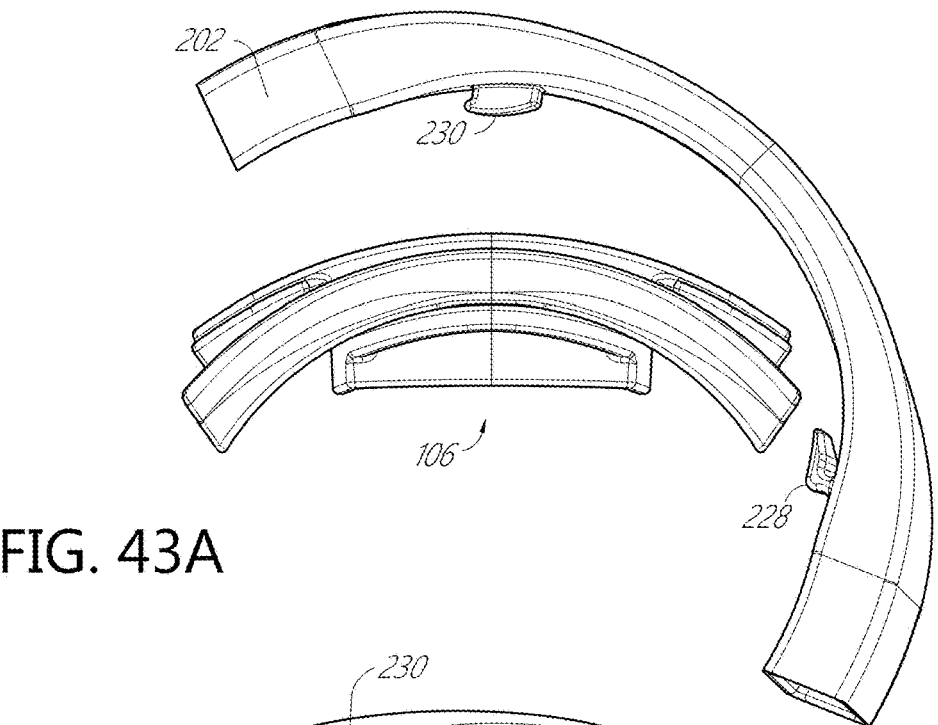
FIGS. 43A to 43C are further schematic views of the FIG. 42A from above and illustrating how the yoke may be attached to the frame.
Figure 43B:
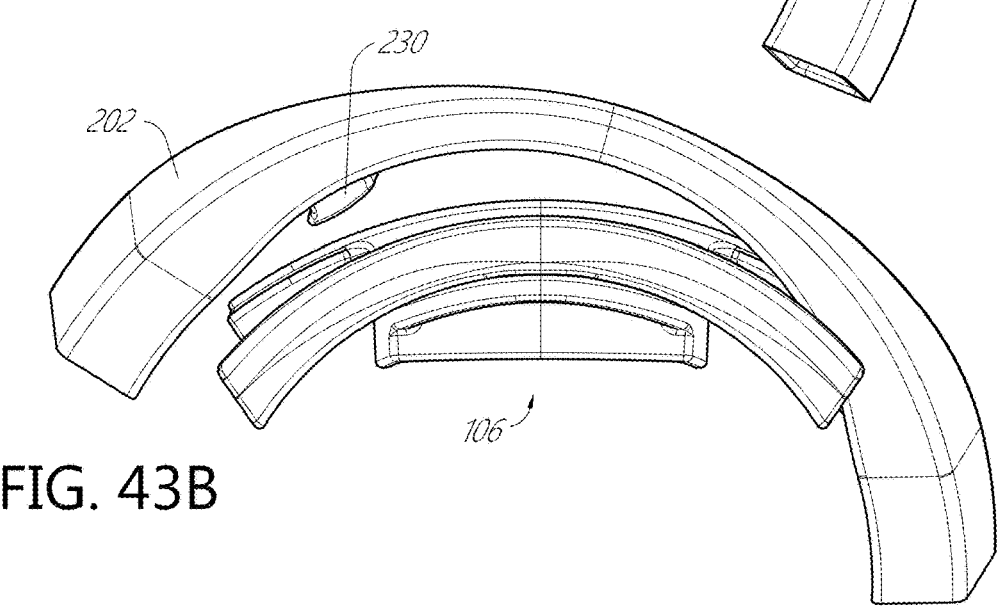
Figure 43C:
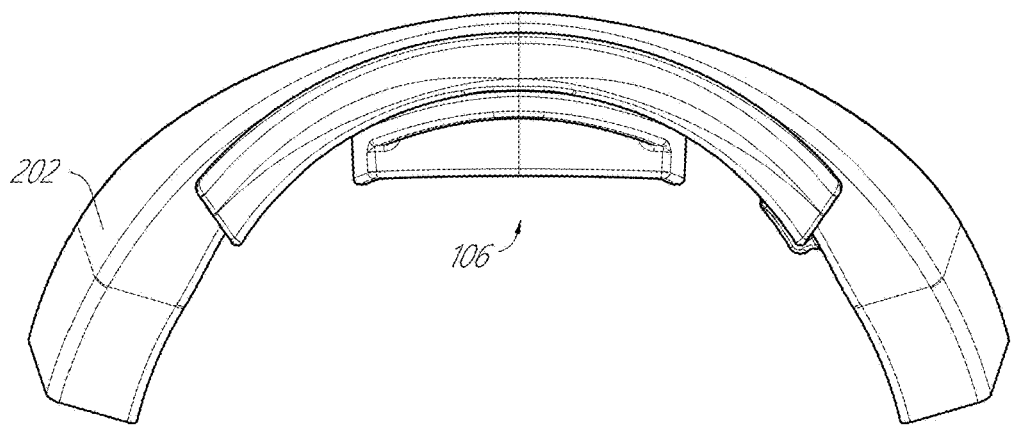
Figure 44:
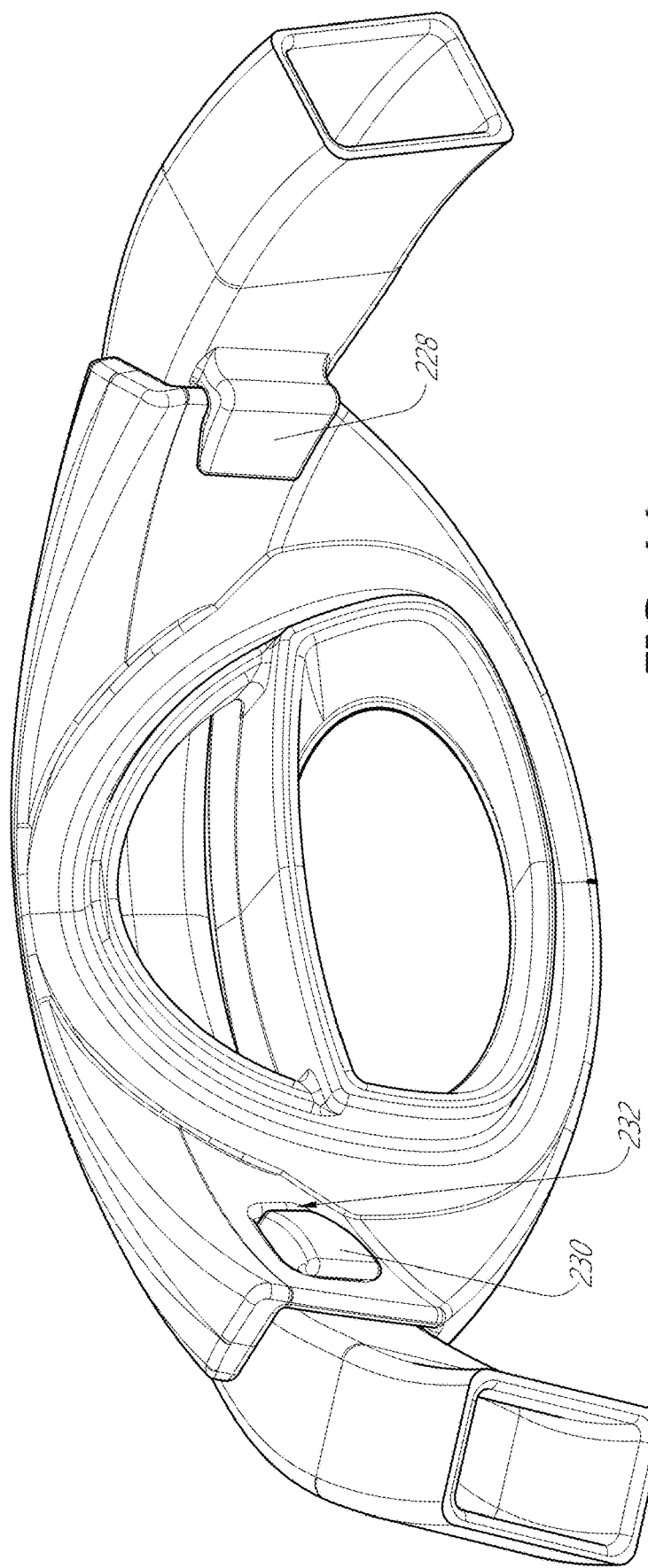
FIG. 44 is another rear perspective view of the frame and yoke configuration of FIG. 42A.
Figure 45:
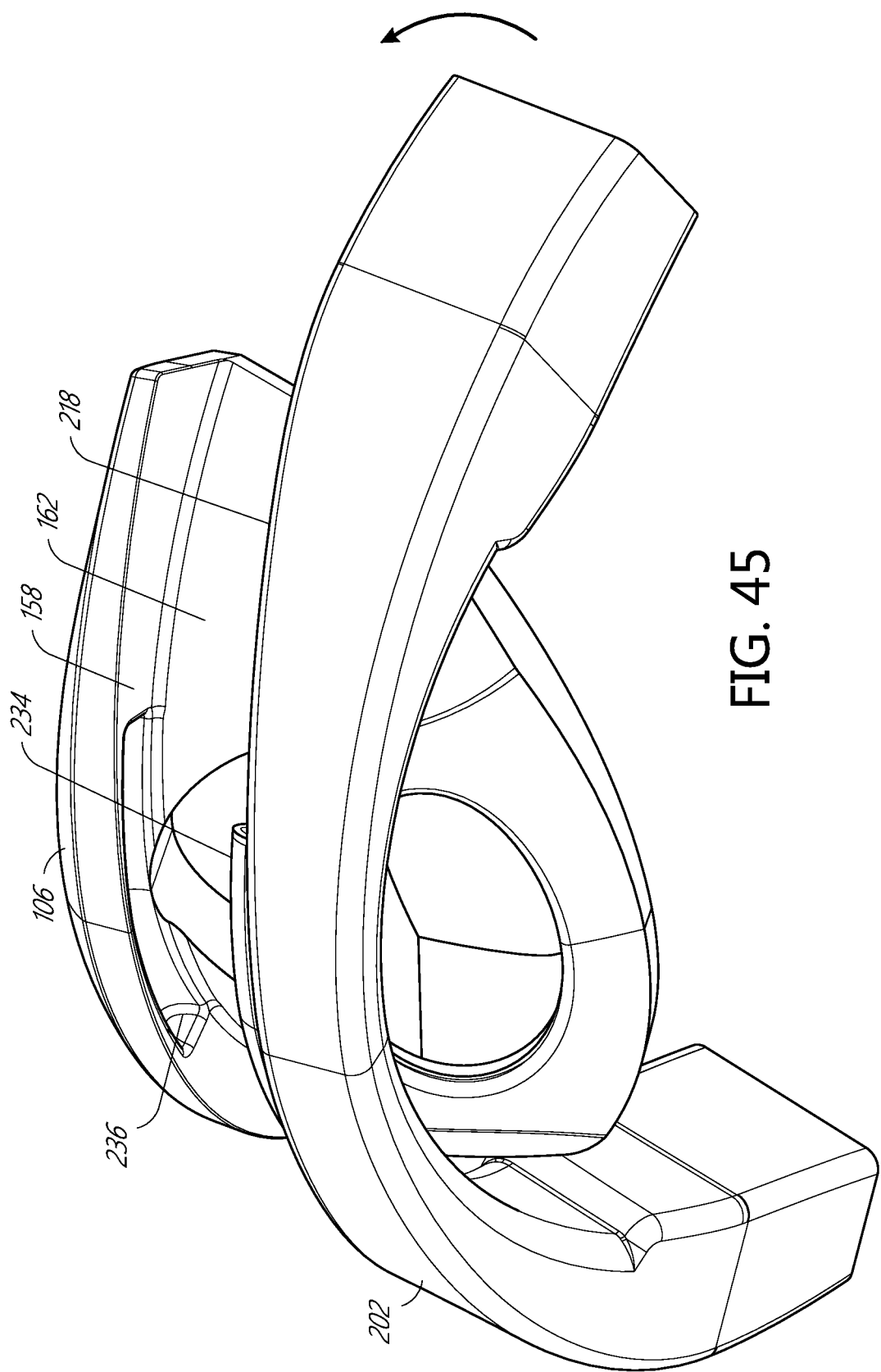
FIG. 45 is a front perspective view from below showing another form of frame and yoke configuration.

In one form, as shown in FIGS. 41A to 41C, the yoke body may comprise one or more attachment features in the form of locating members. The locating members may help to position the yoke 202 within the channel 154 of the frame 106. The locating members may also be configured to help ensure that the yoke 202 is correctly orientated within the frame 106 (i.e. is the right way up). Preferably, the yoke body comprises a pair of locating members, one of the locating members being located on each side portion 213 of the yoke 202. Each locating member may be in the form of a protrusion 226 that projects from a rear surface 216 of the yoke 202. Each locating member may comprise an alignment surface configured to abut a corresponding alignment surface of the frame to guide the yoke 202 into position on the frame 106.

In one form, a pair of locating members may project from the rear surface 216 or proximal surface of the yoke 202. The alignment surface of at least one of the locating members may be substantially perpendicular to the portion of rear surface 216 of the yoke 202 from which the locating member projects. Alternatively, the alignment surface may slope outwardly from the rear surface 216 in a direction away from the middle portion 212 of the yoke 202. In one form, the locating member and its alignment surface may be orientated at an angle to the bottom surface 220 of the yoke 202. For example, where a pair of substantially opposing locating members are orientated in this manner, the alignment surfaces of the locating members are closer together near the bottom surface than near the top surface of the yoke 202. In this form, the body of the frame 106 or ends of the channel 154 may be sloped at substantially corresponding angles so that the frame 106 abuts the alignment surfaces when the yoke 202 is held within the channel 154 of the frame 106.

In one form, at least one locating member may comprise a substantially curved projection that is formed at or near the ends of the yoke 202 and that may project from the rear surface 216 of the yoke 202. The curved projection may comprise an alignment surface configured to abut a corresponding alignment surface of the frame 106 when the yoke 202 is held within the channel 154 of the frame 106. For example, the frame 106 may comprise a cutaway region in which the curved projection may be located when the yoke 202 is positioned on the frame 106.

At least one locating member may be integrally formed with the yoke body.

In one form, each locating member may be formed from an over-moulding located at or near each end or side portion 213 of the yoke 202. One or more edges of the over-moulding may form one or more alignment surfaces. Optionally, the alignment surfaces angle outwardly from the middle portion 212 of the yoke toward the side portions 213. In this form, outer edges of the frame body may be correspondingly angled so that the frame 106 fits snugly between the over-moulded portions of the yoke 202.

In one form, one locating member may comprise a hook 228 and the other locating member may comprise a post 230. For example, as shown in FIGS. 42A to 44, a hook 228 may project from the rear surface 216 of one side portion 213 of the yoke 202 and a post 230 may project from the rear surface 216 of the other side portion 213. A post aperture 232 may be provided in the channel 154 of the frame 106.

To attach the yoke 202 to the frame 106, one edge of the frame 106 is slid under the hook 228 to attach one end of the yoke 202 to the frame 106. The yoke 202 is maneuvered so that the post 230 is aligned with the post aperture 232. The free end of the yoke 202 is then pushed into the channel 154 of the frame 106 to cause the post 230 to project through the post aperture 232.

The post 230 may also comprise an overhang 233 facing in the direction of the hook 228. In this form, after the yoke 202 is pushed into the channel 154 as described above, the yoke 202 may be pushed in the direction of the hook 228 so that the post overhang 233 hooks over the rear surface of the frame 106.

In another form of frame 106 and yoke 202 connection system, the yoke body may comprise a material that is substantially stretchable along its length and the yoke 202 may comprise one or more attachment features for engaging with one or more corresponding attachment features provided on the frame 106 of a respiratory mask system. For example, the stretchable yoke body may comprise at least one attachment feature comprising a hook configured to engage with a corresponding hook, recess or opening provided on the frame 106.

In another form, the frame 106 and yoke 202 may comprise male and female attachment members configured to engage with each other to help hold and/or locate the yoke 202 within the channel 154 of the frame 106. For example, the yoke 202 may comprise a male member in the form of a projection configured to be held within a female member in the form of an aperture or recess provided on the frame 106. Additionally or alternatively, the male member may be provided on the frame 106 and the female member may be provided on the yoke 202.

In one form, the rear surface 216 of the yoke 202 may comprise a pair of male attachment members in the form of projections configured to project through a pair of corresponding female attachment apertures or recesses provided on the rear surface 162 of the channel 154 of the frame 106. Preferably, the yoke 202 comprises a pair of projections, one on either side of a virtual centre line passing vertically through the frame 106, such as on each side portion 213. In this form, an attachment aperture may be located at each side region of the rear surface 162 of the channel 154.

FIGS. 45 to 47C illustrate one example of a frame 106 and yoke 202 connection system using male and female attachment members. In this form, the yoke 202 may comprise a male attachment member in the form of a tab 234 or flange projecting from the top surface 218 of the yoke. Preferably, the tab 234 projects from the middle portion 212 of the yoke 202. In one form, the tab 234 may extend substantially along the length of the yoke 202.

Figure 46B:
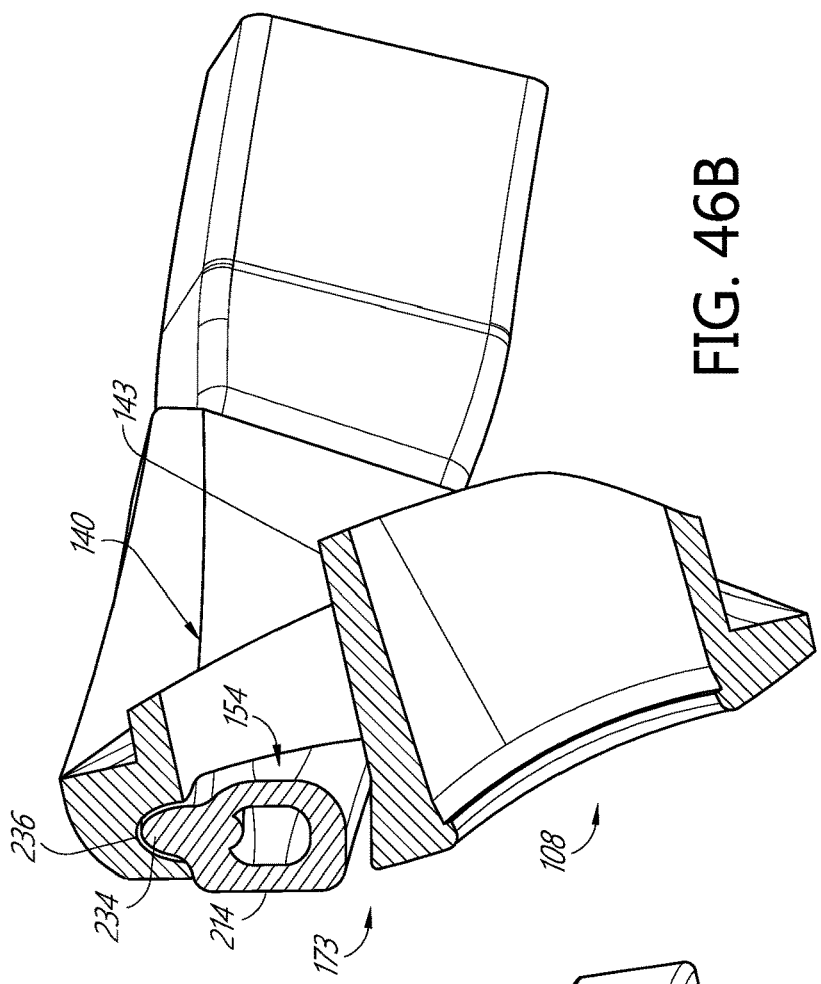
FIG. 46B is a cross-sectional view of the frame and yoke configuration taken along line 46B-46B of FIG. 46A.
Figure 46A:
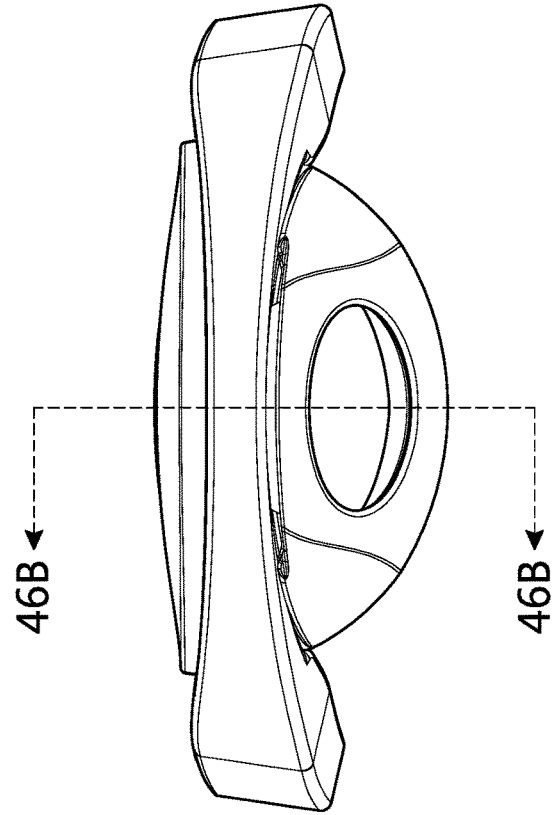
FIG. 46A is a front view of the frame and yoke configuration of FIG. 45 when attached together.
Figure 47A:
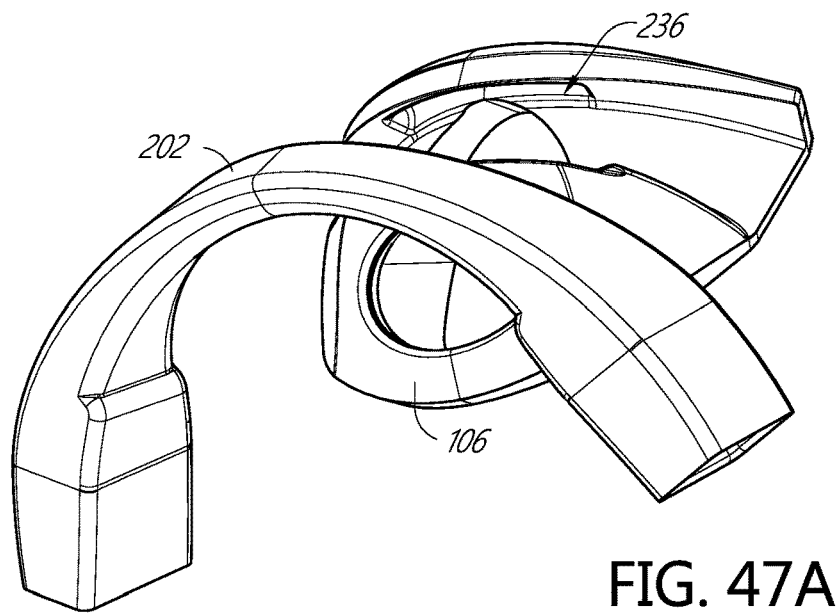
FIGS. 47A to 47C are front perspective views of the configuration of FIG. 45 and show one method of locating the yoke within the channel of the frame.
Figure 47B:
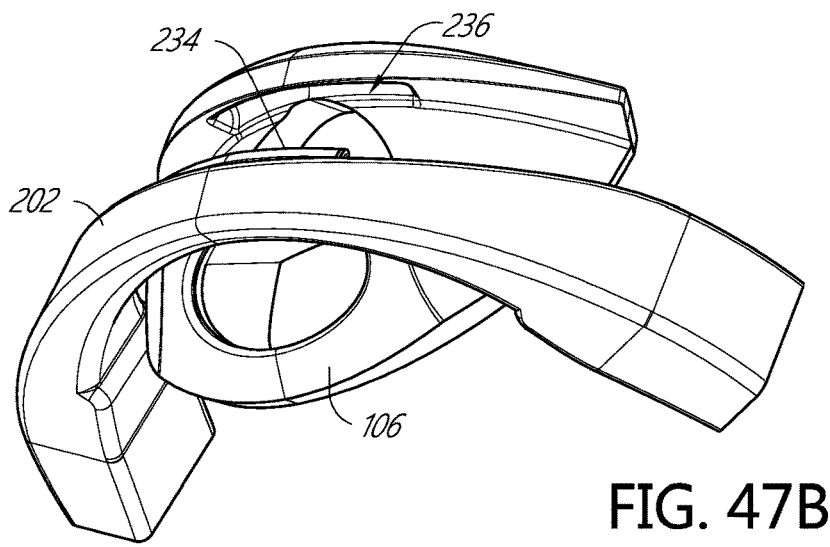
Figure 47C:
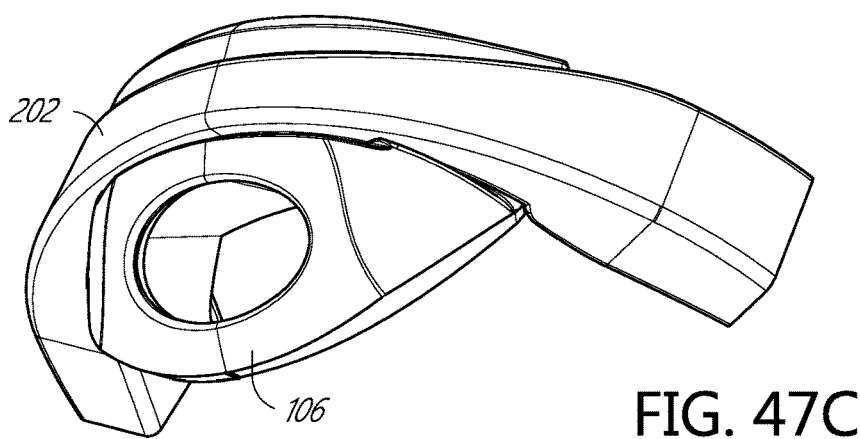
Figure 48A:
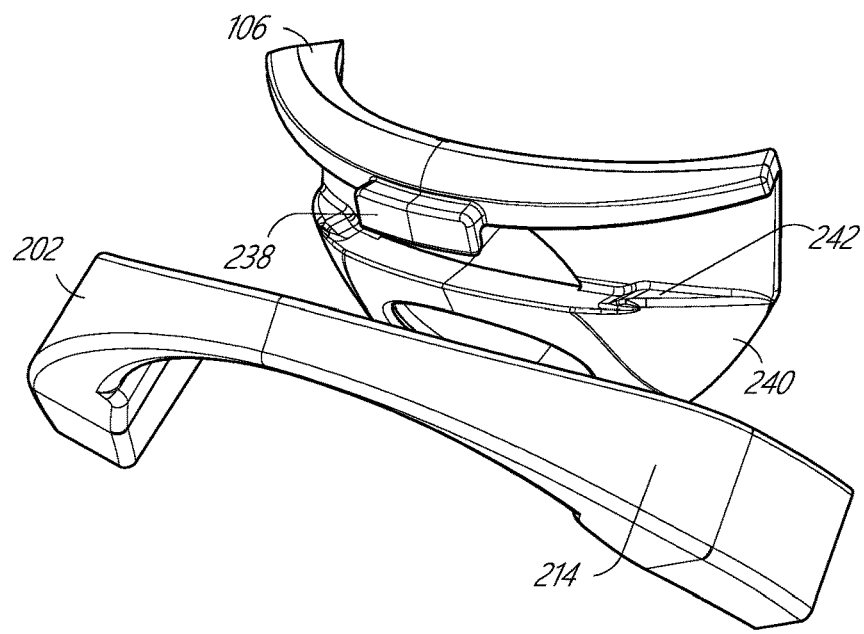
FIGS. 48A to 49C are front perspective views of another configuration of the frame and yoke and show a method of locating the yoke within the channel of the frame.
Figure 48B:
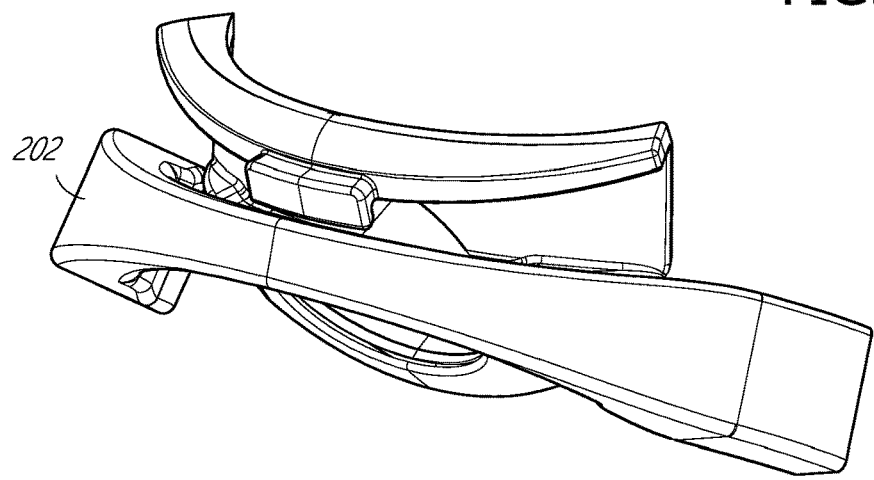
Figure 48C:
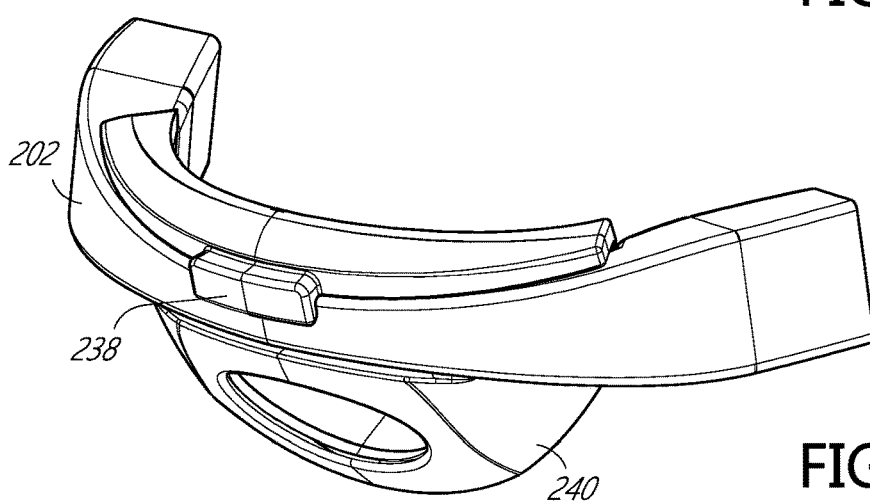
Figure 49A:
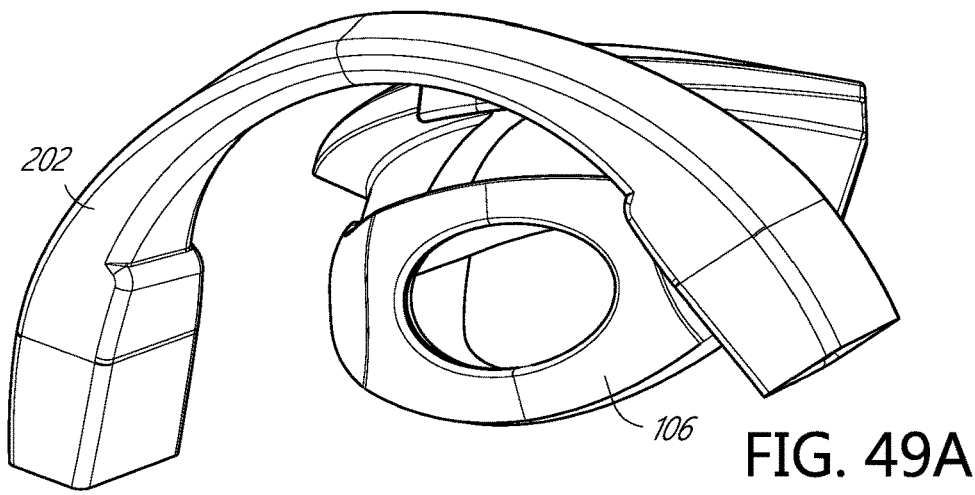
Figure 49B:
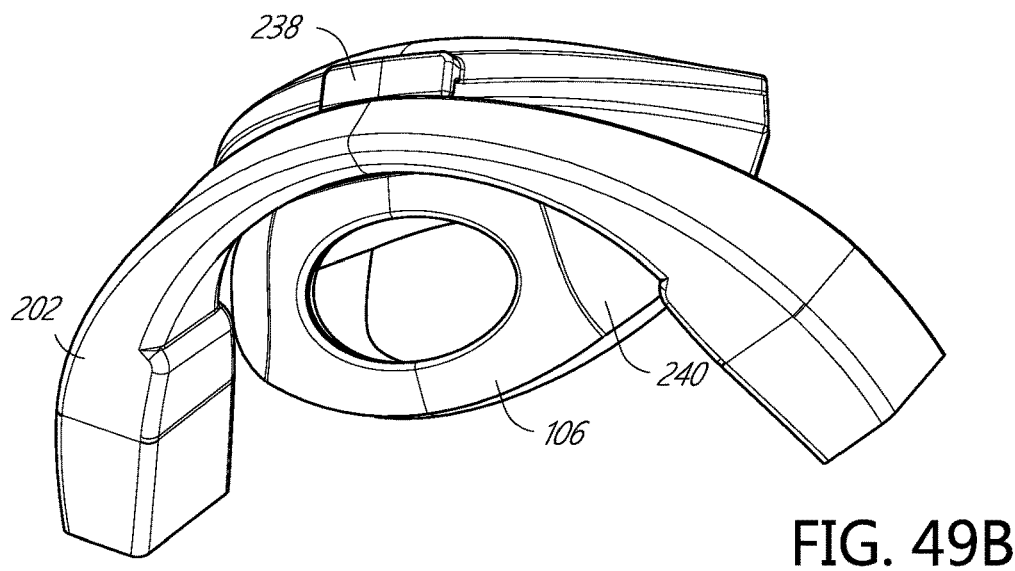
Figure 49C:
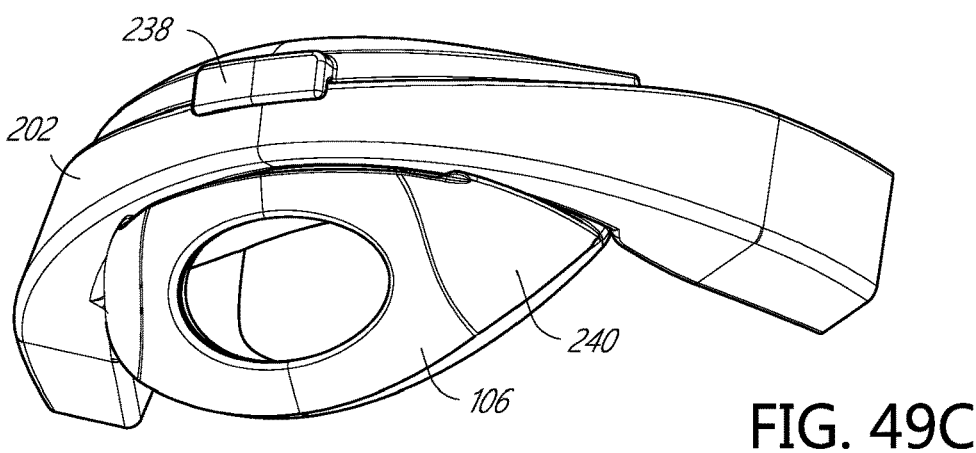
Figure 50C:
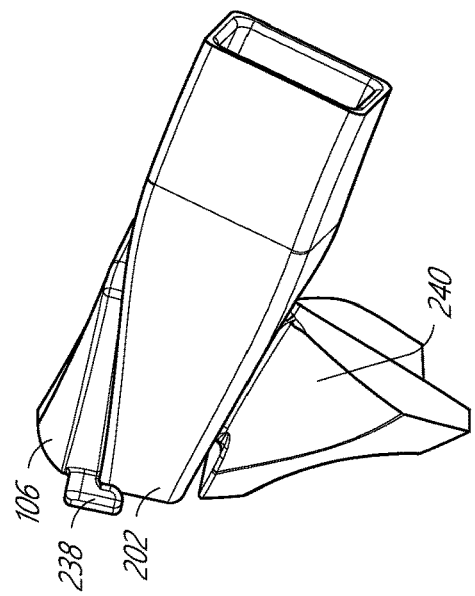
FIGS. 50A to 50C are side views of the configuration of FIG. 48A and show the method of locating the yoke within the channel of the frame.
Figure 50B:
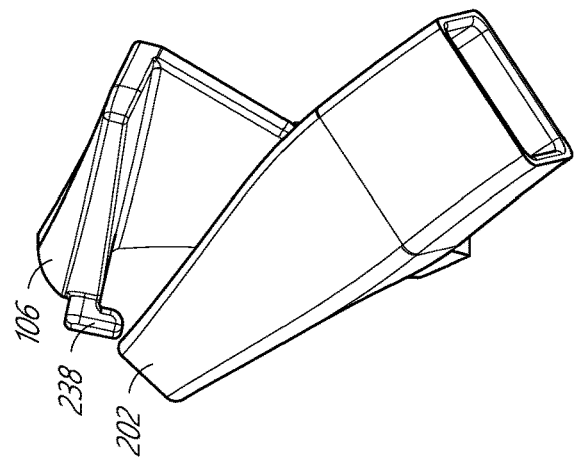
Figure 50A:
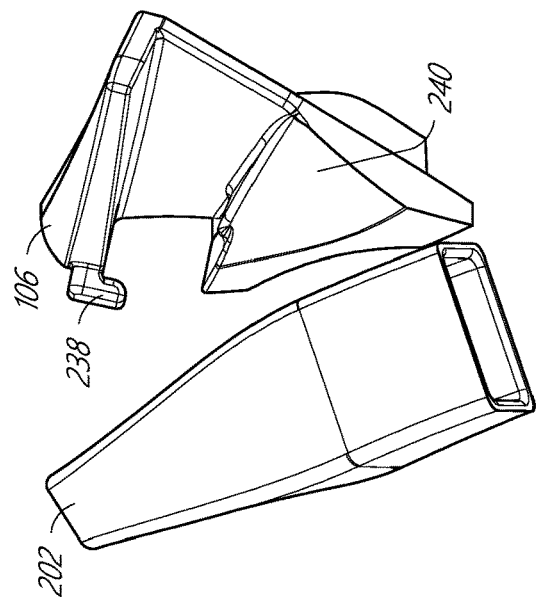
Figure 51A:
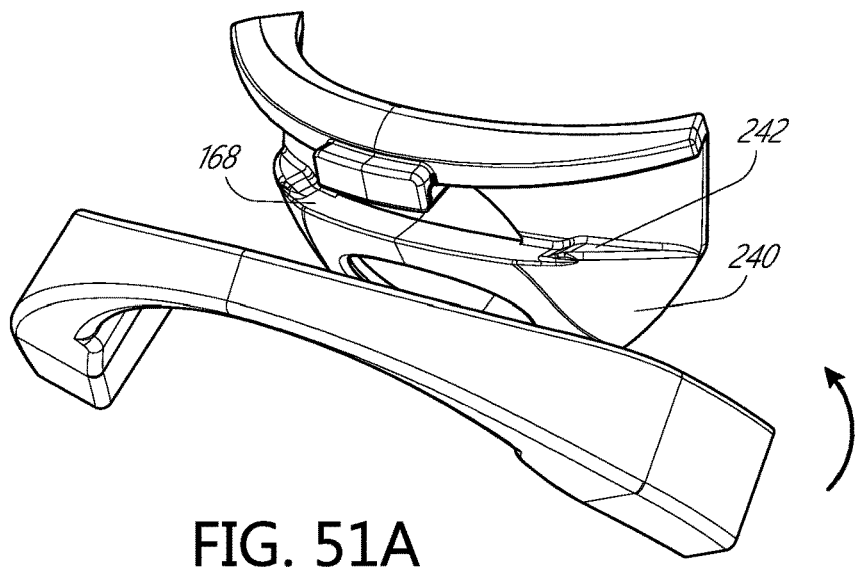
FIG. 51A is another front perspective view of the configuration of FIG. 48A and demonstrate the method of locating the yoke within the channel of the frame.
Figure 51B:
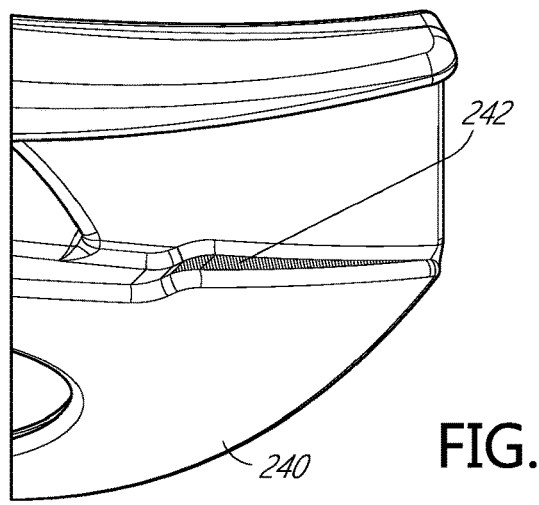
FIG. 51B is an enlarged front view showing a portion of the front surface of the frame body of FIG. 51A.
Figure 51C:
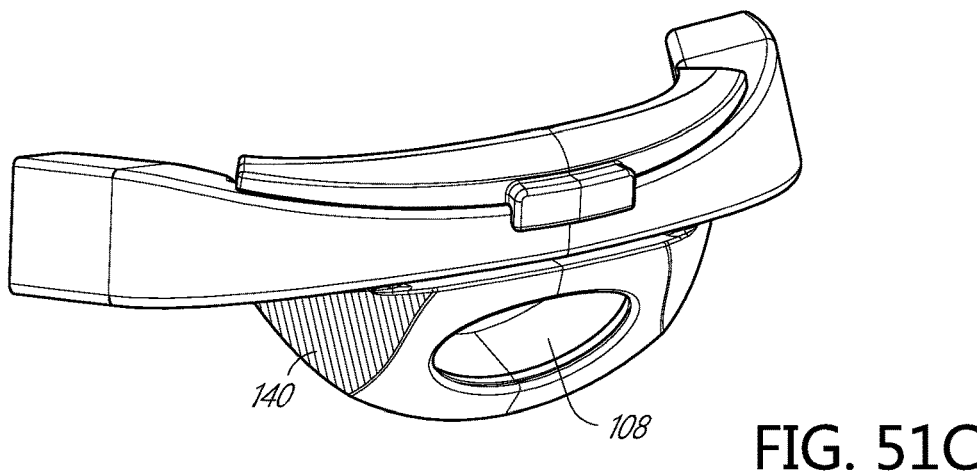
FIG. 51C is a front perspective view of the frame and yoke of FIG. 51A attached together.

The upper surface 158 of the channel 154 may comprise a recess or aperture 236 configured to receive the tab 234 therein. In this form, as shown in FIGS. 47A to 47C, the yoke 202 is pushed upwardly into the channel 154 so that the tab 234 is pushed within the recess 236. The yoke 202 can then be pushed back so that the rear surface 216 of the yoke 202 substantially abuts the rear surface 162 of the channel 154. As shown in FIG. 46B, a gap 173 may exist between the bottom surface of the yoke and the lower surface of the channel 154. Optionally, the yoke 202 also comprises locating members having alignment surfaces that abut corresponding surfaces of the frame 106.

FIGS. 48A to 51C illustrate another form of frame 106 and yoke 202 connection system. In this form, the frame 106 comprises a tab 238 projecting downwardly to partially cover the central region of the channel 154. The front surface 112 of the frame body, below the channel 154, may comprise a relief surface 240 that tapers toward the sides of the frame 106. The lower surface 160 of the channel 154 may also taper towards the ends of the channel 154. As shown, tapered lower surfaces 242 can extend from the recessed lower surface 168 to lateral edges of the frame 106 and/or channel 154. To fit the yoke 202 and frame 106 together, the yoke 202 is angled into the channel 154 so that the body of the yoke 202 sits within the channel 154 and behind the tab 238. In this configuration, the tab 238 covers a portion of the front surface 214 of the yoke 202 and holds the yoke 202 in position within the channel 154. The tapered relief surface 240 and lower surface 160 of the channel 154 help provide space for the curved or angled body of the yoke 202 to be maneuvered into the channel 154 from below. Again, the yoke 202 may comprise alignment surfaces to help position the yoke 202 on the frame 106.

Figure 52A:
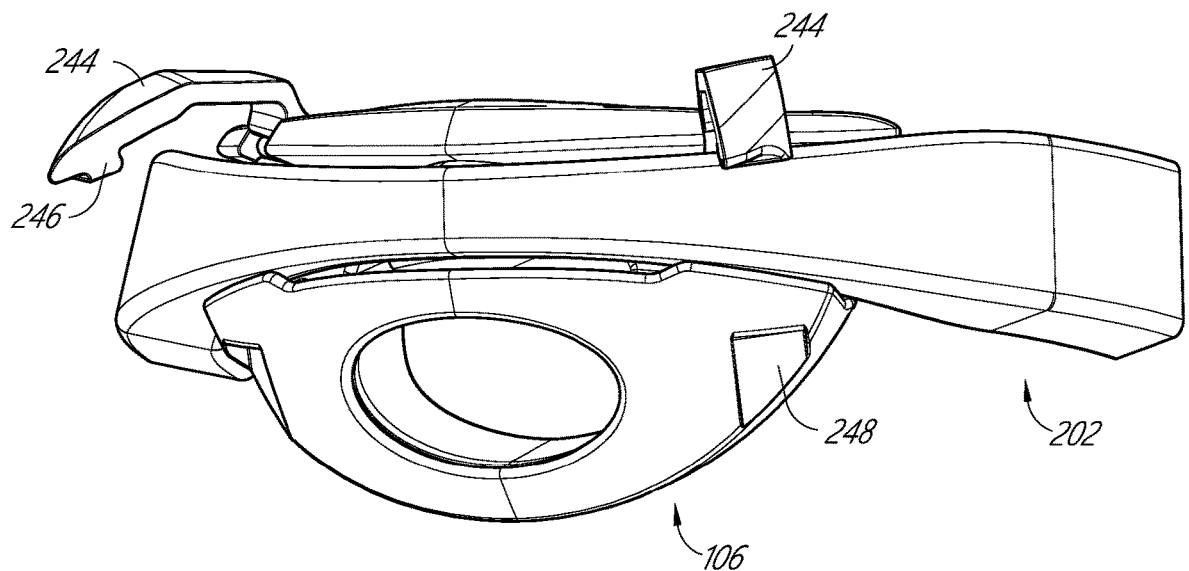
FIGS. 52A and 52B are front perspective views of yet another frame and yoke configuration, this configuration using attachment clips or latches.
Figure 52B:
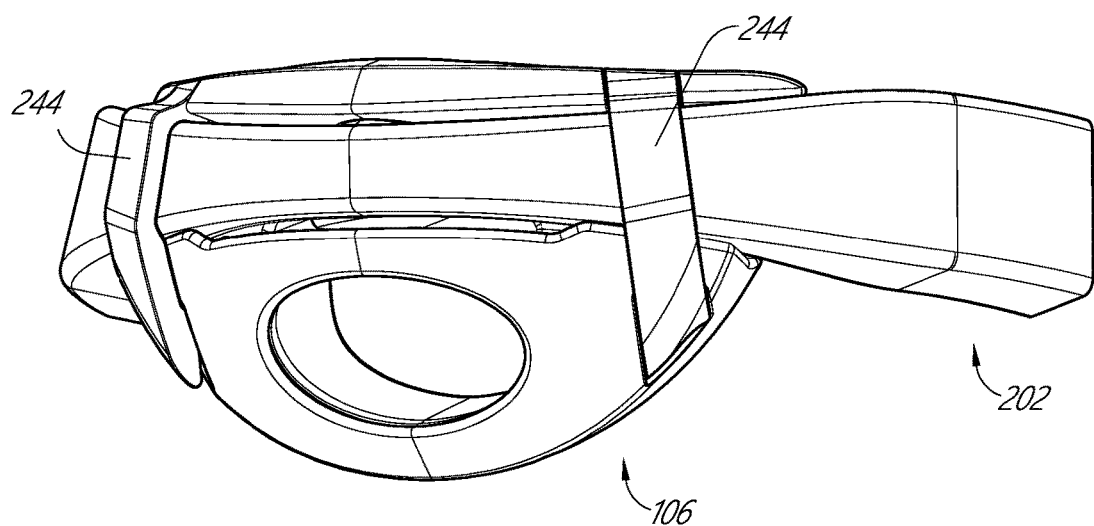
Figure 53A:
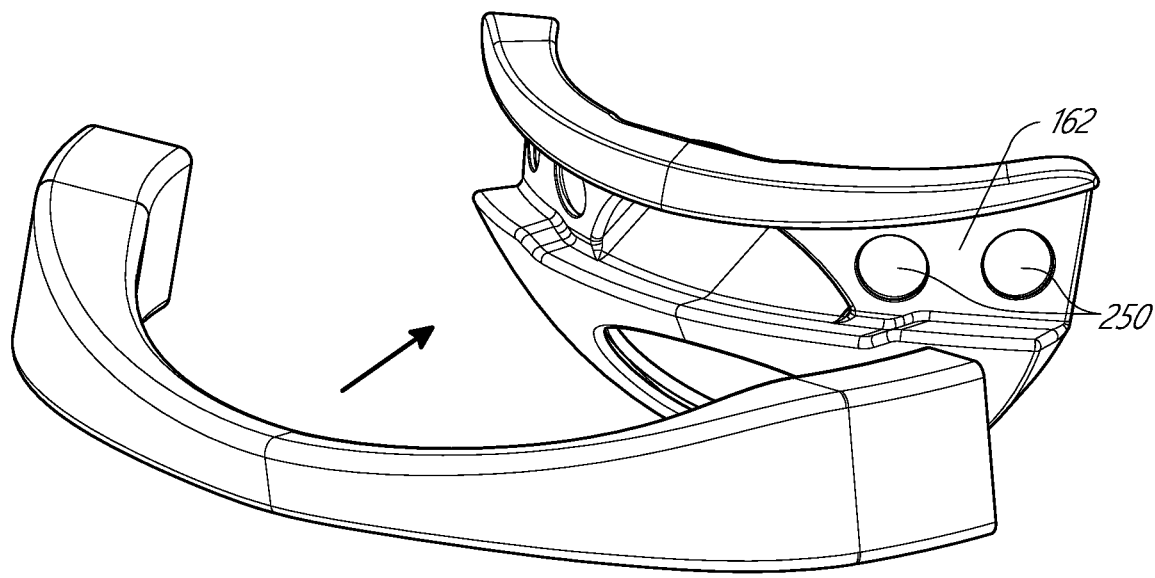
FIG. 53A is a front perspective view showing a frame and yoke configuration comprising magnets and demonstrating one method of locating the yoke within the channel of the frame.
Figure 53B:
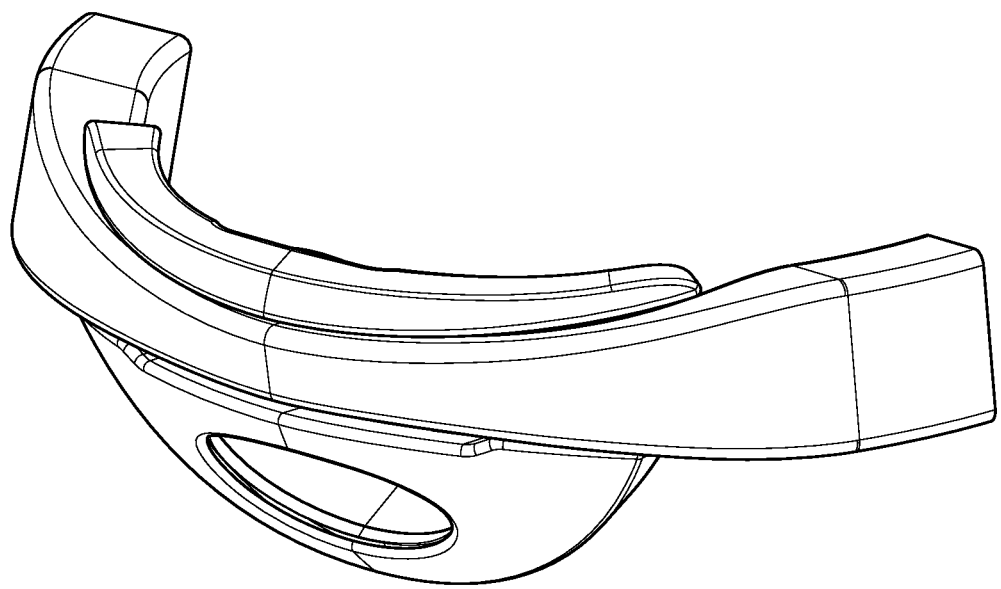
FIG. 53B is a front view of the frame and yoke configuration of FIG. 53A when joined together.
Figure 54A:
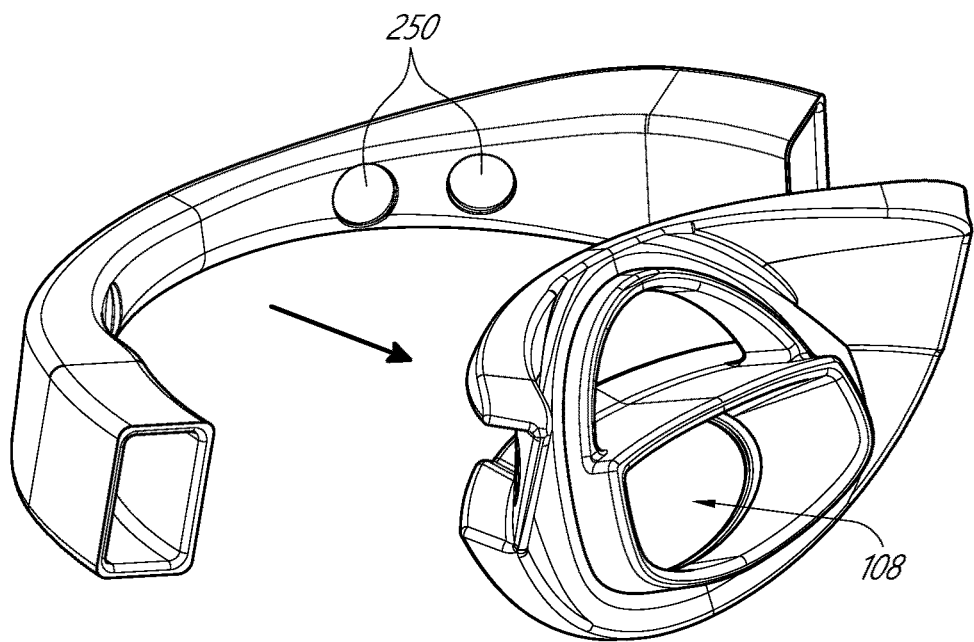
FIG. 54A is a rear perspective view of the frame and yoke configuration of FIG. 53A.
Figure 54B:
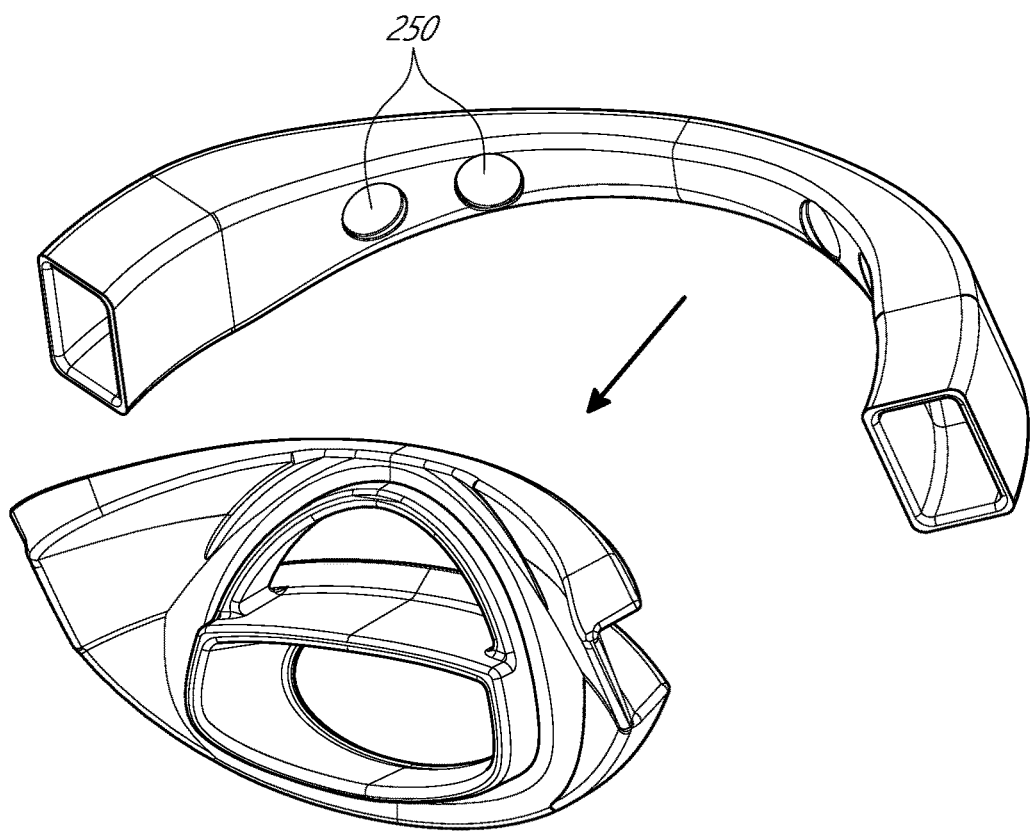
FIG. 54B is another rear perspective view of the frame and yoke configuration of FIG. 53A.
Figure 55A:
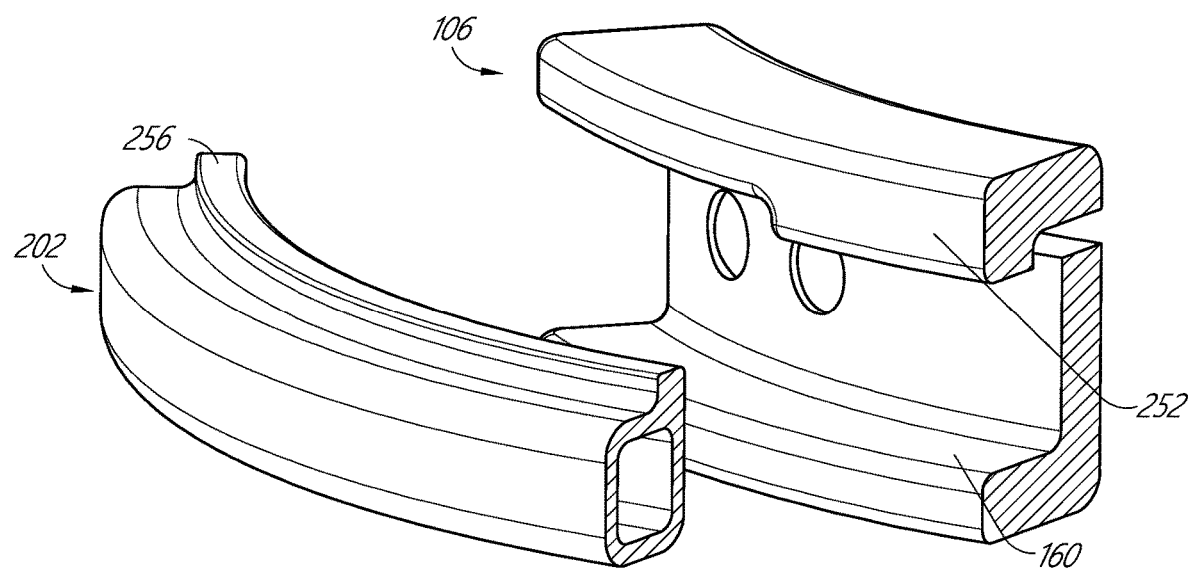
FIGS. 55A and 55B are front perspective views of yet another form of frame and yoke configuration.
Figure 55B:
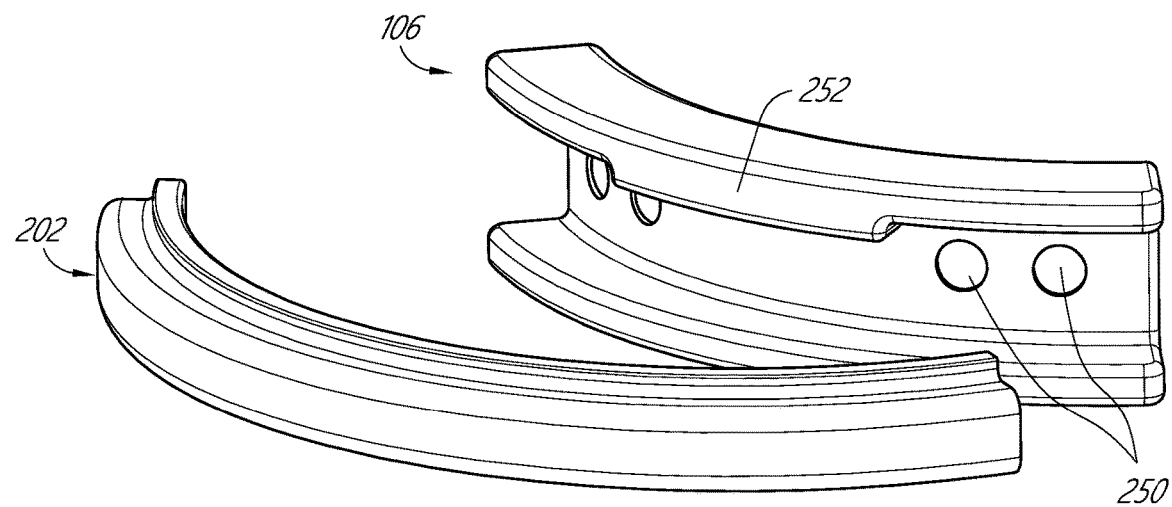
Figure 56:
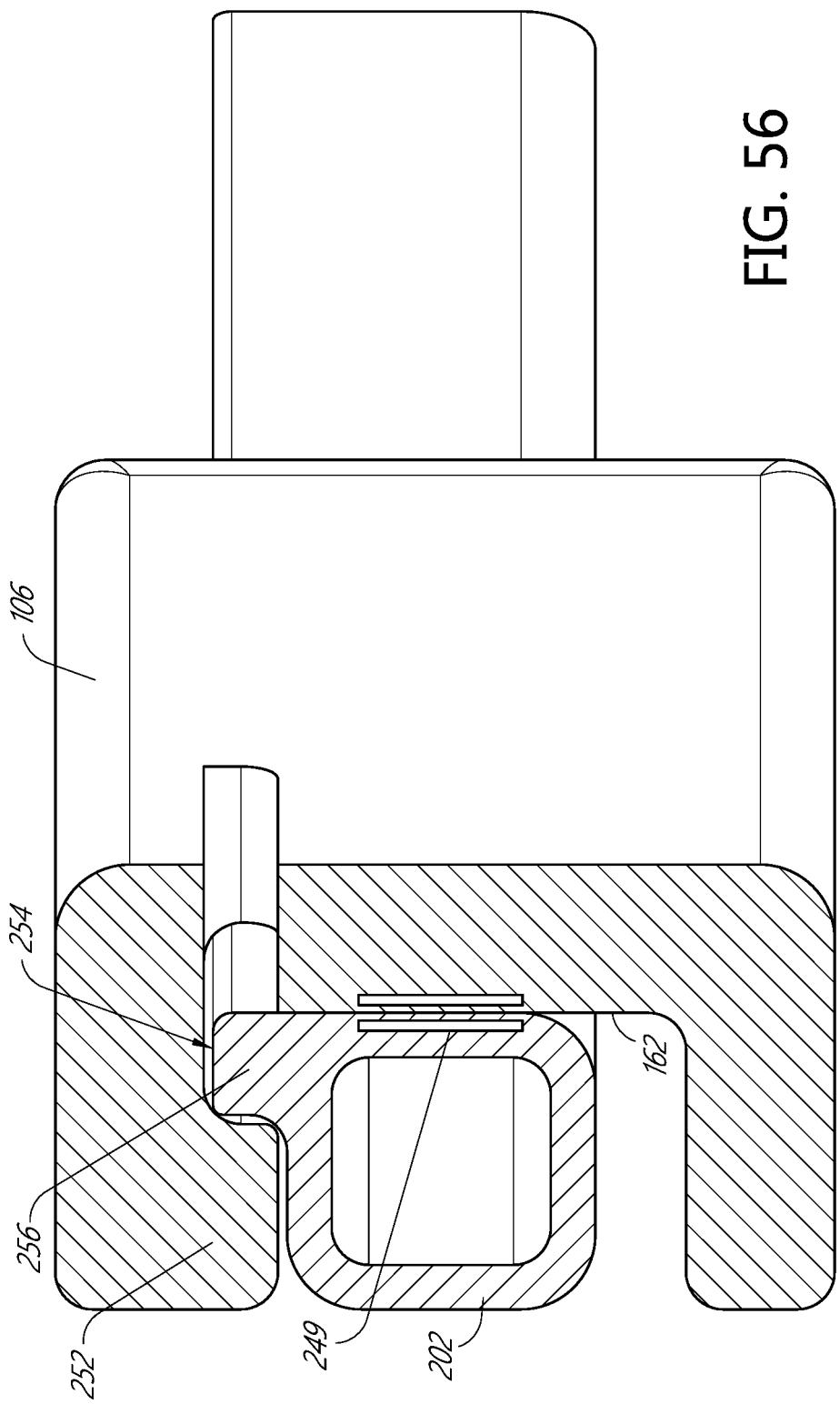
FIG. 56 is a cross-sectional side view of the frame and yoke of FIG. 55A when attached together.
Figure 57C:
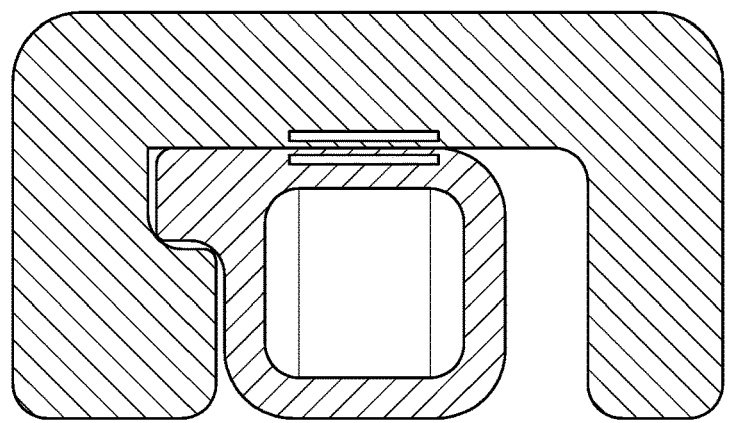
Figure 57B:
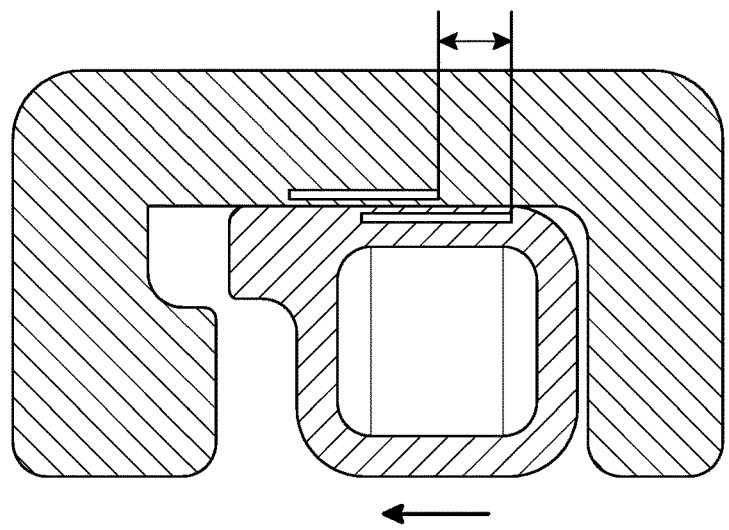
Figure 57A:
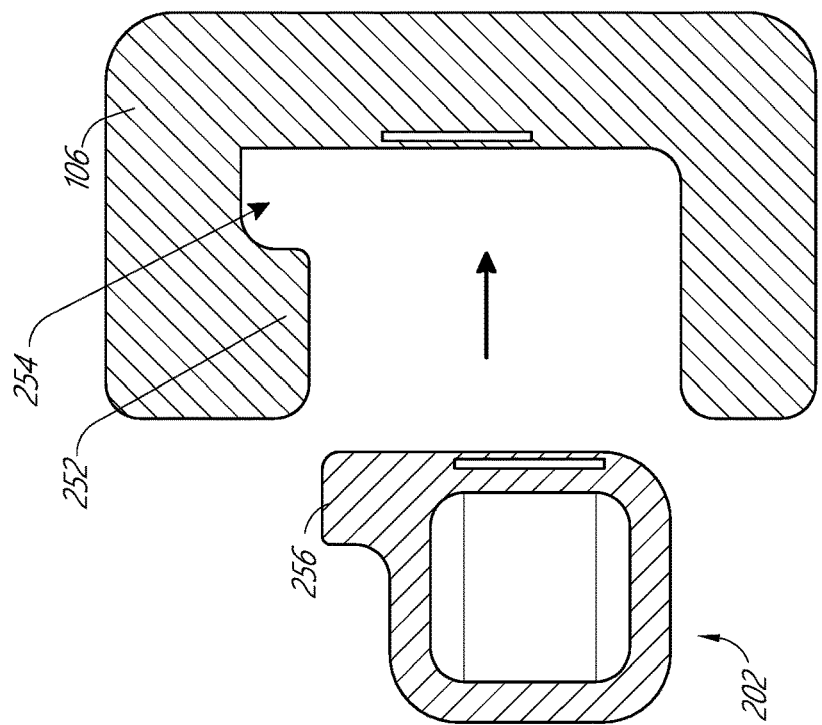

FIGS. 52A and 52B illustrate yet another form of frame 106 and yoke 202 connection system. In this form, one or more latches 244 or clips may be used to attach the yoke 202 to the frame 106. Each latch 244 may be fixedly or removably attached to the frame 106 and may hinge between an open position and a closed position. In the open position, one end of the latch 244 is attached to the frame 106 and the channel 154 of the frame 106 is open. The yoke 202 may be pushed into position within the channel 154 and the latch 244 may then be closed over the yoke 202 and channel 154. In the closed position, the latch 244 extends across the channel 154 and the yoke 202 within it. The free end of each latch 244 engages with a lock provided on the frame 106 to hold the latch 244 in the closed position.

In one form, the latch 244 hinges from an upper portion of the frame body, above the channel 154, and is configured to extend across the channel 154 to engage with a lock provided on a lower portion of the frame body, beneath the channel 154. In an alternative configuration, the latch 244 hinges from the lower portion of the frame 106 and extends across the channel 154 to engage with a lock on the upper portion of the frame 106.

The latch 244 may comprise a locking member, which may be in the form of a protrusion 246, configured to engage with the lock, which may be in the form of a latch engagement recess 248, to hold the latch 244 in the closed position. Preferably, a pair of latches 244 is provided, one latch 244 being located on either side of the central region of the channel 154.

In another form, the lock is provided on the front surface 214 of the yoke 202. In this form, one end of the latch 244 hinges from the frame 106 and the other end engages with the lock provided on the yoke 202 to hold the yoke 202 within the channel 154.

FIGS. 53A to 58 illustrate another form of frame 106 and yoke 202 connection system using attachment features in the form of magnets. The term 'magnets' should be interpreted to include magnetic regions comprising ferromagnetic material, where appropriate. In other words, it is possible to attach the frame 106 and yoke 202 to each other where both parts comprise magnets, or where one part comprises a magnet and the other part comprises a magnetic region comprising ferromagnetic material.

In one form, as shown in FIGS. 53A to 54B, the rear surface 162 of the channel 154 comprises one or more magnets configured to attach to one or more magnets provided on the rear surface of the yoke 202. In one form, a plurality of magnets are located on the rear surface 162 of the channel 15. The magnets may be spaced equidistant from each other. Each channel magnet may be located on a centre-line that extends from one end of the channel 154 to the other. Similarly, each yoke magnet may be located on a centre-line that extends from one end of the yoke 202 to the other. Optionally, each magnet may be embedded within a recess 250 formed in the channel 154 or yoke 202, as the case may be. In this form, the yoke 202 may be placed in the channel 154 of the frame 106 and the magnetic attraction between the magnets on each part holds the yoke 202 in position within the channel 154.

In another form, as shown in FIGS. 55A to 58, the upper surface 158 of the channel 154 may comprise a tab 252 that projects across a portion of the channel 154. The height of the channel 154 opening is defined by which is defined by the distance between the distal end of the projecting tab 252 and the lower surface 160 of the channel 154. A recess 254 is formed between the back of the tab 252 and the rear surface 162 of the channel 154, as seen best in FIGS. 56 to 58. One or more magnets 251 may be positioned off-centre one the rear surface 162 of the channel 154, so that each magnet 251 is closer to the upper surface of the channel 154 than to the lower surface. The yoke 20 may comprise a projection, such as a flange 256, projecting from its top surface. The height of the yoke body is defined by the distance between the bottom surface of the yoke 202 and the free upper edge of the projecting flange 256. The height of the yoke body is less than the height of the channel opening. One or more magnets 249 provided on the rear surface of the yoke 20 may be positioned closer to the bottom surface of the yoke 202 than to the free upper edge of the projecting flange 256. In this arrangement, when the yoke 202 is placed within the channel 154 of the frame 106, the magnetic attraction between the magnets 251, 249 of the frame 106 and yoke 202 cause the yoke 202 to be pulled upwardly so that the projecting flange 256 of the yoke 202 is located in the recess 254 behind the projecting tab 252 of the frame 106. In this way, the tab 252 and magnets 251, 249 hold the yoke 202 in position on the frame 106. Because the magnets 251, 249 pull the yoke 202 upwardly in the channel 154, a gap 258 is formed between the bottom surface 220 of the yoke 202 and the lower surface 160 of the channel 154. In one form, an outlet vent 140 may be located on the rear surface 162 of the channel 154 and the gap 258 provided beneath the yoke 202 forms a fluid flow path through which gas can escape from the outlet vent 140.

Figure 59A:
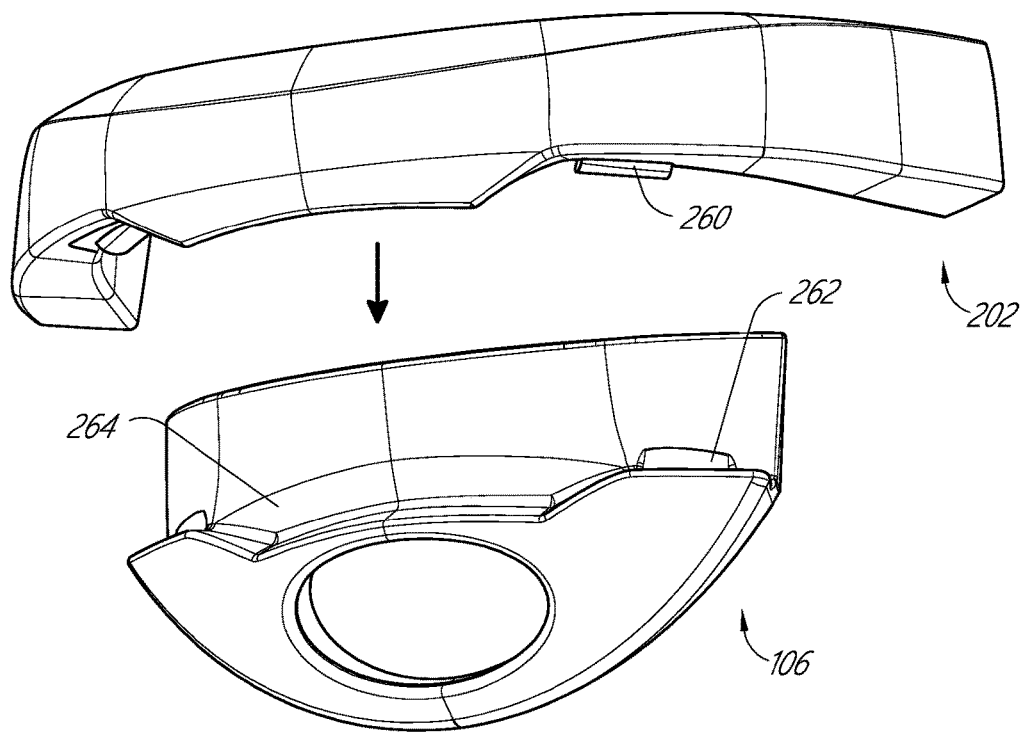
FIG. 59A is an exploded front perspective view of another form of frame and yoke configuration and demonstrating one method of locating the yoke within the channel of the frame.
Figure 59B:
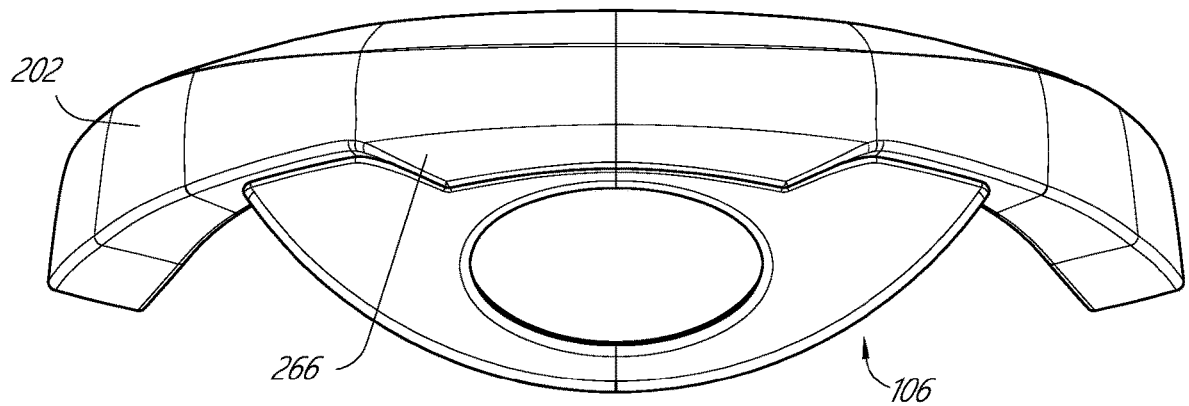
FIG. 59B is a front view of the frame and yoke of FIG. 59A when attached together.

In another form, as shown in FIGS. 59A and 59B, the frame 106 may comprise a recessed region forming a channel that comprises only a rear surface and a lower wall comprising a lower surface. The channel may extend across the body of the frame from the left side to the right side. The yoke may be configured to be positioned within the channel. The yoke and frame may comprise one or more attachment features to hold the yoke in position. For example, the bottom surface of the yoke may comprise one or more projecting tabs or protrusions 260 configured to engage with one or more corresponding engagement recesses 262 formed in the lower surface 160 of the channel 154. Alternatively or additionally, one or more tabs or protrusions may project from the lower surface of the channel and may be configured to engage with one or more corresponding engagement recesses formed in the bottom surface of the yoke. In one form, the lower surface of the channel comprises a recessed region 264 and the bottom surface of the yoke comprises a protruding region 266 configured to sit within the recessed region when the yoke is located within the channel of the frame. Optionally, the rear surfaces of the channel 154 and yoke 202 may each comprise one or more attachment features in the form of magnets for attaching the yoke and frame together. The channel magnet(s) may be positioned off-centre from a centre line extending along the length of the channel, so that the magnet(s) is/are closer to the lower surface of the channel. Similarly, the yoke 202 may comprise one or more magnets that may be positioned off-centre from a centre line extending along the length of the yoke 202, so that the magnets are closer to the top surface of the yoke 202 than to the bottom surface. In this configuration, when the yoke 202 is located within the channel 154, the magnetic attraction between the yoke 202 and frame 106 causes the yoke 202 to be pulled downwardly so that the bottom surface of the yoke 202 abuts the lower surface of the channel 154. As the bottom surface of the yoke 202 abuts the lower surface 160 of the channel 154, any protrusions projecting from the bottom surface of the yoke are received within corresponding recesses formed in the lower surface of the channel. Similarly, any protrusions projecting from the lower surface of the channel are received within corresponding recesses formed in the bottom surface of the yoke.

Figure 60:
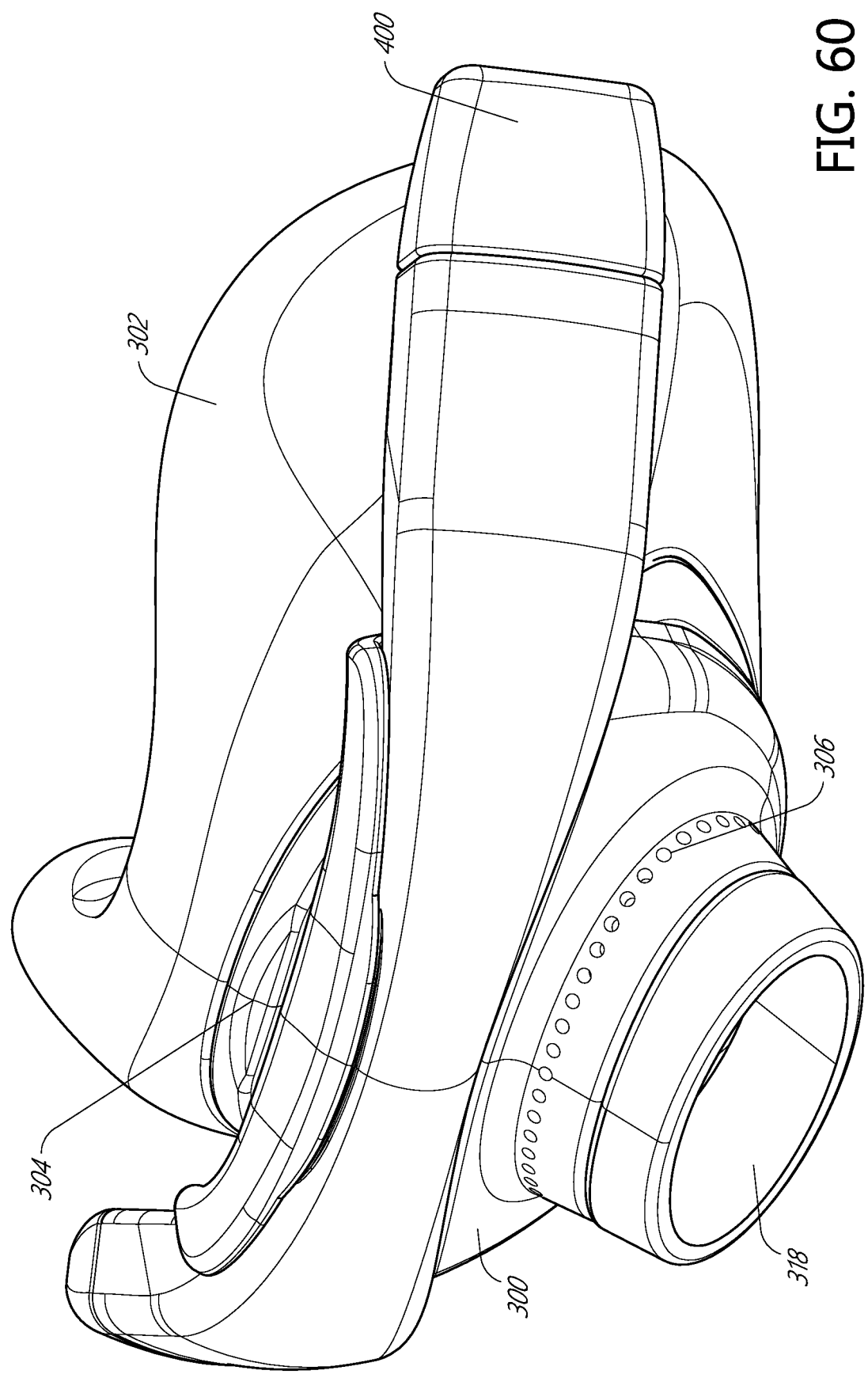
FIG. 60 is a perspective view of an example embodiment of an assembled frame, cushion, and yoke.
Figure 63:
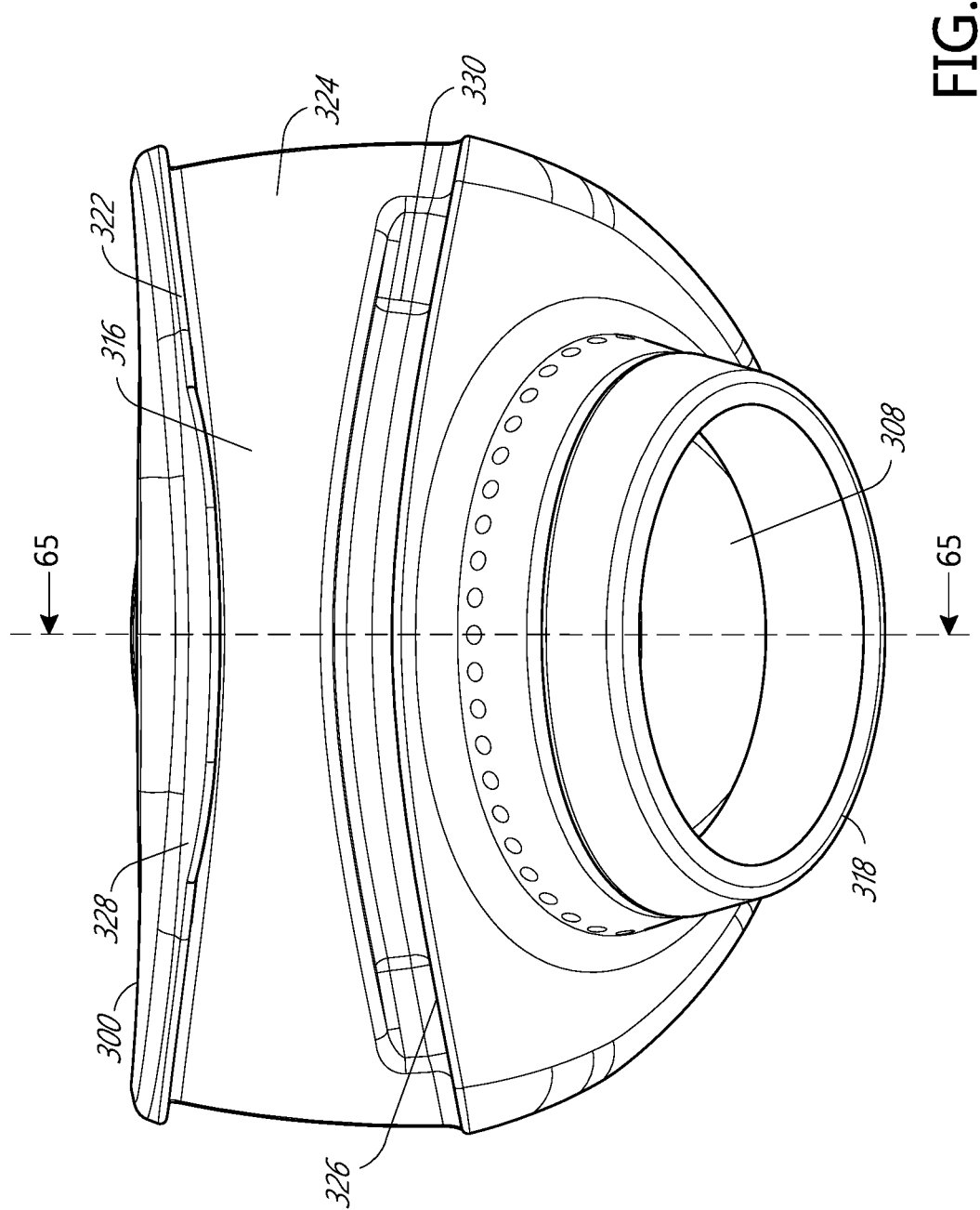
FIG. 63 is a front view of the frame of FIG. 60.
Figure 65:
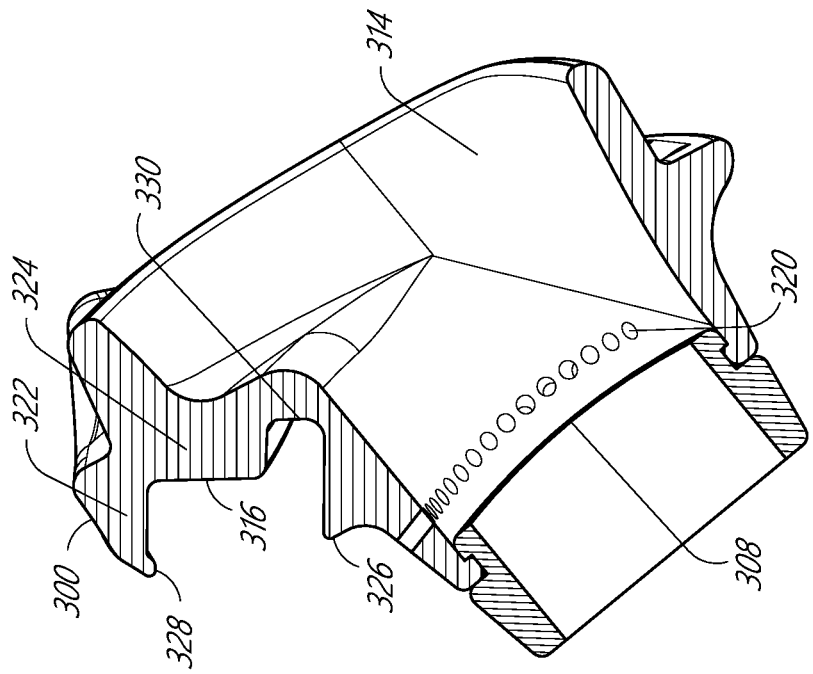
FIG. 65 is a side cross-sectional view of the frame of FIGS. 63-64.
Figure 64:
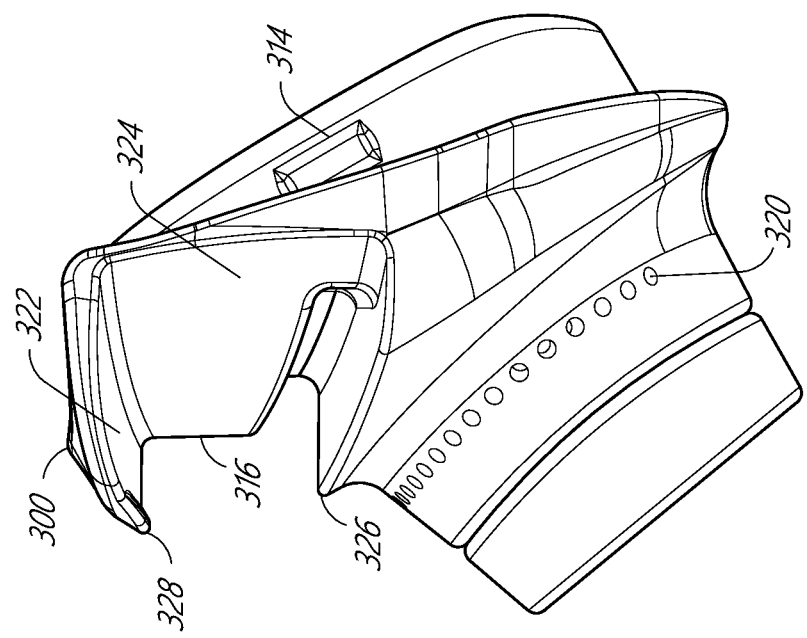
FIG. 64 is a side view of the frame of FIG. 63.

FIG. 60 illustrates another example embodiment of a yoke 400 and cushion 302 coupled to a frame 300. As shown in FIGS. 63-65, the frame 300 includes an inlet 308, a cushion connection flange 314, and a yoke channel 316.

A tube or gases conduit can be coupled to the inlet 308 via a tube over-mold 318 coupled to the inlet 308. In some embodiments, the inlet 308 has an elliptical shape. In some embodiments, the inlet includes a bias vent 320. In the illustrated embodiment, the bias vent 320 includes a plurality of holes extending through a wall of the inlet 308. The holes of the bias vent 320 can extend around part or all of a circumference of the inlet 308. The holes can be laser drilled through the inlet wall.

The cushion connection flange 314 projects rearwardly from the frame 300. For use, the cushion 302 is coupled to the cushion connection flange 314 to secure the cushion 302 to the frame 300. In some embodiments, the cushion 302 includes, or is coupled to, a cushion clip 304, for example, as shown in FIGS. 60-62, and the cushion clip 304 couples to the cushion connection flange 314 in use to secure the cushion 302 to the frame 300. In some embodiments, when the cushion 302 is coupled to the frame 300, the cushion connection flange 314 protrudes slightly into the cushion 302. The cushion connection flange 314 can have a shape or profile that matches or corresponds to a shape or profile of an inlet of the cushion 302.

As shown in FIGS. 63-65, the yoke channel 316 is formed or defined by an upper wall 322, rear wall 324, and lower wall 326. In the illustrated embodiment, the yoke channel 316 extends substantially horizontally across the frame 300. In the illustrated embodiment, the yoke channel 316 is positioned above the inlet 308. The yoke channel 316 is configured to receive the yoke 400 in use. The yoke channel 316 has a shape, profile, and/or geometry that matches or corresponds to the shape, profile, and/or geometry of the yoke 400.

As described herein, the yoke 400 connects headgear to the frame 300 and cushion 302. The yoke 400 can also house core elements, such as filaments 442, of a one-way friction, automatically adjusting, or self-adjusting headgear adjustment mechanism as described herein. In the illustrated embodiment, the yoke 400 is generally C-shaped when viewed from the top or bottom. In the illustrated embodiment, a height of the yoke 400 is greater at lateral ends (e.g., adjacent and/or at end caps 406) than at a center. Such a configuration can advantageously help minimize or reduce the size of the mask as a whole.

As shown in FIGS. 66-71, in the illustrated embodiment, the yoke 400 includes a yoke front 402, a yoke back 404, and two end caps 406, one at each lateral end of the yoke 400. In the illustrated embodiment, the yoke front 402 and yoke back 404 are formed as separate components that are coupled together. In the illustrated embodiment, the yoke front 402 includes a top wall 408, a front wall 409, and a bottom wall 410. An external side or surface of the front wall 409 can be rounded. The top wall 408 and bottom wall 410 extend substantially perpendicularly from upper and lower edges, respectively, of the front wall 409. The top wall 408 and bottom wall 410 are therefore substantially parallel to each other. The yoke front 402 can form a D-shaped cross-sectional profile.

Figure 71:
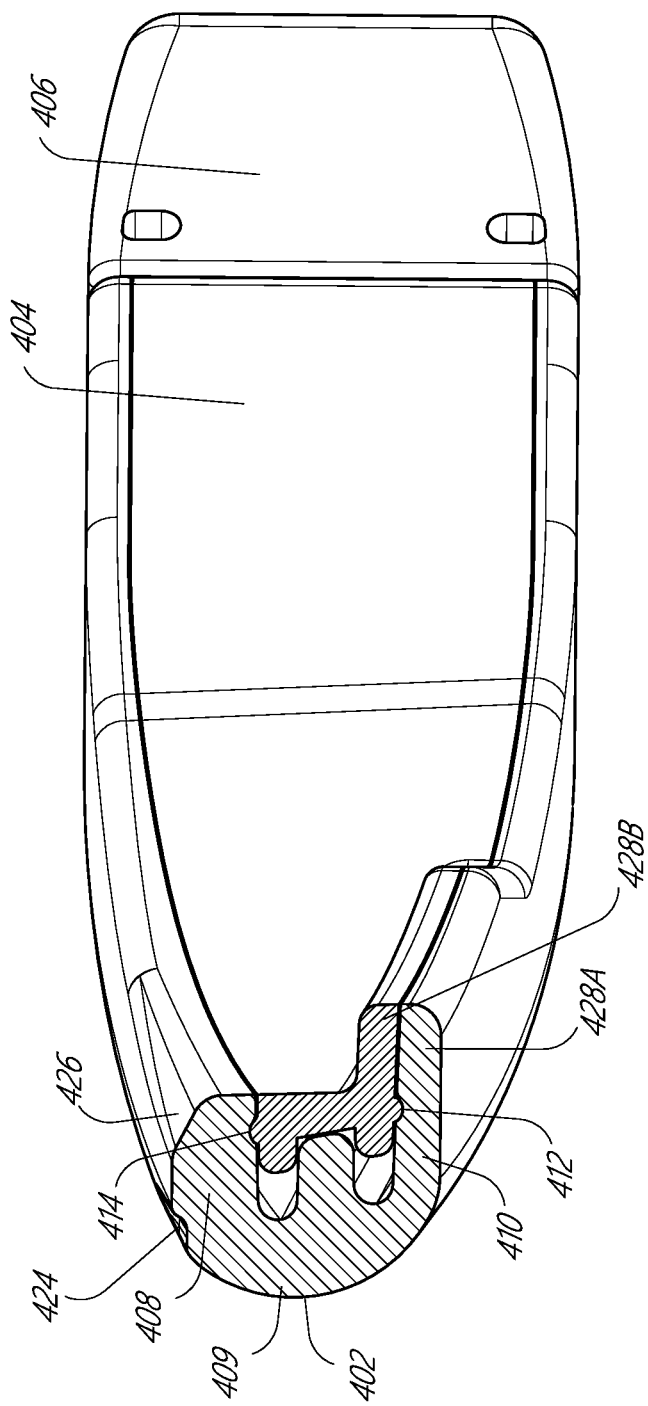
FIG. 71 is a side cross-sectional view of the yoke of FIG. 66.

The yoke front 402 and yoke back 404 can be coupled together via a snap fit. The yoke back 404 snap fits between the top wall 408 and bottom wall 410 as shown in FIG. 71. In the illustrated embodiment, the yoke back 404 includes snap-fit bumps 412 positioned on upper and lower edges or surfaces of the yoke back 404. In some embodiments, the snap-fit bumps 412 extend longitudinally between the lateral ends along a portion or an entirety of a length of the yoke 400. As shown in FIG. 71, the snap-fit bumps 412 fit into corresponding snap-fit grooves 414 formed in internal surfaces of the top wall 408 and bottom wall 410 of the yoke front 402. In some embodiments, the yoke back 404 may include only one of the snap-fit bumps 412 and the yoke front 402 may include only the corresponding snap-fit groove 414. In some embodiments, the yoke front 402 includes snap-fit bump(s) 412 and the yoke back 404 includes corresponding snap-fit groove(s) 414. A cavity or space is formed between the yoke front 402 and yoke back 404. In other words, the yoke 400 is hollow.

The end caps 406 can also help secure the yoke front 402 and yoke back 404 together by clipping over or snap fitting over or onto the lateral ends of the yoke front 402 and yoke back 404. As shown in FIGS. 73A-73B, the lateral ends of the yoke front 402 include or are formed by end cap inserts 418. The end cap inserts 418 can be integrally formed with or attached, permanently or removably, to the lateral ends of the yoke front 402. The end cap inserts 418 have walls that are inwardly offset from the top wall 408, front wall 409, and bottom wall 410 of the yoke front 402. As shown in FIGS. 74-77, lateral ends of the yoke back 404 can include or be formed by end cap inserts 420. The end cap inserts 420 can be integrally formed with or attached, permanently or removably, to the lateral ends of the yoke back 404. As shown in FIGS. 74-77, each of the end cap inserts 420 includes an alignment peg 422 that fits inside the corresponding end cap insert 418 of the yoke front 402. In the illustrated embodiment, the alignment peg 422 of one of the end cap inserts 420 (on one end of the yoke back 404) is positioned proximate a top or upper surface of the yoke back 404, and the other of the end cap inserts 420 (on the other end of the yoke back 404) is positioned proximate a bottom or lower surface of the yoke back 404. When the yoke front 402 and yoke back 404 are coupled together, the alignment pegs 422 fit inside the end cap inserts 418 of the yoke front 402.

When assembled, the end caps 406 snap onto and at least partially cover the end cap inserts 418, 420. The yoke front 402 can include end cap snap fit bump(s) 416 positioned on or proximate the lateral ends on upper and/or lower edges or surfaces of the yoke front 402. In the illustrated embodiment, the end cap snap fit bumps 416 extend transversely across a portion or entirety of a thickness or width of the yoke front 402. The end cap snap fit bumps 416 can be positioned on top and bottom surfaces of the end cap inserts 418 as shown in FIGS. 73A-73B. Each of the end caps 406 can be coupled to one of the front straps of the headgear. In some embodiments, the end caps 406 can be over-molded onto an end of a braided element of an automatic headgear adjustment mechanism, for example, braided elements as shown and described in U.S. Provisional Patent Application No. 62/343,711, entitled "Directional Lock for Interface Headgear Arrangement" and filed May 31, 2016, and PCT Application No. PCT/NZ2014/000074, the entireties of which are hereby incorporated by reference herein. The core elements or filaments 442 can extend within the braided elements. The end caps 406 can connect the braided element, and therefore the headgear, to the yoke 400 and create a closed loop headgear system.

Figure 61A:
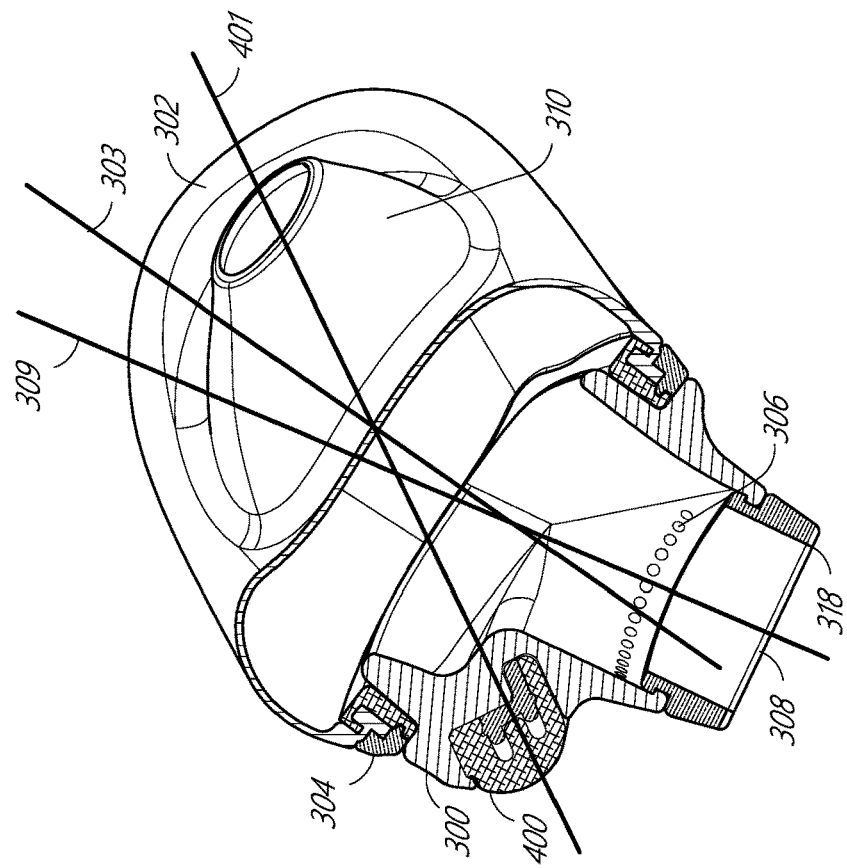
FIG. 61A is a side view of the assembly of FIG. 60 showing planes of connection between the illustrated components.
Figure 61B:
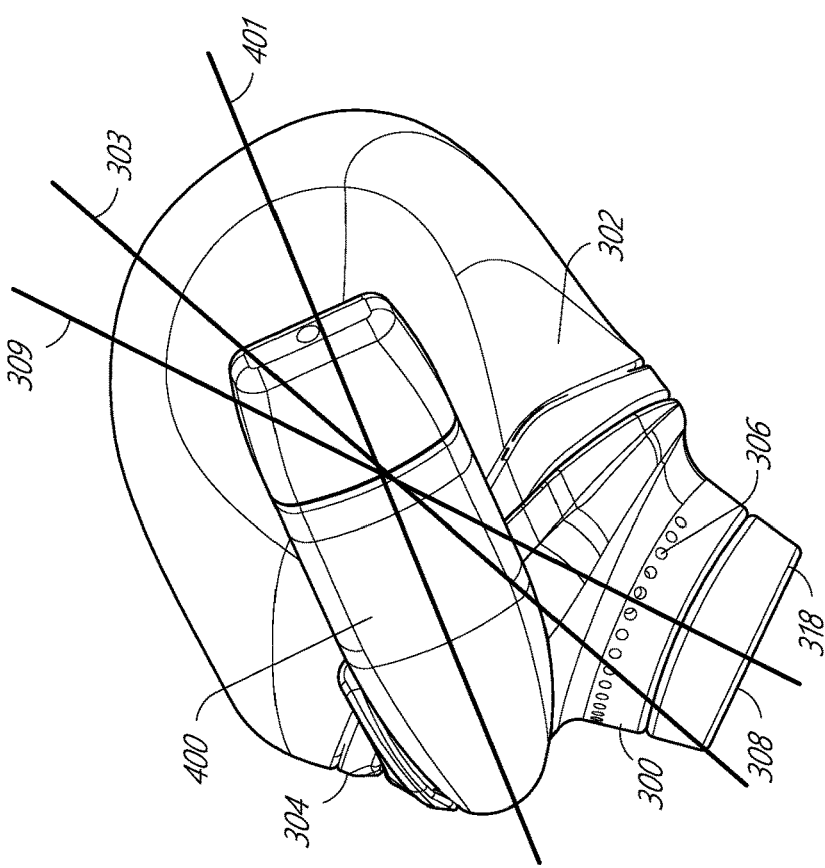
FIG. 61B is a side cross-sectional view of the assembly of FIGS. 60-61A showing the planes of connection.
Figure 62:
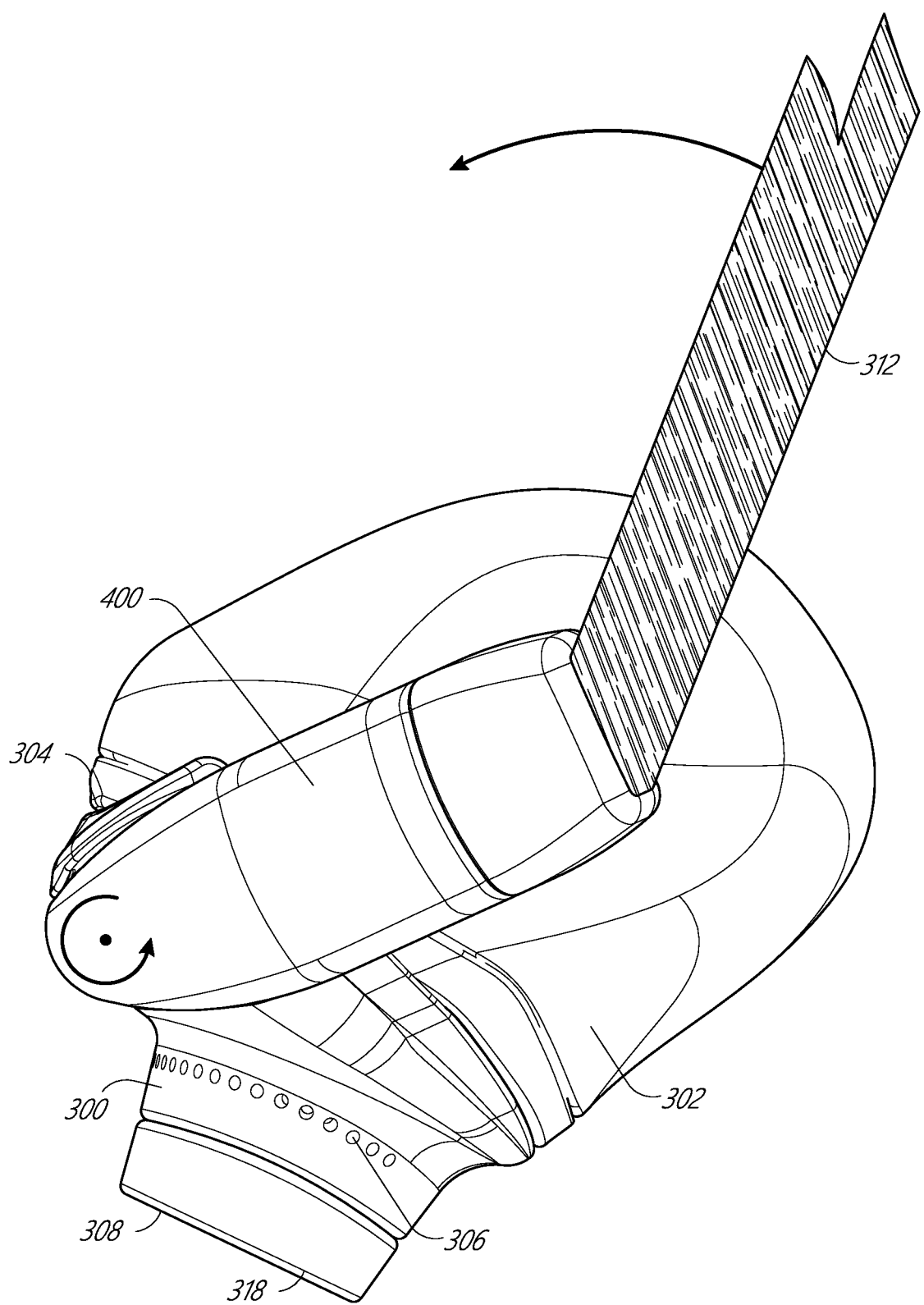
FIG. 62 is a side view of the assembly of FIG. 60 including a portion of a headgear strap showing forces that may be applied to or by the headgear strap in use.

As shown in FIGS. 61A-61B, the yoke 400 is assembled or coupled to the frame 300 in a plane (or along an axis) 401 different than a central plane (or axis) 309 extending through the inlet 308 and different than a plane (or axis) 303 along which the cushion 302 is coupled to the frame 300. In the illustrated embodiment, the inlet plane 309 is different than the cushion connection plane 303. As shown in FIG. 61B, the yoke plane 401 is aligned with or extends through the nasal prongs 310. When the mask system is disposed on the user's face, the alignment of the yoke plane 401 with the nasal prongs 310 advantageously allows the headgear to apply a force through the yoke 400 to pull the nasal prongs 310 toward the user's nares. In the illustrated embodiment, the cushion connection plane 303 and inlet plane 309 are more closely aligned (or closer to being aligned) with each other than either is with the yoke plane 401. This allows the cushion 302 to be coupled or attached to the frame 300 in a direction that is close to being aligned with the inlet 308, which may advantageously be intuitive for the user.

Due to the difference in angles between the cushion connection plane 303 and the yoke plane 401, the yoke 400 is coupled to the frame 300 in a different direction than the cushion 302 is coupled to the frame 300. This may be counter-intuitive for some users. If the user attempts to remove the yoke 400 from the frame 300 along the same direction as the cushion connection plane 303, the yoke 400 may bind or catch on the frame 300, increasing removal forces and making it more difficult to disconnect the yoke 400. Therefore, it can be beneficial if the yoke 400 is relatively easy and requires minimal force to connect to and disconnect from the frame 300 while still maintaining an effective connection during use. During donning and doffing of the mask, the headgear 312 may be pulled upwards at an angle relative to the yoke plane 401, as shown in FIG. 62. This can create a rotational force or torque on the connection between the yoke 400 and the frame 300. If the torque generated is great enough, the yoke 400 could become unintentionally disconnected from the frame 300, making it more difficult to don and/or doff the mask. Various features as described herein can help address these potential issues.

Figure 66:
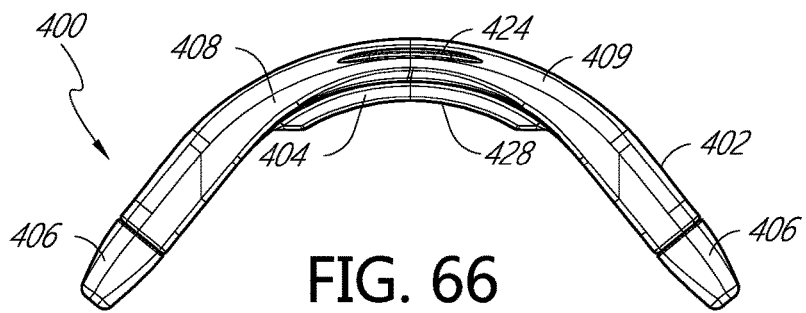
FIG. 66 is a top view of the yoke of FIG. 60
Figure 69:
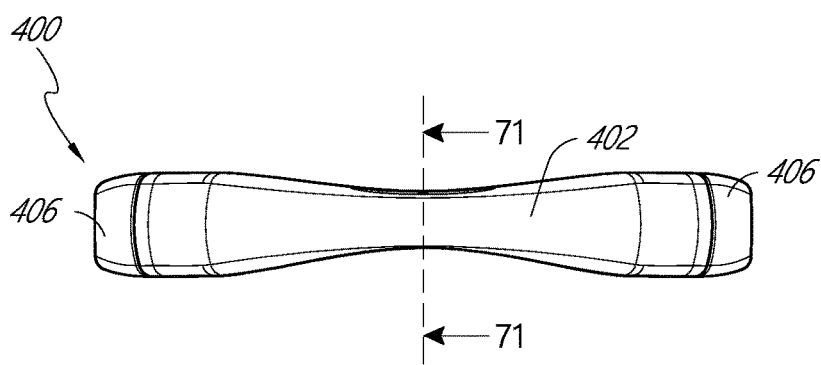
FIG. 69 is a front view of the yoke of FIG. 66.

As shown in FIGS. 63-65, the frame 300 can include a retention bump 328. The retention bump 328 protrudes downwardly from a forward and bottom edge of the upper wall 322 toward and/or into the yoke channel 316. In the illustrated embodiment, the retention bump 328 extends from a mid-portion of the upper wall 322. The retention bump 328 forms a relatively narrower opening for a portion of the yoke channel 316. As shown in FIGS. 66 and 69, the yoke 400 (the yoke front 402 in the illustrated embodiment) includes a retention notch 424. In the illustrated embodiment, the retention notch 424 is located at or near a corner formed between the top wall 408 and front wall 409 of the yoke front 402. The retention notch 424 can form a scalloped region. In the illustrated embodiment, the retention notch 424 is located at a mid-portion of the yoke front 402. The retention notch 424 is configured to receive the retention bump 328 of the frame 300 when the frame 300 and yoke 400 are coupled together to form a snap-fit connection between the frame 300 and yoke 400. A width of the retention bump 328 and retention notch 424 can affect or at least partially determine the force needed to connect and/or disconnect the yoke 400 and frame 300. In the illustrated embodiment, the retention bump 328 and retention notch 424 are narrower than the yoke channel 316 such that the force needed to connect and/or disconnect the yoke 400 and frame 300 is sufficiently low to allow for an easy connection that is still effective in securing the yoke 400 to the frame 300.

Figure 67:
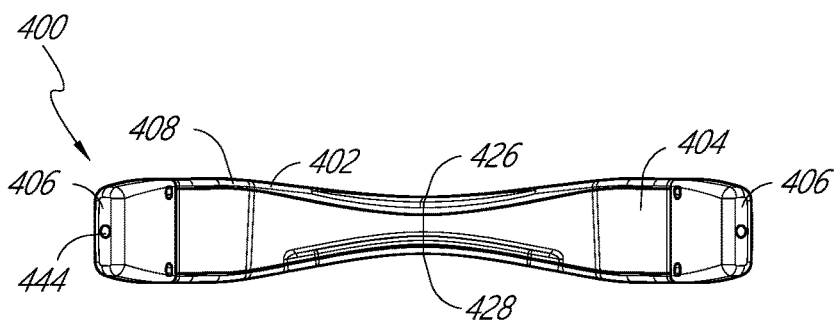
FIG. 67 is a back or rear view of the yoke of FIG. 66.
Figure 68:
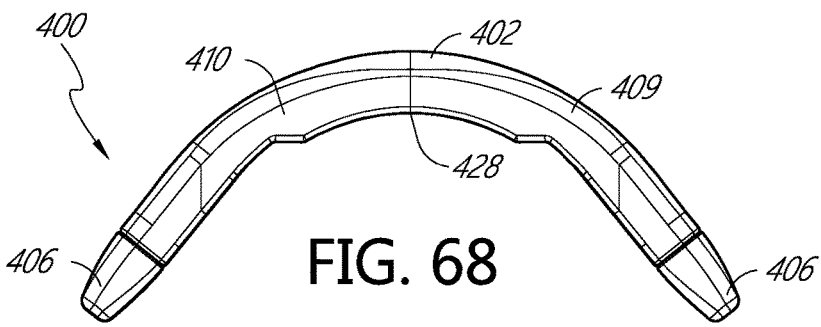
FIG. 68 is a bottom view of the yoke of FIG. 66.

In some embodiments, for example as shown in FIGS. 67 and 71-72, the yoke front 402 includes a lead-in chamber 426. The lead-in chamfer 426 is a chamfered or radiused edge along a rear upper edge of the top wall 408. The lead-in chamfer 426 can help guide the yoke 400 past the retention bump 328 to help improve the ease of insertion of the yoke 400 into the yoke channel 316. In some embodiments, the frame 300 and yoke 400 need not include the retention bump 328 and retention notch 424, respectively. Tension applied to the yoke 400 and/or frame 300 by the headgear can help secure the yoke 400 and frame 300 together instead of or in addition to a snap fit between a retention bump 328 and retention notch 424.

The yoke channel 316 can include an anti-rotation groove 330 that is recessed into the rear wall 324 and extends along a portion or an entirety of the length of the yoke channel 316 as shown in FIGS. 63-65. In the illustrated embodiment, the anti-rotation groove 330 is positioned adjacent the lower wall 326 of the frame 300. The yoke 400 includes a corresponding tongue 428 (shown in FIGS. 66-68) that is received in the anti-rotation groove 330 when the yoke 400 and frame 300 are coupled together. As shown in FIG. 71, a central region of the bottom wall 410 of the yoke front 402 extends deeper or protrudes rearward to a greater extent than lateral ends of the yoke front 402 to form a front tongue 428a. As shown in FIGS. 71 and 77, a central region of a bottom of the yoke back 404 extends rearward to a greater extent than lateral ends of the yoke back 404 to form a back tongue 428b. The back tongue 428b protrudes perpendicularly from the central region of the bottom of the yoke back 404 to form an "L" shaped cross-section. The front tongue 428a and back tongue 428b are aligned with and abut each other such that the front tongue 428a is positioned beneath the back tongue 428b as shown in FIG. 71. Having the tongue 428 formed in two parts (the front tongue 428a and back tongue 428b) can advantageously help improve the connection between the yoke front 402 and yoke back 404. A two-part configuration can allow rotational forces applied to the yoke 400 and/or frame 300 to be applied to both the yoke front 402 and yoke back 404 simultaneously to help reduce or minimize distortion of the yoke front 402 and yoke back 404 relative to each other that could cause disconnection of the yoke front 402 and yoke back 404. During rotation, the front tongue 428a and back tongue 428b are pinched together by contact with the anti-rotation groove 330 (as shown in FIG. 82), which can help reinforce the connection between the yoke front 402 and yoke back 404.

Figure 80:
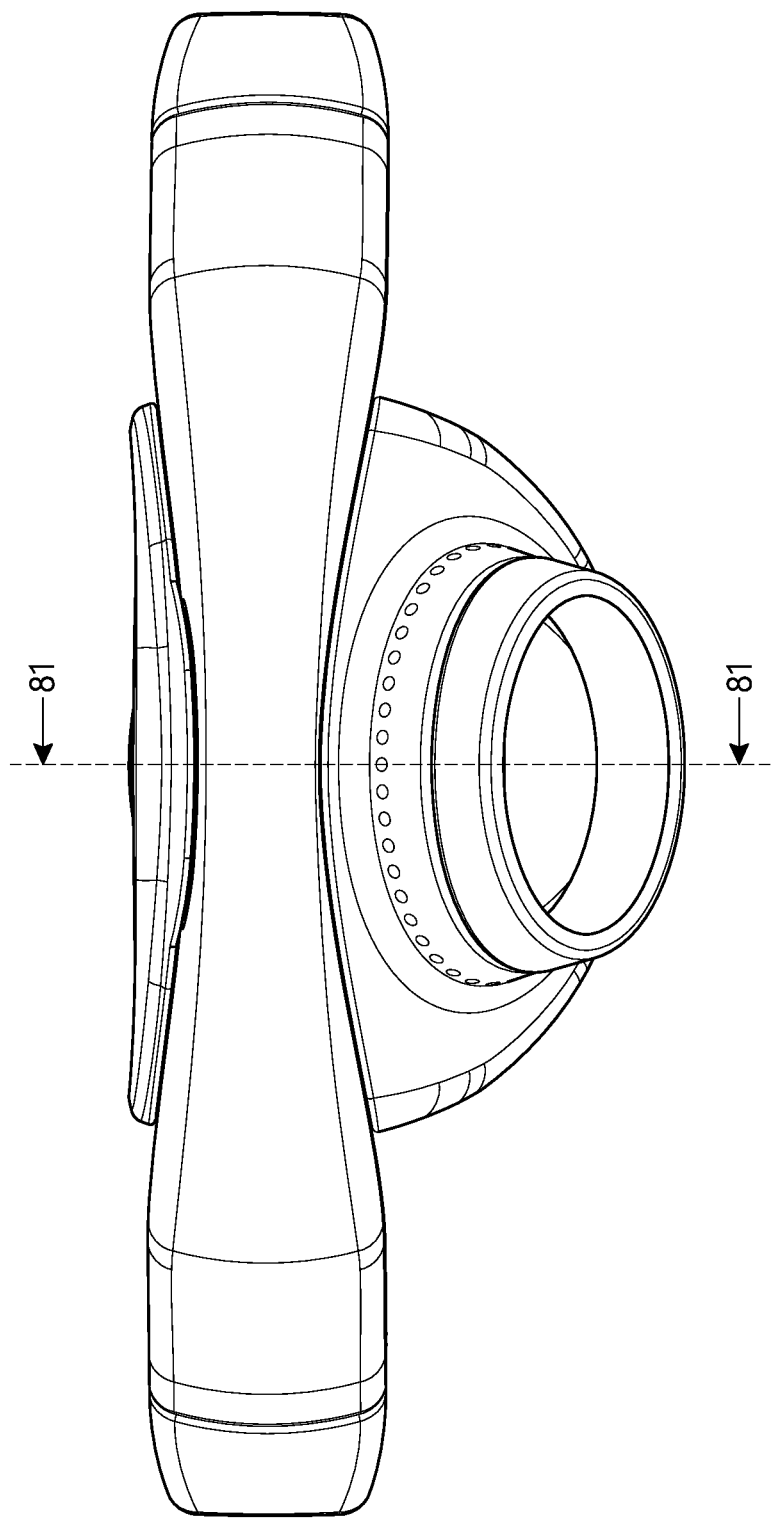
FIG. 80 is a front view of the yoke assembled to the frame.
Figure 81:
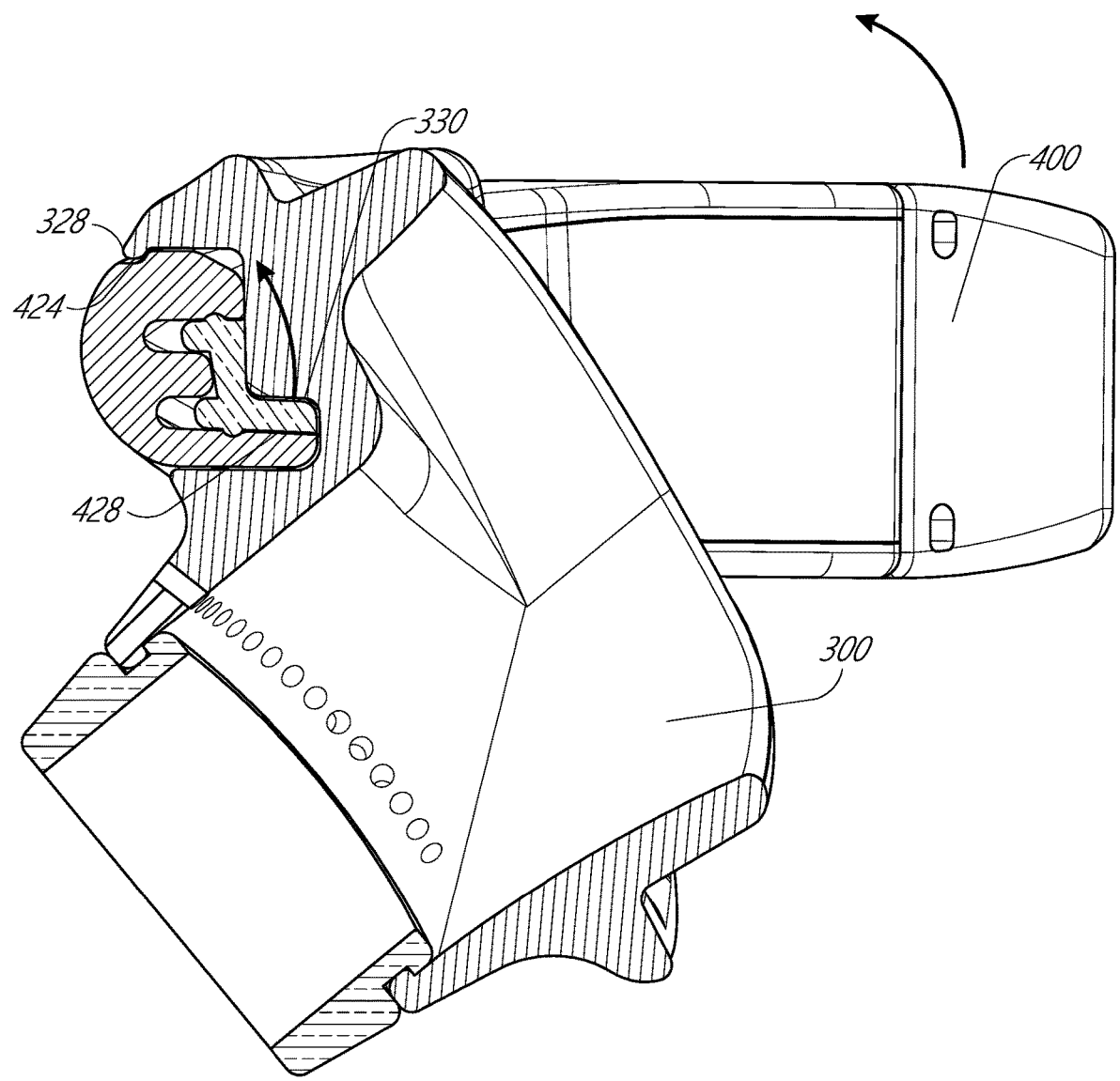
FIG. 81 is a section view of the yoke and frame taken along line 81-81 in FIG. 80.
Figure 82:
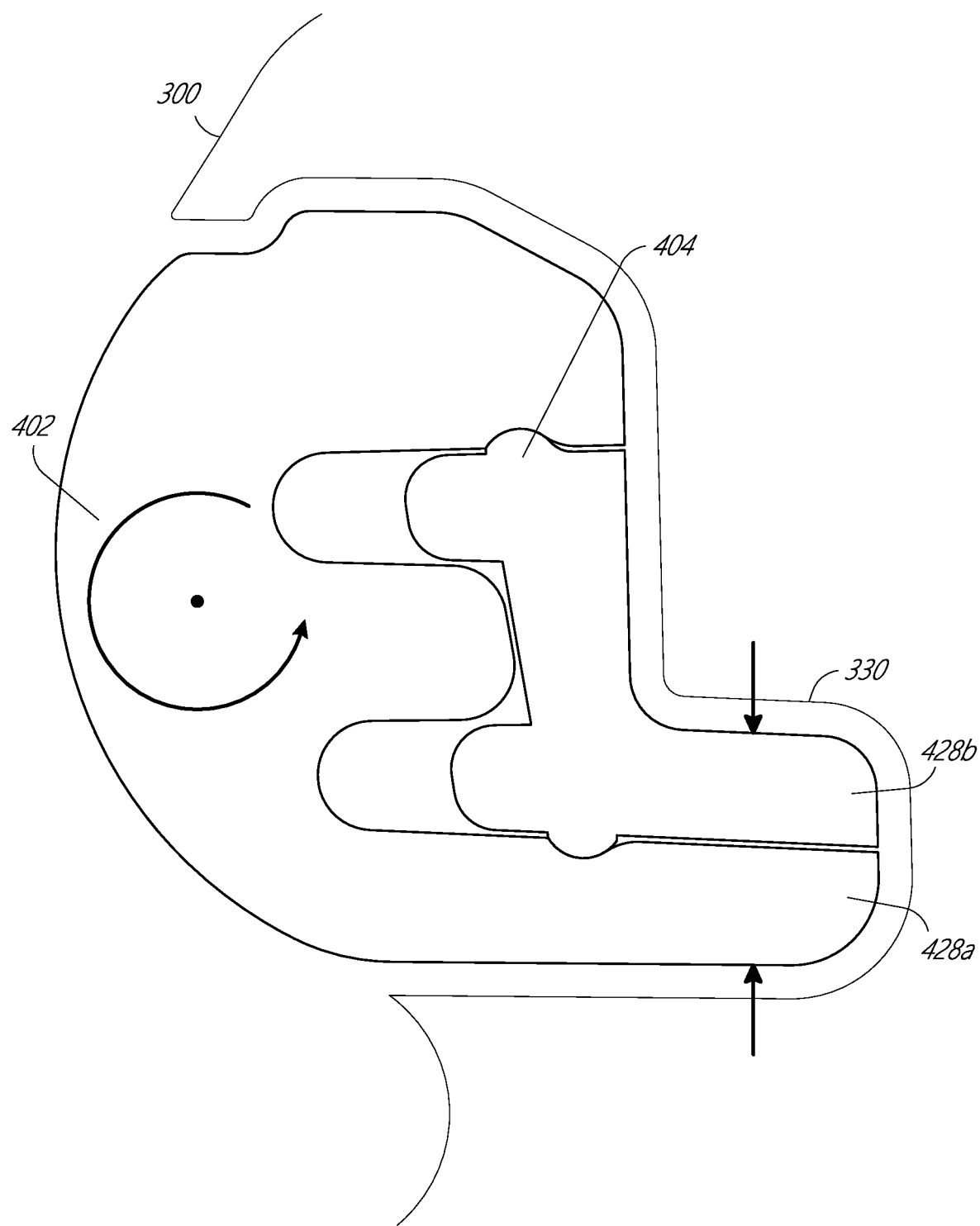
FIG. 82 is a schematic partial section view of the yoke coupled to the frame.
Figure 91:
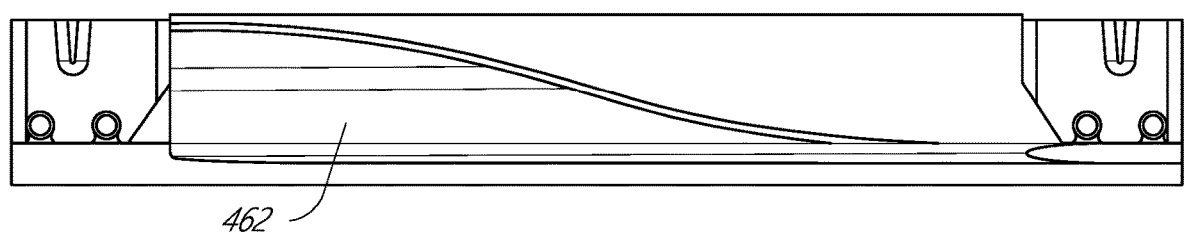
FIG. 91 is a rear view of an alternative embodiment of the yoke.
Figure 92:
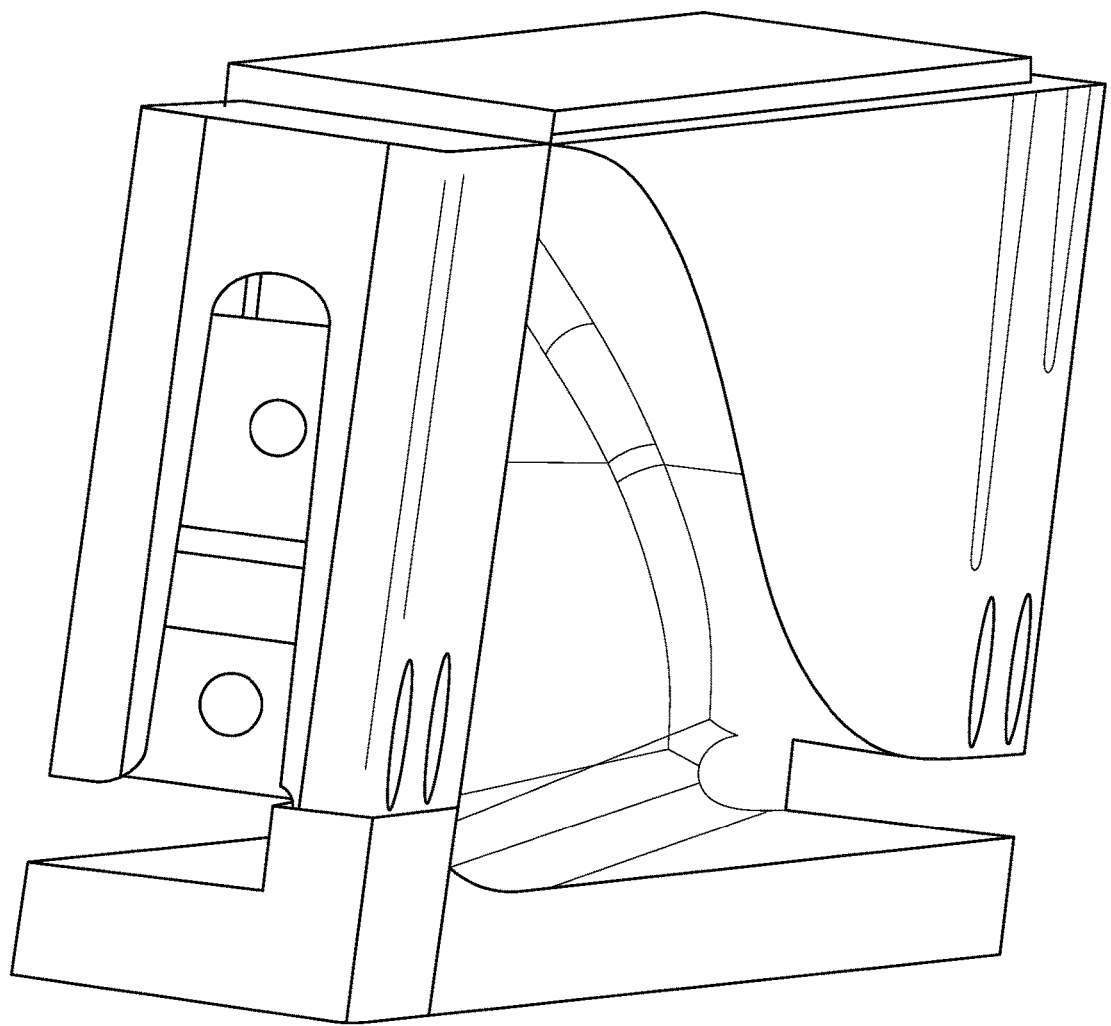
FIG. 92 is an end perspective view of the yoke of FIG. 91.
Figure 93:
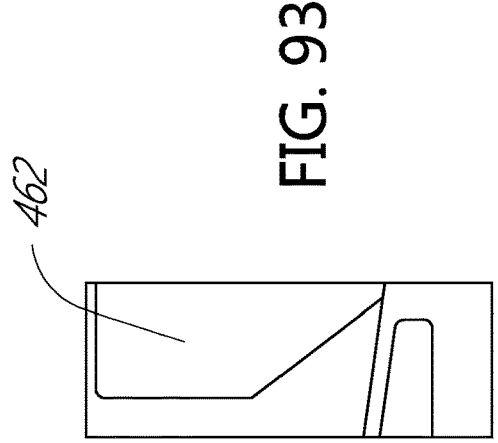
FIG. 93 is a schematic sectional view of the yoke of FIG. 91.
Figure 94:
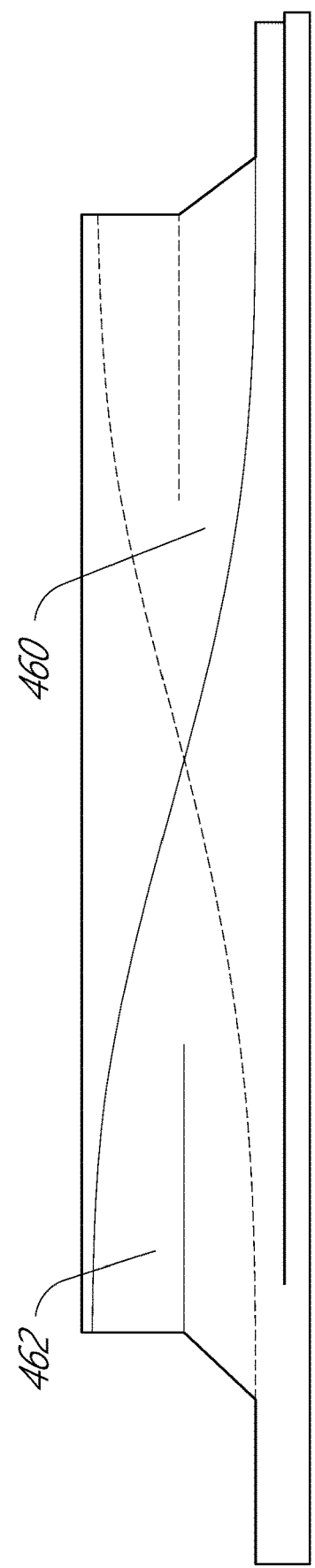
FIG. 94 is a schematic of the interior of the yoke of FIG. 91.

When the tongue 428 is disposed within the anti-rotation groove 330, as shown in FIGS. 80-82, the interaction between the tongue 428 and anti-rotation groove 330 helps prevent or inhibit the yoke 400 from rotating out of the yoke channel 316 if and when a rotational force is applied to the yoke 400, for example, via the headgear. In embodiments, including a retention bump 328 and retention notch 424, the retention bump 328 and retention notch 424 can help resist rotational disconnection of the yoke 400 from the frame 300 instead of or in addition to interaction between the tongue 428 and anti-rotation groove 330.

As described herein, in some embodiments, the yoke 400 may form a collector for core elements, such as filaments 442, used in an automatically adjustable or self-adjusting headgear system. As shown in FIGS. 71-73B, the yoke front 402 includes an upper line track 430 and a lower line track 432. A line track divider 434 protrudes rearwardly from a rear or internal surface of the front wall 409 of the yoke front 402. As shown in FIGS. 72-73A, the line track divider 434 extends generally at a diagonal across a portion of the length of the yoke front 402. In other words, one end of the line track divider 434 is proximate the top wall 408, and the other, opposite end of the line track divider 434 is proximate the bottom wall 410. The upper line track 430 is therefore bounded and/or defined by a bottom surface of the top wall 408, the rear surface of the front wall 409, and an upper surface of the line track divider 434. The lower line track 432 is bounded and/or defined by a top surface of the bottom wall 410, the rear surface of the front wall 409, and a lower surface of the line track divider 434.

Figure 70:
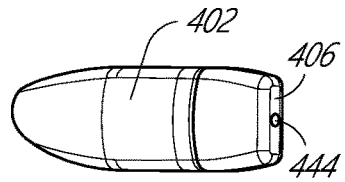
FIG. 70 is a side view of the yoke of FIG. 66.
Figure 74:
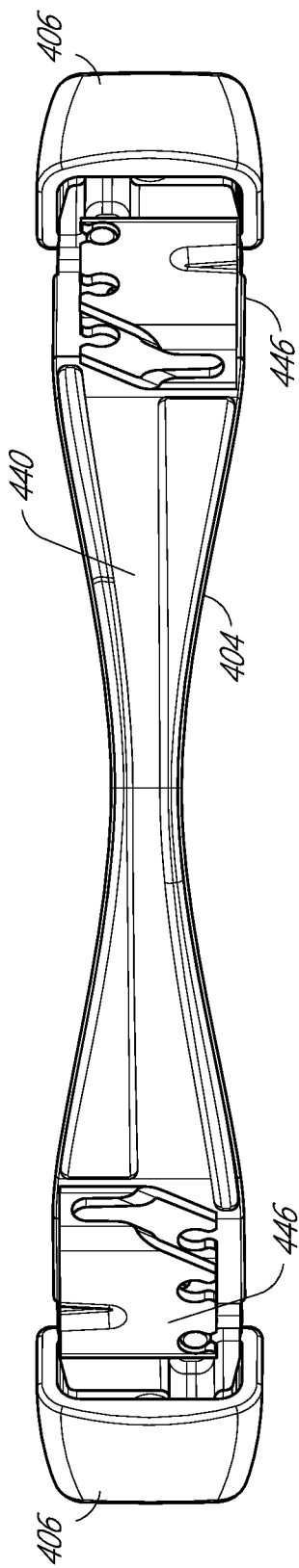
FIG. 74 is a front view of a yoke back portion of the yoke of FIG. 66 including the washer housings and end caps.
Figure 79:
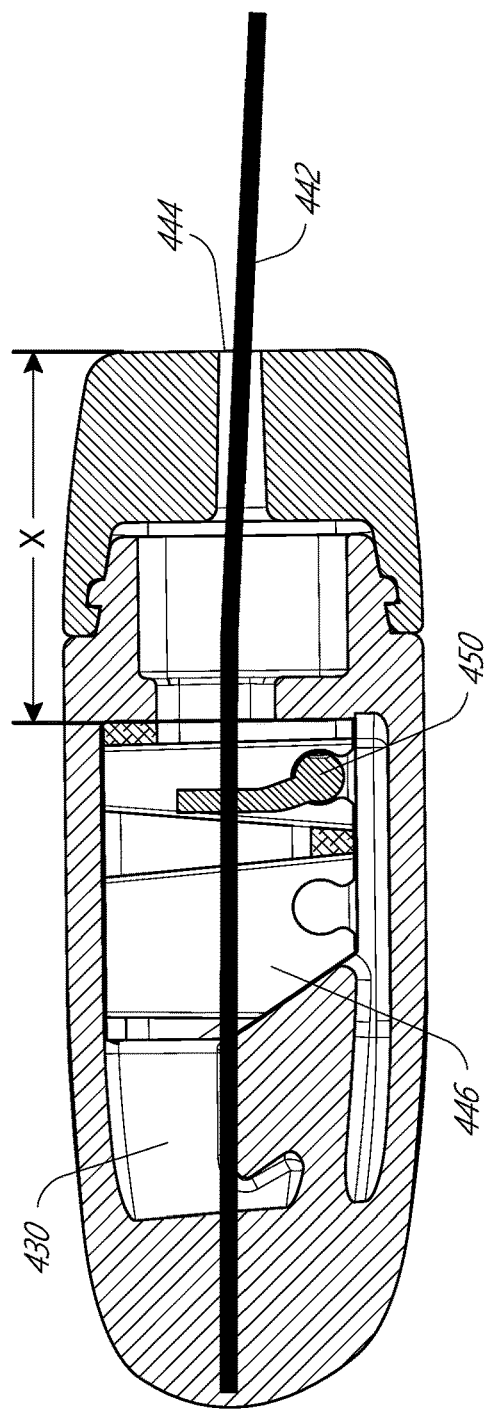
FIG. 79 is a section view of a lateral portion of the yoke front.

The upper 430 and lower 432 line tracks receive the filaments 442 of the automatically adjustable headgear system. The filaments 442 extend from portions of the headgear coupled to and/or adjacent the yoke 400. As shown in FIGS. 67 and 70, the end caps 406 include filament entry holes 444. The filament entry holes 444 help guide filaments 442 into the yoke 400, for example, from the braid component of the headgear. The filaments 442 pass from the headgear, through the entry holes 444, into the hollow yoke 400. As shown in FIGS. 72 and 74, the yoke 400 includes a washer housing 446 disposed adjacent (and medial of) each end cap 406. Each washer housing 446 can fit or be disposed in a washer housing pocket 448 formed by the yoke front 402, as shown in FIG. 73A. The washer housings 446 house one or more washers 450 (as shown in FIG. 79) that act as part of a locking mechanism for the automatically adjustable headgear system. An example of such a locking mechanism is shown and described in U.S. Provisional Patent Application No. 62/343,711, which has been incorporated by reference herein. A first filament passes through a first of the end caps 406 and washer(s) 450 in a first of the washer housings 446 into the upper line track 430. A second filament passes through a second of the end caps 406 and washer(s) 450 in a second of the washer housings 446 into the lower line track 432.

As shown in FIGS. 72-73A, the upper line track 430 is wider toward a first end of the yoke front 402 and narrows toward a second end. The lower line track 432 is wider toward the second end of the yoke front 402 and narrows toward the first end. The upper 430 and lower 432 line tracks have greater heights or widths at the end at which a filament 442 enters the line track. This can advantageously help prevent or inhibit sharp bends from forming in the filament 442 immediately or soon after the filament 442 exits the washer housing 446, which can help the washer(s) 450 properly engage with the filament 442. This can also or alternatively help prevent or inhibit the filament 442 from getting caught on internal geometry of the yoke 400 during retraction of the filament 442 and headgear.

Figure 78:
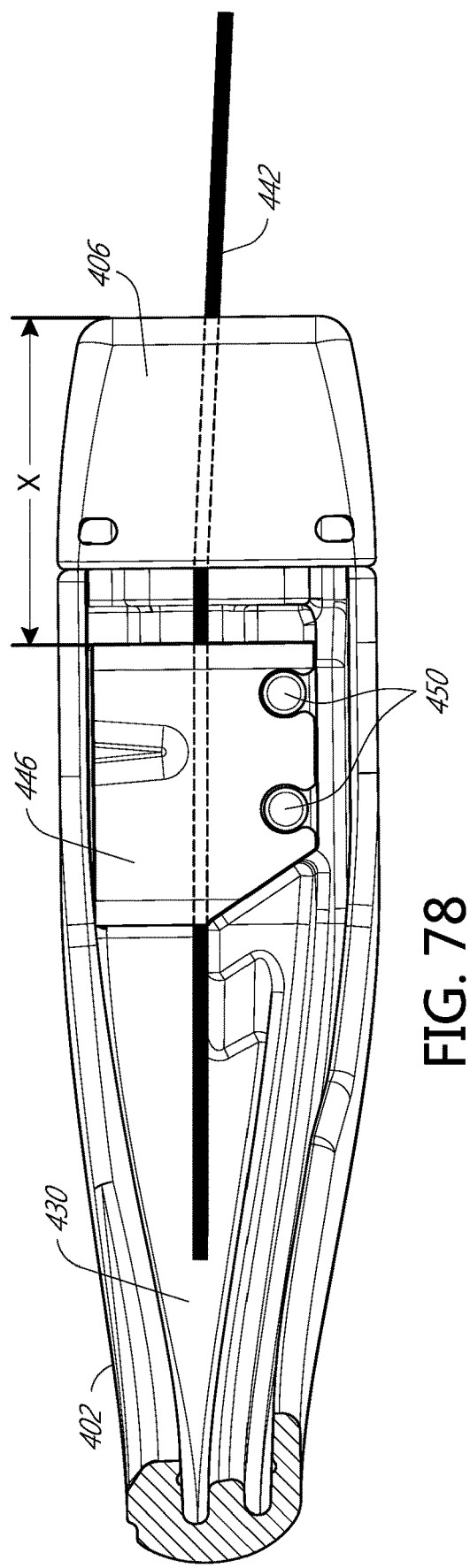
FIG. 78 is a view of the rear or interior of one lateral half of the yoke front.

As shown in FIGS. 78-79, the end caps 406 and/or filament entry holes 444 act as guides for the filaments 442, which can help improve the reliability of the function of the adjustment mechanism. In use, if the filament 442 is bent (for example, by the user) at a sharp angle close to where the filament 442 exits the washer housing 446, the washer(s) 450 may not be able to properly engage the filament 442 during extension of the headgear, which may distort the force displacement profile of the adjustment mechanism and prevent or inhibit the adjustment mechanism from working properly and/or effectively. Each end cap 406 provides an extension of the length or distance (indicated by X in FIGS. 78 and 79) that the filament 442 extends within the yoke 400 before entering the washer housing 446. The filament 442 is prevented or inhibited from being bent within the yoke 400 and end cap 406. The filament 442 may be bent by the user once the filament 442 exits the end cap 406 through the filament entry hole 444. However, the extended length X provided by the end cap 406 allows any bends formed in the filament 442 outside the yoke 400 to be offset or spaced from the washer housing 446 to a greater extent. This advantageously helps the filament 442 extend through the washer housing 446 substantially parallel to the walls of the washer housing 446 and/or end cap 406, which can help the washer(s) fully and properly engage the filament 442 during adjustment.

In the illustrated embodiment, the upper line track 430 extends above the washer housing 446 on the second end of the yoke 400 (the end opposite that at which a filament 442 enters the upper line track 430), and the lower line track 432 extends below the washer housing 446 on the first end of the yoke 400 (the end opposite that at which a filament 442 enters the lower line track 432). The extension of the upper 430 and lower 432 line tracks above and below, respectively, the opposite washer housings 446 advantageously allows a shorter yoke 400 to accommodate the same length filaments 442 (compared to a yoke 400 in which the upper 430 and lower 432 line tracks end medial to the washer housings 446). A shorter yoke 400 can advantageously prevent or inhibit the lateral ends of the yoke 400 from digging into the user's cheeks in use. With this configuration (with the upper 430 and lower 432 line tracks extending above and below the opposite washer housings 446), the washer housings 446 are vertically offset from one another, as shown in FIG. 74, to allow the yoke 400 to be symmetrical.

Figure 75:
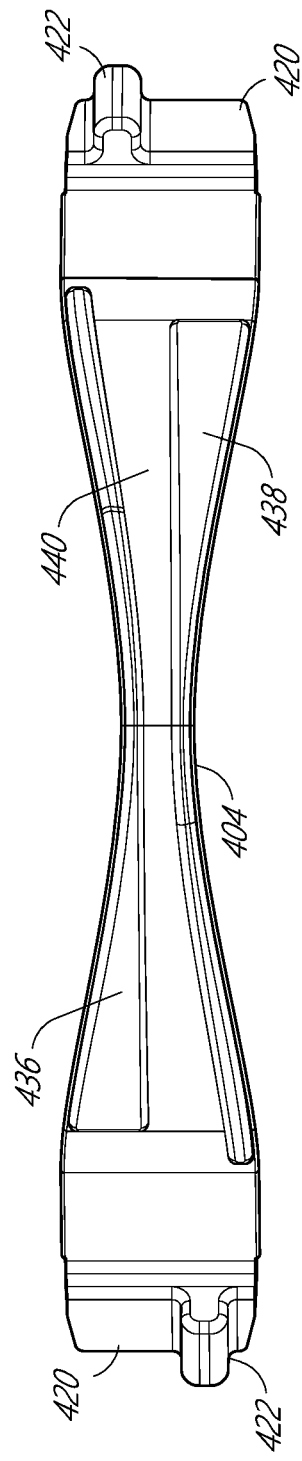
FIG. 75 is a front view of the yoke back with the washer housings and end caps removed.

As shown in FIGS. 74-75, the yoke back 404 includes an upper line track insert 436 and a lower line track insert 438. The upper line track insert 436 and lower line track insert 438 protrude forward from a front or internal surface the yoke back 404. The upper line track insert 436 at least partially fits within the upper line track 430 of the yoke front 402, and the lower line track insert 438 at least partially fits within the lower line track 432 of the yoke front 402. The upper line track insert 436 and lower line track insert 438 can have shapes that correspond to the shapes of the upper 430 and lower 432 line tracks, respectively. For example, the upper line track insert 436 is wider proximate a first end of the yoke back 404 configured to be placed adjacent the first end of the yoke front 402, and the lower line track insert 438 is wider proximate a second end of the yoke back 404 configured to be placed adjacent the second end of the yoke front 402. A divider channel 440 extends longitudinally between and is defined by the upper line track insert 436 and lower line track insert 438. The yoke back 404 has a reduced wall thickness in the region of the divider channel 440 compared to in the regions of the upper line track insert 436 and lower line track insert 438. The divider channel 440 receives the line track divider 434 of the yoke front 402. This can advantageously help promote the correct alignment of the yoke front 402 and yoke back 404 and/or can help reduce or minimize the overall depth or thickness of the yoke 400.

The upper line track insert 436 and lower line track insert 438 reduce the depth or height of the line tracks 430, 432. The reduced depth or height helps to better guide the filaments 442 within the line tracks 430, 432. The upper line track insert 436 and lower line track insert 438 can also or alternatively provide increased structure and rigidity to the yoke back 404, which can help prevent or inhibit the yoke back 404 from become detached from the yoke front 402 if the yoke 400 is bent. The interaction between the upper line track insert 436 and lower line track insert 438 and the upper 430 and lower 432 line tracks, respectively, can help align the yoke front 402 and yoke back 404 to help prevent or inhibit incorrect assembly.

FIGS. 83-84 illustrate an alternative embodiment of the yoke back 404 and end caps 406. In the illustrated embodiment, the alignment peg 422 has an increased height (indicated by "H" in FIG. 84) relative to the alignment peg 422 shown in the embodiment of FIG. 45. The increased height of the alignment peg 422 reduces the space available inside the end cap 406. The reduced space can help improve guidance of the filament 442 through the end cap insert 418. In the illustrated embodiment, the space within the end cap insert 418 through with the filament 442 passes above the alignment peg 422 is positioned above or higher than the opening in the first washer 450a through which the filament 442 extends. The filament 442 can therefore flex over the alignment peg 422 as shown in FIG. 83, which increases the friction between the filament 442 and the first washer 450a. This can help ensure the first washer 450a is engaged and pivots during elongation and/or extension of the headgear. In this embodiment, the filament entry hole 444 can be extended (relative to the embodiment of, for example, FIG. 67) to form an elongate slot having a height greater than its depth. As the increased height of the alignment peg 422 provides additional guidance to the filament 442 within the yoke 400, less support for the filament 442 is required of the filament entry hole 444. An elongated slot rather than a circular hole for the filament entry hole 444 can allow the filament 442 to pass freely through the filament entry hole 444 without having to bend through a torturous path. An elongated slot rather than a circular hole can also allow a single symmetrical end cap 406 to be used on both sides of the yoke 400.

FIGS. 85-87 illustrate another alternative embodiment of the yoke back 404. In the illustrated embodiment, the alignment peg 422 has a height H that is approximately the same as, but slightly smaller or less than, an internal height of the yoke front 402 end cap insert 418 such that the alignment peg 422 abuts, or nearly abuts, upper and lower internal surfaces of the end cap insert 418 as shown in FIG. 85. The alignment peg 422 includes a filament slot 452 that allows the filament 442 to pass through the alignment peg 422 to the washer housing 446. The alignment peg 422 and/or filament slot 452 help guide the filament 442 through the end cap 406.

FIGS. 88-90 illustrate an alternative yoke 400 embodiment including variation in the line tracks 430, 432. As shown, the line tracks 430, 432 overlap with the washer housings 446 to reduce the yoke length needed for a given filament length, similar to the embodiment shown in and described with respect to FIGS. 72-73A. In the embodiment of FIGS. 88-90, each of the line tracks 430, 432 passes in front of the opposite washer housing 446 rather than above or below the washer housing 446. The line tracks 430, 432 are cut or formed into the front wall 409 of the yoke front 402 (for example, of the end cap insert 418) where the line tracks 430, 432 pass in front of the washer housings 446, as shown toward the lateral ends of FIG. 88 and in FIG. 90. This configuration can allow for a reduced yoke height ("H" in FIG. 89) compared to the embodiment of FIGS. 72-73A. A reduced height H can help the mask as a whole appear smaller and/or less obtrusive. However, the embodiment of FIGS. 72-73A may allow for a reduced depth of the yoke 400 compared to the embodiment of FIGS. 88-90.

FIGS. 91-94 illustrate another alternative embodiment of the line tracks. Similar to previously described embodiments, the line tracks overlap with the washer housings 446 to reduce the yoke length needed for a given filament length. In the embodiment of FIGS. 91-94, the yoke is divided diagonally by a helical wall that at least partially forms or defines a front line track 460 and a rear line track 462. The line tracks 460, 462 overlap front-to-back and then extend to finish below the washer housings 446. This arrangement allows the washer housings 446 to be horizontally aligned with each other. This arrangement can help reduce or limit the increase in height of the yoke 400 caused by the line tracks 460, 462 as both line tracks 460, 462 pass under the washer housings 446 rather than one passing below a washer housing 446 and one passing above the other washer housing 446 as in the embodiment of FIG. 72. Although FIGS. 91-94 illustrate the yoke 400 as straight or linear, a yoke 400 having the line track 460, 462 arrangement shown in FIGS. 91-94 can be curved in plan view similar to previously shown and described embodiments.

Figure 134:
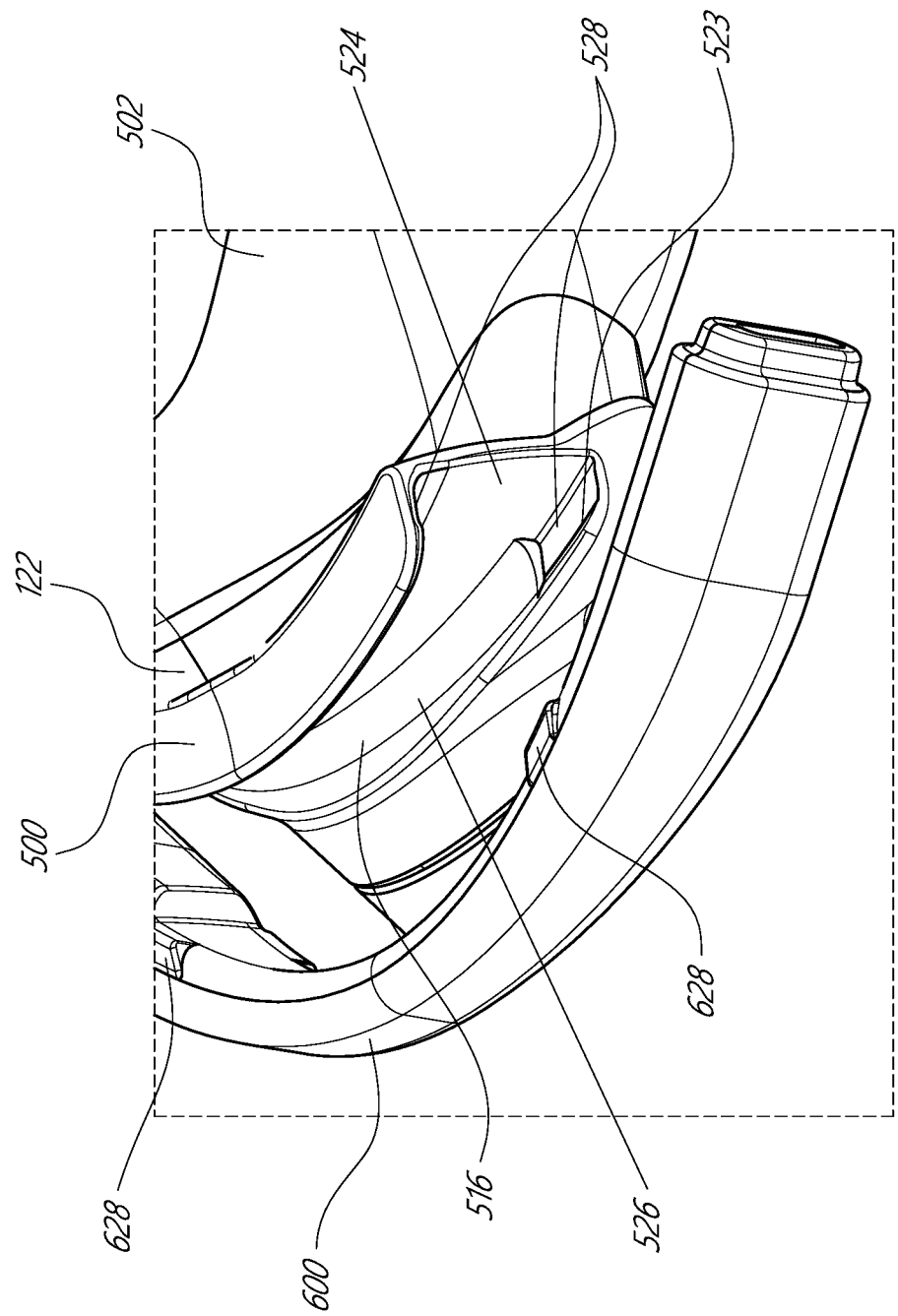
Figure 135:
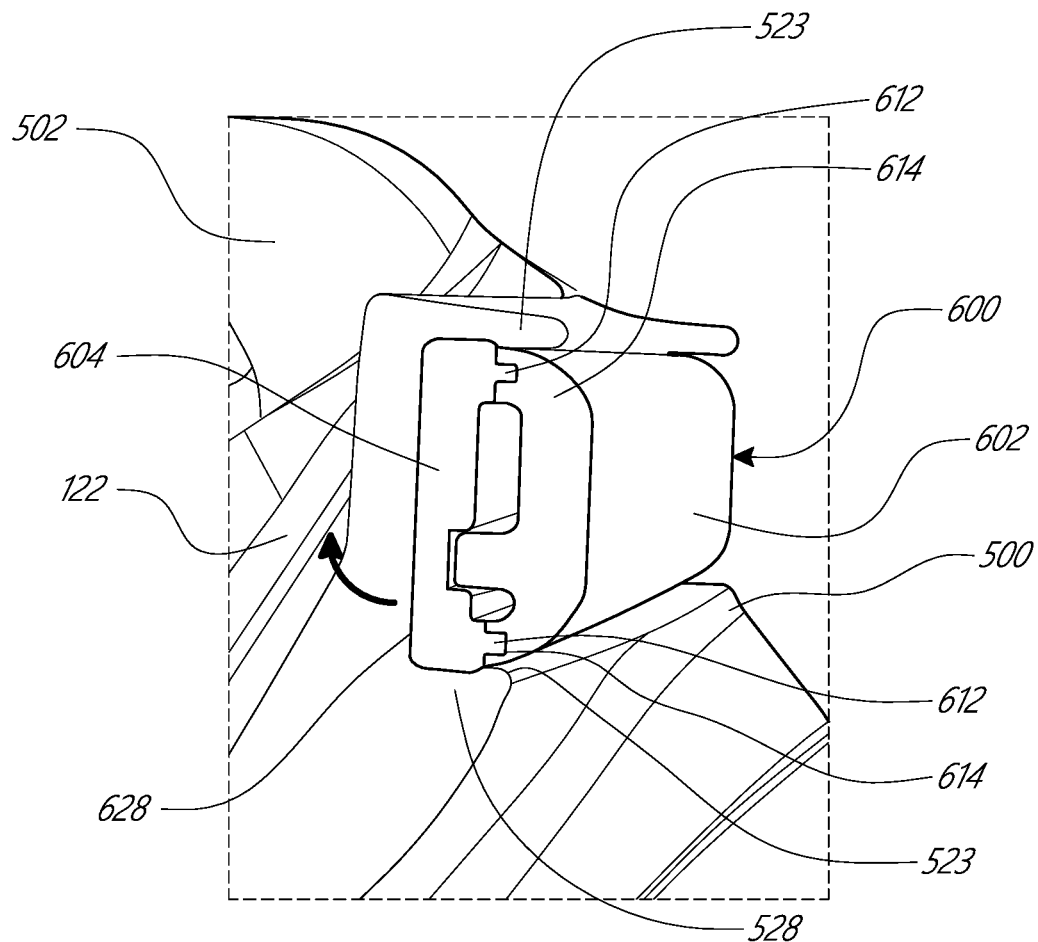

FIGS. 133 to 135 illustrate another example embodiment of a yoke 600 and cushion or seal 502 coupled to a frame 500. The yoke 600, seal 502, and/or frame 500 can be similar in some ways to the yoke 400, cushion 302, and/or frame 300, respectively. The frame 500 includes a yoke channel 516 configured to receive the yoke 600 in use. The yoke channel 516 is formed or defined by an upper wall 522, rear wall 524, and lower wall 526. The yoke 600 has increased asymmetry between upper and lower edges of the yoke 600, for example, compared to the yoke 400. In the illustrated embodiment, the upper edge of the yoke 600 is straighter than the lower edge. The asymmetry advantageously provides improved visual cues as to the correct orientation for assembly of the yoke 600 to the frame 500 and helps inhibit incorrect assembly.

As shown in FIG. 134, the yoke channel 516 includes connector recesses 528 in the upper wall 522 and lower wall 526. In the illustrated embodiment, a connector recess 528 is positioned at, adjacent, or proximate each lateral end of the yoke channel 516. The connector recesses 528 at least partially define or form retention lips 523 at or along front edges of the yoke channel 516 (e.g., at or along front edges of internally facing surfaces of the upper wall 522 and lower wall 526). The yoke 600 includes connector protrusions 628 protruding rearwardly from upper, lower, and/or rear surfaces of the yoke 600. In the illustrated embodiment, the yoke 600 includes a connector protrusion 628 on each side of a center of the yoke 600. In the illustrated embodiment, the yoke 600 includes a yoke front 602 and yoke back 604 that are coupled together, as described in greater detail herein, and the connector protrusions 628 are formed in the yoke back 604. The connector recesses 528 are configured to receive the connector protrusions 628 when the frame 500 and yoke 600 are coupled together to form a snap-fit connection between the frame 500 and yoke 600. When the frame 500 and yoke 600 are coupled together, the retention lips 523 engage the yoke 600 forward of the connector protrusions 628 to contribute to the snap-fit connection and retain the yoke 600 in the yoke channel 516. In the illustrated embodiment, the connector protrusions 628 and connector recesses 528 have a square or rectangular profile, which inhibits the yoke 600 from rotating out of the yoke channel 516, for example, in the direction indicated by the arrow in FIG. 135.

Figure 136A:
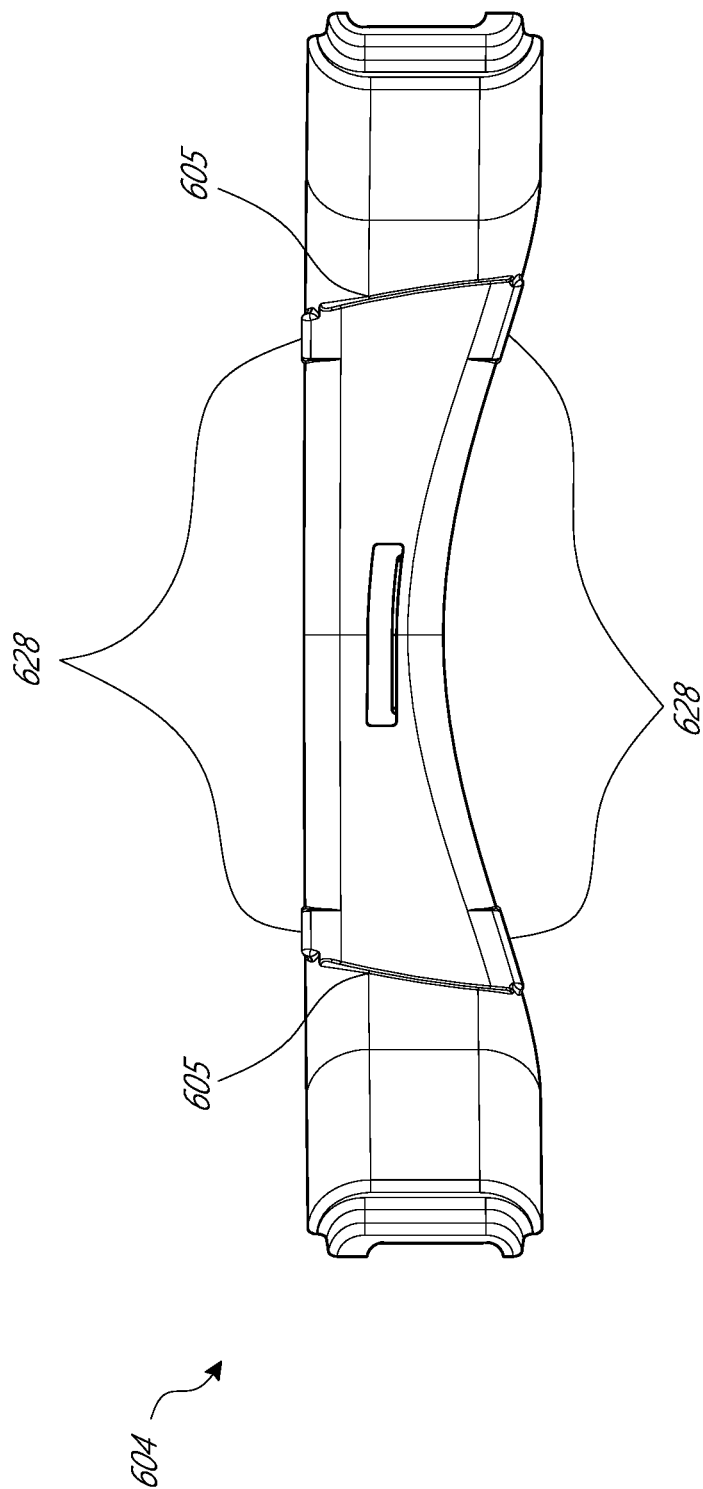
Figure 136B:
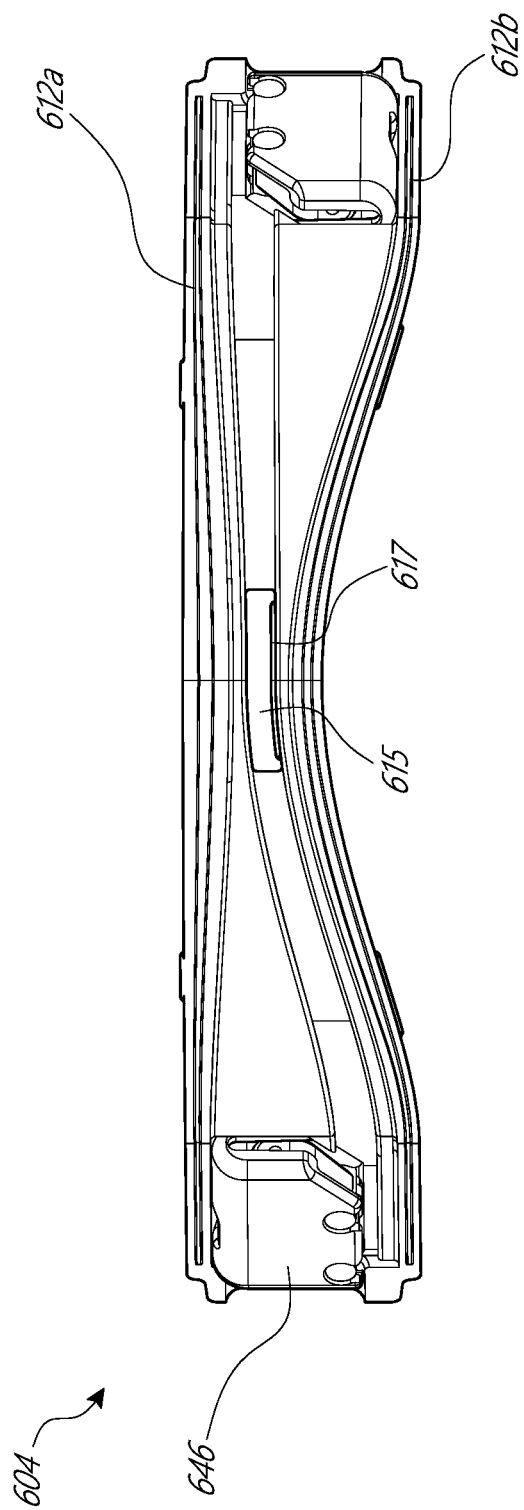
Figure 136C:
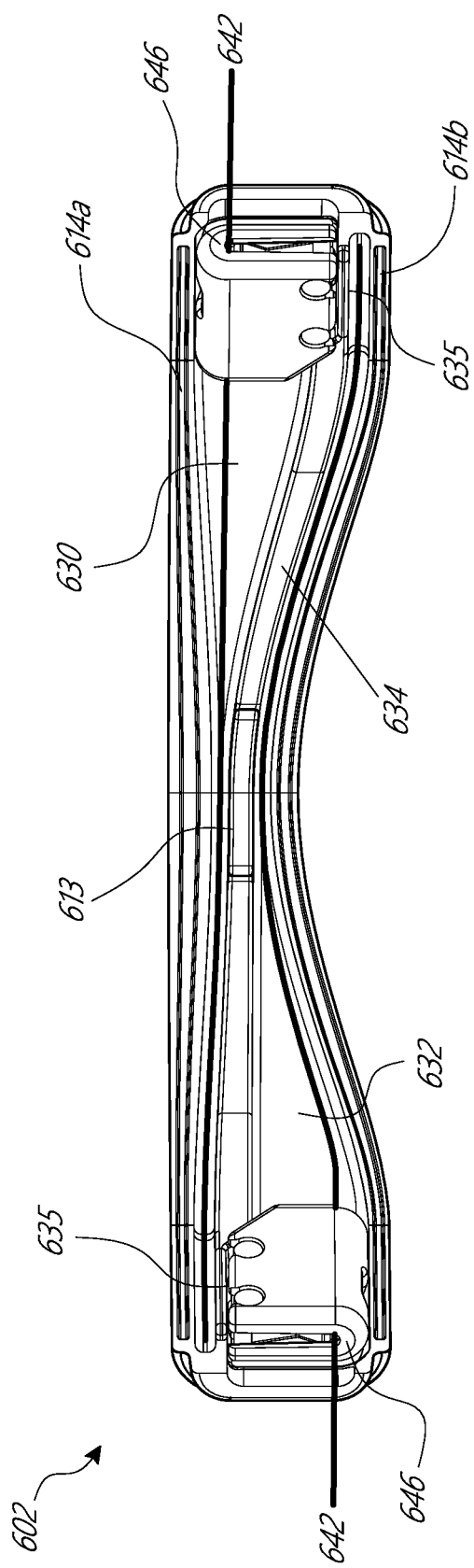

In some embodiments, the yoke 600 has an oval or substantially oval cross-section, for example, as shown in FIG. 137. This shape advantageously reduces the size or bulk of the yoke 600 and/or provides an improved aesthetic appearance. The washer housings 646, discussed in greater detail herein, can have a D-shaped, substantially D-shaped, U-shaped, or substantially U-shaped cross-section, for example as shown in FIGS. 136A-136C, to allow for and/or contribute to the overall oval or substantially oval cross-section of the yoke 600. The washer housings 646 can be oriented opposite each other. In other words one of the washer housings 646, e.g., the left washer housing 646 as shown in FIG. 136C, can be oriented as an upward-facing U-shape, and the other washer housing 646, e.g., the right washer housing 646 in FIG. 136C, can be oriented as a downward-facing U-shape. This arrangement and orientation can advantageously help allow the line tracks 630, 632 to extend above and below the left and right washer housings 646, respectively, as discussed in greater detail herein. As shown in FIG. 137, in the illustrated embodiment, the yoke 600, or a central portion of the yoke 600, has a depth D that is the same as or similar to or corresponds to a depth of the yoke channel 516 such that the yoke 600 does not protrude, or does not substantially protrude, from the yoke channel 516. This advantageously reduces the overall size of the frame 500 and yoke 600 assembly.

As shown in FIGS. 136A and 138, in the illustrated embodiment, a rear or back surface of the yoke 600 includes a rearward step on each side or lateral end of the central portion of the yoke 600 such that the yoke 600 has a stepped depth. In other words, lateral portions of the yoke 600, which are positioned laterally outside of the yoke channel 516 when the yoke 600 is coupled to the frame 500, have a greater depth than the depth D of the central portion of the yoke 600, which is positioned in the yoke channel 516 when the yoke 600 is coupled to the frame 500. The steps form or define frame abutment surfaces 605 at the transitions between the central portion and lateral portions of the yoke 600. When the yoke 600 is coupled to the frame 500, each of the frame abutment surfaces 605 abuts or is positioned adjacent or proximate one of the lateral edges 505 of the frame 500 as shown in FIG. 138. The frame abutment surfaces 605 and lateral edges 505 help properly align the yoke 600 with the frame 500 during assembly. The frame abutment surfaces 605 and lateral edges 505 also or alternatively provide a more secure connection between the yoke 600 and frame 500. The reduced depth of the central portion of the yoke 600 advantageously reduces the overall size of the frame 500 and yoke 600 assembly.

As shown in FIGS. 135-137, in the illustrated embodiment, the yoke 600 includes a yoke front 602 and a yoke back 604. The yoke 600 can also include two end caps 606 (as shown in FIG. 140), one at each lateral end of the yoke 600. In the illustrated embodiment, the yoke front 602 and yoke back 604 are formed as separate components that are coupled together. In the embodiment of FIGS. 135-137, a split line 603 (shown in FIG. 137) between the yoke front 602 and yoke back 604 is centered or generally centered. This can improve ease of manufacturing.

The yoke front 602 and yoke back 604 can be coupled together via a snap fit. In the illustrated embodiment, the yoke front 602 includes a yoke fastener 613 projecting rearwardly from a rear surface of the yoke front 602. In the illustrated embodiment, the yoke fastener 613 is positioned centrally or generally centrally with respect to the yoke front 602. The yoke back 604 includes a fastener aperture 615 that is sized, shaped, and positioned to receive the yoke fastener 613 to form a snap-fit connection when the yoke front 602 and yoke back 604 are coupled together. The central connection between the yoke front 602 and yoke back 604 via the yoke fastener 613 and fastener aperture 615 provides more rigidity to the connection between the yoke front 602 and yoke back 604 and/or provides support against or inhibits twisting between the yoke front 602 and yoke back 604. In some embodiments, the yoke front 602 instead includes the fastener aperture 615 and the yoke back 604 includes the yoke fastener 613. In some embodiments, the fastener aperture 615 includes one or more fastener bumps 617 extending along (e.g., laterally along) upper and/or lower edges of the fastener aperture 615 and protruding into the fastener aperture 615 from the upper and/or lower edges. The yoke fastener 613 includes one or more corresponding notches 619 (shown in FIG. 137) extending along (e.g., laterally along) upper and/or lower surfaces of the yoke fastener 613 that are sized, shaped, and positioned to receive the fastener bump(s) 617 to form a snap-fit connection. In some embodiments, the fastener aperture 615 includes one or more notches 619 and the yoke fastener 613 includes one or more fastener bumps 617.

FIGS. 148-150 illustrate a variation of the yoke 600 in which the yoke back 604 includes a fastener recess 615' instead of a fastener aperture 615. The fastener recess 615' does not extend all the way through the thickness of the yoke back 604. The yoke front 602 includes a rearwardly-extending yoke fastener 613'. The fastener recess 615' is sized, shaped, and positioned to receive the yoke fastener 613' to form a friction-fit connection when the yoke front 602 and yoke back 604 are coupled together. In some such embodiments, the fastener recess 615' includes one or more interference bumps 617' on the upper and/or lower surfaces or edges of the fastener recess 615'. In the illustrated embodiment, the interference bumps 617' are elongate and extend an entire depth of the fastener recess 615'. The interference bumps 617' interfere with and help create a friction fit between the fastener recess 615' and the yoke fastener 613' to help secure the yoke front 602 and yoke back 604 together. This configuration can advantageously allow for easier manufacturing, provide a neater finish (without an aperture in the yoke back 604), and/or inhibit the ingress of dirt or other debris into the line tracks 630, 632 (due to the lack of aperture, which allows the yoke 600 to be fully enclosed along its length), which can help maintain the function of the automatic headgear adjustment mechanism.

In the embodiment of FIGS. 135-137, the yoke back 604 includes an upper alignment bead 612a protruding forward from the yoke back 604 and extending along a length of the yoke back 604 adjacent or proximate the upper surface of the yoke back 604, and/or a lower alignment bead 612b protruding forward from the yoke back 604 and extending a length of the yoke back 604 adjacent or proximate the lower surface of the yoke back 604. The yoke front 602 includes an upper alignment groove 614a in a rear surface of the yoke front 602 extending along a length of the yoke front 602 adjacent or proximate the upper surface of the yoke front 602, and/or a lower alignment groove 614b in the rear surface of the yoke front 602 extending a length of the yoke front 602 adjacent or proximate the lower surface of the yoke front 602. The upper and/or lower alignment grooves 614a, 614b receive the upper and/or lower alignment beads 612a, 612b, respectively, when the yoke front 602 and yoke back 604 are coupled together. The alignment beads 612a, 612b and alignment grooves 614a, 614b help correctly align the yoke front 602 and yoke back 604. The alignment beads 612a, 612b and alignment grooves 614a, 614b can also or alternatively resist or support against torsion, e.g., between the yoke front 602 and yoke back 604. In some embodiments, the alignment beads 612a, 612b and alignment grooves 614a, 614b can be positively engaged with each other, for example, in the form of a friction fit or snap fit connection.

The end caps 606 can help secure the yoke front 602 and yoke back 604 together by clipping over or snap fitting over or onto the lateral ends of the yoke front 602 and yoke back 604. The end caps 606 can also allow for connection of a front strap of a headgear to the yoke 600. In some embodiments, each end cap 606 is over-molded onto a braided portion of the front strap.

As shown in FIGS. 141-147, the lateral ends of the yoke front 602 and yoke back 604 include or are formed by end cap inserts 618. The end cap inserts 618 can be integrally formed with or attached to the lateral ends of the yoke front 602 and yoke back 604. The end cap inserts 618 have a reduced dimension or profile compared to the lateral portions of the yoke 600. The end caps 606 have internal cavities 609 that receive the end cap inserts 618. During assembly, the end caps 606 are connected over or snapped onto the end cap inserts 618 in a hinged manner, as shown in FIG. 141.

As shown in FIG. 146, each end cap 606 includes a retention hole 605 on one side (e.g., in a rear side in the illustrated embodiment) and a retention notch 607 on an opposite side (e.g., a front side in the illustrated embodiment). In other embodiments, the position of the retention hole 605 and retention notch 607 can be reversed. The positioning of the retention hole 605 in the rear of the end cap 606 in the illustrated embodiment, advantageously hides the retention hole 605 in use, which provides an improved aesthetic appearance. The retention notch 607 extends from the internal cavity 609 forward into the end cap 606. The end cap inserts 618 include a first retention feature 616 on one of the front and back surfaces (e.g., extending rearwardly from the yoke back 604 portion of the end cap insert 618 in the illustrated embodiment) and a second retention feature 611 on an opposite surface (e.g., extending forward from the yoke front 602 portion of the end cap insert 618 in the illustrated embodiment). To attach the end cap 606 to the yoke 600, e.g., to the end cap insert 618, the retention hole 605 is engaged with the first retention feature 616 as shown in FIG. 141. The first retention feature 616 then acts as a hinge or pivot point, and the end cap 606 is pivoted over the end cap insert 618 in the direction indicated by the arrow in FIG. 141 until the second retention feature 611 and retention notch 607 engage, e.g., in a bump or snap fit connection. The hinged connection can provide a strong connection between the yoke 600 and end caps 606 with a reduced end cap insert 618 length L (indicated in FIG. 144). The end caps 606 can therefore taper more steeply. The reduced length of the end cap inserts 618, end caps 606, and/or overall yoke 600 can advantageously reduce or minimize the yoke 600 digging into the patient's face.

In the illustrated embodiment, the first retention feature 616 is or includes an oval or stadium shaped post extending rearward from the yoke back 604. The first retention feature 616 has a length or depth selected such that an outer or rearmost surface of the first retention feature 616 is flush or substantially flush with the rear surface of the yoke back 604. This increases the contact area and interaction between the end caps 606 and end cap inserts 618 and increases the retention forces. The connection between the end caps 606 and end cap inserts 618 can therefore resist greater torsional forces along the length of the yoke 600 and/or rotational forces about the joint.

In the illustrated embodiment, the second retention feature 611 is or includes a raised tab extending forward from the yoke front 602. The second retention feature 611 has a reduced length or depth compared to the first retention feature 616, which allows the end cap 606 to pass over the second retention feature 611 during assembly. In the illustrated embodiment, the second retention feature 611 has a chamfered lead-in 617a on one edge, e.g., on the lateral (relative to the yoke 600) edge in the illustrated embodiment, which allows the end cap 606 to be hinged or pivoted over and/or onto the second retention feature 611 more easily.

In some embodiments, the end caps 606 can be overmolded onto an end of a braided element of an automatic headgear adjustment mechanism, for example, braided elements as shown and described in U.S. Provisional Patent Application No. 62/343,711, entitled "Directional Lock for Interface Headgear Arrangement" and filed May 31, 2016, and PCT Application No. PCT/NZ2014/000074, the entireties of which are hereby incorporated by reference herein. The core elements or filaments 642 can extend within the braided elements. The end caps 606 can connect the braided element, and therefore the headgear, to the yoke 600 and create a closed loop headgear system.

As described herein, in some embodiments, the yoke 600 may form a collector for core elements, such as filaments 642, used in an automatically adjustable or self-adjusting headgear system. As shown in FIG. 136C, the yoke front 602 includes an upper line track 630 and a lower line track 632. A line track divider 634 protrudes rearwardly from a rear or internal surface of the yoke front 602. The line track divider 634 extends generally at a diagonal across a portion of the length of the yoke front 602. In the illustrated embodiment, a divider wall 635 extends between each of the washer housings 646 and the opposing line track. The divider wall 635 separates the opposing line track from the washer housing 646 so that a free end of the filament 642 is inhibited from being caught in the opposing washer housing 646 during retraction. In the illustrated embodiment, the line tracks 630, 632 are not symmetrically mirrored due to the asymmetry of the upper and lower edges of the yoke 600.

FIG. 140 illustrates a variation of the yoke 600 in which the line tracks 630, 632 extend into and terminate within the end caps 606. The lengths of the line tracks 630, 632 are therefore extended beyond the ends of the yoke front 602 and yoke back 604. This increases the length of filament 642 that can be stored within the yoke 600, which increases the range of adjustment or variability in the size of the headgear. The headgear 200 defines a headgear loop that extends around a user's head in use. The filament 642 forms part of the automatic headgear adjustment mechanism that allows a total length of the headgear loop to be extended during donning and doffing of the mask system. In some such embodiments, the length of each of the line tracks 630, 632 can be increased or extended by about 5 mm. In such embodiments, the total length of the headgear loop, in an extended state, can therefore increase by about 10 mm.

FIG. 139 illustrates an example embodiment of a seal 502, for example that can be used with the frame 500 and yoke 600. In the illustrated embodiment, the seal 502 includes a lip pad 503 that protrudes outwardly from the seal clip 122 along a lower edge of the sealing surface to form a convex region that pads or cushions the seal clip 122. The lip pad 503 can minimize the lower edge of the seal 502 from bottoming out on the seal clip 122 by providing additional cushioning, which may improve patient comfort, particularly in the upper lip region.

Figure 95B:
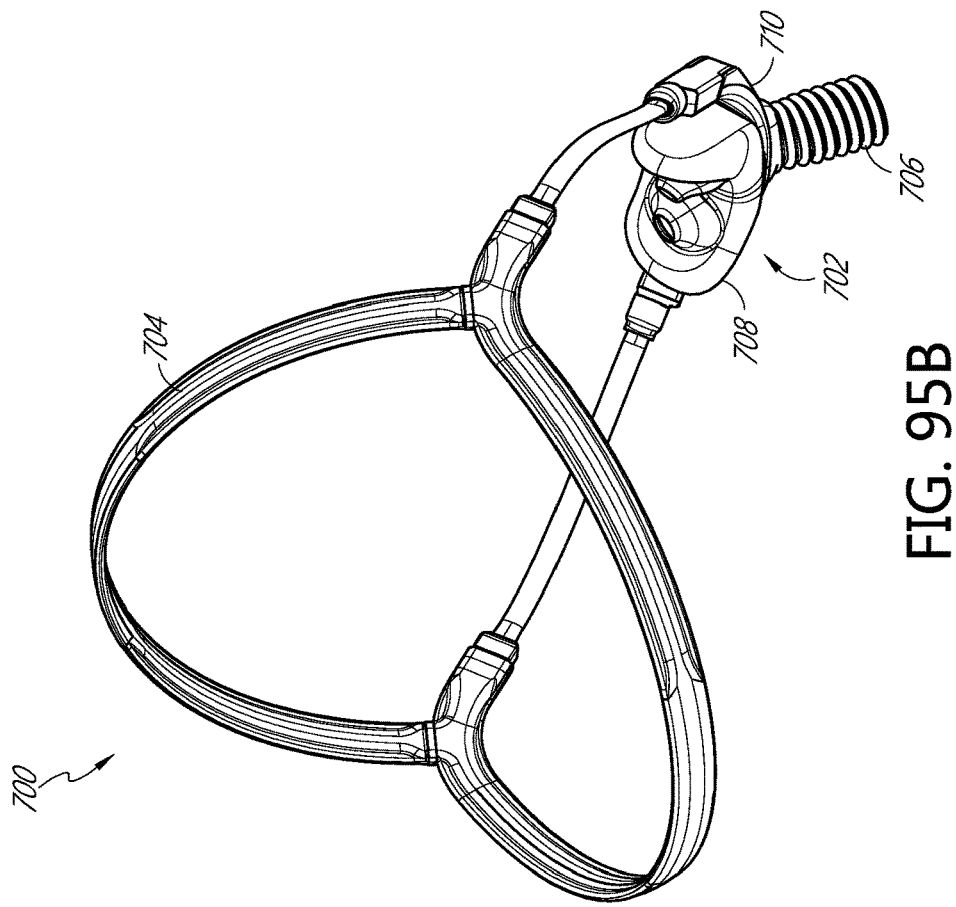
FIG. 95 shows front and rear perspective views of a mask assembly, including a headgear assembly, a seal assembly, and a frame assembly.
Figure 95A:
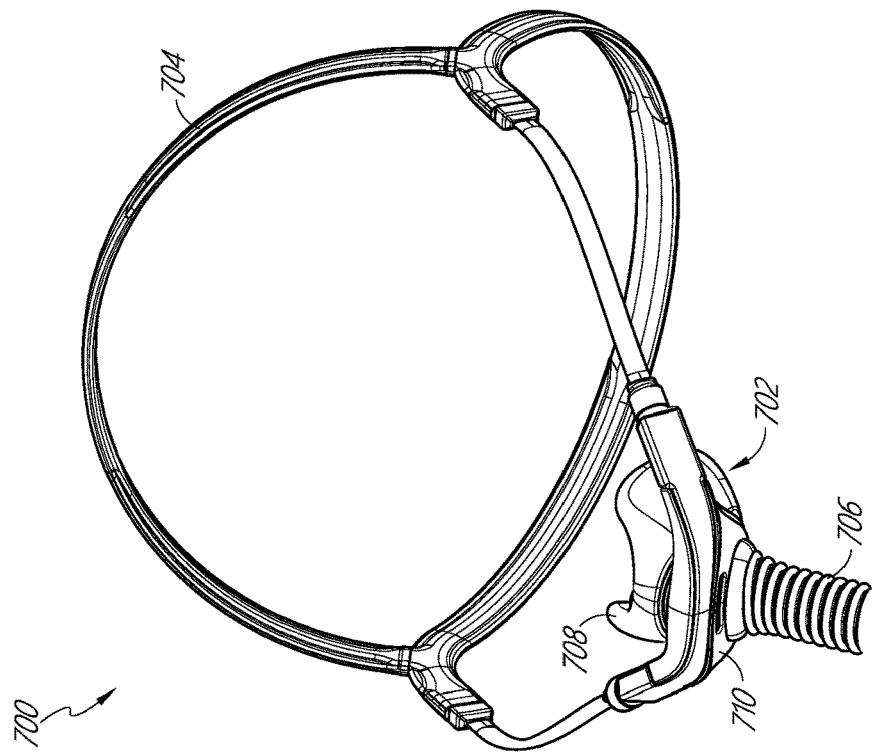

FIGS. 95A and 95B illustrate front and rear views, respectively, of a nasal mask assembly 700 comprising a seal and frame assembly 702, a headgear assembly 704 and a gas conduit 706. The seal and frame assembly 702 comprises a seal 708 supported by a frame 710. The seal 708, alone or in combination with the frame 710, defines a breathing chamber of the nasal mask assembly 700. The seal 708 can be in the form of a direct nasal cushion (e.g., a nasal pillows cushion). The gas conduit 706 delivers a flow of breathing gas from a gases source to the breathing chamber of the nasal mask assembly 700. The headgear assembly 704 supports the seal and frame assembly 702 in a desired position on the face of a user.

FIGS. 96-107 illustrate an embodiment of the seal cushion or seal 708 of the interface or mask assembly of FIG. 95 next to an example of a prior art nasal seal or reference seal 708R for the sake of comparison. As illustrated, the seal 708 is smaller than the prior art seal 708R. One aspect of the present disclosure involves a seal (e.g., the seal 708) that has a smaller overall size/volume than the prior art seal 708R, while sealing well and being stable on the face of the user when incorporated in a mask assembly (e.g., the nasal mask assembly 700). In some configurations, the seal 708 is used in combination with an automatically adjustable headgear or a headgear having directional locking capabilities, as described above. Such a headgear allows a seal to be held in place with a reduced or minimal force that balances blow-off or hose drag forces that may be applied to a mask. The force applied by the headgear to the user without pressurization of the mask assembly can be less than the force required to balance blow-off forces. It has been discovered by the present inventors that the reduced or minimal force applied to the user's head by such a system allows the sealing surface of the seal to be reduced or minimized. This is because it is no longer necessary to disperse higher headgear forces over a greater sealing surface in order to reduce pressure points. The lower forces can be dispersed over a smaller sealing surface without significant pressure points occurring. This allows a smaller seal with a smaller contact surface to form an effective and comfortable seal with a user's face. It is advantageous for respiratory masks to be as small as possible or practical such that they are as unobtrusive as possible and avoid feelings of claustrophobia for the user. Because in some configurations of an automatically adjustable headgear or a headgear having directional locking capabilities, such as the headgear of FIG. 95, the system is highly flexible between a rear portion of the headgear and the mask frame, it is beneficial for the seal to be more stable on the face than prior art seal 708R or other seals used in combination with other types of headgear. The inflatable nature of the prior art seal 708R allows it to rotate or roll about the user's nose.

Several factors limit how small the seal can be made. For example, in general, a minimum size of the seal is influenced or limited by the size of the inlet aperture and the sealing surface. The seal forms part of an air path and therefore must be connected to a gas conduit that delivers pressurized gas to the seal and the patient's airways. There is a limit to how small the diameter of the gas conduit can be whilst minimizing pressure drop between the CPAP (blower or flow generator) and the patient interface/mask. In some configurations, the internal diameter of the gas conduit being used with the disclosed seals is equal to or greater than 15 mm.

Some prior art masks use an elbow to connect the gas conduit to the mask frame. The elbow adds extra weight and bulk to the mask, which can contribute to instability of the mask. In at least some configurations of the presently disclosed interfaces, the elbow has been omitted in favour of a direct connection between the gas conduit and mask frame (e.g., gas conduit 706 and frame 710). Removal of the elbow shifts the centre of gravity towards the user's face, in use, and therefore reduces the moment of rotation and improves stability of the seal.

Bias flow or exhaust vents are typically located in the elbow for direct nasal (e.g., pillows) masks. If there is no elbow, the bias vents need to be located elsewhere. The bias vents should be located within the air path of the mask and therefore the inlet aperture of the seal preferably is large enough to accommodate a path through which exhausted air can be vented. The inlet aperture of the seal therefore preferably is large enough to accommodate a gas inlet, a bias vent and clipping or other connection structure to attach a mask frame to the seal. The sealing surface of the seal should be large enough to form an air-tight seal between the seal and the nares of a range of patients.

Figure 96:
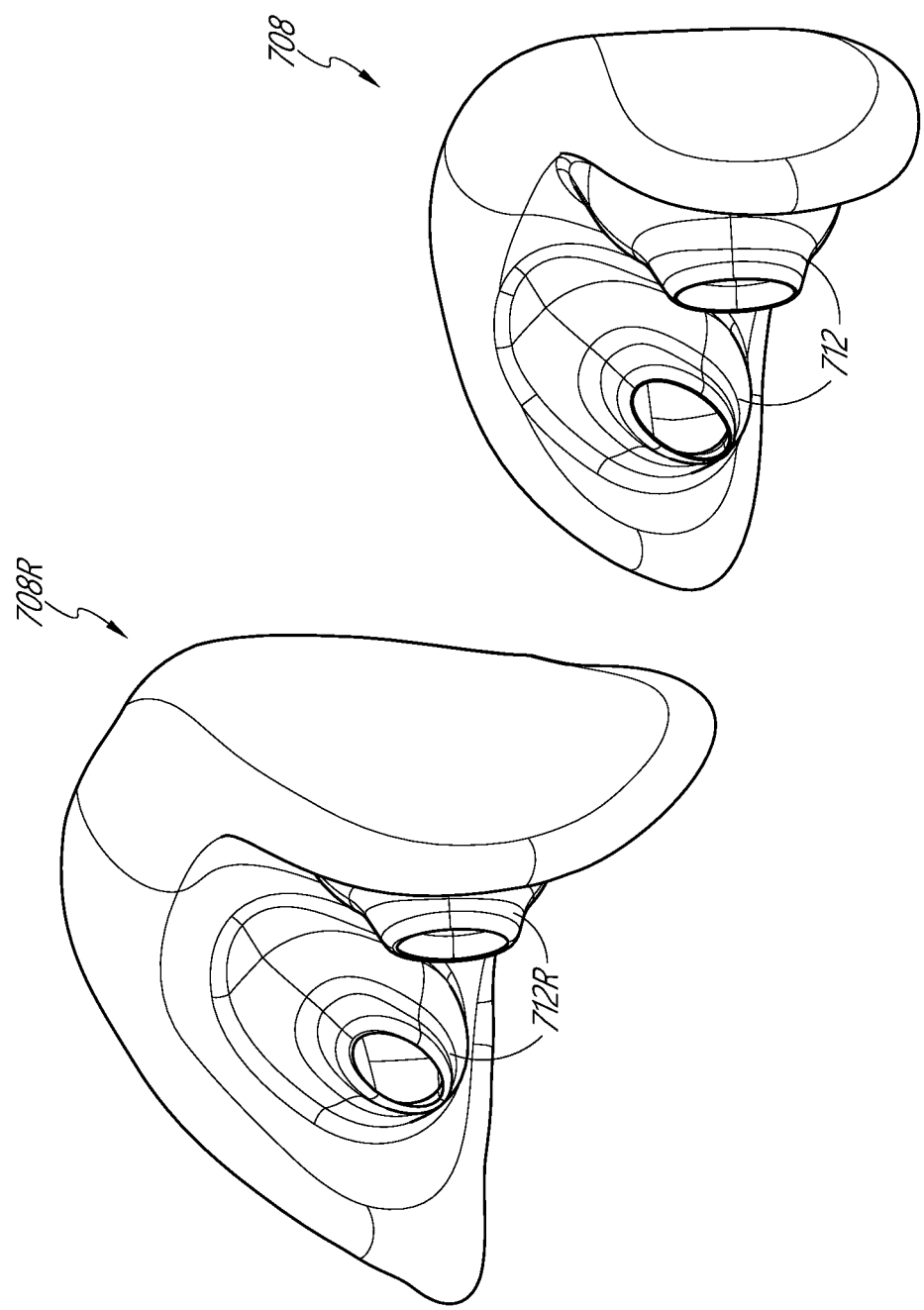
FIG. 96 shows rear perspective views of the seal of FIG. 95 (right) and a prior art nasal seal (left)

With reference to FIG. 96, a prior art nasal seal 708R is shown next to a seal 708 of the present disclosure for the sake of comparison. The prior art seal 708R can be the same as or similar to the seals disclosed in Applicant's PCT Publication No. WO2015/009172, the entirety of which is incorporated by reference herein. The prior art seal 708R cushion and the seal 708 are generally similar in shape; however, in the illustrated arrangement, an overall size of the seal 708 is smaller than the prior art seal 708R cushion. Both of the seal cushions 708, 708R comprise a pair of nasal prongs or pillows 712, 712R, respectively, that are configured to engage with and form a substantial seal with the nares of a user, such that a supply of pressurized air may be delivered to the airways of the user. In at least some configurations, the nasal prongs 712, 712R provide a primary sealing surface that provides the primary contact between the nares and the seal 708, 708R to provide a substantially airtight seal. The nasal prongs 712 of the seal 708 can be the same or substantially similar in shape as the nasal prongs 712R of the prior art seal 708R.

With reference to FIG. 97, the prior art seal 708R comprises a secondary sealing surface 714R that encircles and links the nasal prongs 712R. The secondary sealing surface 714R forms a back-up or secondary seal with the lower nasal surfaces of the user's nose. The secondary sealing surface 714R is configured to catch air leaks that may occur between the nasal prong 712R and the user's nares, and substantially inhibit or prevent it escaping outside of the seal cushion.

The illustrated seal 708 comprises a secondary sealing surface 714 that is smaller than the prior art secondary sealing surface 714R. The secondary sealing surface 714 of the seal 708 extends primarily between the two nasal prongs 712 and forms a link between them, without extending radially outward from the nasal prongs 712. In some configurations, the secondary sealing surface 714 has an upper boundary that is at or below the uppermost extent of the nasal prongs 712 and a lower boundary that is at or above the lowermost extent of the nasal prongs 712. In some configurations, the secondary sealing surface 714 is defined by the concave portion of the user-facing surface of the seal 708 between or surrounding the nasal prongs 712. The secondary sealing surface 714 or surround region of the seal 708 may perform less of a role as a secondary seal in comparison to that of the prior art seal 708R due to its smaller size. In some configurations, the secondary sealing surface 714 of the seal 708 may be configured to only catch leaks on the underside of the user's nose and may not provide a substantial secondary seal on the outside edges of the user's nares for at least some users. However, in some configurations, the secondary sealing surface 714 of the seal 708 can be configured to provide a secondary seal around an entire periphery of the seal 708.

Figure 98:
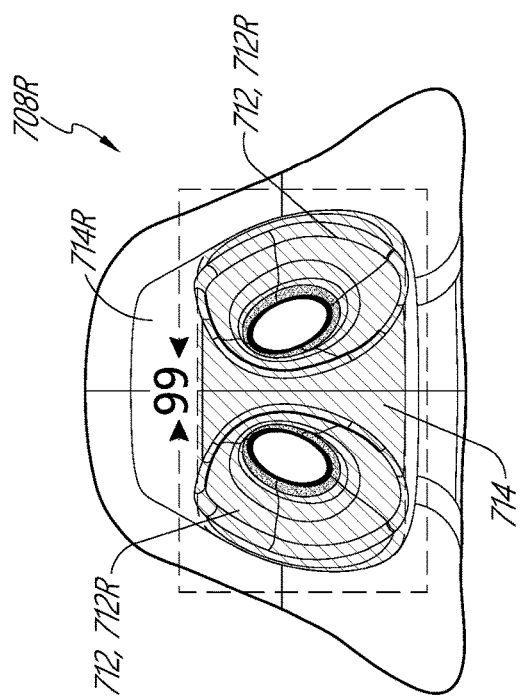
FIG. 98 shows a rear view of the seals of FIG. 96 superimposed on one another.
Figure 99:
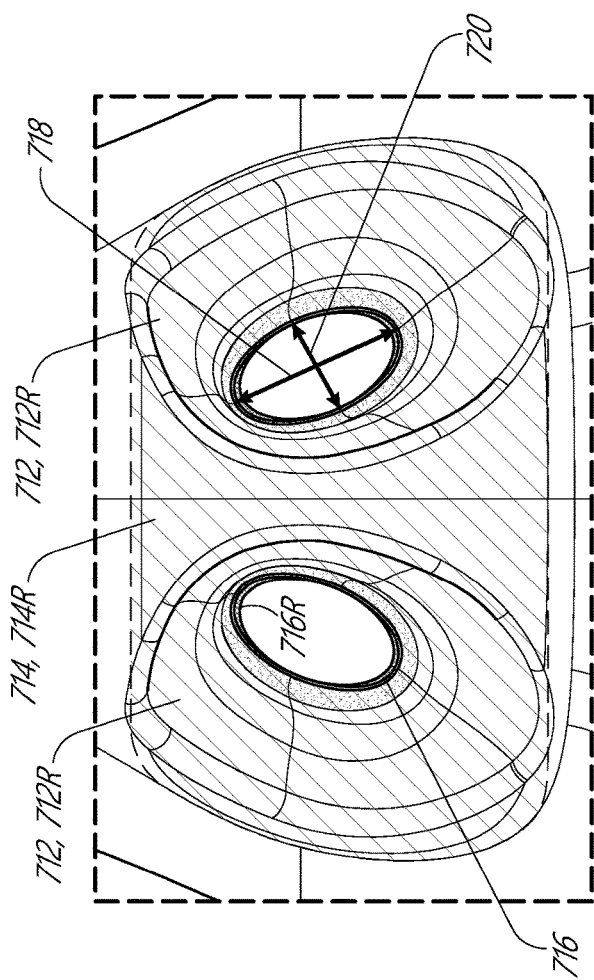
FIG. 99 is an enlarged view of a portion of the superimposed seals of FIG. 98.

In some configurations, the secondary sealing surface 714 of the seal 708 is substantially similar or identical in contour to a corresponding portion of the secondary sealing surface of the prior art seal 708R, as shown by the overlapping geometry in FIGS. 98 and 99. As discussed above, the primary sealing surfaces of the nasal prongs 712, 712R of both seals 708, 708R can be substantially similar as well.

With reference to FIG. 99, the nasal prongs 712, 712R of both seal cushions 708, 708R comprise an outlet 716, 716R through which the supply of pressurized air passes. The outlets 716, 716R comprise an elliptical aperture that is formed at a truncated apex of the nasal prongs 712, 712R. The elliptical apertures have a major axis 718 and a minor axis 720. In the illustrated arrangement, a dimension along the major axis 718 of the outlet 716 of the seal 708 is longer than a corresponding dimension along the major axis 718 of the prior art outlet 716R. In at least some configurations, the difference is present only on the internal perimeter surface of the outlet 716, 716R. The dimensions along the major axes 718 of the outlets 716, 716R are the same length on the external perimeter surface of the outlets 716, 716R. This configuration provides a uniform wall thickness at the outlet 716 of the seal 708, which also provides a uniform softness to improve comfort and fit for the wearer. The dimensions of the outlets 716, 716R along the minor axes 720 of both the seal 708 and the prior art seal 708R are substantially the same.

Figure 100:
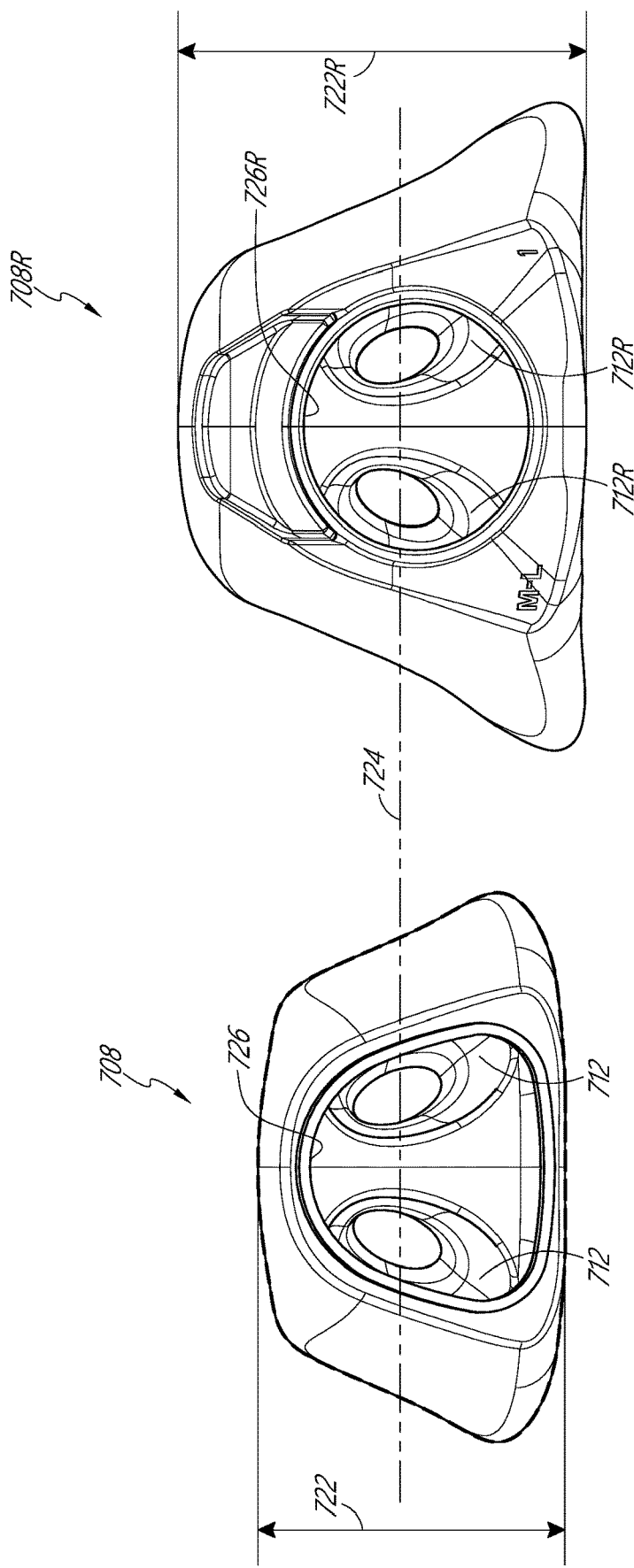
FIG. 100 shows front views of the seals of FIG. 96.

With reference to FIG. 100, the overall height 722 of the seal 708 is less than the height 722R of the prior art seal 708R. The dimension along the direction of the height 722 of the seal 708 has been reduced at both the top and bottom in comparison to the prior art seal 708R. In the illustrated arrangement, the height 722 has been reduced predominantly at the top of the seal 708. This is shown by the difference in height 722, 722R above the centre line 724 through which the nasal prongs 712, 712R of both seals 708, 708R are aligned. The reduced height 722 makes the seal 708 less obtrusive to the wearer. The reduced height 722 also means that the seal 708 sits lower on the wearer's nose and in some cases may not cover the tip of the wearer's nose. In some configurations, the height 722 can be equal to or less than about 38 mm, 35 mm or 33 mm. In some configurations, the height 722 is equal to about 32 mm (e.g., 32.2 mm). The illustrated prior art seal 708R, for sake of comparison, has a height 722R of 42.3 mm.

As illustrated, an inlet 726R of the prior art seal 708R comprises a circular profile. An inlet 726 of the seal 708 is shaped like a trapezoid or trapezium that has been rounded. Described another way, the inlet 726 of the seal 708 is substantially 'D-shaped' and somewhat follows the outer silhouette of the seal 708 (when viewed from the front). The inlet 726 is configured to be surrounded by a clipping mechanism (not shown, but can be the same as or similar to the clipping mechanism of FIGS. 119-122) that is configured to clip the seal 708 to a mask frame (e.g., mask frame 710). The inlet 726 of the seal 708 provides an alignment feature between the seal 708 and a mask frame (e.g., mask frame 710) that prevents incorrect assembly and, thus, improves ease of use.

Figure 101:
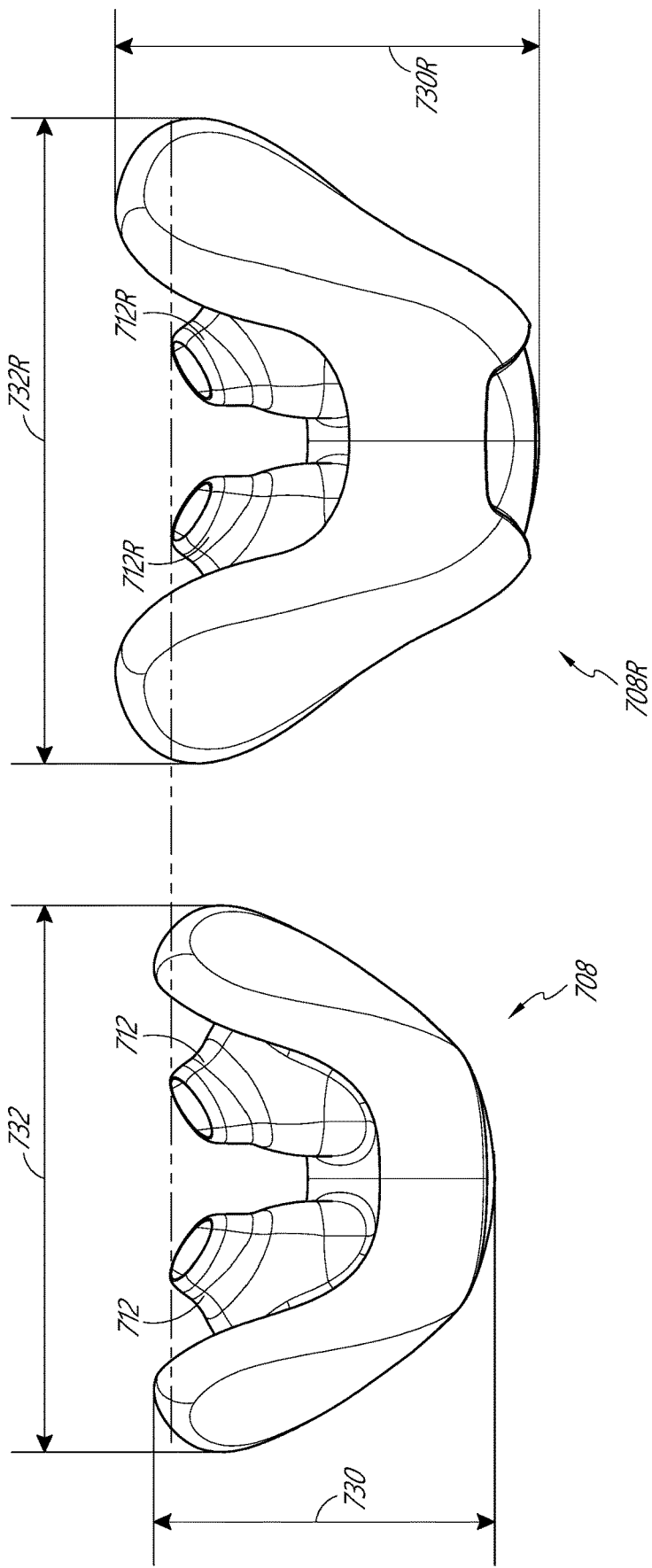
FIG. 101 shows top views of the seals of FIG. 96.

With reference to FIG. 101, an overall depth 730 of the seal 708 is less than a depth 730R of the prior art seal 708R. The depth 730 of the seal 708 is reduced at both the front and back in comparison to the prior art seal 708R. The reduced depth 730 contributes to the seal 708 being less obtrusive to the wearer and may help to reduce rotational movement (in a vertical plane about a lateral axis) of the seal 708 with respect to the wearer's face. The smaller depth 730 reduces the moment of the seal 708 on the face by moving the centre of gravity closer to the face. As described above, this is beneficial when the seal 708 is used in combination with automatically adjustable headgear or headgear incorporating one or more directional locks. In some configurations, an overall depth 730 of the seal 708 is equal to or less than 40 mm, equal to or less than 38 mm or is about 35 mm (e.g., 35.7 mm) in comparison to an overall depth 730R of 44.4 mm for the prior art seal 708R. In some configurations, an overall width 732 of the seal 708 is equal to or less than 60 mm or is about 57 mm (e.g., 57.4 mm) in comparison to an overall width 732R of 68.1 mm for the prior art seal 708R.

Figure 102:
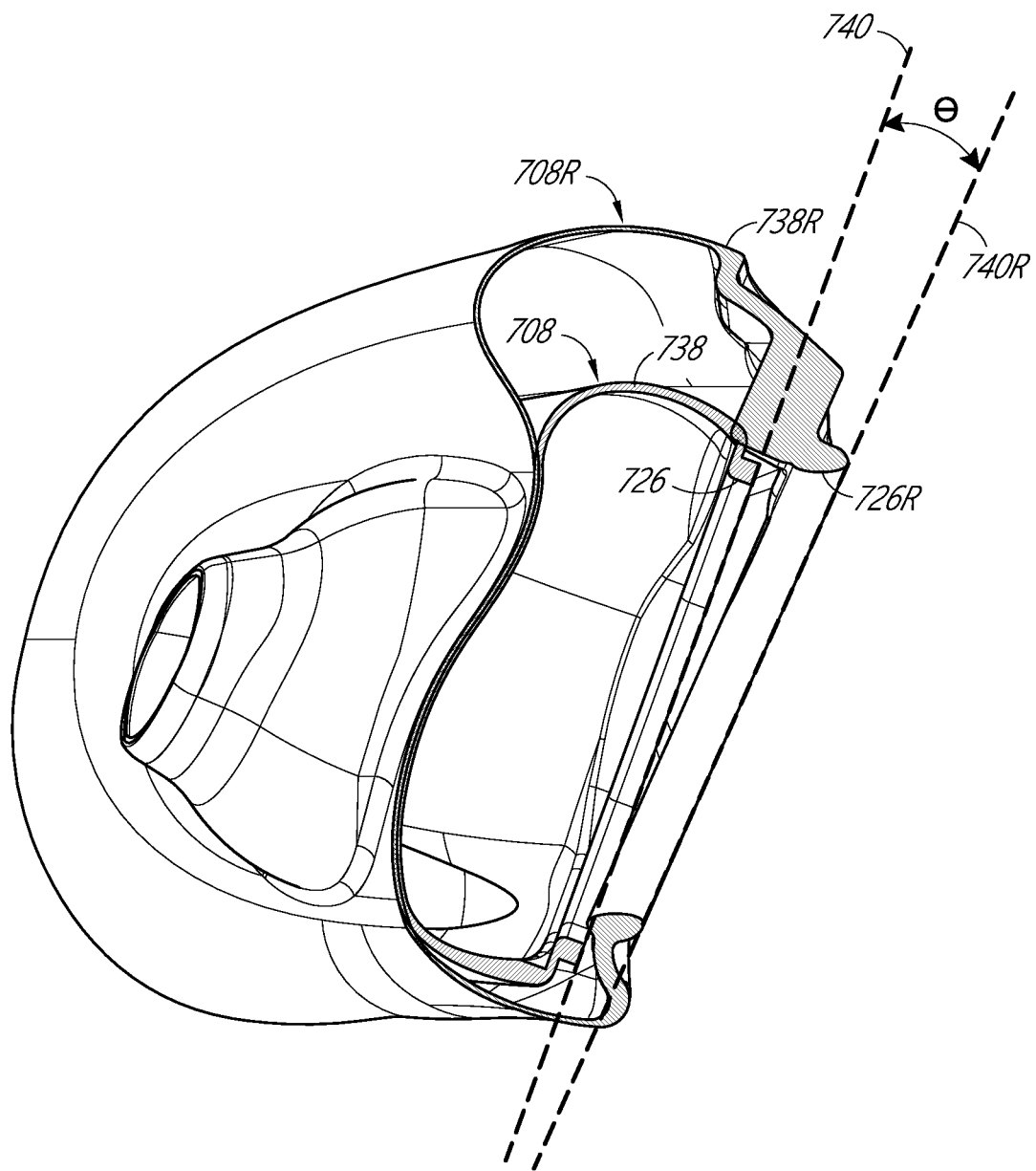
FIG. 102 is a sectioned view of the superimposed seals of FIG. 98.

With reference to FIG. 102, as a result of the reduced height 722 and depth 730 of the seal 708 in relation to the prior art seal 708R, in at least some configurations, an upper or rolling bridge portion 738 of the seal 708 is smaller (has a smaller depth or fore-aft dimension) than an upper or rolling bridge portion 738R of the prior art seal 708R. The rolling bridge portion 738R of the prior art seal 708R comprises a thin region or region of reduced wall thickness that is configured to roll or deform in order to allow the seal 708R to accommodate a wider range of nasal geometries. The reduced size of the rolling bridge portion 738 of the seal 708 can reduce instability between the seal 708 and the wearer's face, by minimizing the amount of deformation in the seal 708.

The inlet 726R of the prior art seal 708R and the inlet 726 of the seal 708 are both relatively planar when viewed from a side of the seal cushions 708, 708R. The inlet 726 of the seal 708 is angled at a greater angle 740 to a horizontal plane (in FIG. 102) than an angle 740R of the inlet 726R of the prior art seal 708R when the nasal prongs 712, 712R are in the same position. In other words, the inlet 726 of the seal 708 is closer to vertical than the inlet 726R of the prior art seal 708R when the nasal prongs 712, 712R are in the same position. In addition, the inlet 726 of the seal 708 is offset towards the wearer's face (in use) in comparison to the inlet 726R of the prior art seal 708R.

Figure 103:
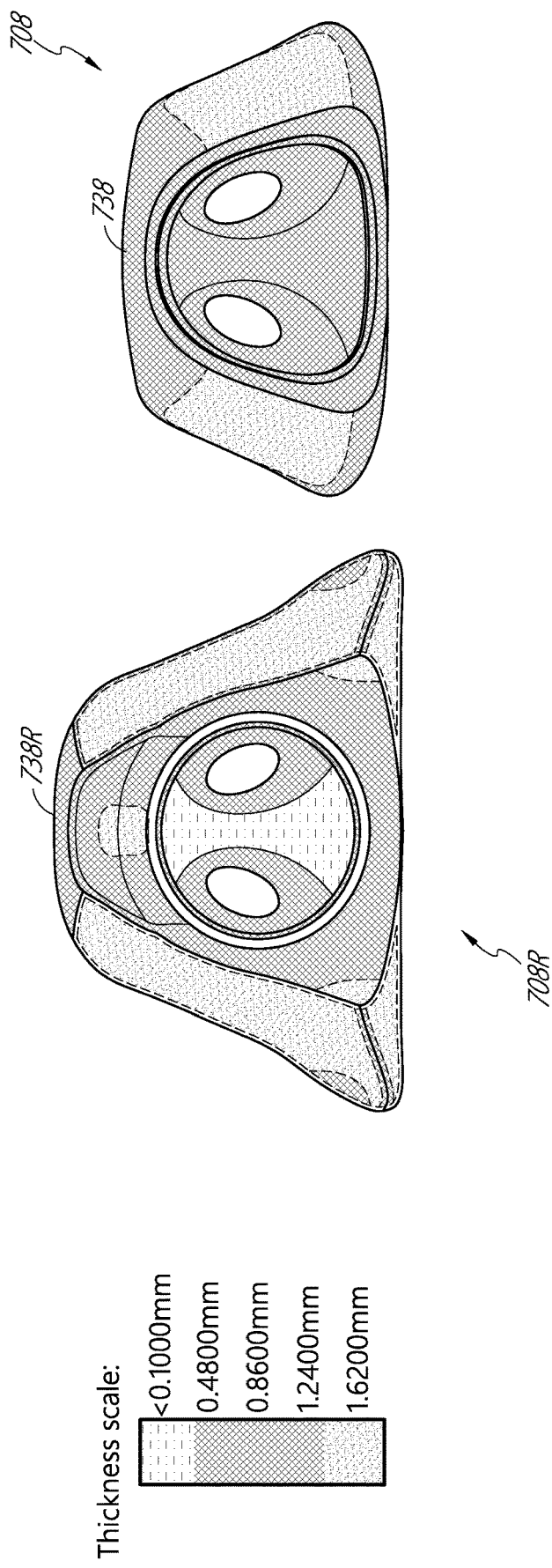
FIG. 103 shows front views of the seals of FIG. 96 showing regions of different thickness.

FIGS. 103 and 104 illustrate thickness maps of the prior art seal 708R and the seal 708 for the sake of comparison. Different thicknesses are indicated by different hatching patterns. The prior art seal 708R comprises three thickness zones or regions 742R, 744R, 746R in order from thinnest to thickest. The seal 708 comprises two thickness zones or regions 744, 746 in order from thinnest to thickest. The zone or region 742R can have thicknesses equal to or less than about 0.3 or 0.4 mm. The zones or regions 744, 744R can have thicknesses between about 0.4 or 0.5 mm to about 0.8 or 1 mm. The zones or regions 746, 746R can have thicknesses equal to or greater than 1 or 1.5 mm. The rolling bridge portion 738 of the seal 708 has a smoother transition and increased wall thickness in a least a portion thereof relative to the rolling bridge portion 738R of the prior art seal 708R (as shown in FIG. 102). Such an arrangement inhibits or prevents folds or creases forming at sudden thickness transitions and provides a more uniform distortion under applied forces, which improves stability. As illustrated in FIG. 103, thickened side regions 746 of the seal 708 are limited to the side walls of the seal 708. That is, a thinner region extends from the top and bottom walls through transition regions and toward or onto the side walls. In some configurations, the thickened side regions 746 have a wall thickness that is equal to or greater than 1 mm and the relatively thinner regions of the top and bottom walls have a wall thickness that is equal to or less than 1 mm. In the illustrated arrangement, the wall thicknesses greater than 1 mm are limited to the side regions 746 and the wall thicknesses less than 1 mm extend onto the transitions between the side walls and the top and bottom walls.

With reference to FIG. 105, the size and wall thickness of outwardly protruding corners 748, 748R has been reduced in the seal 708 relative to the prior art seal 708R. The smaller size of the seal 708 means that the outwardly protruding corners 748 are less likely to come into contact with the wearer's face to provide stability. To counteract the reduction in stability provided by the outwardly protruding corners 748R in the prior art seal 708R, the seal 708 has been made more stable by increasing the internal wall thickness and reducing the size of the rolling bridge portion 738, thus making the outwardly protruding corners 748 less important in providing stability. This means that the outwardly protruding corners 748 of the seal 708 do not need to contact the upper lip surface with as much force to provide stability and can therefore be smaller and have a thinner wall thickness. The reduced wall thickness of the outwardly protruding corners 748 may render them more compliant and capable of flexing to suit the facial geometry of the wearer.

With reference to FIG. 106, the primary sealing surfaces of the nasal prongs 712, 712R and secondary sealing surfaces 714, 714R form the internal surfaces of both of the seal cushions 708, 708R, wherein the internal surfaces are adjacent the wearer's face, in use. The seal 708 has a greater wall thickness in the internal surfaces than the prior art seal 708R. In some configurations, the internal surfaces of the seal 708 have a wall thickness of greater than 0.3 mm, greater than 0.4 mm or approximately 0.45 mm in comparison to the prior art internal surface wall thickness of 0.25 mm. The increased wall thickness of the internal surfaces of the seal 708 are less susceptible to deformation than those of the prior art seal 708R, which provides increase stability on the wearer's face. In some cases, this may improve manufacturability as it is easier to mould parts with thicker walls.

FIG. 106 also illustrates a depth 750 of a valley defined by a user-contacting surface of the seal 708 and a depth 750R of a valley of the prior art seal 708R for the sake of comparison. The valley depth 750, 750R is defined as a maximum depth relative to a line defined by rearward-most points of an upper and lower portion of the user-contacting surface of the seal, which occurs along a vertical central plane of each of the illustrated seals 708, 708R. As illustrated, the valley depth 750 of the seal 708 is significantly smaller than the valley depth 750R of the prior art seal 708R. In some configurations, the valley depth 750 of the seal 708 is less than about 1.2 mm. For example, the valley depth 750 of the seal 708 can be between about 0.9 mm and 1.2 mm, or can be about 1.125 mm. In comparison, the valley depth 750R of the prior art seal 708R is about 4.5-5 mm. In the illustrated seals 708, 708R, at least a substantial portion of the difference results from the larger rolling bridge portion 738R in the prior art seal 708R.

FIG. 107, illustrate bottom view thickness maps of the prior art seal 708R and the seal 708 for the sake of comparison using the same hatching of FIGS. 103-105. FIG. 107 illustrates that the seal 708 has a smoother thickness transition between a front and bottom wall (as shown in FIGS. 102 and 106). Such an arrangement inhibits or prevents folds or creases forming at sudden thickness transitions and provides a more uniform distortion under applied forces, which improves stability.

Figure 108:
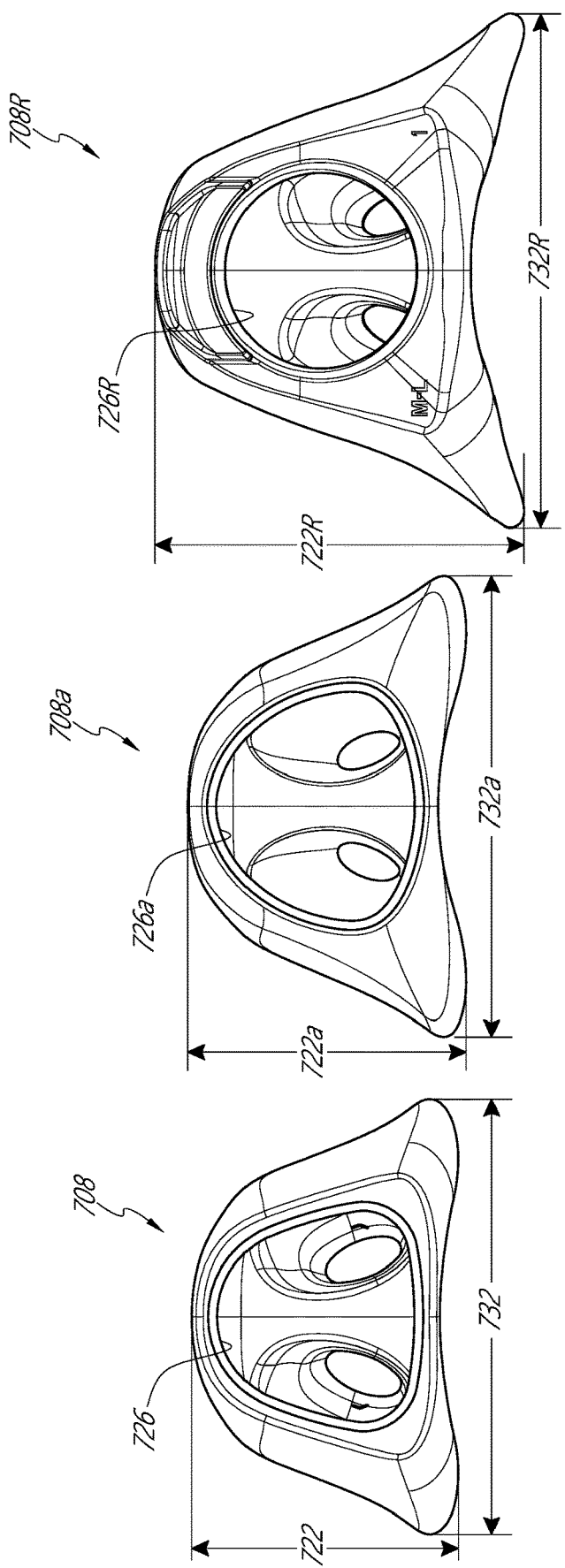
FIG. 108 shows front views of a first seal (left), a second seal (middle) and a prior art seal (right); the first seal and the prior art seal may be the same as or substantially similar to the respective seals of FIG. 96.

FIG. 108 provides front views of the seal 708 (left, which can be referred to herein as a "first seal"), the prior art seal 708R (right) and another embodiment of a seal referred to herein as a "second seal" 708*a*. The inlets 726, 726*a*, 726R of all of the illustrated seal cushions 708, 708*a*, 708R are configured to receive a seal clip that connects the seal 708, second seal 708*a*, or prior art seal 708R to a mask frame. The inlets 726, 726*a* of the first and second seals 708, 708*a* are sized to allow for a gas inlet and a bias vent to fit within the seal clip. A lower edge of the inlet 726*a* of the second seal 708*a* is more curved than a lower edge of the inlet 726 and a maximum width of the inlet 726*a* is larger than a maximum width of the inlet 726. In addition, the front surface surrounding the inlet 726*a* is more curved than the relatively planar front surface surrounding the inlet 726. FIG. 108 also illustrates overall relative heights 722, 722*a*, 722R and widths 732, 732*a*, 732R of the first seal 708, second seal 708*a* and prior art seal 708R. The first and second seals 708, 708*a* can have a height 722, 722*a* of less than or equal to 40 mm and a width 732, 732*a* of less than or equal to 65 mm. The illustrated first seal 708 has a height 722 of about 35 mm (e.g., 35.2 mm) and a width 732 of about 58-60 mm (e.g., 58.5 mm). The illustrated second seal 708*a* has a height 722*a* of about 35-36 mm (e.g., 35.5 mm) and a width 732*a* of about 60-62 mm (e.g., 61 mm). The illustrated prior art seal 708R has a height 722R of 48.2 mm and a width 732R of 68 mm.

Figure 109:
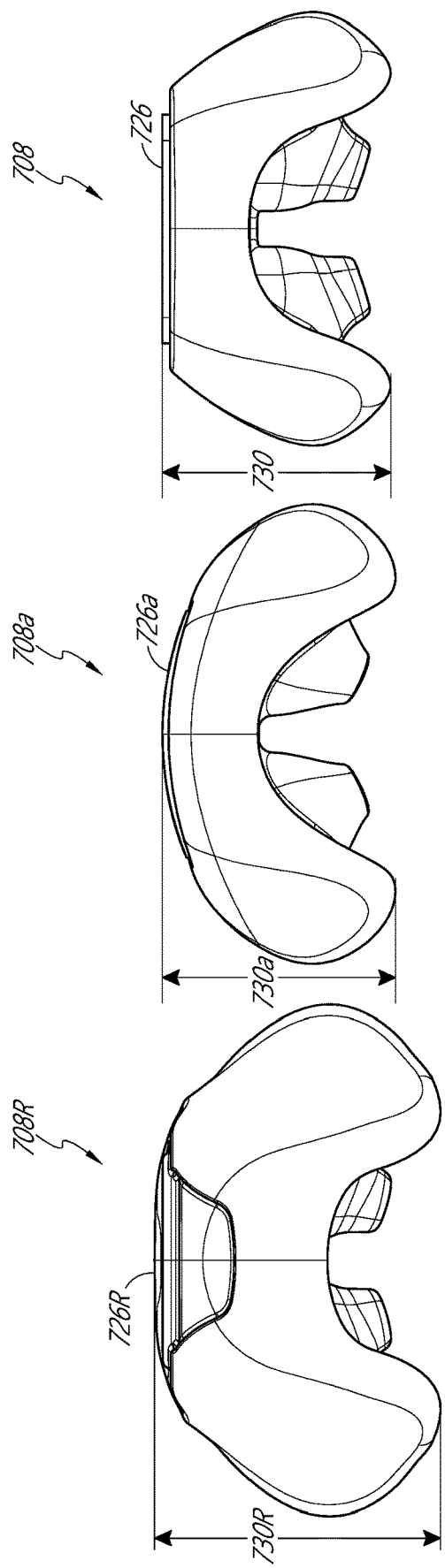
FIG. 109 shows top views of the seals of FIG. 108.

FIG. 109 provides top views of the seal 708, the second seal 708*a* and the prior art seal 708R. The inlet 726*a* of the second seal 708*a* is curved allowing for reduced depth towards the lateral edges of the second seal 708*a* in comparison to the seal 708. This makes the seal 708*a* appear smaller and helps to shift the centre of gravity of the seal 708*a* closer to the wearer's face, in use. FIG. 109 illustrates the overall depths 730R, 730, 730*a*, respectively, of the prior art seal 708R (left), the seal 708 (right) and the second seal 708*a* (middle). The seal 708 has a depth 730 of about 30 mm, the second seal 708*a* has a depth 730*a* of about 32-33 mm (e.g., 32.5 mm) and the prior art seal 708R has a depth 730R of about 38-40 mm (e.g., 38.2 mm).

Figure 110:
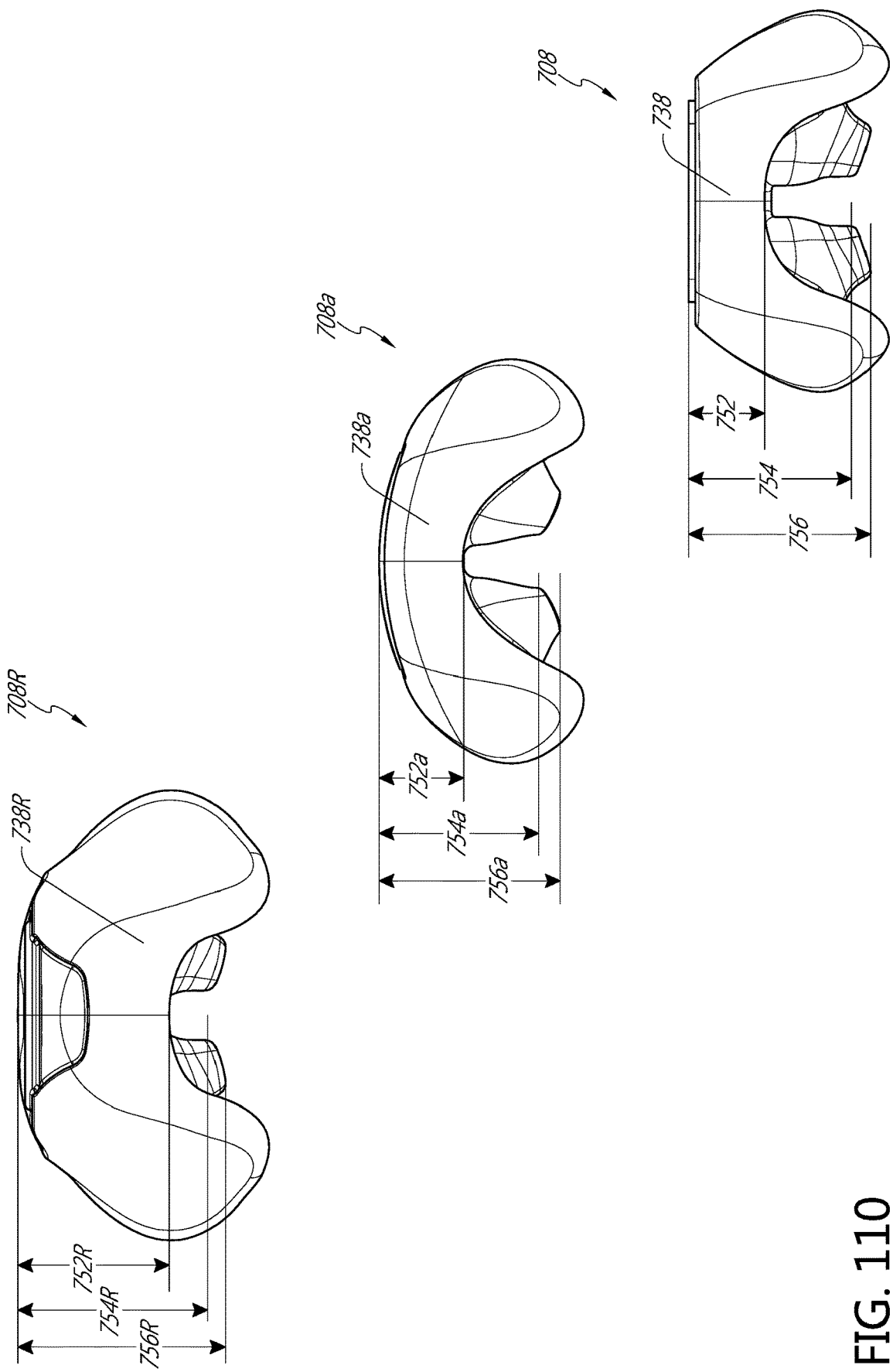
FIG. 110 shows top views of the seals of FIG. 108 comparing certain depth dimensions.

With reference to FIG. 110, the seal 708, second seal 708*a*, and prior art seal 708R have a bridge depth 752, 752*a*, 752R, respectively, defined as a depth of the top surface of the along a vertical, central plane of the seal 708, second seal 708*a*, and prior art seal 708R. The bridge depths 752, 752*a* have been reduced in the seal 708 and the second seal 708*a* in comparison to the prior art seal 708R, which reduces or minimizes instability and rolling of the seal 708 and second seal 708*a* on the user's nose. The rolling bridge portions 738, 738*a* have a greater wall thickness in the seal 708 and the second seal 708*a*, which also improves stability. The thickness map of FIG. 104 shows the increased thickness of the seal 708 and also the smoother thickness transition. The second seal 708*a* can have a similar thickness and/or thickness transition as the seal 708.

The bridge depths 752, 752*a* of the first and second seals 708, 708*a* can be less than or equal to 15 mm. In the illustrated arrangement, the bridge depth 752 of the seal 708 is 11 mm, the bridge depth 752*a* of the second seal 708*a* is 13.5 mm and the bridge depth 752R of the prior art seal 708R is 21.7 mm. Thus, with reference to the depths 730, 730*a*, 730R identified in FIG. 109, the bridge depth 752 of the seal 708 is less than one-half of the overall depth 730 of the seal 708. In some configurations, the bridge depth 752 is about one-third of the overall depth 730. The bridge depth 752*a* of the second seal 708*a* is less than one-half of the overall depth 730*a* of the second seal 708*a*. In some configurations, the bridge depth 752*a* is about two-fifths of the overall depth 730*a*. In contrast, the bridge depth 752R of the prior art seal 708R is greater than one-half of the overall depth 730R of the prior art seal 708R. In particular, the bridge depth 752R of the prior art seal 708R is about four-fifths of the overall depth 730R of the prior art seal 708R.

The seal 708, second seal 708*a*, and prior art seal 708R also define, respectively, inner prong depths 754, 754*a*, 754R from the front surface to an inner portion of the prongs 712, 712*a*, 712R and outer prong depths 756, 756*a*, 756R from the front surface to an outer portion of the prongs 712, 712*a*, 712R. Both the inner prong depths 754, 754*a* and the outer prong depths 756, 756*a* of the seal 708 and second seal 708*a* are smaller than the respective inner prong depth 754R and outer prong depth 756R of the seal 708R, which can be partially or primarily a result of the smaller bridge depths 752, 752*a*. In the illustrated seal 708, second seal 708*a*, and prior art seal 708R, the inner prong depths 754, 754*a*, 754R are 24.5 mm, 25.8 mm and 29.8 mm, respectively, and the outer prong depths are 27 mm, 28.9 mm and 32.2 mm, respectively.

Figure 111:
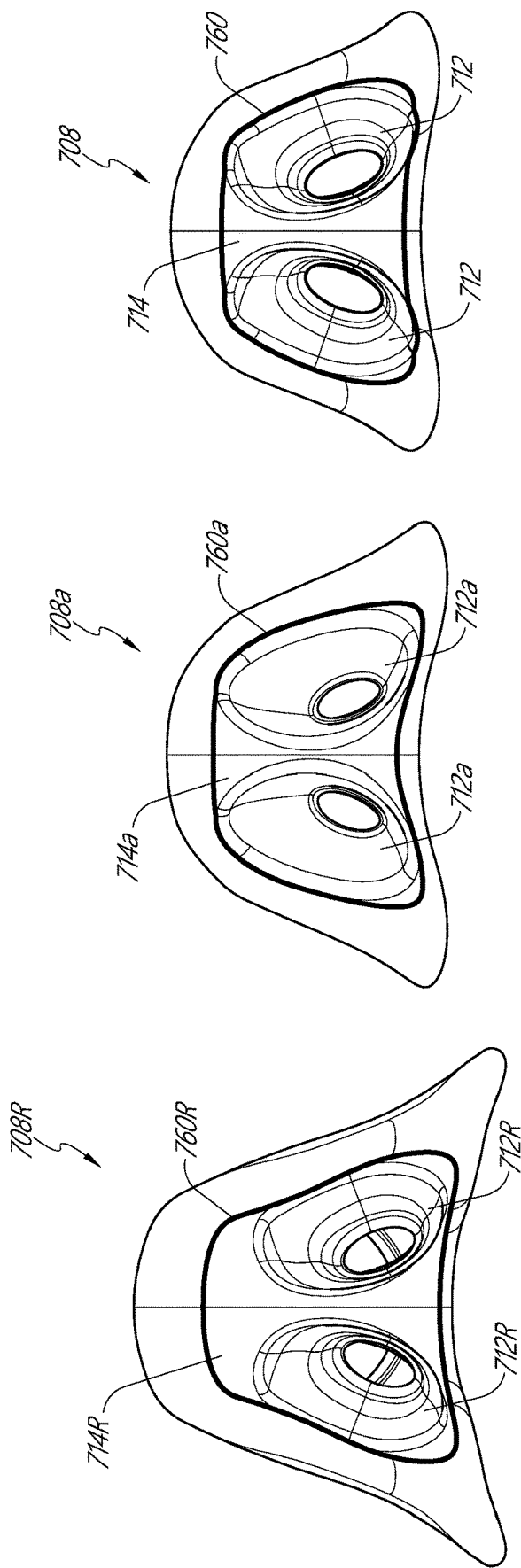
FIG. 111 shows rear views of the seals of FIG. 108 comparing certain sealing areas.

With reference to FIG. 111, the geometry of the prongs 712*a* of the second seal 708*a* is more conical and less curvaceous than geometry of the prongs 712 of the seal 708 and the geometry of the prongs 712R of the prior art seal 708R. The more conical and less curvaceous shape helps the prongs 712*a* seal with a larger range of nasal geometries without extending too far into larger nares.

FIG. 111 also illustrates an area of a sealing surface 760, 760*a*, 760R (including the prongs 712, 712*a*, 712R and the secondary sealing surface 714, 714*a*, 714R), respectfully, of each of the seal 708, the second seal 708*a* and the prior art seal 708R for the sake of comparison. As illustrated, the sealing area 760R of the prior art seal 708R is greater than 1000 mm$^2$ and is, in particular, about 1100 mm$^2$ (1102 mm$^2$). In contrast, the sealing areas 760, 760*a* of each of the seal 708 and the second seal 708*a* are less than 1000 mm$^2$. In particular, the sealing area 760 of the seal 708 is about 900 mm$^2$ (e.g., 907 mm$^2$) and the sealing area 760*a* of the second seal 708*a* is about 880 mm$^2$ (e.g., 883 mm$^2$).

Figure 112:
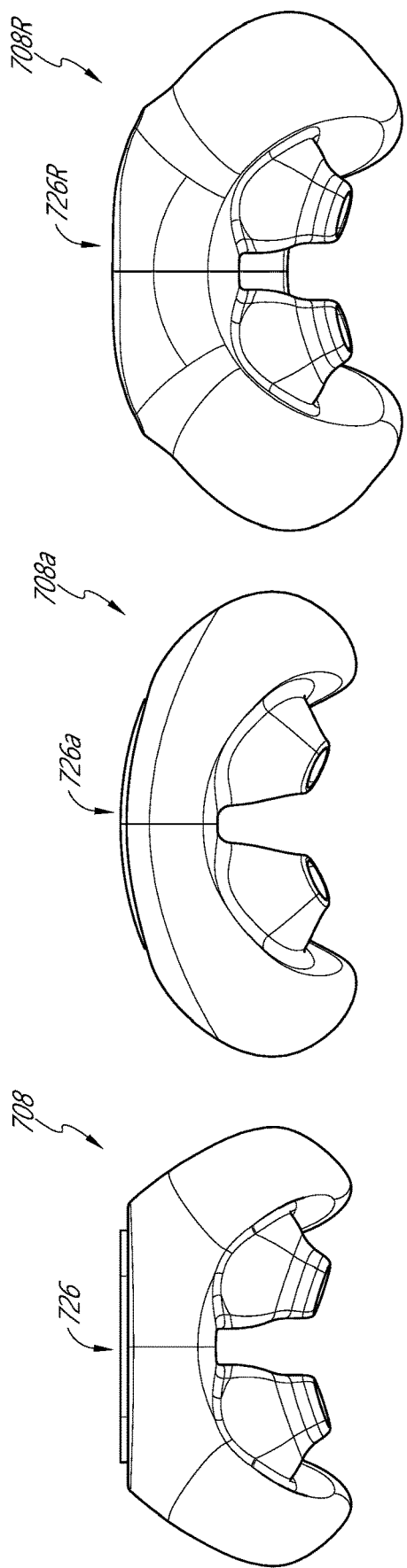
FIG. 112 shows bottom views of the seals of FIG. 108.

FIG. 112 provides bottom views of the seal 708, the second seal 708*a* and the prior art seal 708R for the sake of comparison. As described in connection with FIG. 109, the second seal 708*a* includes an inlet 726*a* (laterally curved). The seal 708 includes an inlet 726 (planar).

Figure 114:
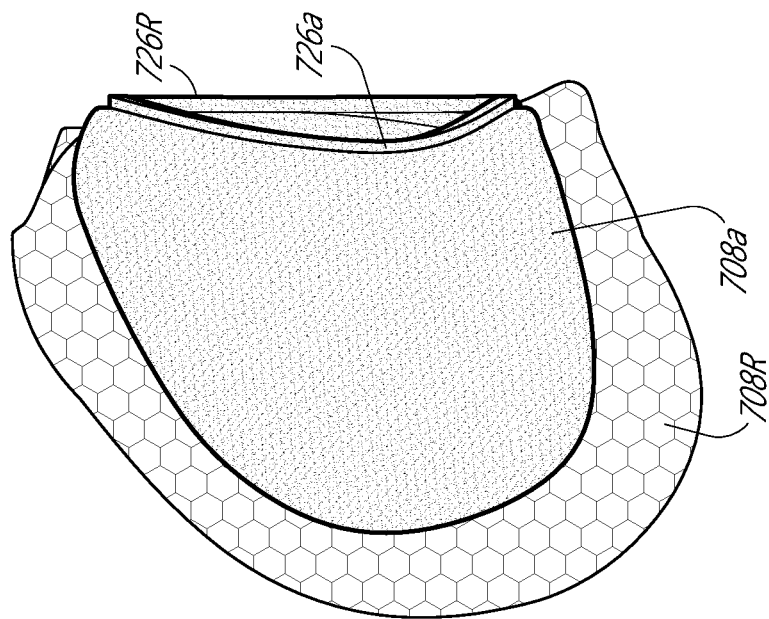
FIG. 114 is a side view of the second seal and the prior art seal of FIG. 108 superimposed on one another.
Figure 113:
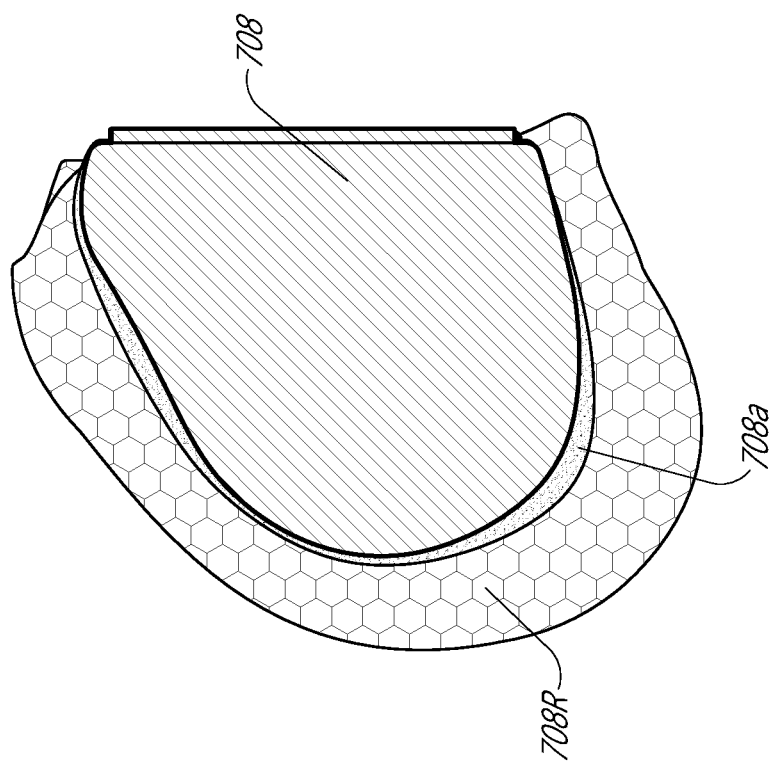
FIG. 113 is a side view of the seals of FIG. 108 superimposed on one another.

FIG. 113 illustrates a side view of the seal 708, the second seal 708*a* and the prior art seal 708R superimposed on one another. FIG. 114 illustrates the second seal 708*a* superimposed on the prior art seal 708R. As described above, the seal 708 and the second seal 708*a* have a significantly smaller height and depth compared to the prior art seal 708R.

Figure 116:
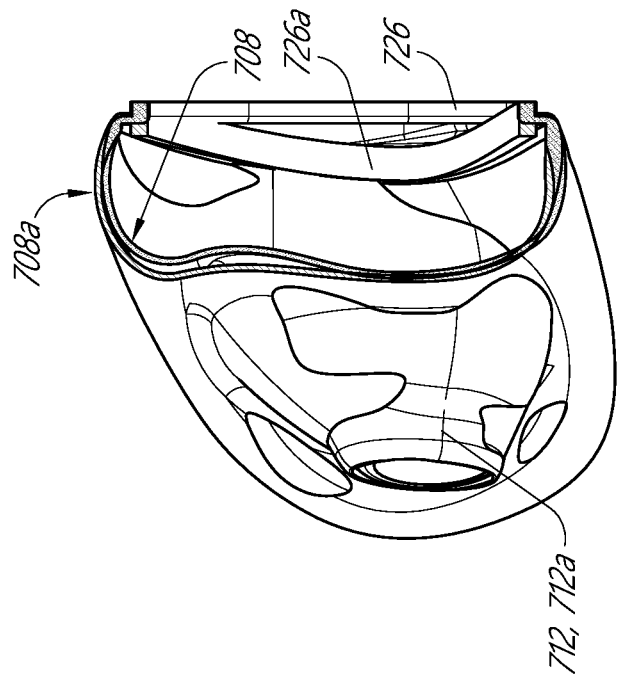
FIG. 116 is a vertical sectioned view of the superimposed seals of FIG. 114.
Figure 115:
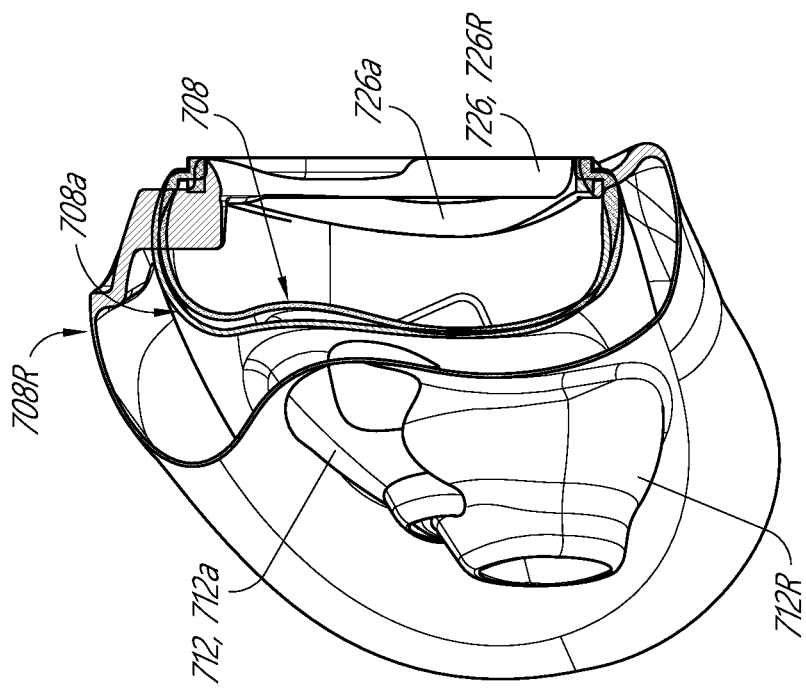
FIG. 115 is a vertical sectioned view of the superimposed seals of FIG. 113.

FIG. 115 is a sectioned view along a central, vertical plane of the seal 708, the second seal 708*a* and the prior art seal 708R superimposed on one another. FIG. 115 illustrates that the internal (user-facing) wall thickness of the first and second seals 708, 708*a* is greater than the internal wall thickness of the prior art seal 708R. FIG. 116 is a sectioned view of the seal 708 and the second seal 708*a* superimposed on one another. FIG. 116 illustrates the inlet 726*a* (laterally curved) of the second seal 708*a* compared to the inlet 726 (planar) of the seal 708.

Figures 117, 118:
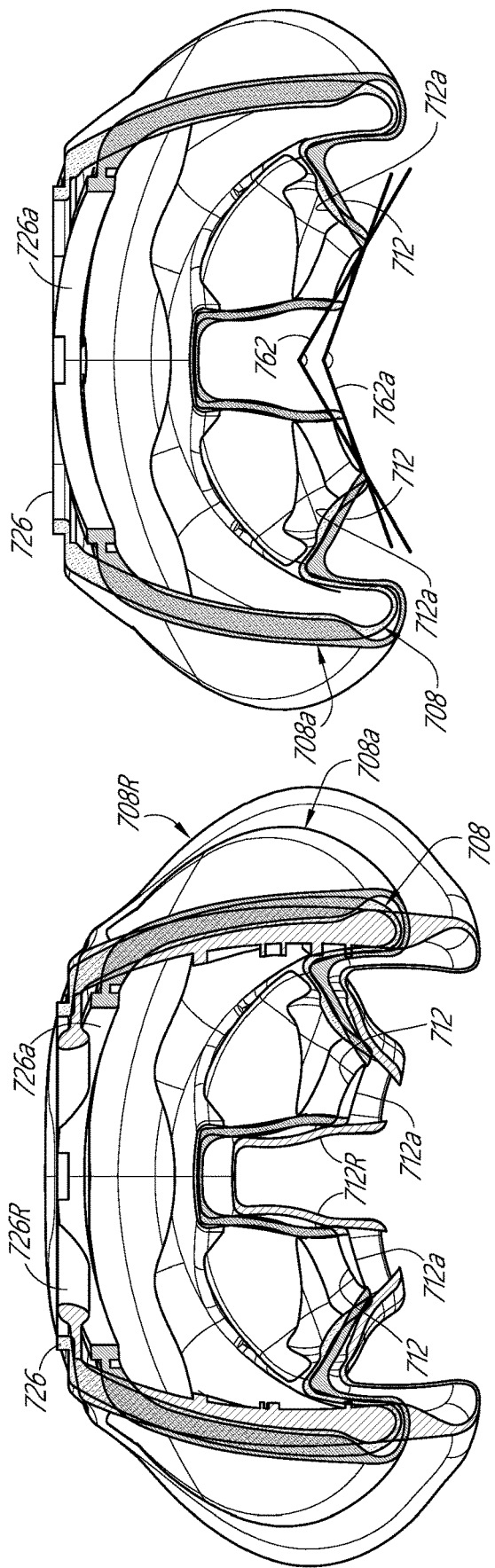
FIG. 117 is a horizontal sectioned view of the superimposed seals of FIG. 113.

FIG. 117 illustrates a sectioned view along a central, horizontal plane of the seal 708, the second seal 708*a* and the prior art seal 708R superimposed on one another. FIG. 117 illustrates that the wall thickness of both the first and second seals 708, 708*a* is reduced on the outer surfaces in comparison to the prior art seal cushion 708R.

FIG. 118 is the same sectioned view as FIG. 117 but omits the prior art seal 708R. FIG. 118 illustrates that an angle of the prong tips has been altered between the seal 708 and the second seal 708*a*. In the illustrated arrangement, the prong angle 762 of the seal 708 is approximately 120 degrees and the prong angle 762*a* of the second seal is approximately 140 degrees. The increased angle 762*a* between the prong tips of the second seal 708*a* is intended to reduce pressure on the septum of a user and may make the prongs 712*a* less intrusive.

Figure 119:
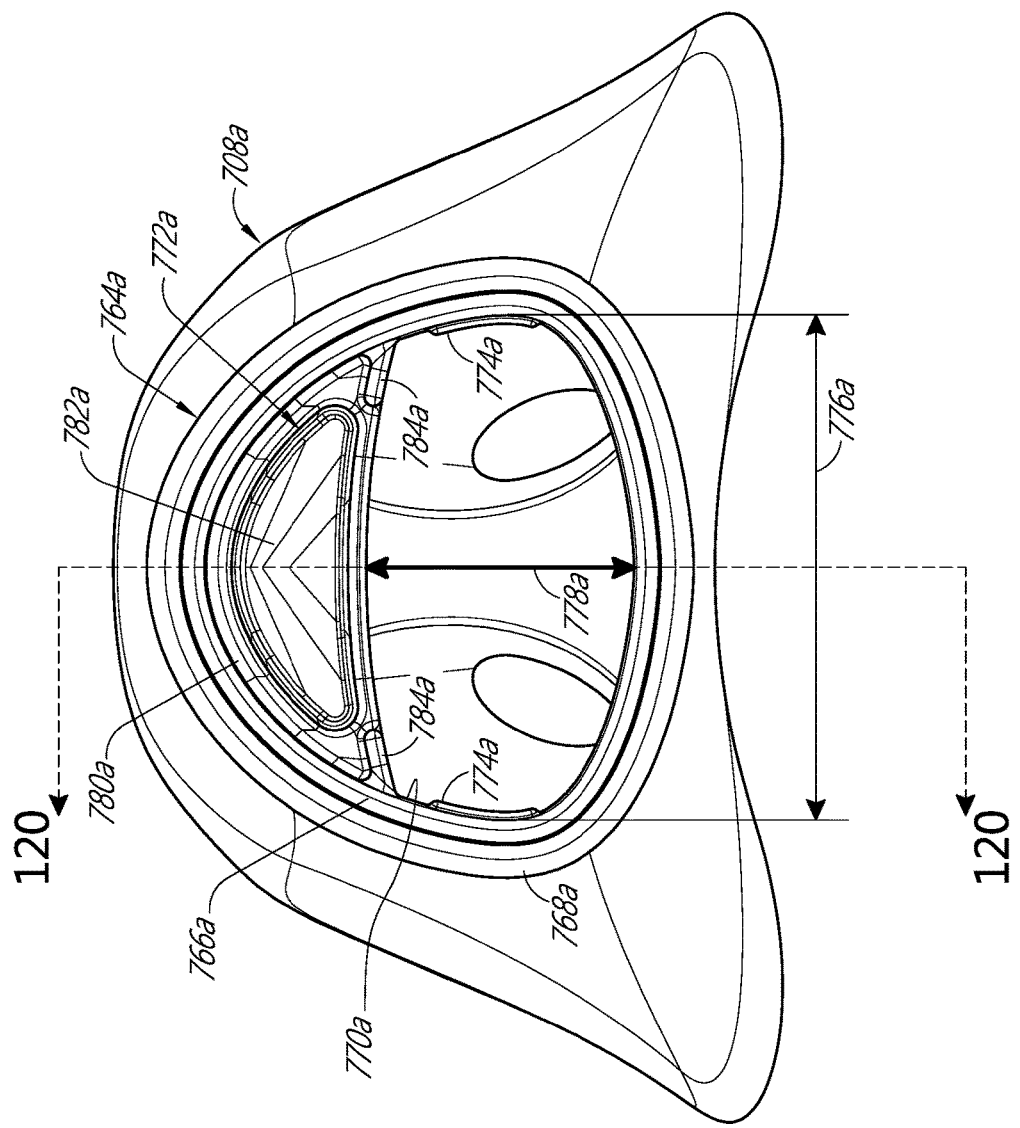
Figure 120:
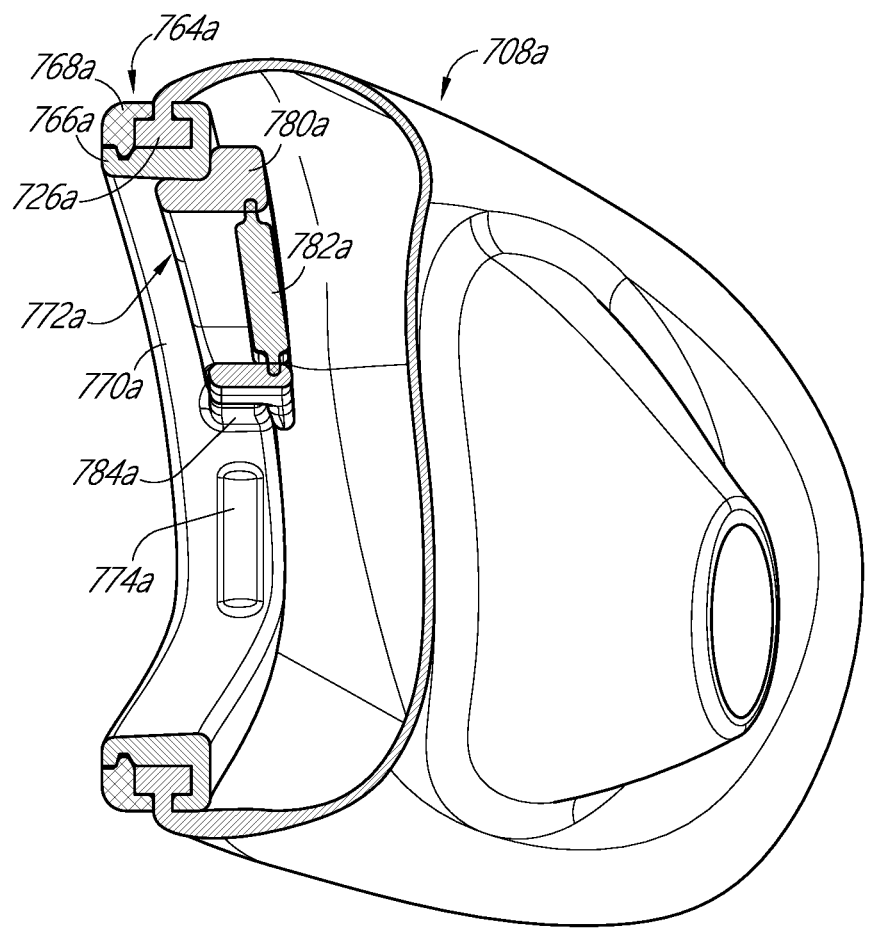

With reference to FIGS. 119 and 120, the second seal 708*a* includes a seal clip 764*a*. The seal clip 764*a* comprises an inner clip portion or inner clip 766*a* and an outer clip portion or outer clip 768*a* that are configured to clip together such that they sandwich the edges of the inlet 726*a* of the seal. In some configurations, the inner clip 766*a* and the outer clip 768*a* are permanently joined to each other by snap fit geometry or any other suitable means (welded, glued, etc.). The inner clip 766*a* defines a gas inlet opening 770*a* and a vent region 772*a*. The gas inlet opening 770*a* has a larger area than the vent region 772*a* and is positioned below the vent region 772*a*.

The gas inlet opening 770*a* is configured to receive and connect to a flange of the mask frame (e.g., frame 710). The connection between the flange and the inner clip 766*a* is provided by snap fit bumps 774*a* in the illustrated arrangement and is configured such that the second seal 708*a* can be repeatedly connected and disconnected to the frame. The flange is configured to surround a connection between the frame and the gas conduit. The gas inlet opening 770*a* is thus sized according to the size of the gas conduit and the connection to the frame. In the illustrated arrangement, the gas inlet opening 770*a* has a maximum width 776*a* of approximately 27 mm and a maximum height 778*a* of approximately 14 mm.

The vent region 772*a* is configured to receive and retain a diffuser clip 780*a* that holds a diffuser 782*a* within the vent region 772*a* such that all air/gas that passes through the vent region 772*a* passes through the diffuser 782*a*. The diffuser clip 780*a* can be permanently or temporarily connected to the inner clip 766*a* by a snap fit connection or other suitable arrangements (e.g., welding).

The diffuser 782*a* comprises a fibrous textile that air can pass through. The area of the diffuser 782*a* in combination with the density of the diffuser 782*a* is configured to allow enough air to flow through the vent region 772*a* to flush expired $CO_2$ from within the mask (e.g., mask 702) of which the second seal 708*a* is a part. A flow rate of approximately 31 L/min may be desired in some embodiments.

In the illustrated arrangement, the diffuser 782*a* is permanently bonded to the diffuser clip 780*a* by means such as over-moulding or welding. The diffuser clip 780*a* comprises an aperture that is filled by the diffuser 782*a*.

The vent region 772*a* is bounded at its lower limits by a pair of separators 784*a* that extend inwardly from the inner perimeter of the inner clip 766*a*. The separators 784*a* extend part way across the width such that they do not meet at the middle. The separators 784*a* are configured to support the diffuser clip 780*a* within the inner clip 766*a*.

Figure 121:
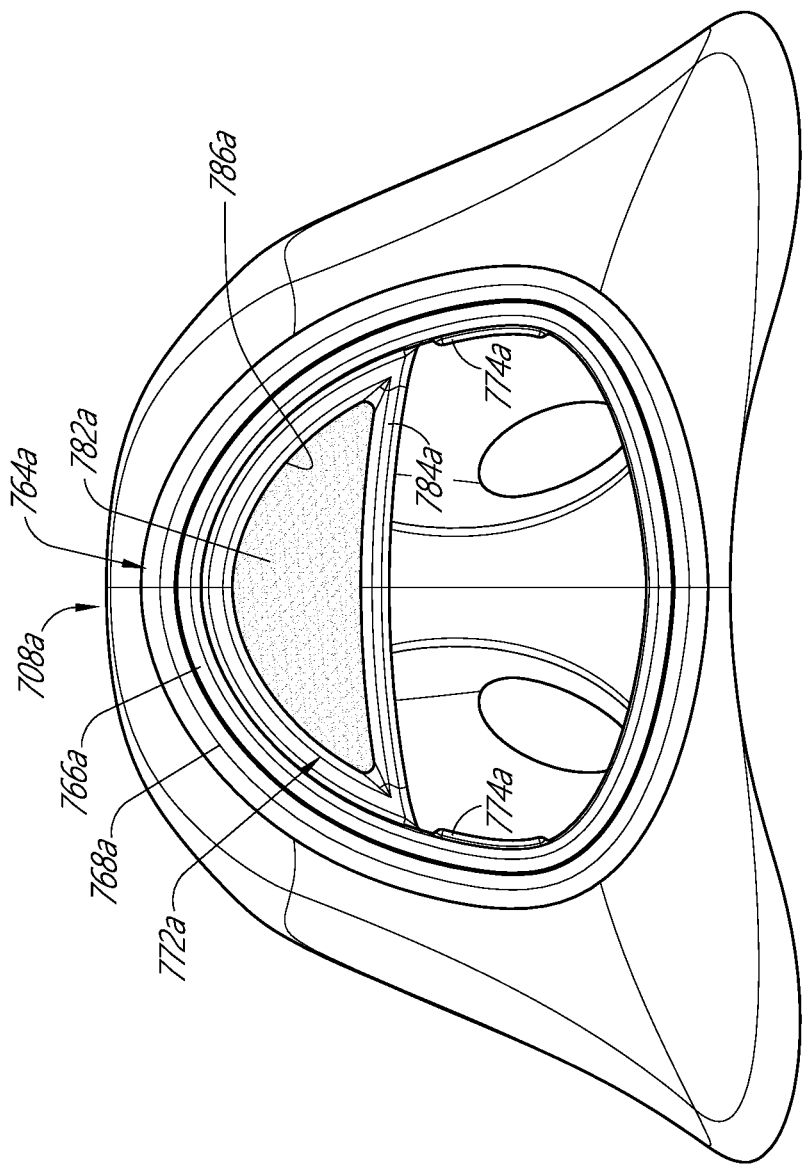
Figure 122:
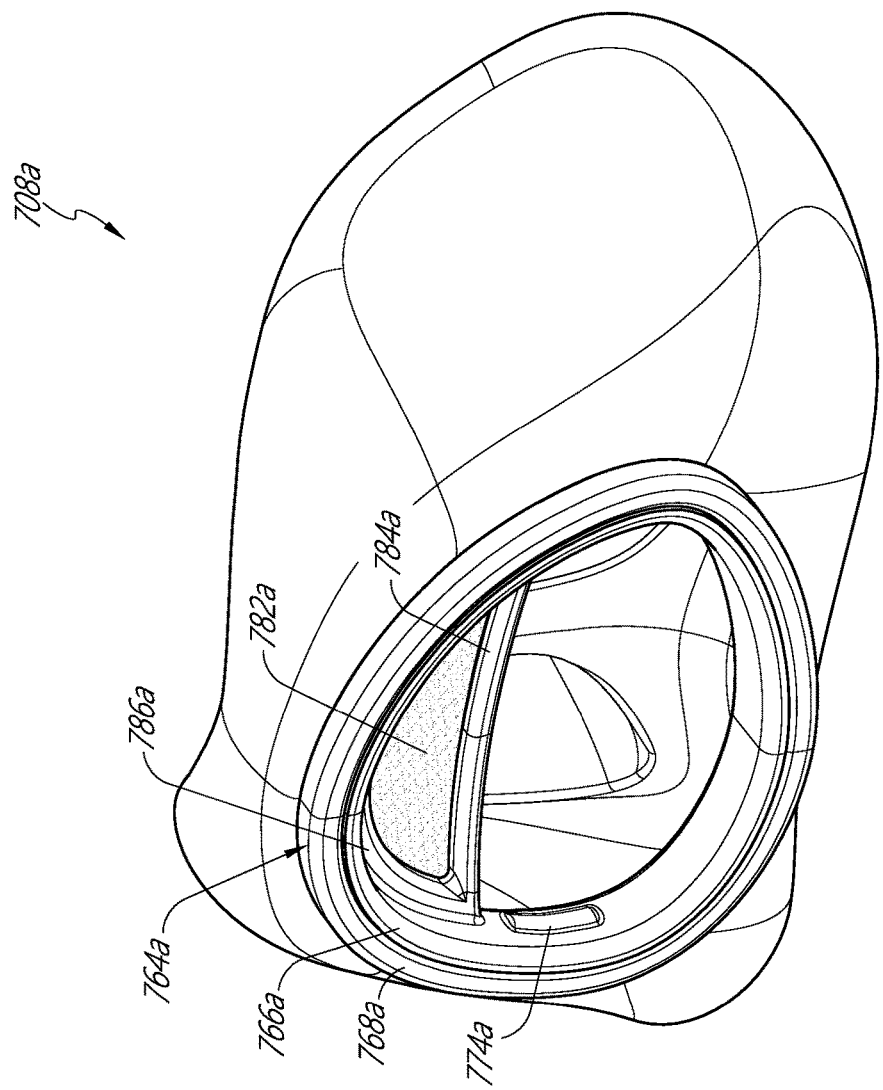

With reference to FIGS. 121 and 122, a modified embodiment of the inner clip 766*a* comprises a single separator 784*a* that extends across the entire width of the inner clip 766*a* to define a vent aperture 786*a*. The diffuser clip 780*a* is permanently bonded to the inner clip 766*a* within the vent aperture 786*a*. The diffuser clip 780*a* may be bonded to the inner clip 766*a* by over-moulding, welding or adhesives etc.

FIG. 123 illustrates the outlet end of the prong 712*a* of the second seal 708*a* along with the end of the prong 712R of the prior art seal 708R for the sake of comparison. As illustrated, each outlet end of the prongs 712*a*, 712R defines a major axis 718*a*, 718R and a minor axis 720*a*, 720R. The outlet end of the prong 712R is symmetrical about the major axis 718R and the minor axis 720R. The outlet end has a width 790R that is defined by a width 792R of the inner portion and a width 794R of the outer portion. The widths 792R, 794R are equal to one another. Each width 792R, 794R has a dimension of 2.90 mm, such that the total width 790R has a dimension of 5.8 mm. The outlet end has a height 796R that is defined by a height 798R of the upper portion and a height 800R of the lower portion. The heights 798R, 800R are equal to one another. Each height 798R, 800R has a dimension of 4.6 mm, such that the total height 796R has a dimension of 9.2 mm. In contrast, the outlet end of the prong 712*a* is asymmetrical about at least one of the major axis 718*a* and the minor axis 720*a*. In the illustrated arrangement, the width 790*a* is made up of the width 792*a* of the inner portion and the width 794*a* of the outer portion, wherein the width 794*a* is larger than the width 792*a*. In the illustrated arrangement, the width 792*a* is 2.6 mm and the width 794*a* is 3.0 mm for a total width 790*a* of 5.6 mm. The height 796*a* is made up of the height 798*a* of the upper portion and a height 800*a* of the lower portion, which are equal to one another. In the illustrated arrangement, the height 798*a* and the height 800*a* each have a dimension of 4.25 mm such that the total height 796*a* has a dimension of 8.5 mm.

Figure 124:
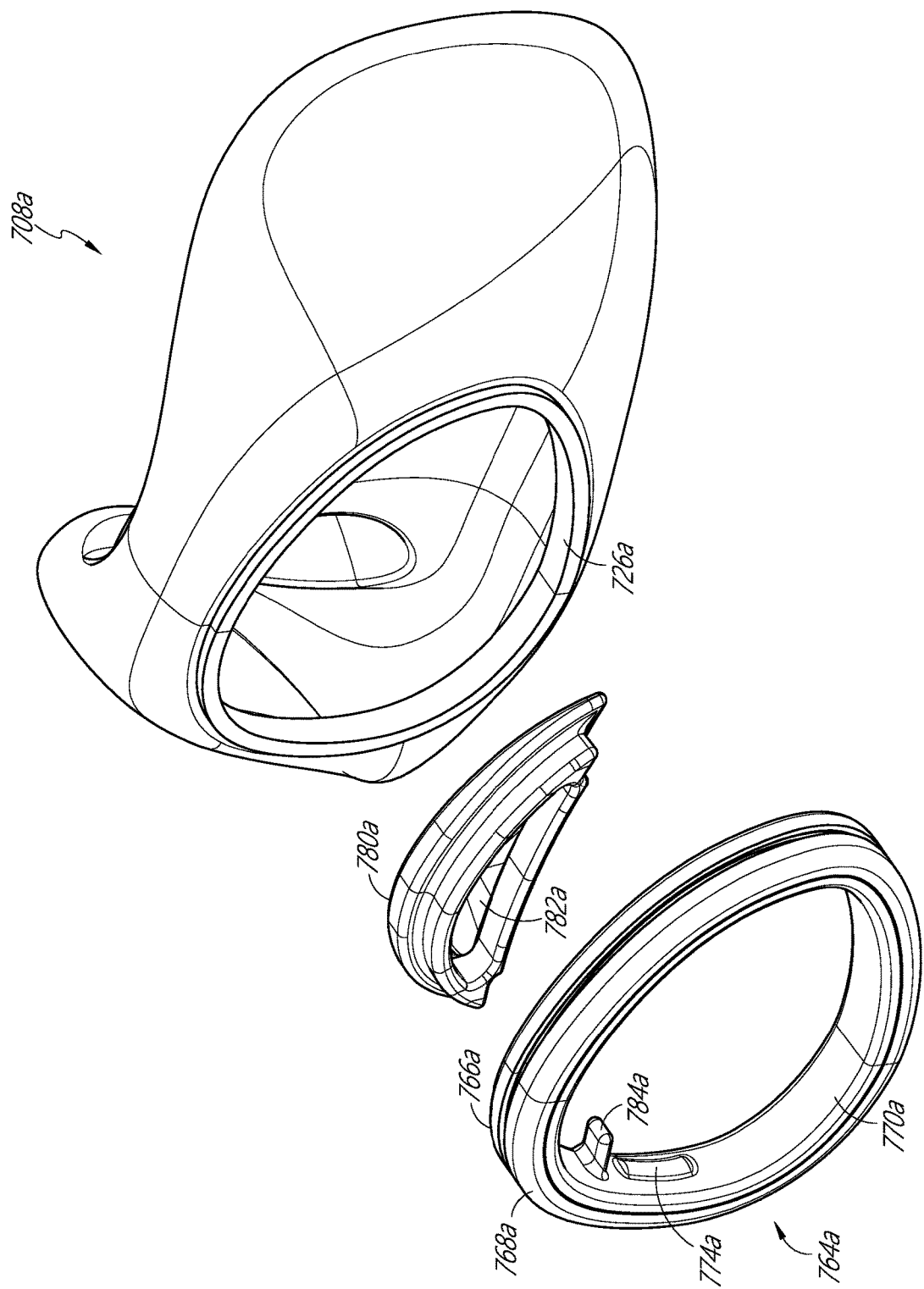

FIG. 124 is an exploded view of the second seal 708*a*, seal clip 764*a* and diffuser clip 780*a*. In FIG. 124, the seal clip 764*a* illustrates the inner clip 766*a* and the outer clip 768*a* clipped together separate from the second seal 708*a*. The diffuser clip 780*a* is also shown separate from the second seal 708*a* and the seal clip 764*a*.

Figure 125:
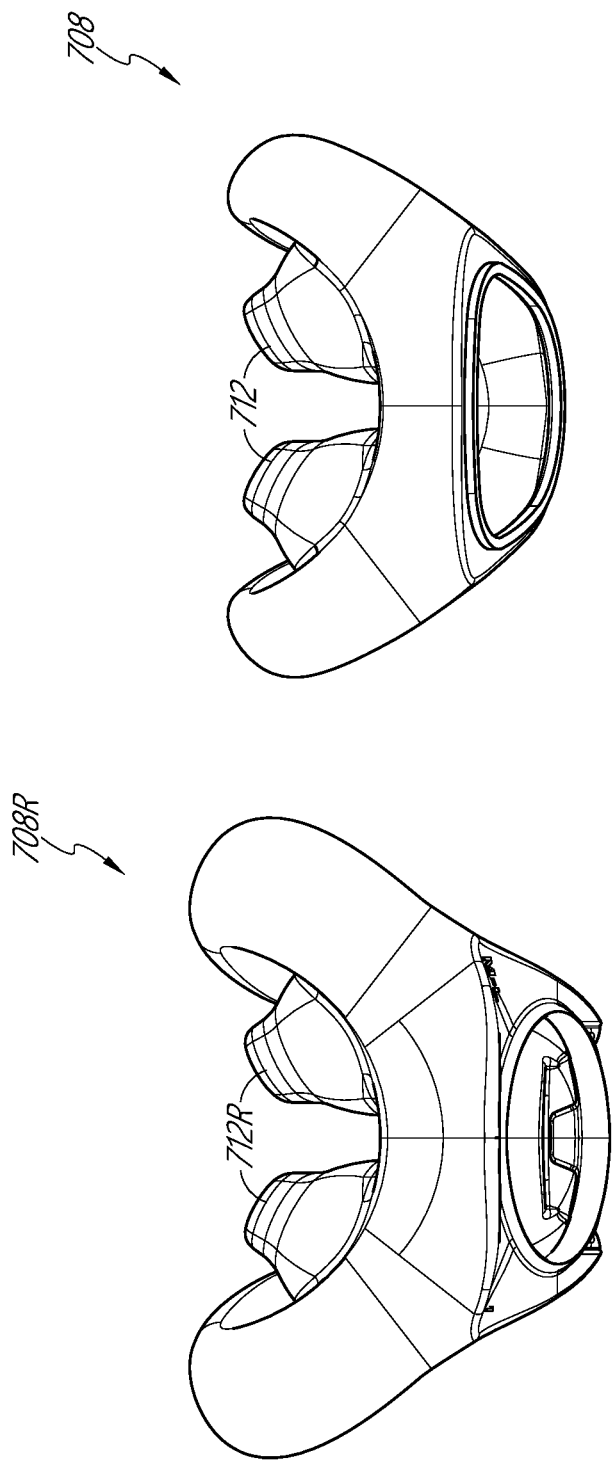
Figure 126:
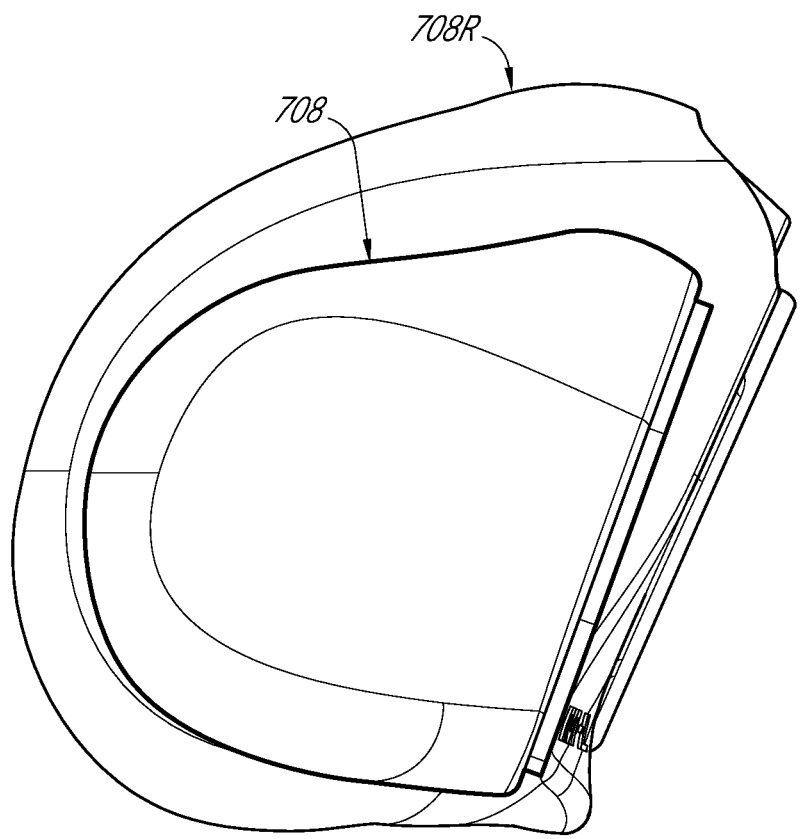

FIGS. 125 and 126 illustrate a top view and a side view, respectively, of the prior art seal 708R next to the first seal 708 for the sake of comparison. As noted, the portion of the seal 708 surrounding the nasal prongs 712 is substantially smaller for a given seal or nasal prong size than the portion of the seal 708R that surrounds the nasal prongs 712R.

Figure 127:
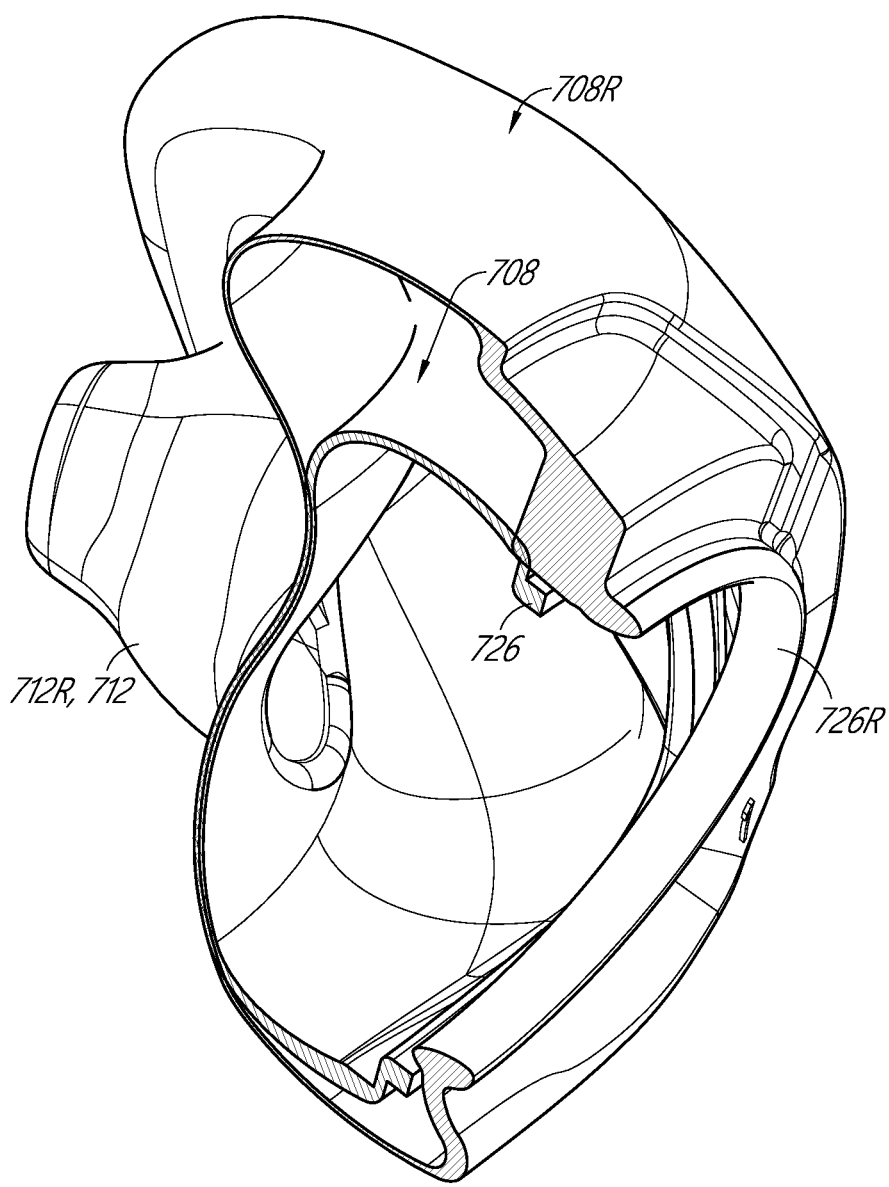
Figure 129:
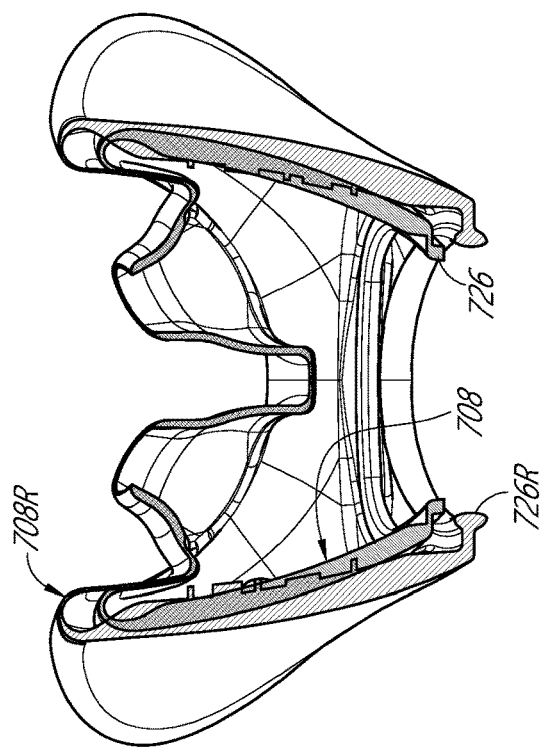
Figure 128:
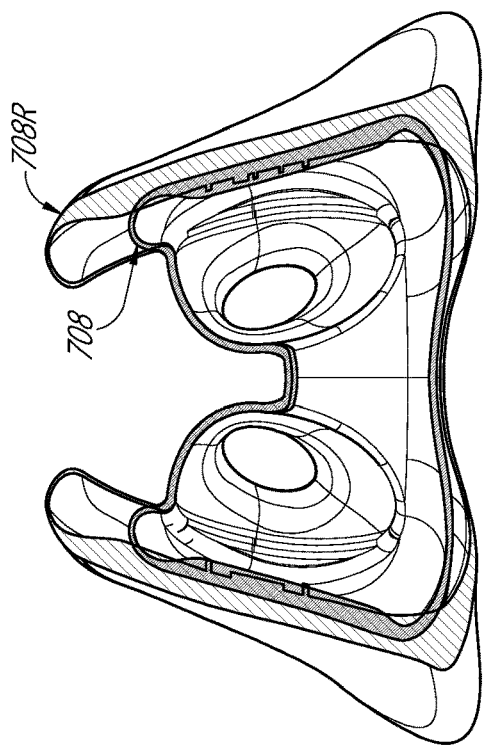

FIGS. 127-129 illustrate several views of the prior art seal 708R overlying the first seal 708 with the nasal prongs 712R, 712 substantially aligned with one another. FIGS. 127-129 illustrate, among other differences, the different in wall thicknesses in various portions of the seals 708, 708R, the different in attitude or angle of the inlet 726, 726R and the different in overall size and shape.

Figure 130:
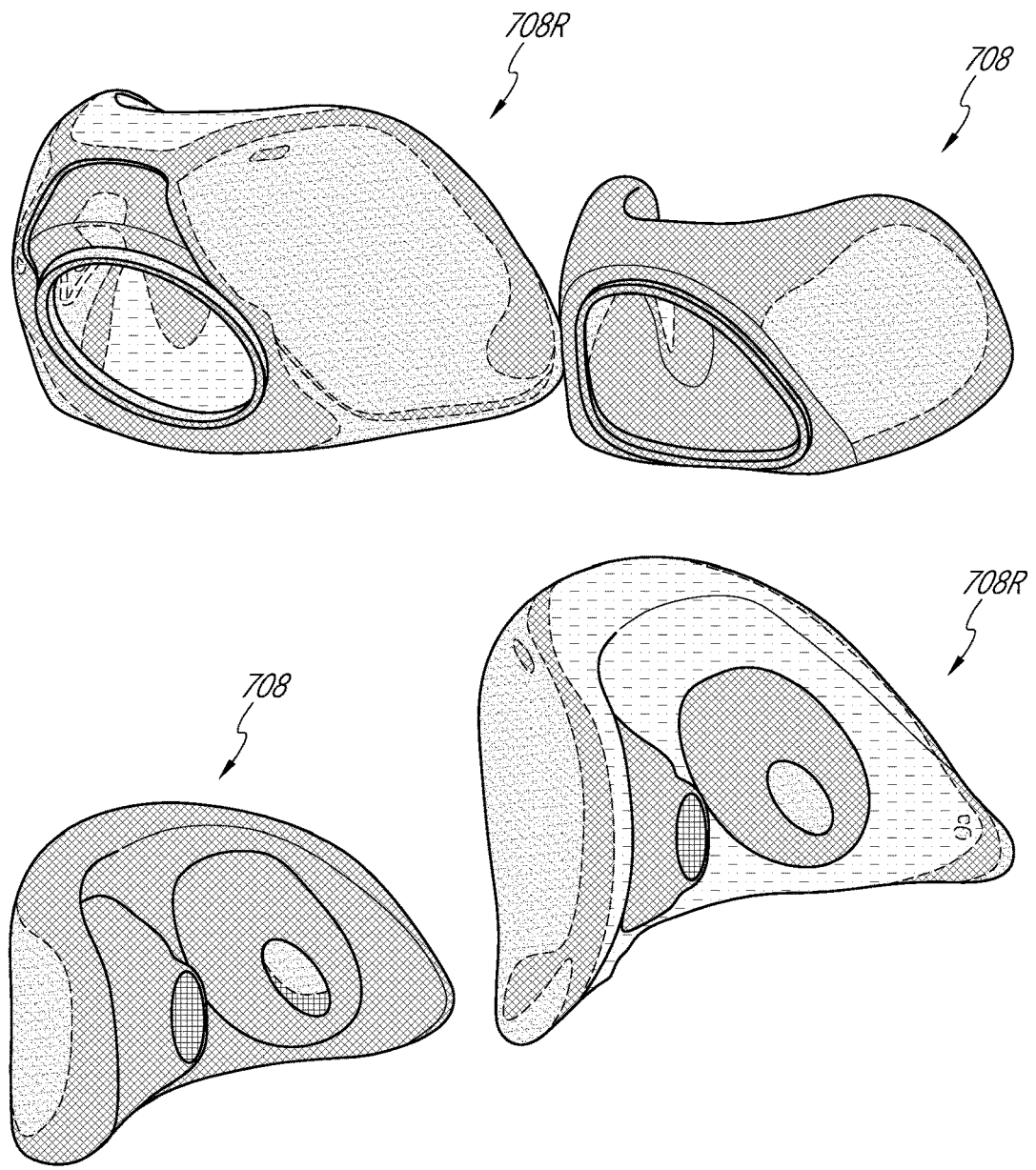

FIG. 130 illustrates thickness maps of the prior art seal 708R and the first seal 708 with the seals 708, 708R in front and rear perspective views. FIG. 130 utilizes the same hatching patterns to denote wall thickness ranges as described in connection with FIGS. 103-105 and 107.

Figure 131:
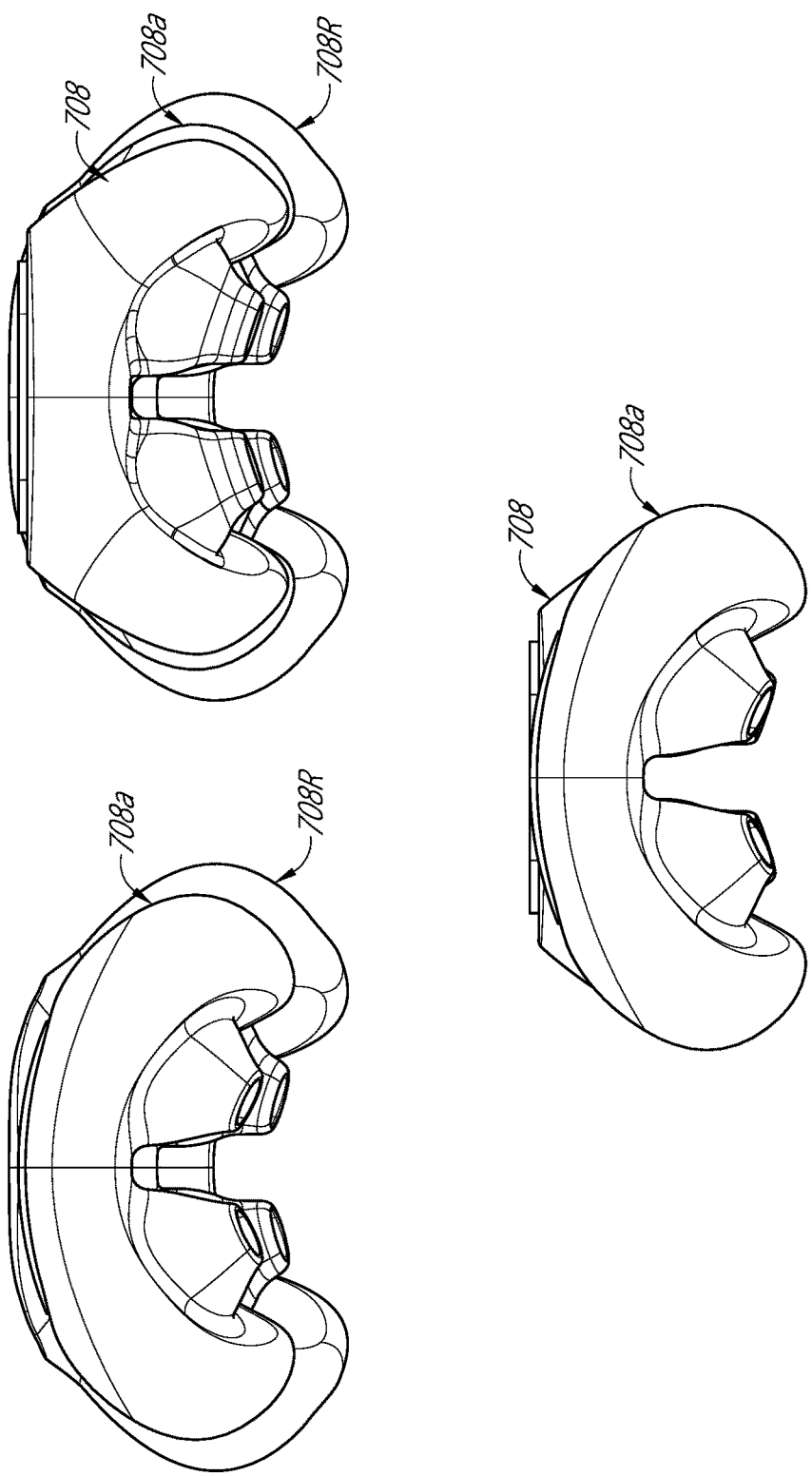

FIG. 131 illustrates top views of different combinations of the seal 708, second seal 708a, and prior art seal 708R overlying one another for the sake of comparison.

FIG. 132 illustrates sectional views taken along a vertical, lateral plane of the seal 708, second seal 708a, and prior art seal 708R overlying one another and the seal 708, second seal 708a overlying one another for the sake of comparison.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A yoke configured to be coupled to a mask frame of a respiratory mask system comprising:
   a front wall extending from a first lateral end to a second lateral end;
   a rear wall extending from a first lateral end to a second lateral end, the front wall and the rear wall defining an inner cavity therebetween;
   a first end cap coupled to the first lateral ends of the front wall and the rear wall and a second end cap coupled to the second lateral ends of the front wall and the rear wall, each end cap comprising an entry hole configured to receive a filament of a self-adjusting headgear;

a first housing disposed between the front wall and the rear wall adjacent the first end cap;

a second housing disposed between the front wall and the rear wall adjacent the second end cap; and a divider dividing the inner cavity into an upper track and a lower track, wherein the upper track extends from the first housing to the second end cap above the second housing, and wherein the lower track extends from the second housing to the first end cap below the first housing.

2. The yoke of claim 1, wherein the yoke comprises a yoke front comprising the front wall and a yoke back comprising the rear wall, and wherein the yoke front and the yoke back are coupled together.

3. The yoke of claim 2, wherein one of the yoke front and yoke back comprises at least one snap-fit bump and the other of the yoke front and yoke back comprises at least one corresponding snap-fit groove that receives the snap-fit bump to couple the yoke front and the yoke back together.

4. The yoke of claim 3, wherein a plurality of snap-fit bumps extend along a portion of a length of one of the yoke front or the yoke back and a plurality of corresponding snap-fit grooves extend along the other of the yoke front or the yoke back.

5. The yoke of claim 2, wherein the upper track is at least partially defined by an upper wall of the yoke front and the divider, and the lower track is at least partially defined by a lower wall of the yoke front and the divider.

6. The yoke of claim 2, wherein the divider protrudes rearwardly from a rear internal surface of the front wall of the yoke front.

7. The yoke of claim 2, wherein the yoke front comprises a first end located at the first lateral end of the front wall, wherein the yoke front comprises a second end located at the second lateral end of the front wall, wherein the upper track is wider toward the first end of the yoke front and narrower toward the second end of the yoke front, and wherein the lower track is wider toward the second end of the yoke front and narrower toward the first end of the yoke front.

8. The yoke of claim 2, wherein the yoke front forms a D-shaped cross-sectional profile.

9. The yoke of claim 1, wherein each of the first and second end caps comprise a locking mechanism for the self-adjusting headgear.

10. The yoke of claim 1, wherein a height of the yoke is greater at the first and second lateral ends than at a centre portion between the first and second lateral ends.

11. The yoke of claim 1, wherein the entry hole of at least one of the first and second end caps comprises a slot.

12. The yoke of claim 1, wherein the upper track extends into the second end cap and the lower track extends into the first end cap.

13. The yoke of claim 1, wherein the first and second end caps are configured to be hinged onto the first and second lateral ends of the front wall and the rear wall, respectively, during assembly.

14. The yoke of claim 1, wherein each of the first and second end caps are attached to a front strap of the headgear.

15. The assembly of claim 1, wherein the first and second housings are U-shaped.

* * * * *

UNITED STATES PATENT AND TRADEMARK OFFICE
CERTIFICATE OF CORRECTION

PATENT NO. : 11,083,862 B2
APPLICATION NO. : 16/085156
DATED : August 10, 2021
INVENTOR(S) : Melissa Catherine Bornholdt Page 1 of 1

It is certified that error appears in the above-identified patent and that said Letters Patent is hereby corrected as shown below:

On the Title Page

In Column 2, item (74), Attorney, Agent or Firm, Line 1, delete "Marten," and insert --Martens,--.

In the Specification

In Column 2, Line 5, delete "450" and insert --45°--.

In Column 8, Line 35, delete "frontl" and insert --front--.

In Column 9, Line 65, delete "f" and insert --of--.

In Column 11, Line 59, delete "60" and insert --60;--.

In Column 13, Line 18, delete "113." and insert --113;--.

In Column 15, Line 63, delete "450" and insert --45°--.

In the Claims

In Column 52, Line 28, Claim 15, delete "assembly" and insert --yoke--.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*